US008921369B2

(12) United States Patent
Zhong et al.

(10) Patent No.: US 8,921,369 B2
(45) Date of Patent: Dec. 30, 2014

(54) INHIBITORS OF HCV NS5A

(75) Inventors: Min Zhong, San Francisco, CA (US);
Leping Li, San Francisco, CA (US)

(73) Assignee: Presidio Pharmaceuticals, Inc., San Francisco, CA (US)

( * ) Notice: Subject to any disclaimer, the term of this patent is extended or adjusted under 35 U.S.C. 154(b) by 393 days.

(21) Appl. No.: 13/132,605

(22) PCT Filed: Dec. 2, 2009

(86) PCT No.: PCT/US2009/066459
§ 371 (c)(1),
(2), (4) Date: Jan. 20, 2012

(87) PCT Pub. No.: WO2010/065674
PCT Pub. Date: Jun. 10, 2010

(65) Prior Publication Data
US 2012/0122864 A1   May 17, 2012

Related U.S. Application Data

(60) Provisional application No. 61/119,723, filed on Dec. 3, 2008, provisional application No. 61/173,590, filed on Apr. 28, 2009, provisional application No. 61/214,881, filed on Apr. 28, 2009, provisional application No. 61/182,958, filed on Jun. 1, 2009, provisional application No. 61/182,952, filed on Jun. 1, 2009.

(51) Int. Cl.

| | | |
|---|---|---|
| *A01N 43/58* | (2006.01) |
| *A01N 43/60* | (2006.01) |
| *A61K 31/50* | (2006.01) |
| *A61K 31/495* | (2006.01) |
| *A01N 27/00* | (2006.01) |
| *A61K 31/015* | (2006.01) |
| *A01N 43/54* | (2006.01) |
| *A01N 43/90* | (2006.01) |
| *A61K 31/517* | (2006.01) |
| *A61K 31/519* | (2006.01) |
| *A01N 43/42* | (2006.01) |
| *A61K 31/44* | (2006.01) |
| *C07D 235/02* | (2006.01) |
| *C07D 403/00* | (2006.01) |
| *C07D 209/52* | (2006.01) |
| *C07D 209/04* | (2006.01) |
| *C07D 498/02* | (2006.01) |
| *C07D 513/02* | (2006.01) |
| *C07D 515/02* | (2006.01) |
| *C07D 513/00* | (2006.01) |
| *C07D 239/70* | (2006.01) |
| *C07D 471/02* | (2006.01) |
| *C07D 491/02* | (2006.01) |
| *C07D 413/00* | (2006.01) |
| *C07D 263/52* | (2006.01) |
| *C07D 498/00* | (2006.01) |
| *C07D 263/60* | (2006.01) |
| *C07D 249/08* | (2006.01) |
| *C07D 249/00* | (2006.01) |
| *C07D 407/14* | (2006.01) |
| *C07D 413/14* | (2006.01) |
| *C07D 471/04* | (2006.01) |
| *C07D 403/14* | (2006.01) |
| *C07D 401/14* | (2006.01) |
| *C07D 417/14* | (2006.01) |
| *C07D 405/14* | (2006.01) |

(52) U.S. Cl.
CPC ............ *C07D 471/04* (2013.01); *C07D 407/14* (2013.01); *C07D 413/14* (2013.01); *C07D 403/14* (2013.01); *C07D 401/14* (2013.01); *C07D 417/14* (2013.01); *C07D 405/14* (2013.01)
USPC ........ 514/250; 514/258.1; 514/299; 514/765; 544/253; 546/113; 548/151; 548/217; 548/262.4; 548/302.7; 548/516

(58) Field of Classification Search
CPC ..... A61K 31/015; A61K 31/34; A61K 31/40; A61K 31/41; A61K 31/341; A61K 31/381; A61K 31/403; A61K 31/407; A61K 31/415; A61K 31/4164; A61K 31/4245; A61K 31/425; A61K 31/4353; A61K 31/4985; A61K 31/5025; A61K 31/519; C07C 15/24; C07D 207/30; C07D 209/04; C07D 231/10; C07D 231/56; C07D 233/54; C07D 235/04; C07D 249/08; C07D 261/02; C07D 261/06; C07D 263/54; C07D 271/06; C07D 277/20; C07D 277/62
USPC ............... 514/765, 250, 258.1, 299; 544/253; 546/113; 548/151, 217, 262.4, 302.7, 548/516; 549/49, 462
See application file for complete search history.

(56) References Cited

U.S. PATENT DOCUMENTS 4,048,185 A * 9/1977 Pintschovius et al. ......... 548/220
5,236,619 A * 8/1993 Iwaki et al. .............. 252/299.61

FOREIGN PATENT DOCUMENTS

| WO | 2008021936 A2 | 2/2008 |
| WO | 2010132601 A1 | 11/2010 |
| WO | 2011031904 A1 | 3/2011 |
| WO | 2011059850 A1 | 5/2011 |

OTHER PUBLICATIONS

Extended European Search Report dated Jun. 29, 2012 issued in PCT/US2009/066459.

* cited by examiner

*Primary Examiner* — Sarah Pihonak
(74) *Attorney, Agent, or Firm* — Sam K. Tahmassebi; TechLaw LLP

(57) ABSTRACT

Provided herein are compounds, pharmaceutical compositions and combination therapies for inhibition of hepatitis C.

17 Claims, No Drawings

INHIBITORS OF HCV NS5A

STATEMENT OF RELATED APPLICATIONS

This application is filed under 35 U.S.C. §371 as the U.S. national phase of International Application PCT/US2009/066459, filed Dec. 2, 2009, which designated the U.S. and claims the benefit of U.S. provisional applications 61/119,723 filed Dec. 3, 2008; 61/173,590 and 61/214,881 filed Apr. 28, 2009; and 61/182,958 and 61/182,952 filed Jun. 1, 2009.

FIELD OF THE INVENTION

The invention relates to compounds useful for inhibiting hepatitis C virus ("HCV") replication, particularly functions of the non-structural 5A ("NS5A") protein of HCV.

BACKGROUND OF THE INVENTION

HCV is a single-stranded RNA virus that is a member of the Flaviviridae family. The virus shows extensive genetic heterogeneity as there are currently seven identified genotypes and more than 50 identified subtypes. In HCV infected cells, viral RNA is translated into a polyprotein that is cleaved into ten individual proteins. At the amino terminus are structural proteins: the core (C) protein and the envelope glycoproteins, E1 and E2. p7, an integral membrane protein, follows E1 and E2. Additionally, there are six non-structural proteins, NS2, NS3, NS4A, NS4B, NS5A and NS5B, which play a functional role in the HCV lifecycle. (see, for example, Lindenbach, B. D. and C. M. Rice, *Nature*. 436:933-938, 2005).

Infection by HCV is a serious health issue. It is estimated that 170 million people worldwide are chronically infected with HCV. HCV infection can lead to chronic hepatitis, cirrhosis, liver failure and hepatocellular carcinoma. Chronic HCV infection is thus a major worldwide cause of liver-related premature mortality.

The present standard of care treatment regimen for HCV infection involves interferon-alpha, alone, or in combination with ribavirin. The treatment is cumbersome and sometimes has debilitating and severe side effects and many patients do not durably respond to treatment. New and effective methods of treating HCV infection are urgently needed.

SUMMARY OF THE INVENTION

Essential features of the NS5A protein of HCV make it an ideal target for inhibitors. The present disclosure describes a class of compounds targeting the NS5A protein and methods of their use to treat HCV infection in humans.

In a first aspect, compounds of formula I are provided:

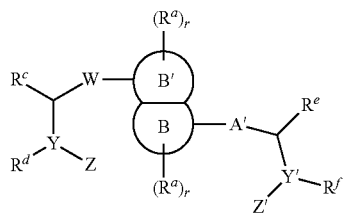

wherein:
A' is selected from the group consisting of single bond, —(CR$_2$)$_n$—C(O)—(CR$_2$)$_p$—, —(CR$_2$)$_n$—O—(CR$_2$)$_p$—, —(CR$_2$)$_n$—N(R$^N$)—(CR$_2$)$_p$—, —(CR$_2$)$_n$—S(O)$_k$—N(R$^N$)—(CR$_2$)$_p$—, —(CR$_2$)$_n$—C(O)—N(R$^N$)—(CR$_2$)$_p$—, —(CR$_2$)$_n$—N(R$^N$)—C(O)—N(R$^N$)—(CR$_2$)$_p$—, —(CR$_2$)$_n$—C(O)—O—(CR$_2$)$_p$—, —(CR$_2$)$_n$—N(R$^N$)—S(O)$_k$—N(R$^N$)—(CR$_2$)$_p$— and —(CR$_2$)$_n$—N(R$^N$)—C(O)—O—(CR$_2$)$_p$— and a heteroaryl group selected from the group consisting of

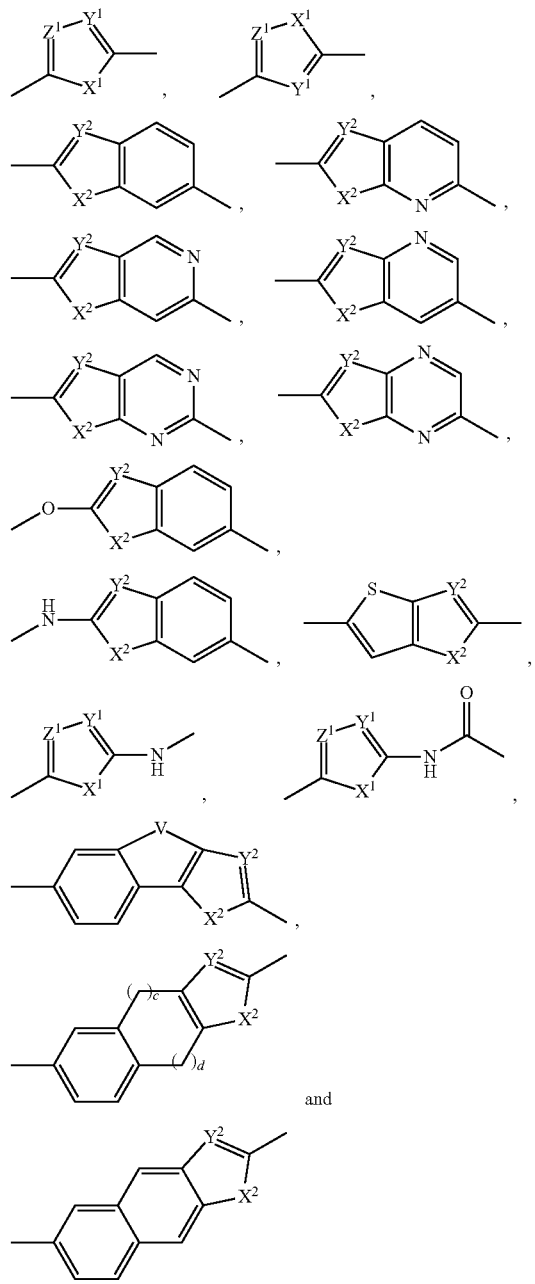

wherein:
X$^1$ is CH$_2$, NH, O or S,
Y$^1$, Y$^2$ and Z$^1$ are each independently CH or N,
X$^2$ is NH, O or S,
V is —CH$_2$—CH$_2$—, —CH=CH—, —N=CH—, —(CH$_2$)$_a$—N(R$^N$)—(CH$_2$)$_b$— or —(CH$_2$)$_a$—O—(CH$_2$)$_b$—, wherein a and b are independently 0, 1, 2, or 3 with the proviso that a and b are not both 0,

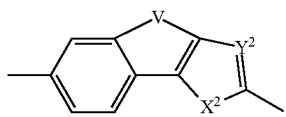

optionally includes 1 or 2 nitrogens as heteroatoms on the phenyl residue, the carbons of the heteroaryl group are each independently optionally substituted with a substituent selected from the group consisting of halogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, the nitrogens, if present, of the heteroaryl group are each independently optionally substituted with a substituent selected from the group consisting of —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, a and b are independently 1, 2, or 3.

c and d are independently 1 or 2, n and p are independently 0, 1, 2 or 3, k is 0, 1, or 2, each R is independently selected from the group consisting of hydrogen, halogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, each R$^N$ is independently selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, and wherein B may be attached to either side of A' so that in the example of A' being

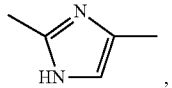

the W—B-A' can be

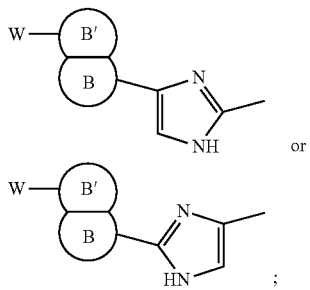

B and B' are each independently a 4- to 8-membered ring that is an aryl, heteroaryl, cycloalkyl, or heterocycle, wherein each hetero atom, if present, is independently N, O or S and wherein at least one of B or B' is aromatic;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and if B or B' is not aromatic, it may also be substituted with one or more oxo;

each r is independently 0, 1, 2 or 3;

W is independently selected from

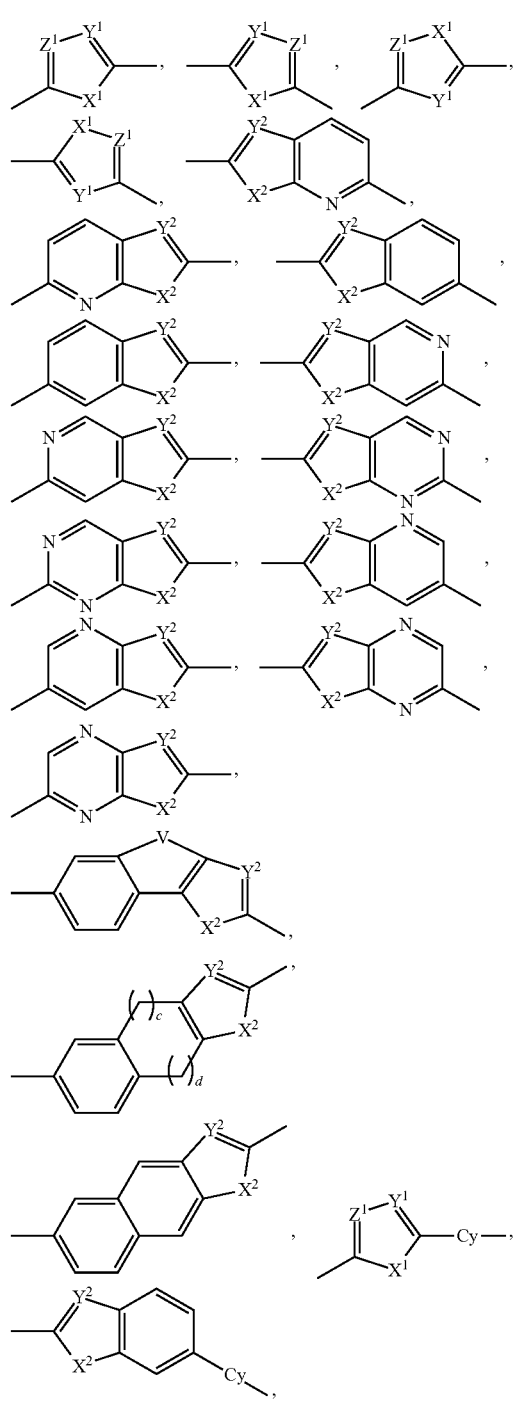

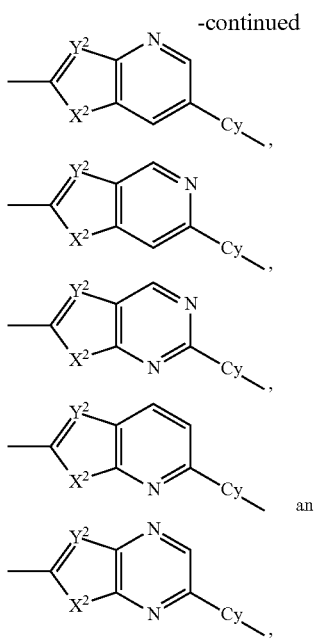

wherein:
X¹ is CH₂, NH, O or S,
Y¹, Y² and Z¹ are each independently CH or N,
X² is NH, O or S,
V is —CH₂—CH₂—, —CH=CH—, —N=CH—, —(CH₂), —N(R$^N$)—(CH₂)$_b$— or —(CH₂)$_a$—O—(CH₂)$_b$—, wherein a and b are independently 0, 1, 2, or 3 with the proviso that a and b are not both 0,

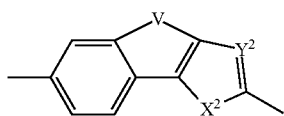

optionally includes 1 or 2 nitrogens as heteroatoms on the phenyl residue,
W is optionally substituted with one or more substituents selected from the group consisting of —OH, —CN, —NO₂, halogen, C₁ to C₁₂ alkyl, C₁ to C₁₂ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
W and ring B' can be connected through either a carbon or a nitrogen atom on B', and
Cy is a monocyclic, bicyclic or tricyclic 5- to 12-membered cycloalkyl, heterocycle, aryl group or heteroaryl group wherein up to three heteroatoms are independently N, S or O and which is optionally substituted with one or more substituents selected from the group consisting of —OH, —CN, —NO₂, halogen, C₁ to C₁₂ alkyl, C₁ to C₁₂ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
each R$^c$, R$^d$, R$^e$ and R$^f$ is independently selected from the group consisting of: hydrogen, C₁ to C₈ alkyl, C₁ to C₈ heteroalkyl, aralkyl and a 4- to 8-membered ring which may be cycloalkyl, heterocycle, heteroaryl or aryl, wherein, each hetero atom, if present, is independently N, O or S,
each of R$^c$, R$^d$, R$^e$ and R$^f$ may optionally be substituted by C₁ to C₈ alkyl, C₁ to C₈ heteroalkyl, aralkyl, or a 4- to 8-membered ring which may be cycloalkyl, heterocycle, heteroaryl or aryl and wherein each heteroatom, if present, is independently N, O or S,
R$^c$ and R$^d$ are optionally joined to form a 4- to 8-membered heterocycle which is optionally fused to another 3- to 5-membered heterocycle or heteroaryl ring, and
R$^e$ and R$^f$ are optionally joined to form a 4- to 8-membered heterocycle which is optionally fused to another 3- to 5-membered heterocycle or heteroaryl ring;
Y and Y' are each independently carbon or nitrogen; and
Z and Z' are independently selected from the group consisting of hydrogen, C₁ to C₈ alkyl, C₁ to C₈ heteroalkyl, cycloalkyl, heterocycle, aryl, heteroaryl, aralkyl, 1-3 amino acids, —[U—(CR⁴₂)$_t$—NR⁵—C(R⁴₂)$_t$]$_u$—U—(CR⁴₂)$_t$—NR⁷—(CR⁴₂)$_t$—R⁸, —U—(CR⁴₂)$_t$—R⁸, and —[U—(CR⁴₂)$_t$—NR⁵—(CR⁴₂)$_t$]$_u$—U—(CR⁴₂)$_t$—O—(CR⁴₂)$_t$—R⁸, wherein,
U is selected from the group consisting of —C(O)—, —C(S)— and —S(O)₂—,
each R⁴, R⁵ and R⁷ is independently selected from the group consisting of hydrogen, C₁ to C₈ alkyl, C₁ to C₈ heteroalkyl, cycloalkyl, heterocycle, aryl, heteroaryl and aralkyl,
R⁸ is selected from the group consisting of hydrogen, C₁ to C₈ alkyl, C₁ to C₈ heteroalkyl, cycloalkyl, heterocycle, aryl, heteroaryl, aralkyl, —C(O)—R⁸¹, —C(S)—R⁸¹, —C(O)—O—R⁸¹, —C(O)—N—R⁸¹₂, —S(O)₂—R⁸¹ and —S(O)₂—N—R⁸¹₂, wherein each R⁸¹ is independently chosen from the group consisting of hydrogen, C₁ to C₈ alkyl, C₁ to C₈ heteroalkyl, cycloalkyl, heterocycle, aryl, heteroaryl and aralkyl,
optionally, R⁷ and R⁸ together form a 4-7 membered ring,
each t is independently 0, 1, 2, 3, or 4, and
u is 0, 1, or 2.
In a first embodiment of the first aspect, A' is selected from the group consisting of a single bond, —(CR₂)$_n$—O—(CR₂)$_p$—, —(CR₂)$_n$—N(R$^N$)—(CR₂)$_p$—, —(CR₂)$_n$—C(O)—N(R$^N$)—(CR₂)$_p$—, —(CR₂)$_n$—N(R$^N$)—C(O)—N(R$^N$)—(CR₂)$_p$— and —(CR₂)$_n$—N(R$^N$)—C(O)—O—(CR₂)$_p$— and a heteroaryl group selected from the group consisting of

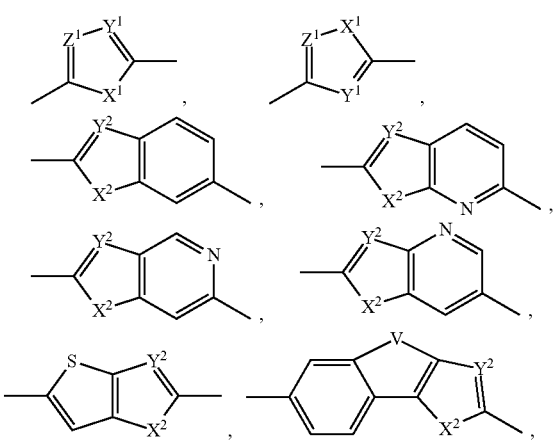

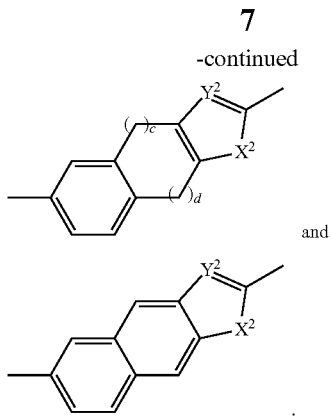

In a second embodiment of the first aspect, A' is selected from the group consisting of a single bond,

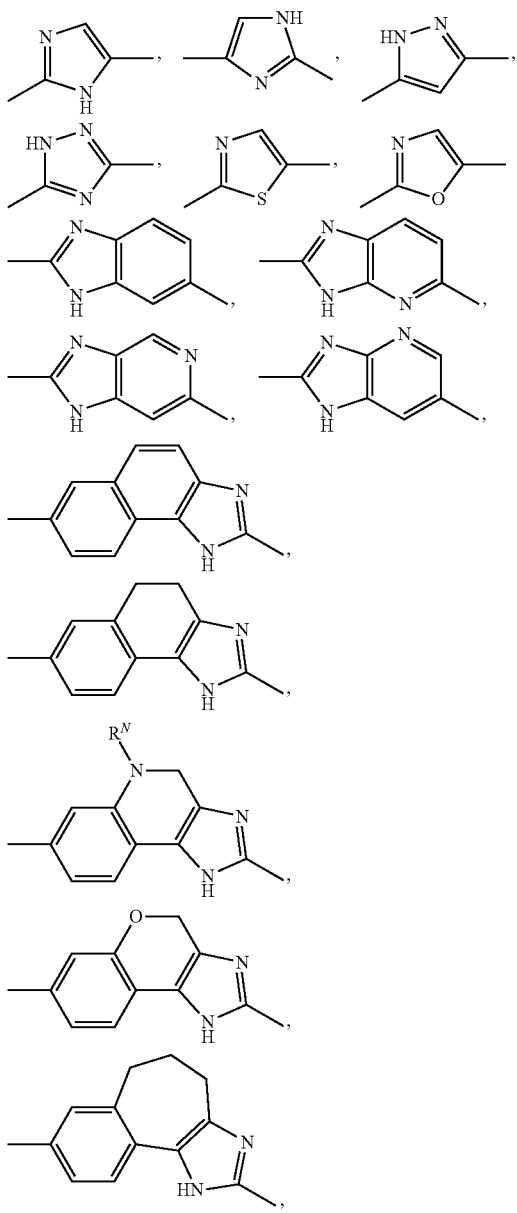

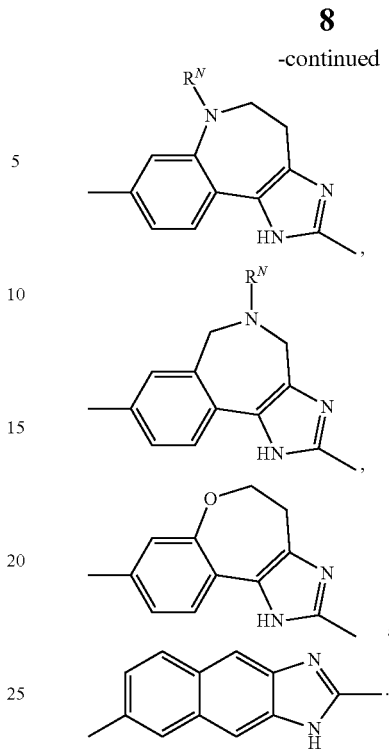

and

In a third embodiment of the first aspect, $R^c$, $R^d$, $R^e$ and $R^f$ are each independently selected from the group consisting of: hydrogen, $C_1$ to $C_8$ alkyl and $C_1$ to $C_8$ heteroalkyl, wherein, each hetero atom, if present, is independently N, O or S, $R^c$ and $R^d$ are optionally joined to form a 4- to 8-membered heterocycle which is optionally fused to another 3- to 6-membered heterocycle, and $R^e$ and $R^f$ are optionally joined to form a 4- to 8-membered heterocycle which is optionally fused to another 3- to 6-membered heterocycle.

In a fourth embodiment of the first aspect, $R^c$ and $R^d$ or $R^e$ and $R^f$ are optionally joined to form a 4- to 8-membered heterocycle which is optionally fused to another 3- to 6-membered heterocycle.

In a fifth embodiment of the first aspect, $R^c$ and $R^d$ are joined and form a heterocyclic fused ring system selected from the group consisting of:

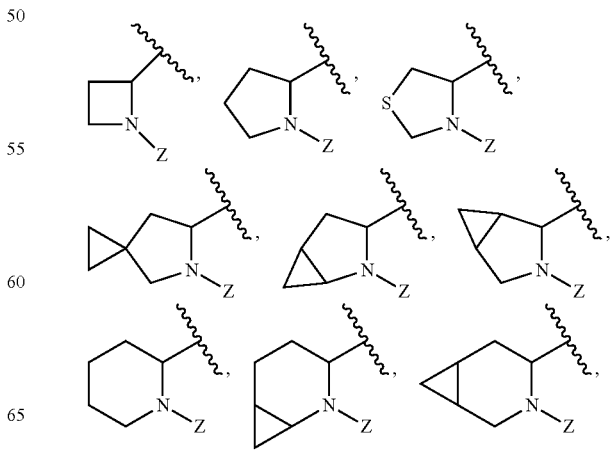

-continued

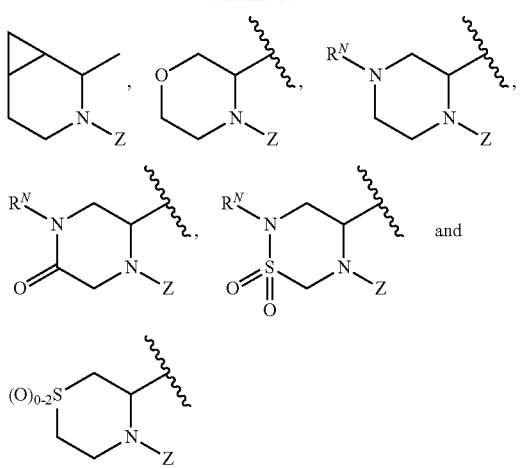

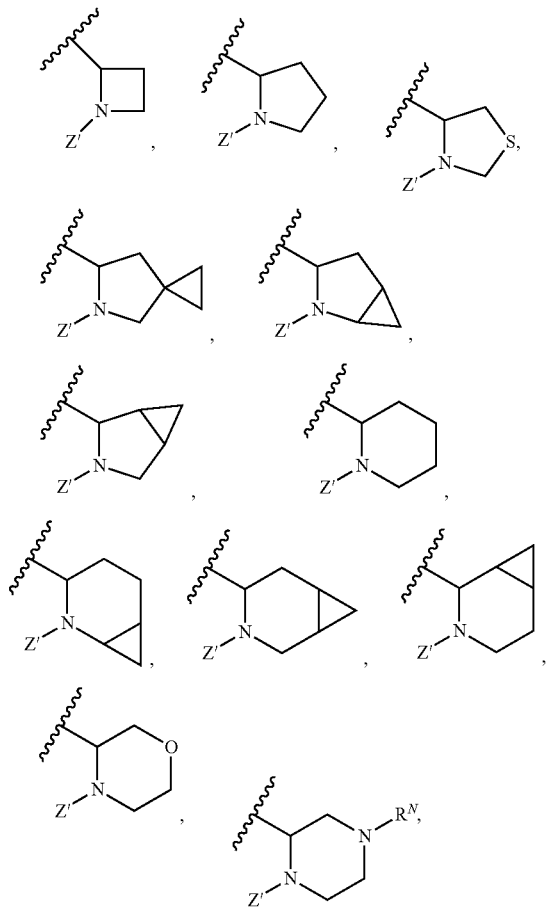

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a sixth embodiment of the first aspect, $R^e$ and $R^f$ are joined and form a heterocyclic fused ring system selected from the group consisting of:

-continued

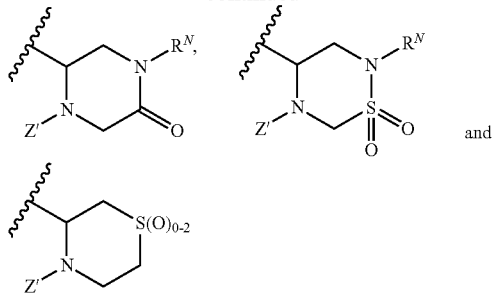

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a seventh embodiment of the first aspect, B and B' together is selected from the group consisting of

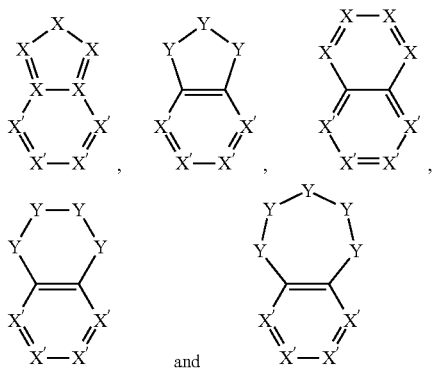

wherein
each X is independently N or C and if C, may include a hydrogen as necessary to complete the valence shell;
each X' is independently —N— or —CH—, with the proviso that no more than two X' are —N—;
each Y is independently selected from —CH$_2$—, —NH—, —O—, —S—, —C(O)$_2$—, or —S(O)$_{1-2}$—; and
B and B' attach to the remainder of the compound at any available attachment point on the molecule.

In an eighth embodiment of the first aspect, B and B' together is

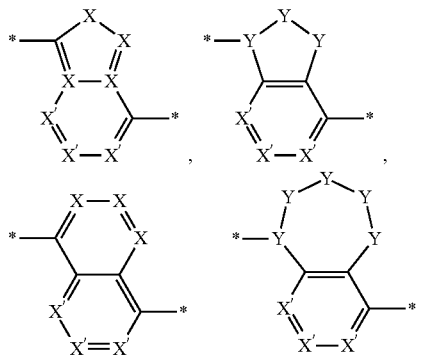

or

-continued

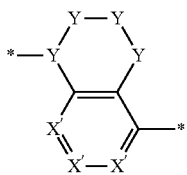

wherein * indicates attachment points to the remainder of the compound.

In a ninth embodiment of the first aspect, B and B' together is

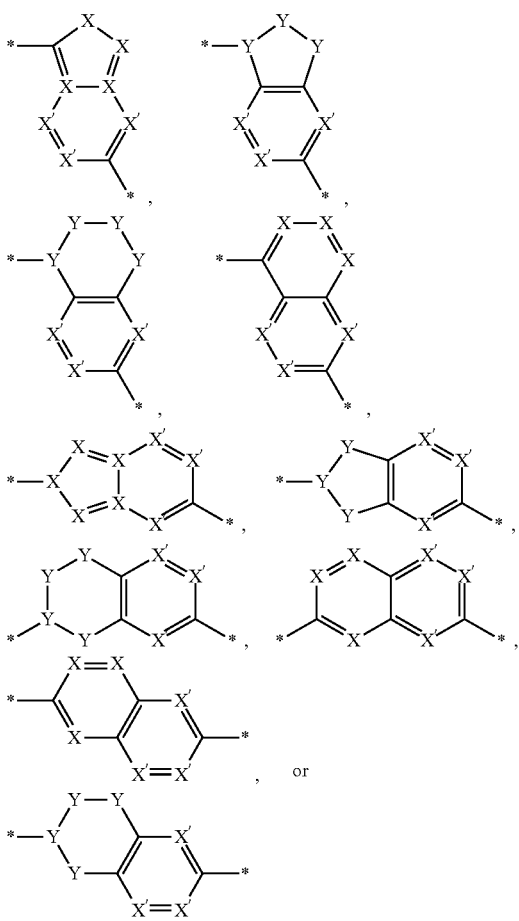

wherein * indicates attachment points to the remainder of the compound.

In a tenth embodiment of the first aspect, B and B' together is

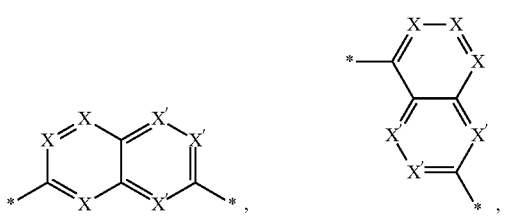

-continued

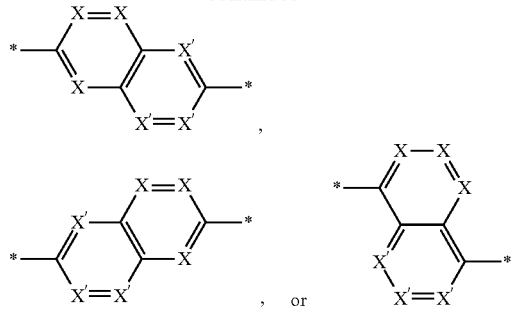

wherein * indicates attachment points to the remainder of the compound wherein no more than 2 of X are nitrogen.

In an eleventh embodiment of the first aspect, B and B' together is

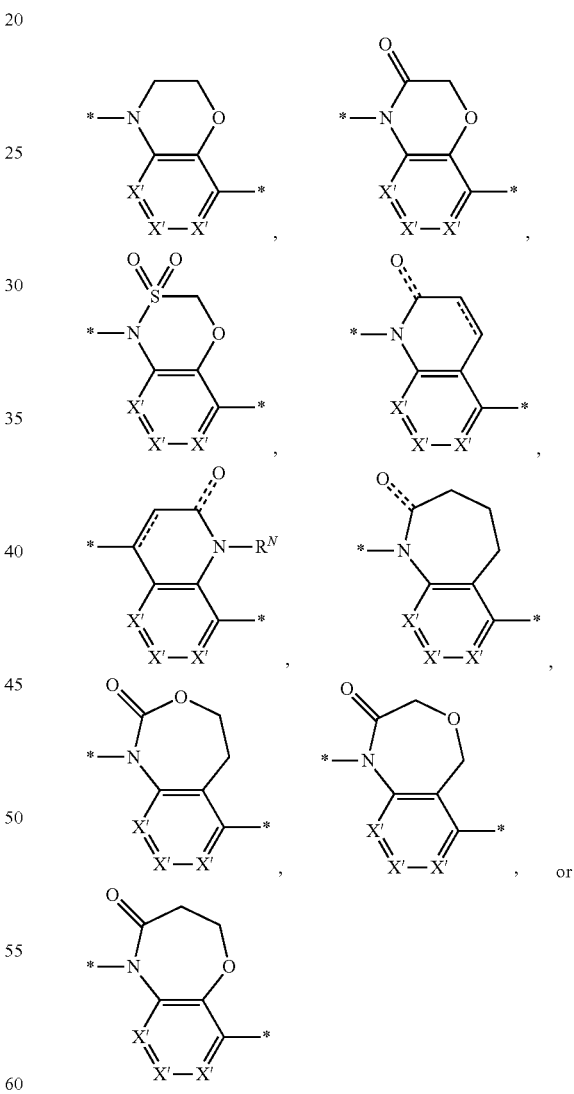

wherein * indicates attachment points to the remainder of the compound and $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a twelfth embodiment of the first aspect, B and B' together is

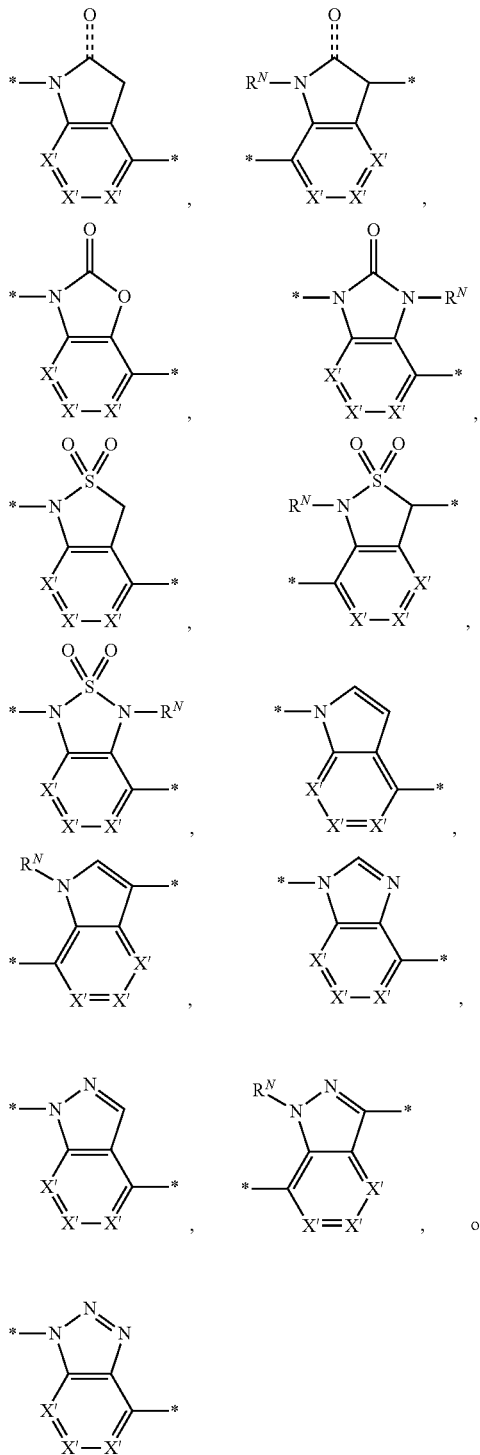

wherein * indicates attachment points to the remainder of the compound and $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a thirteenth embodiment of the first aspect, B and B' together is

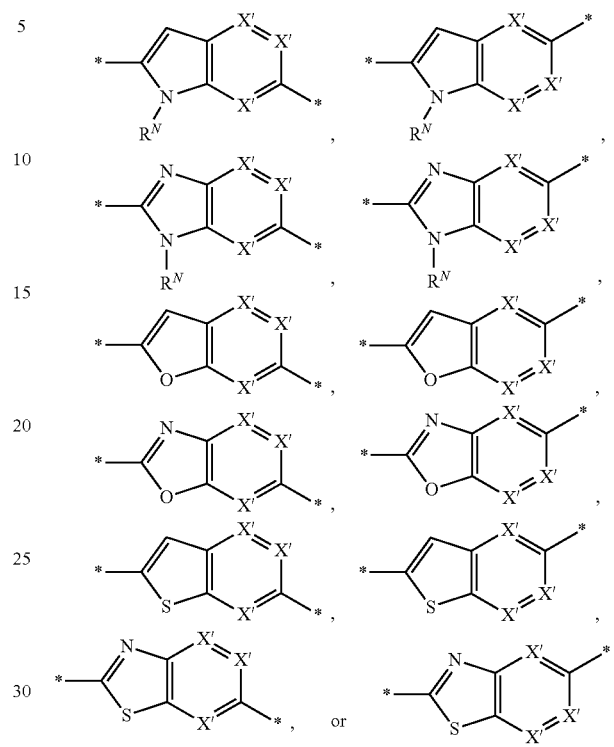

wherein * indicates attachment points to the remainder of the compound and $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a fourteenth embodiment of the first aspect, B and B' together is

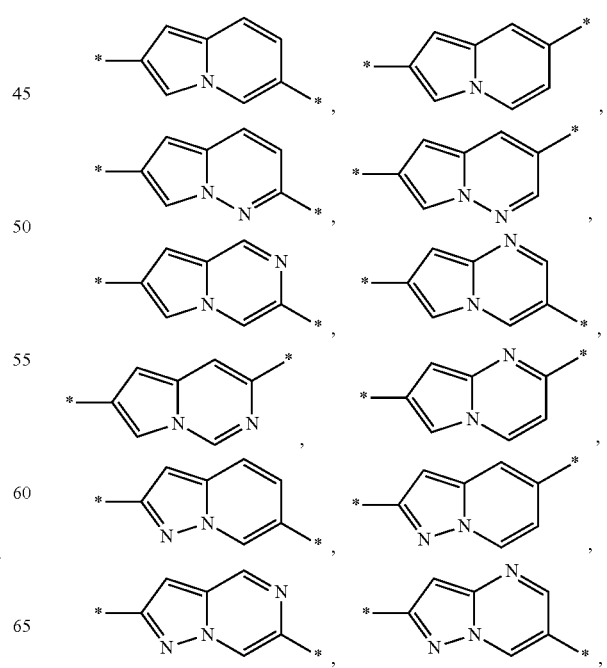

-continued

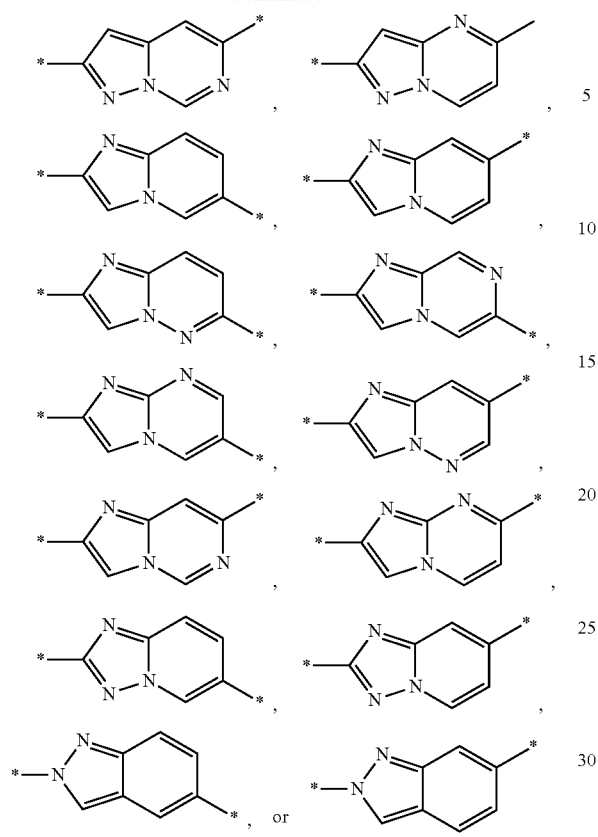

wherein * indicates attachment points to the remainder of the compound and the six-membered ring optionally contains one or two additional nitrogens as heteroatoms with the proviso that the total number of nitrogens in the six-membered ring does not exceed two.

In a fifteenth embodiment of the first aspect, B and B' together is

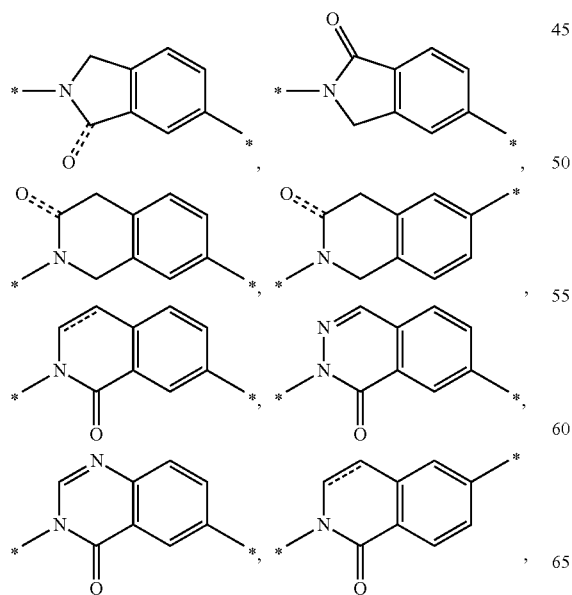

-continued

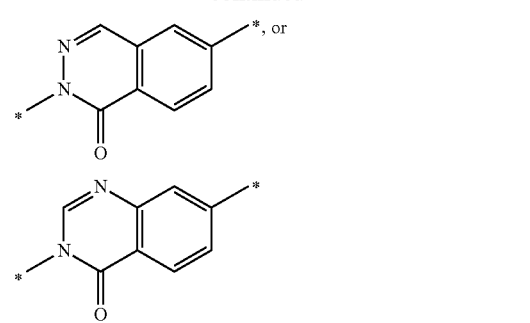

wherein * indicates attachment points to the remainder of the compound and the phenyl moiety optionally contains one or two nitrogens as heteroatoms.

In a sixteenth embodiment of the first aspect, B and B' together is

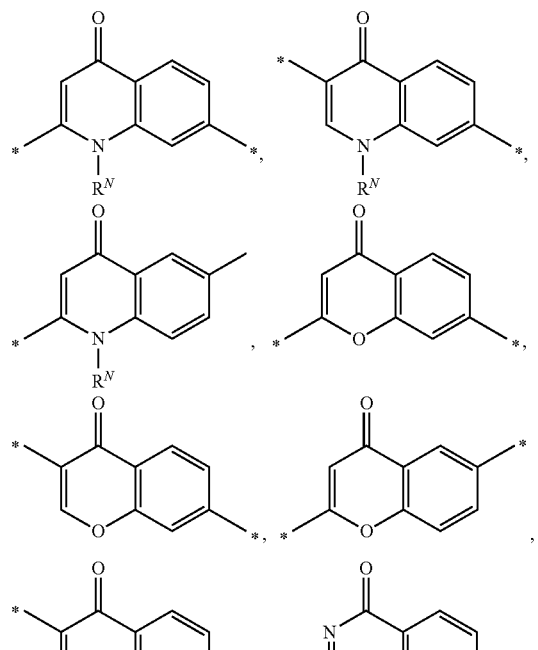

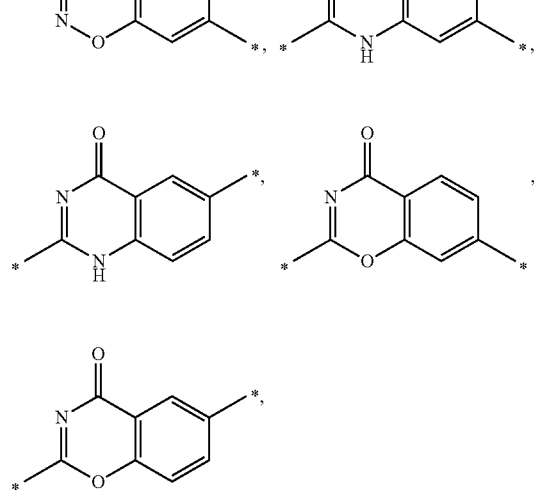

-continued

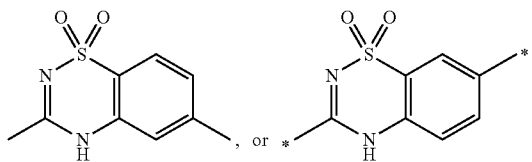

wherein * indicates attachment points to the remainder of the compound; the phenyl moiety optionally contains one or two nitrogens as heteroatoms; and $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a second aspect of the invention, compounds have formula II:

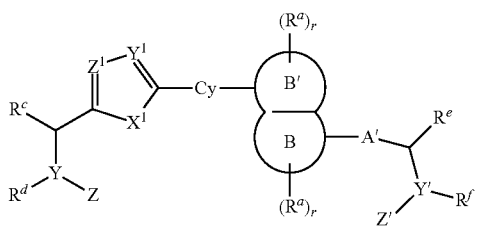

wherein A' is selected from the group consisting of a single bond,

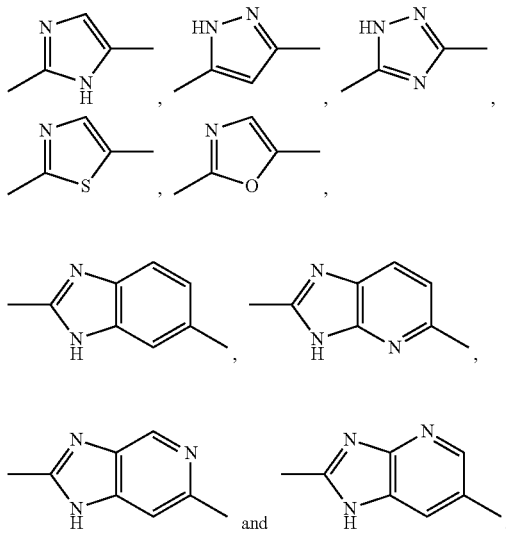

In a first embodiment of the second aspect, compounds have formula II wherein A' is

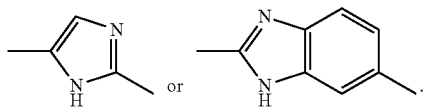

In a second embodiment of the second aspect, compounds have formula IIa:

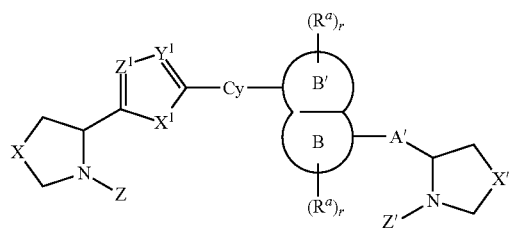

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

In a third embodiment of the second aspect, compounds have formula IIa wherein A' is

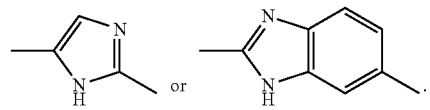

In a fourth embodiment of the second aspect, compounds have formula IIb:

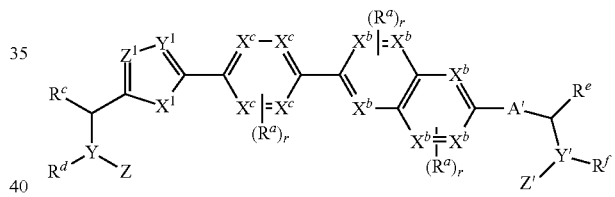

wherein each X$^b$ and X$^c$ is independently C or N.

In a fifth embodiment of the second aspect, compounds have formula IIb wherein A' is

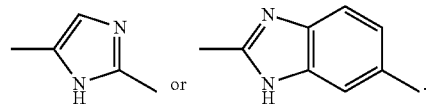

In a sixth embodiment of the second aspect, compounds have formula IIc:

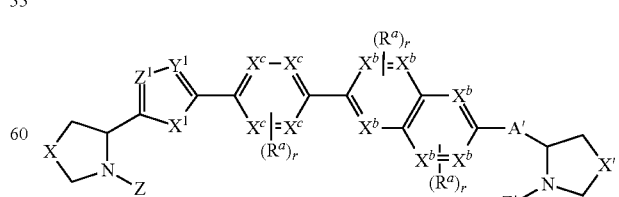

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH₂S—, —CH₂S(O)₁₋₂— and —CH₂N(R¹)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl.

In a seventh embodiment of the second aspect, compounds have formula IIc wherein A' is

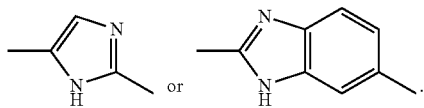

In an eighth embodiment of the second aspect, compounds have formula IId:

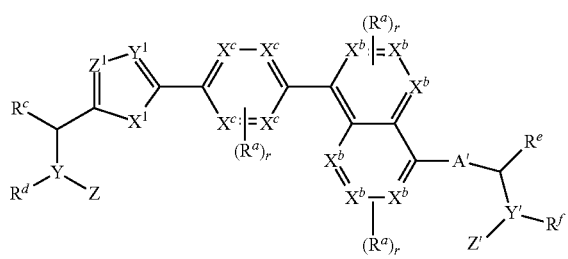

wherein each X^b and X^c is independently C or N.

In a ninth embodiment of the second aspect, compounds have formula IId wherein A' is

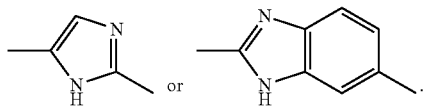

In a tenth embodiment of the second aspect, compounds have formula IIe:

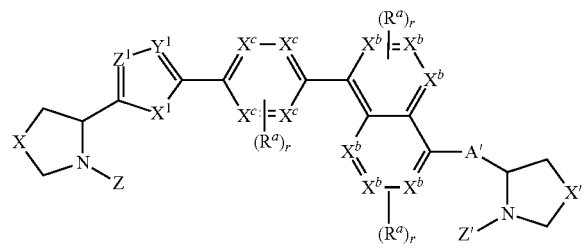

wherein X and X' are each independently selected from the group consisting of a bond, —CH₂—, —CH₂—CH₂—, —CH=CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl.

In an eleventh embodiment of the second aspect, compounds have formula IIe wherein A' is

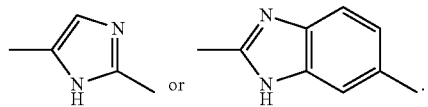

In a twelfth embodiment of the second aspect, compounds have formula IIf:

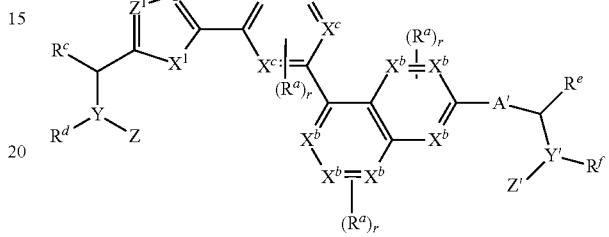

wherein each X^b and X^c is independently C or N.

In a thirteenth embodiment of the second aspect, compounds have formula IIf wherein A' is

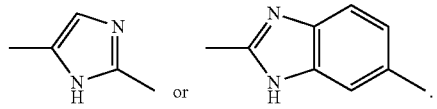

In a fourteenth embodiment of the second aspect, compounds have formula IIg:

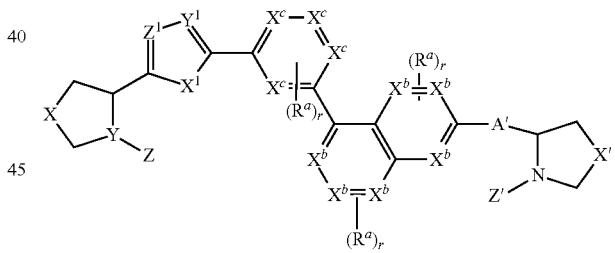

wherein X and X' are each independently selected from the group consisting of a bond, —CH₂—, —CH₂—CH₂—, —CH=CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl.

In a fifteenth embodiment of the second aspect, compounds have formula IIg wherein A' is

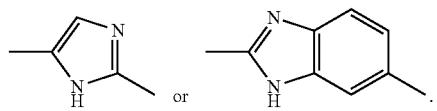

In a sixteenth embodiment of the second aspect, compounds have formula IIh:

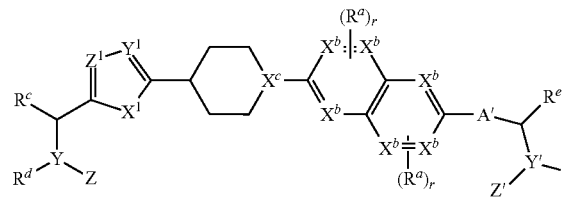

wherein $X^c$ and each $X^b$ is independently C or N.

In a seventeenth embodiment of the second aspect, compounds have formula IIh wherein A' is

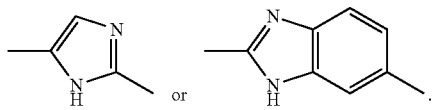

In an eighteenth embodiment of the second aspect, compounds have formula IIi:

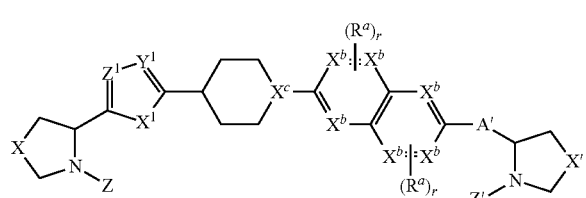

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a nineteenth embodiment of the second aspect, compounds have formula IIi wherein A' is

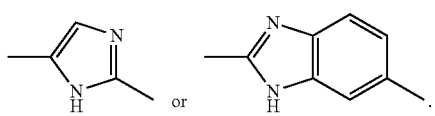

In a twentieth embodiment of the second aspect, compounds have formula IIh or IIi wherein $X^c$ is C.

In an twenty-first embodiment of the second aspect, compounds have formula IIh or IIi wherein $X^c$ is N.

In a twenty-second embodiment of the second aspect, compounds have formula IIj:

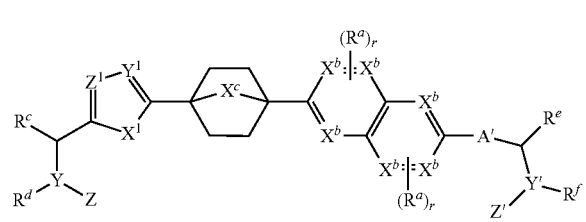

wherein
$X^c$ is —CH$_2$—, —NH— or —CH$_2$—CH$_2$—, and
each $X^b$ is independently C or N.

In a twenty-third embodiment of the second aspect, compounds have formula IIj wherein A' is

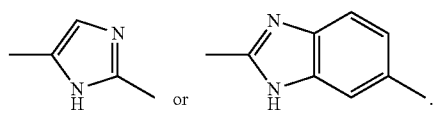

In a twenty-fourth embodiment of the second aspect, compounds have formula IIk:

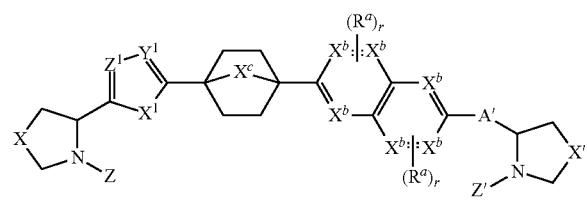

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a twenty-fifth embodiment of the second aspect, compounds have formula IIk wherein A' is

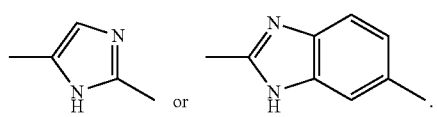

In a twenty-sixth embodiment of the second aspect, compounds have formula III:

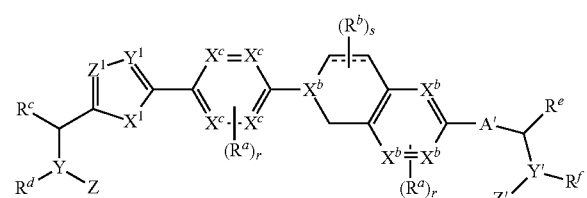

wherein:
each $X^b$ and $X^c$ is independently C or N;
each $R^b$ is selected from the group consisting of oxo, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and
s is 0, 1, 2, or 3.

In a twenty-seventh embodiment of the second aspect, compounds have formula III wherein A' is

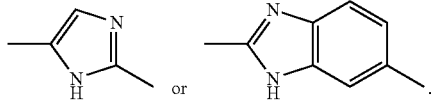 or .

In a twenty-eighth embodiment of the second aspect, compounds have formula IIm:

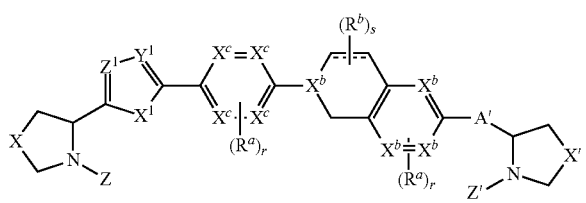

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a twenty-ninth embodiment of the second aspect, compounds have formula IIm wherein A' is

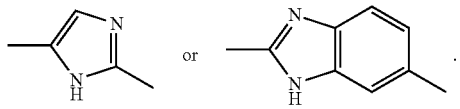 or .

In a thirtieth embodiment of the second aspect, compounds have formula IIn:

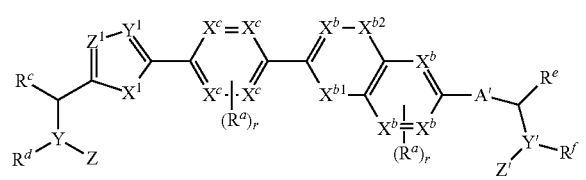

wherein:
each X$^b$ and X$^c$ is independently C or N;
X$^{b1}$ is N or O; and
X$^{b2}$ is S(O)$_2$ or C(O).

In a thirty-first embodiment of the second aspect, compounds have formula IIn wherein A' is

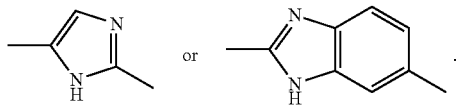 or .

In a thirty-second embodiment of the second aspect, compounds have formula IIo:

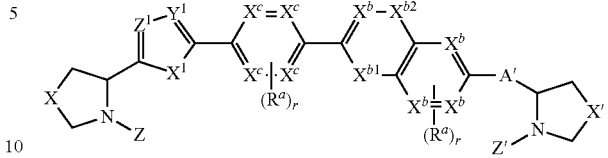

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a thirty-third embodiment of the second aspect, compounds have formula IIo wherein A' is

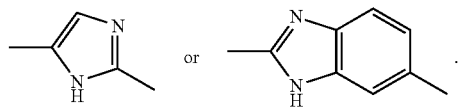 or .

In an thirty-fourth embodiment of the second aspect, compounds have formula IIp:

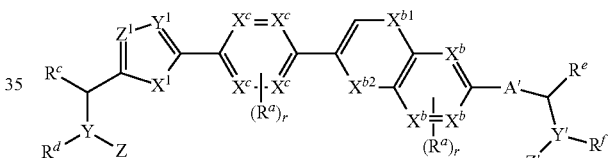

wherein:
each X$^b$ and X$^c$ is independently C or N;
X$^{b1}$ is N or O; and
X$^{b2}$ is S(O)$_2$ or C(O).

In a thirty-fifth embodiment of the second aspect, compounds have formula IIp wherein A' is

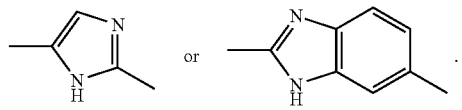 or .

In a thirty-sixth embodiment of the second aspect, compounds have formula IIq:

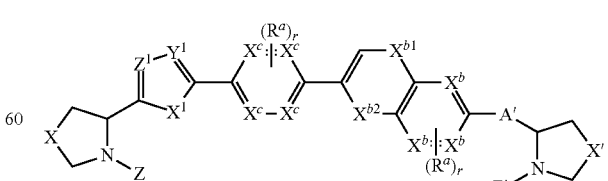

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a thirty-seventh embodiment of the second aspect, compounds have formula IIq wherein A' is

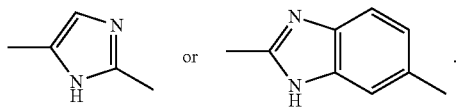

In a third aspect of the invention, compounds have formula III:

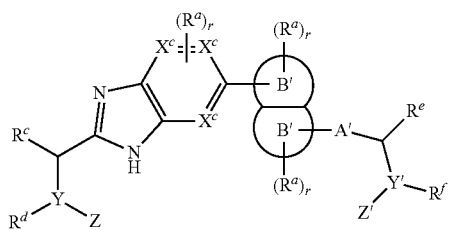

wherein

A' is selected from the group consisting of a single bond,

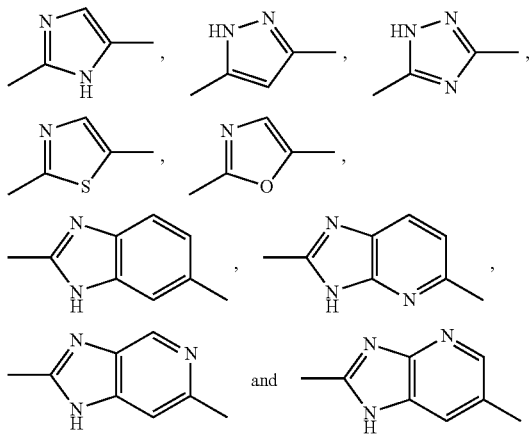

and each X$^c$ is independently C or N.

In a first embodiment of the third aspect, compounds have formula III wherein A' is

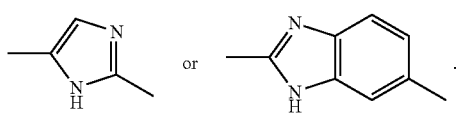

In a second embodiment of the third aspect, compounds have formula IIa:

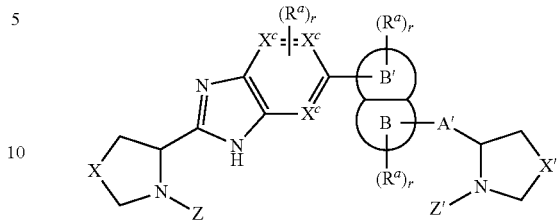

wherein X and X' are each independently selected from the group consisting of a bond, —CH$_2$—, —CH$_2$—CH$_2$—, —CH═CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a third embodiment of the third aspect, compounds have formula IIa wherein A' is

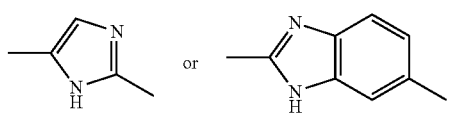

In a fourth embodiment of the third aspect, compounds have formula IIIb:

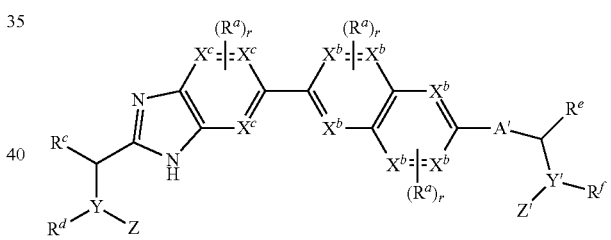

wherein each X$^b$ is independently C or N.

In a fifth embodiment of the third aspect, compounds have formula IIIb wherein A' is

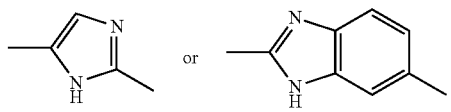

In a sixth embodiment of the third aspect, compounds have formula IIIc:

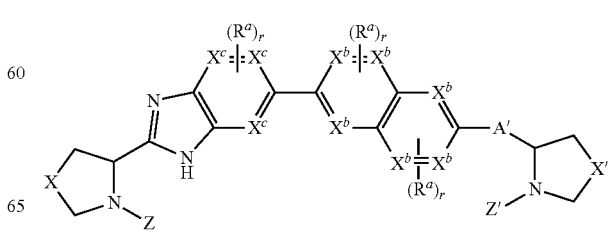

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a seventh embodiment of the third aspect, compounds have formula IIIc wherein A' is

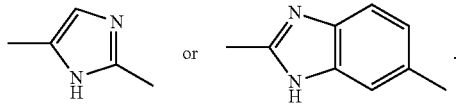

In an eighth embodiment of the third aspect, compounds have formula IIId:

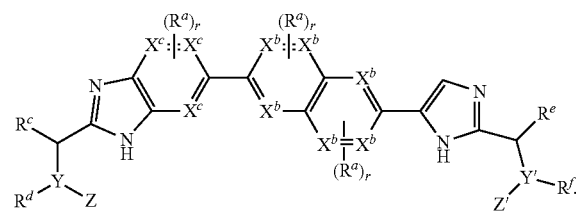

In a ninth embodiment of the third aspect, compounds have formula IIIe:

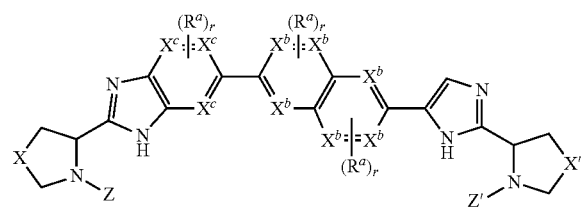

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a tenth embodiment of the third aspect, compounds have formula IIIf:

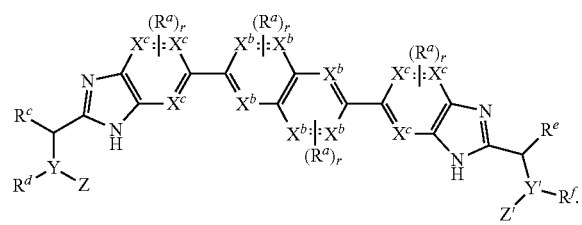

In an eleventh embodiment of the third aspect, compounds have formula IIIg:

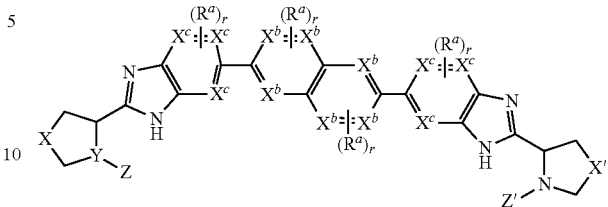

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a twelfth embodiment of the third aspect, compounds have formula IIIh:

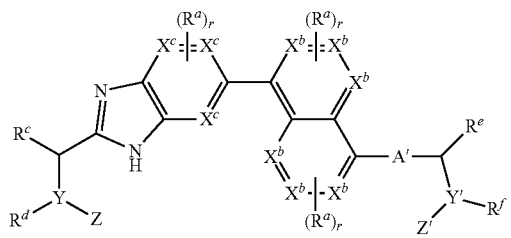

wherein each X$^b$ is independently C or N.

In a thirteenth embodiment of the third aspect, compounds have formula IIIh wherein A' is

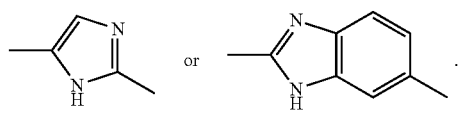

In a fourteenth embodiment of the third aspect, compounds have formula IIIi:

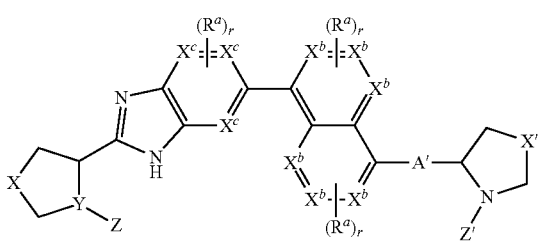

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fifteenth embodiment of the third aspect, compounds have formula IIIi wherein A' is

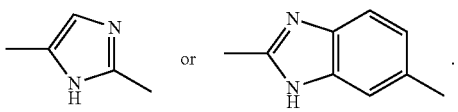

In a sixteenth embodiment of the third aspect, compounds have formula IIIj:

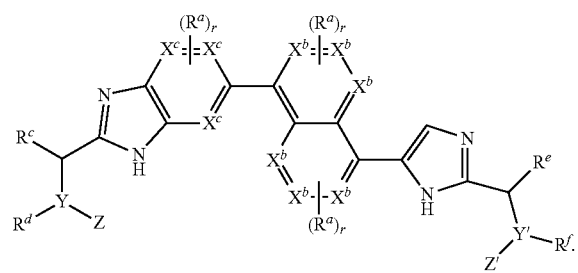

In a seventeenth embodiment of the third aspect, compounds have formula IIIk:

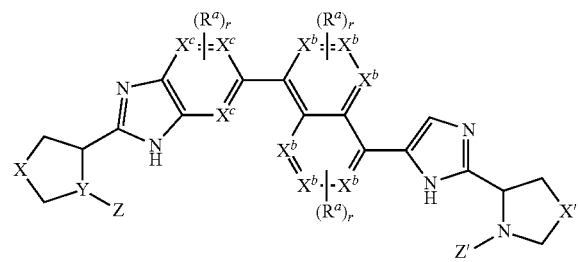

wherein X and X' are each independently selected from the group consisting of a bond, —CH$_2$—, —CH$_2$—CH$_2$—, —CH═CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In an eighteenth embodiment of the third aspect, compounds have formula IIIl:

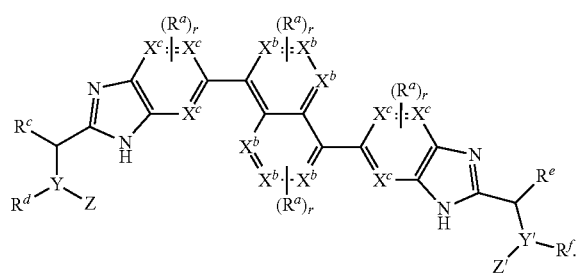

In a nineteenth embodiment of the third aspect, compounds have formula IIIm:

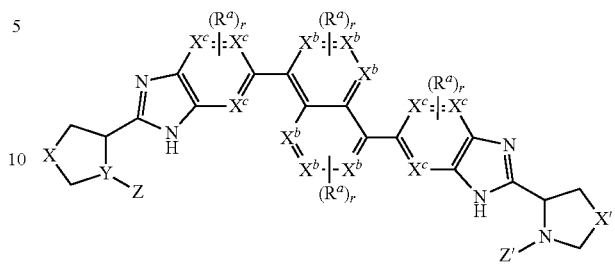

wherein X and X' are each independently selected from the group consisting of a bond, —CH$_2$—, —CH$_2$—CH$_2$—, —CH═CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a twentieth embodiment of the third aspect, compounds have formula IIIn:

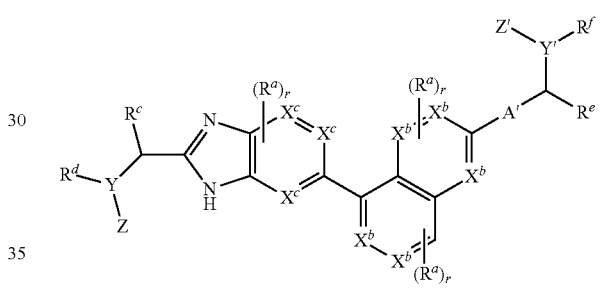

wherein each X$^b$ is independently C or N.

In a twenty-first embodiment of the third aspect, compounds have formula IIIn wherein A' is

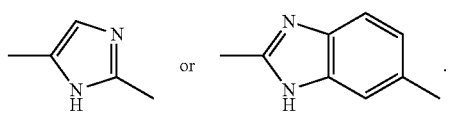

In a twenty-second embodiment of the third aspect, compounds have formula IIIo:

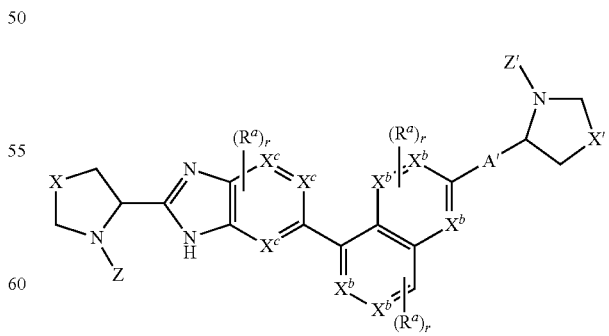

wherein X and X' are each independently selected from the group consisting of a bond, —CH$_2$—, —CH$_2$—CH$_2$—, —CH═CH—, —O—, —S—, —S(O)$_{1-2}$—, —CH$_2$O—, —CH$_2$S—, —CH$_2$S(O)$_{1-2}$— and —CH$_2$N(R$^1$)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl.

In a twenty-third embodiment of the third aspect, compounds have formula IIIo wherein A' is

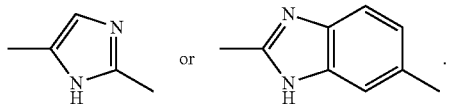

In a twenty-fourth embodiment of the third aspect, compounds have formula IIIp:

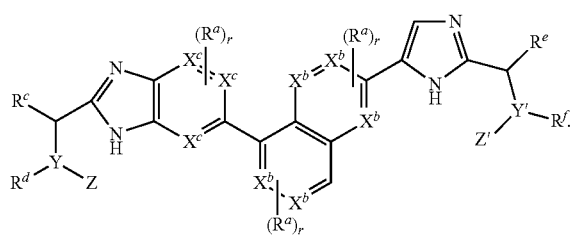

In a twenty-fifth embodiment of the third aspect, compounds have formula IIIq:

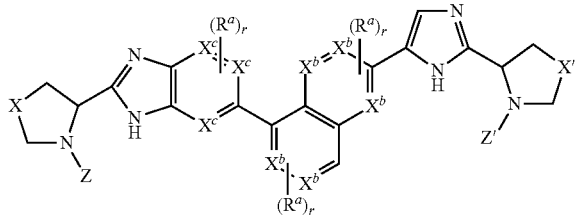

wherein X and X' are each independently selected from the group consisting of a bond, —CH₂—, —CH₂—CH₂—, —CH═CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl.

In a fourth aspect of the invention, compounds have formula IV:

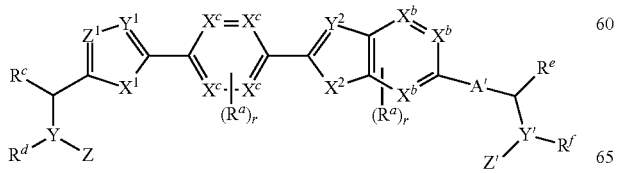

wherein:

A' is selected from the group consisting of a single bond,

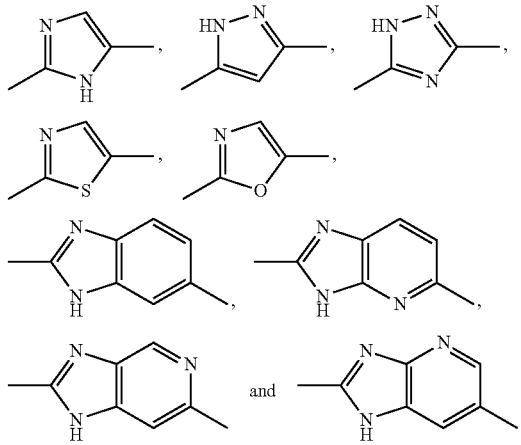

and each X^b and X^c is independently C or N.

In a first embodiment of the fourth aspect, compounds have formula IV wherein A' is

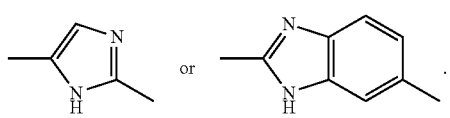

In a second embodiment of the fourth aspect, compounds have formula IVa:

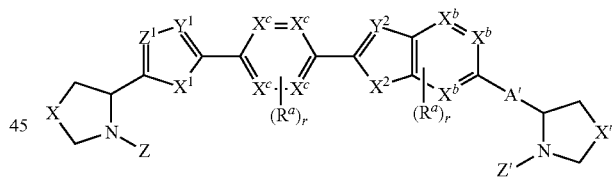

wherein X and X' are each independently selected from the group consisting of a bond, —CH₂—, —CH₂—CH₂—, —CH═CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl.

In a third embodiment of the fourth aspect, compounds have formula IVa wherein A' is

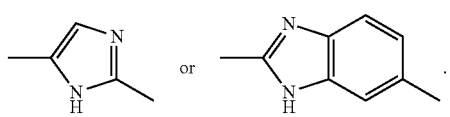

In a fifth aspect of the invention, compounds have formula V:

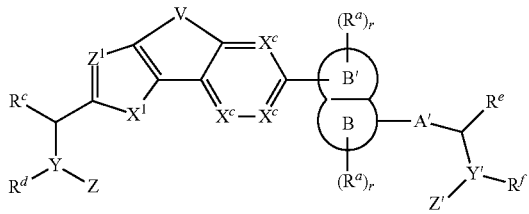

wherein:
A' is selected from the group consisting of a single bond,

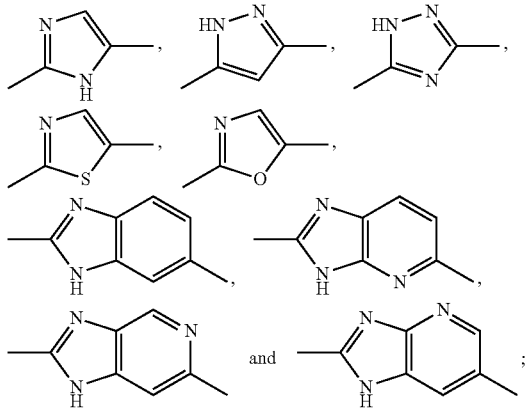

and
each $X^c$ is independently C or N with the proviso that no more than two $X^c$ are N.

In a first embodiment of the fifth aspect, compounds have formula V wherein A' is

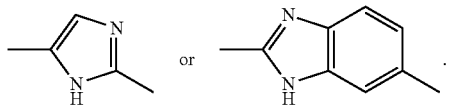

In a second embodiment of the fifth aspect, compounds have formula Va:

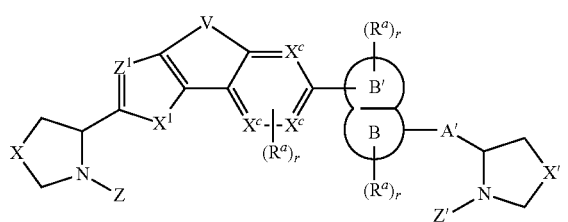

wherein X and X' are each independently selected from the group consisting of a bond, —$CH_2$—, —$CH_2$—$CH_2$—, —CH=CH—, —O—, —S—, —$S(O)_{1-2}$—, —$CH_2O$—, —$CH_2S$—, —$CH_2S(O)_{1-2}$— and —$CH_2N(R^1)$—, wherein $R^1$ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

In a third embodiment of the fifth aspect, compounds have formula Va wherein A' is

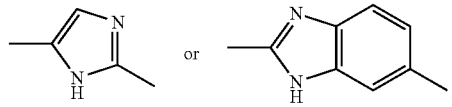

In a fourth embodiment of the fifth aspect, compounds have formula Vb:

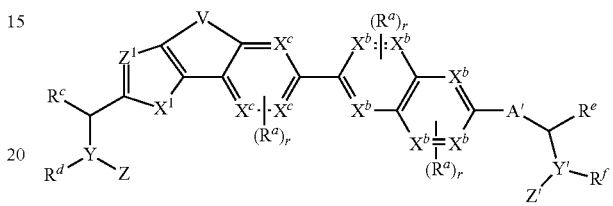

wherein
each $X^b$ is independently C or N.

In a fifth embodiment of the fifth aspect, compounds have formula Vb wherein A' is

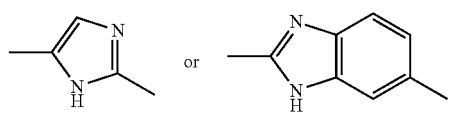

In a sixth embodiment of the fifth aspect, compounds have formula Vc:

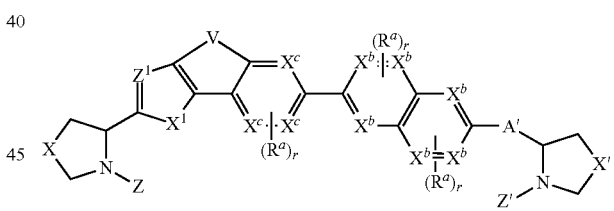

wherein X and X' are each independently selected from the group consisting of a bond, —$CH_2$—, —$CH_2$—$CH_2$—, —CH=CH—, —O—, —S—, —$S(O)_{1-2}$—, —$CH_2O$—, —$CH_2S$—, —$CH_2S(O)_{1-2}$— and —$CH_2N(R^1)$—, wherein $R^1$ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

In a seventh embodiment of the fifth aspect, compounds have formula Vc wherein A' is

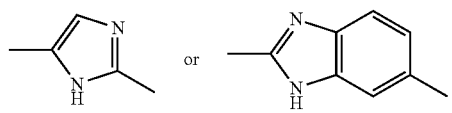

In an eighth embodiment of the fifth aspect, compounds have formula Vd:

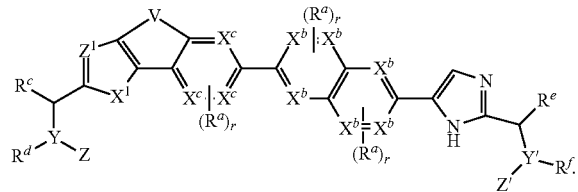

In a ninth embodiment of the fifth aspect, compounds have formula Ve:

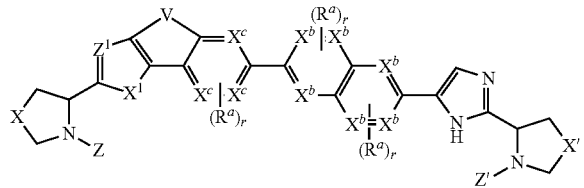

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a sixth aspect of the invention, in any compound of any of the second through fifth aspects, R$^c$, R$^d$, R$^e$ and R$^f$ are each independently selected from the group consisting of: hydrogen, C$_1$ to C$_8$ alkyl and C$_1$ to C$_8$ heteroalkyl, wherein,
  each hetero atom, if present, is independently N, O or S,
  R$^c$ and R$^d$ are optionally joined to form a 4- to 8-membered heterocycle which is optionally fused to another 3- to 6-membered heterocycle, and
  R$^e$ and R$^f$ are optionally joined to form a 4- to 8-membered heterocycle which is optionally fused to another 3- to 6-membered heterocycle.

In a first embodiment of the sixth aspect, R$^c$ and R$^d$ or R$^e$ and R$^f$ are joined to form a 4- to 8-membered heterocycle which is optionally fused to another 3- to 6-membered heterocycle.

In a second embodiment of the sixth aspect, both of R$^c$ and R$^d$ and R$^e$ and R$^f$ are joined to form a 4- to 8-membered heterocycle which is optionally fused to another 3- to 6-membered heterocycle.

In a seventh aspect of the invention, each R$^a$, if present in any of the other aspects of the invention, is independently —CN, —OCHF$_2$, —OCF$_3$, —CF$_3$, or —F.

In an eighth aspect of the invention, if present in any compound of any of the other aspects, one of Y and Y' is N.

In a first embodiment of the eighth aspect, both Y and Y' are N.

In a ninth aspect of the invention, Z and Z' in any of the previous aspects are each 1-3 amino acids.

In a first embodiment of the ninth aspect, the amino acids are in the D configuration.

In a tenth aspect of the invention, Z and Z' in any of the previous aspects are each independently selected from the group consisting of —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$, —U—(CR$^4_2$)$_t$—R$^8$ and —[U—(CR$^4_2$)$_t$—NR$^5$—(CR$^4_2$)$_t$]$_u$—U—(CR$^4_2$)$_t$—O—(CR$^4_2$)$_t$—R$^8$.

In a first embodiment of the tenth aspect, both of Z and Z' are —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$.

In a second embodiment of the tenth aspect, one or both of Z and Z' are —U—(CR$^4_2$)$_t$—NR$^5$—(CR$^4_2$)$_t$—U—(CR$^4_2$)$_t$—NR$^7$—(CR$^4_2$)$_t$—R$^8$.

In a third embodiment of the tenth aspect, one or both of Z and Z' are —U—(CR$^4_2$)$_t$—NR$^7$—(CR$^4_2$)$_t$—R$^8$.

In a fourth embodiment of the tenth aspect, one or both of Z and Z' are —[C(O)—(CR$^4_2$)$_t$—NR$^5$—(CR$^4_2$)$_t$]$_u$—U—(CR$^4_2$)$_t$—NR$^7$—(CR$^4_2$)$_t$—R$^8$.

In a fifth embodiment of the tenth aspect, one or both of Z and Z' are —C(O), —(CR$^4_2$)$_t$—NR$^5$—(CR$^4_2$)$_t$—U—(CR$^4_2$)$_t$—NR$^7$—(CR$^4_2$)$_t$—R$^8$.

In a sixth embodiment of the tenth aspect, one or both of Z and Z' are —[C(O)—(CR$^4_2$)$_t$—NR$^5$—(CR$^4_2$)$_t$]$_u$—C(O)—(CR$^4_2$)$_t$—NR$^7$—(CR$^4_2$)$_t$—R$^8$.

In a seventh embodiment of the tenth aspect, one or both of Z and Z' are —C(O)—(CR$^4_2$)$_t$—NR$^5$—(CR$^4_2$)$_t$—C(O)—(CR$^4_2$)$_t$—NR$^7$—(CR$^4_2$)$_t$—R$^8$.

In an eighth embodiment of the tenth aspect, one or both of Z and Z' are —C(O)—(CR$^4_2$)$_t$—NR$^7$—(CR$^4_2$)$_t$—R$^8$.

In a ninth embodiment of the tenth aspect, one or both of Z and Z' are —C(O)—(CR$^4_2$)$_n$—NR$^7$—(CR$^4_2$)$_n$—C(O)—R$^{81}$.

In a tenth embodiment of the tenth aspect, one or both of Z and Z' are —C(O)—(CR$^4_2$)$_n$—NR$^7$—C(O)—R$^{81}$.

In an eleventh embodiment of the tenth aspect, one or both of Z and Z' are —C(O)—(CR$^4_2$)$_n$—NR$^7$—(CR$^4_2$)$_n$—C(O)—O—R$^{81}$.

In a twelfth embodiment of the tenth aspect, one or both of Z and Z' are —C(O)—(CR$^4_2$)$_n$—NR$^7$—C(O)—O—R$^{81}$.

In a thirteenth embodiment of the tenth aspect, one or both of Z and Z' are —U—(CR$^4_2$)$_t$—R$^8$.

In a fourteenth embodiment of the tenth aspect, one or both of Z and Z' are —C(O)—(CR$^4_2$)$_t$—R$^8$.

In a fifteenth embodiment of the tenth aspect, one or both of Z and Z' are —[U—(CR$^4_2$)$_t$—NR$^5$—(CR$^4_2$)$_t$]$_u$—U—(CR$^4_2$)$_t$—O—(CR$^4_2$)$_t$—R$^8$.

In a sixteenth embodiment of the tenth aspect, one or both of Z and Z' are —U—(CR$^4_2$)$_t$—NR$^5$—(CR$^4_2$)$_t$—U—(CR$^4_2$)$_t$—O—(CR$^4_2$)$_t$—R$^8$.

In a seventeenth embodiment of the tenth aspect, one or both of Z and Z' are —C(O)—(CR$^4_2$)$_t$—NR$^5$—(CR$^4_2$)$_t$—C(O)—(CR$^4_2$)$_t$—O—(CR$^4_2$)$_t$—R$^8$.

In an eighteenth embodiment of the tenth aspect, one or both of Z and Z' are —U—(CR$^4_2$)$_t$—O—(CR$^4_2$)$_t$—R$^8$.

An eleventh aspect of the invention provides a pharmaceutical composition comprising the compounds of the invention.

A twelfth aspect of the invention provides use of the compounds of the invention in the manufacture of a medicament.

In a first embodiment of the twelfth aspect, the medicament is for the treatment of hepatitis C.

A thirteenth aspect of the invention provides a method of treating hepatitis C comprising administering to a subject in need thereof, a therapeutically effective amount of any one of the compounds of the invention.

DETAILED DESCRIPTION

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (2007) "Advanced Organic Chemistry 5th Ed." Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology.

The term "alkanoyl" as used herein contemplates a carbonyl group with a lower alkyl group as a substituent.

The term "alkenyl" as used herein contemplates substituted or unsubstituted, straight and branched chain alkene radicals, including both the E- and Z-forms, containing from two to eight carbon atoms. The alkenyl group may be optionally substituted with one or more substituents selected from the group consisting of halogen, —CN, —NO$_2$, CO$_2$R, C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, S(O)R, SO$_2$R, —SO$_3$R, —S(O)$_2$N(R$^N$)$_2$, phosphate, phosphonate, cycloalkyl, cycloalkenyl, aryl and heteroaryl.

The term "alkoxy" as used herein contemplates an oxygen with a lower alkyl group as a substituent and includes methoxy, ethoxy, butoxy, trifluoromethoxy and the like. It also includes divalent substituents linked to two separated oxygen atoms such as, without limitation, —O—(CH$_2$)$_{1-4}$—O—, —O—CF$_2$—O—, —O—(CH$_2$)$_{1-4}$—O—(CH$_2$CH$_2$—O)$_{1-4}$— and —(O—CH$_2$CH$_2$—O)$_{1-4}$—.

The term "alkoxycarbonyl" as used herein contemplates a carbonyl group with an alkoxy group as a substituent.

The term "alkyl" as used herein contemplates substituted or unsubstituted, straight and branched chain alkyl radicals containing from one to fifteen carbon atoms. The term "lower alkyl" as used herein contemplates both straight and branched chain alkyl radicals containing from one to six carbon atoms and includes methyl, ethyl, propyl, isopropyl, butyl, isobutyl, tert-butyl and the like. The alkyl group may be optionally substituted with one or more substituents selected from halogen, —CN, —NO$_2$, —C(O)$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The term "alkylene," "alkenylene" and "alkynylene" as used herein refers to the groups "alkyl," "alkenyl" and "alkynyl" respectively, when they are divalent, ie, attached to two atoms.

The term "alkylsulfonyl" as used herein contemplates a sulfonyl group which has a lower alkyl group as a substituent.

The term "alkynyl" as used herein contemplates substituted or unsubstituted, straight and branched carbon chain containing from two to eight carbon atoms and having at least one carbon-carbon triple bond. The term alkynyl includes, for example ethynyl, 1-propynyl, 2-propynyl, 1-butynyl, 3-methyl-1-butynyl and the like. The alkynyl group may be optionally substituted with one or more substituents selected from halo, —CN, NO$_2$, CO$_2$R, C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The term "amino" as used herein contemplates a group of the structure —NR$^N$$_2$.

The term "amino acid" as used herein contemplates a group of the structure

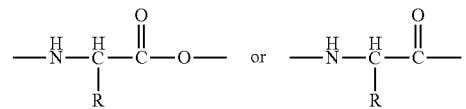

in either the D or the L configuration and includes but is not limited to the twenty "standard" amino acids: isoleucine, leucine, lysine, methionine, phenylalanine, threonine, tryptophan, valine, alanine, asparagine, aspartate, cysteine, glutamate, glutamine, glycine, proline, serine, tyrosine, arginine and histidine. The present invention also includes, without limitation, D-configuration amino acids, beta-amino acids, amino acids having side chains as well as all non-natural amino acids known to one skilled in the art.

The term "aralkyl" as used herein contemplates a lower alkyl group which has as a substituent an aromatic group, which aromatic group may be substituted or unsubstituted. The aralkyl group may be optionally substituted with one or more substituents selected from halogen, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The terms "aryl," "aromatic group" or "aromatic ring" as used herein contemplates substituted or unsubstituted single-ring and multiple aromatic groups (for example, phenyl, pyridyl and pyrazole, etc.) and polycyclic ring systems (naphthyl and quinolinyl, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from halogen, alkyl, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, —SiR$_3$, —P(O)R, phosphate, phosphonate, cycloalkyl, cycloalkenyl, aryl and heteroaryl.

The term "arylsulfonyl" as used herein contemplates a sulfonyl group which has as a substituent an aryl group. The term is meant to include, without limitation, monovalent as well as multiply valent aryls (eg, divalent aryls).

The term "carbamoyl" as used herein contemplates a group of the structure

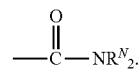

The term "carbonyl" as used herein contemplates a group of the structure

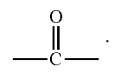

The term "carboxyl" as used herein contemplates a group of the structure

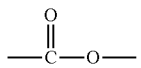

The term "cycloalkyl" as used herein contemplates substituted or unsubstituted cyclic alkyl radicals containing from three to twelve carbon atoms and includes cyclopropyl, cyclopentyl, cyclohexyl and the like. The term "cycloalkyl" also includes polycyclic systems having two rings in which two or more atoms are common to two adjoining rings (the rings are "fused"). The cycloalkyl group may be optionally substituted with one or more substituents selected from halo, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —S(O)$_2$N(R$^N$)$_2$, phosphate, phosphonate, alkyl, cycloalkenyl, aryl and heteroaryl.

The term "cycloalkenyl" as used herein contemplates substituted or unsubstituted cyclic alkenyl radicals containing from four to twelve carbon atoms in which there is at least one double bond between two of the ring carbons and includes cyclopentenyl, cyclohexenyl and the like. The term "cycloalkenyl" also includes polycyclic systems having two rings in which two or more atoms are common to two adjoining rings (the rings are "fused"). The cycloalkenyl group may be optionally substituted with one or more substituents selected from halo, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —S(O)$_2$N(R$^N$)$_2$, phosphate, phosphonate, alkyl, cycloalkenyl, aryl and heteroaryl.

The term "halo" or "halogen" as used herein includes fluorine, chlorine, bromine and iodine.

The term "heteroalkyl" as used herein contemplates an alkyl with one or more heteroatoms.

The term "heteroatom", particularly within a ring system, refers to N, O and S.

The term "heterocyclic group," "heterocycle" or "heterocyclic ring" as used herein contemplates substituted or unsubstituted aromatic and non-aromatic cyclic radicals having at least one heteroatom as a ring member. Preferred heterocyclic groups are those containing five or six ring atoms which includes at least one hetero atom and includes cyclic amines such as morpholino, piperidino, pyrrolidino and the like and cyclic ethers, such as tetrahydrofuran, tetrahydropyran and the like. Aromatic heterocyclic groups, also termed "heteroaryl" groups, contemplates single-ring hetero-aromatic groups that may include from one to three heteroatoms, for example, pyrrole, furan, thiophene, imidazole, oxazole, thiazole, triazole, pyrazole, oxodiazole, thiadiazole, pyridine, pyrazine, pyridazine, pyrimidine and the like. The term heteroaryl also includes polycyclic hetero-aromatic systems having two or more rings in which two or more atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, cinnoline, tetrahydroisoquinoline, quinoxaline, quinazoline, benzimidazole, benzofuran, benzothiophene, benzoxazole, benzothiazole, indazole, purine, benzotriazole, pyrrolepyridine, pyrrazolopyridine and the like. The heterocyclic group may be optionally substituted with one or more substituents selected from the group consisting of halo, alkyl, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, —SiR$_3$, —P(O)R, phosphate, phosphonate, cycloalkyl, cycloalkenyl, aryl and heteroaryl.

The term "oxo" as used herein contemplates an oxygen atom attached with a double bond.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

"Pharmaceutically acceptable salt" refers to a salt of a compound of the invention which is made with counterions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like and salts of organic acids like glucurmic or galactunoric acids and the like (see, e.g., Berge et al., 1977, *J. Pharm. Sci.* 66:1-19).

The terms "phosphate" and "phosphonate" as used herein refer to the moieties having the following structures, respectively:

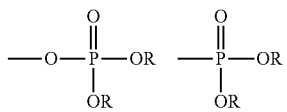

The terms "salts" and "hydrates" refers to the hydrated forms of the compound that would favorably affect the physical or pharmacokinetic properties of the compound, such as solubility, palatability, absorption, distribution, metabolism and excretion. Other factors, more practical in nature, which those skilled in the art may take into account in the selection include the cost of the raw materials, ease of crystallization, yield, stability, solubility, hygroscopicity, flowability and manufacturability of the resulting bulk drug.

The term sulfonamide as used herein contemplates a group having the structure

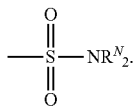

The term "sulfonate" as used herein contemplates a group having the structure

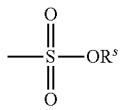

wherein $R^s$ is selected from the group consisting of hydrogen, $C_1$-$C_{10}$ alkyl, $C_2$-$C_{10}$ alkenyl, $C_2$-$C_{10}$ alkynyl, $C_1$-$C_{10}$ alkanoyl, or $C_1$-$C_{10}$ alkoxycarbonyl.

The term "sulfonyl" as used herein contemplates a group having the structure

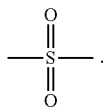

"Substituted sulfonyl" as used herein contemplates a group having the structure

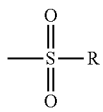

including, but not limited to alkylsulfonyl and arylsulfonyl.

The term "thiocarbonyl," as used herein, means a carbonyl wherein an oxygen atom has been replaced with a sulfur.

Each R is independently selected from hydrogen, —OH, —CN, —NO$_2$, halogen, $C_1$ to $C_{12}$ alkyl, $C_1$ to $C_{12}$ heteroalkyl, alkenyl, alkynyl, cycloalkyl, heterocycle, aryl, heteroaryl, aralkyl, alkoxy, alkoxycarbonyl, alkanoyl, carbamoyl, substituted sulfonyl, sulfonate, sulfonamide, amino, and oxo.

Each $R^N$ is independently selected from the group consisting of hydrogen, —OH, $C_1$ to $C_{12}$ alkyl, $C_1$ to $C_{12}$ heteroalkyl, alkenyl, alkynyl, cycloalkyl, heterocycle, aryl, heteroaryl, aralkyl, alkoxy, alkoxycarbonyl, alkanoyl, carbamoyl, substituted sulfonyl, sulfonate and sulfonamide. Two $R^N$ may be taken together with C, O, N or S to which they are attached to form a five to seven membered ring which may optionally contain a further heteroatom.

The compounds of the present invention may be used to inhibit or reduce the activity of HCV, particularly HCV's NS5A protein. In these contexts, inhibition and reduction of activity of the NS5A protein refers to a lower level of the measured activity relative to a control experiment in which the cells or the subjects are not treated with the test compound. In particular aspects, the inhibition or reduction in the measured activity is at least a 10% reduction or inhibition. One of skill in the art will appreciate that reduction or inhibition of the measured activity of at least 20%, 50%, 75%, 90% or 100%, or any number in between, may be preferred for particular applications.

In a first aspect, compounds of formula I are provided:

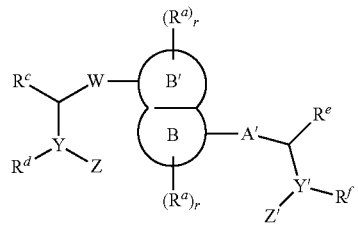

wherein:

A' is selected from the group consisting of single bond, —(CR$_2$)$_n$—C(O)—(CR$_2$)$_p$—, —(CR$_2$)$_n$—O—(CR$_2$)$_p$—, —(CR$_2$)$_n$—N(R$^N$)—(CR$_2$)$_p$—, —(CR$_2$)$_n$—S(O)$_k$—N(R$^N$)—(CR$_2$)$_p$—, —(CR$_2$)$_n$—C(O)—N(R$^N$)—(CR$_2$)$_p$—, —(CR$_2$)$_n$—N(R$^N$)—C(O)—N(R$^N$)—(CR$_2$)$_p$—, —(CR$_2$)$_n$—C(O)—O—(CR$_2$)$_p$—, —(CR$_2$)$_n$—N(R$^N$)—S(O)$_k$—N(R$^N$)—(CR$_2$)$_p$— and —(CR$_2$)$_n$—N(R$^N$)—C(O)—O—(CR$_2$)$_p$— and a heteroaryl group selected from the group consisting of

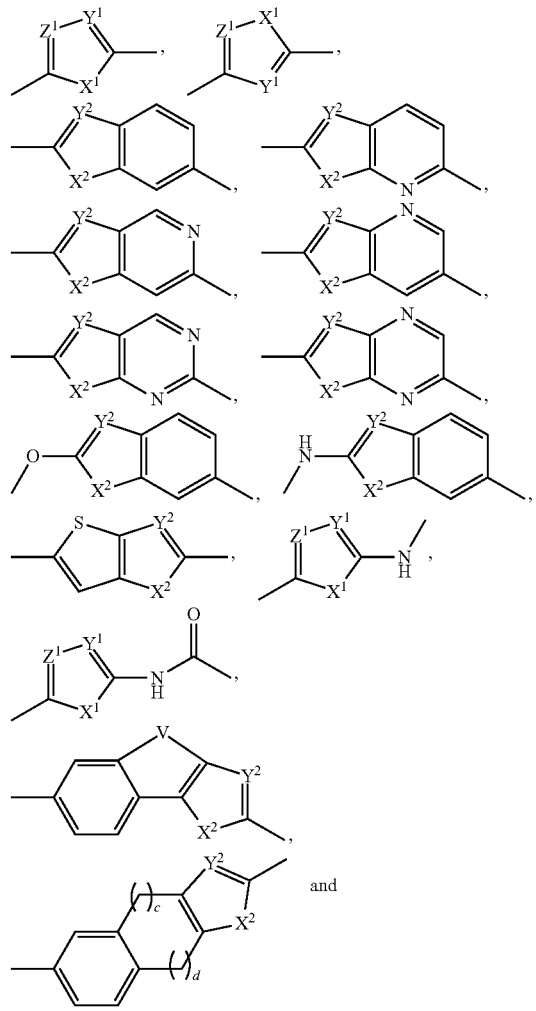

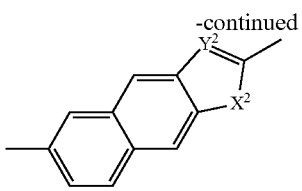

wherein:
X$^1$ is CH$_2$, NH, O or S,
Y$^1$, Y$^2$ and Z$^1$ are each independently CH or N,
X$^2$ is NH, O or S,
V is —CH$_2$—CH$_2$—, —CH=CH—, —N=CH—, (CH$_2$), —N(R$^N$)—(CH$_2$)$_b$— or —(CH$_2$)$_a$—O—(CH$_2$)$_b$—, wherein a and b are independently 0, 1, 2, or 3 with the proviso that a and b are not both 0,

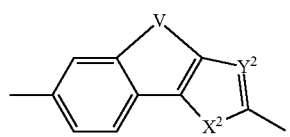

optionally includes 1 or 2 nitrogens as heteroatoms on the phenyl residue,
the carbons of the heteroaryl group are each independently optionally substituted with a substituent selected from the group consisting of halogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
the nitrogens, if present, of the heteroaryl group are each independently optionally substituted with a substituent selected from the group consisting of —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide,
a and b are independently 1, 2, or 3.
c and d are independently 1 or 2,
n and p are independently 0, 1, 2 or 3,
k is 0, 1, or 2,
each R is independently selected from the group consisting of hydrogen, halogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
each R$^N$ is independently selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide and
wherein B may be attached to either side of A' so that in the example of A' being

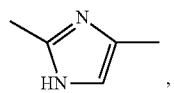

the W—B-A' can be

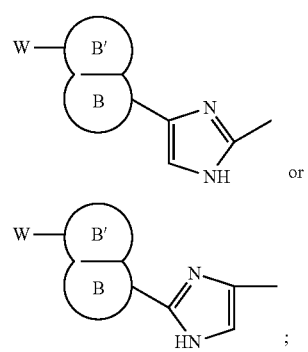

B and B' are each independently a 4- to 8-membered ring that is an aryl, heteroaryl, cycloalkyl, or heterocycle, wherein each hetero atom, if present, is independently N, O or S and wherein at least one of B or B' is aromatic;
each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and if B or B' is not aromatic, it may also be substituted with one or more oxo;
each r is independently 0, 1, 2 or 3;
W is independently selected from

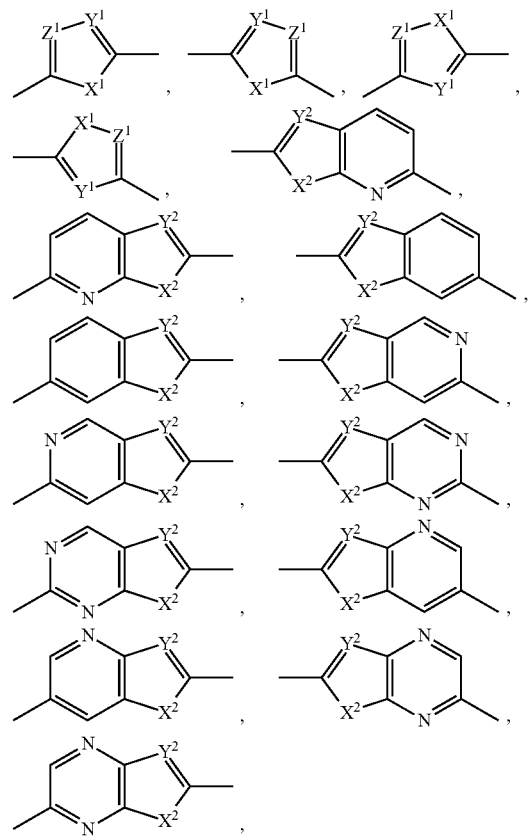

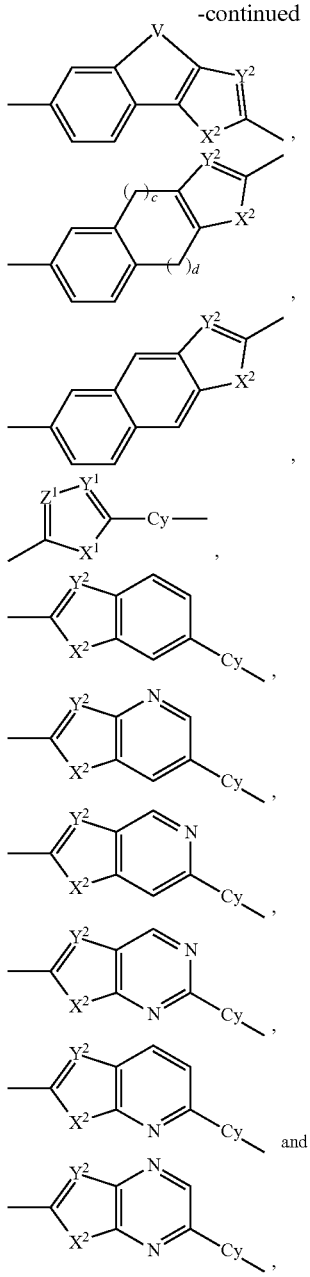

wherein:
X¹ is CH₂, NH, O or S,
Y¹, Y² and Z¹ are each independently CH or N,
X² is NH, O or S,
V is —CH₂—CH₂—, —CH=CH—, —N=CH—, (CH₂)$_a$—N(R$^N$)—(CH₂)$_b$— or —(CH₂)$_a$—O—(CH₂)$_b$—, wherein a and b are independently 0, 1, 2, or 3 with the proviso that a and b are not both 0,

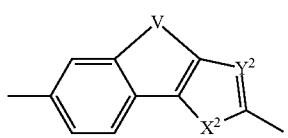

optionally includes 1 or 2 nitrogens as heteroatoms on the phenyl residue,

W is optionally substituted with one or more substituents selected from the group consisting of —OH, —CN, —NO₂, halogen, C₁ to C₁₂ alkyl, C₁ to C₁₂ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, W and ring B' can be connected through either a carbon or a nitrogen atom on B', and Cy is a monocyclic, bicyclic or tricyclic 5- to 12-membered cycloalkyl, heterocycle, aryl group or heteroaryl group wherein up to three heteroatoms are independently N, S or O and which is optionally substituted with one or more substituents selected from the group consisting of —OH, —CN, —NO₂, halogen, C₁ to C₁₂ alkyl, C₁ to C₁₂ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each R$^c$, R$^d$, R$^e$ and R$^f$ is independently selected from the group consisting of: hydrogen, C₁ to C₈ alkyl, C₁ to C₈ heteroalkyl, aralkyl and a 4- to 8-membered ring which may be cycloalkyl, heterocycle, heteroaryl or aryl, wherein, each hetero atom, if present, is independently N, O or S, each of R$^c$, R$^d$, R$^e$ and R$^f$ may optionally be substituted by C₁ to C₈ alkyl, C₁ to C₈ heteroalkyl, aralkyl, or a 4- to 8-membered ring which may be cycloalkyl, heterocycle, heteroaryl or aryl and wherein each heteroatom, if present, is independently N, O or S, R$^c$ and R$^d$ are optionally joined to form a 4- to 8-membered heterocycle which is optionally fused to another 3- to 5-membered heterocycle or heteroaryl ring, and R$^e$ and R$^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, C₁ to C₈ alkyl, C₁ to C₈ heteroalkyl, cycloalkyl, heterocycle, aryl, heteroaryl, aralkyl, 1-3 amino acids, —[U—(CR⁴₂)$_t$—NR⁵—C(R⁴₂)$_t$]$_u$—U—(CR⁴₂)$_t$—NR⁷—(CR⁴₂)$_t$—R⁸, —U—(CR⁴₂)$_t$—R⁸, and —[U—(CR⁴₂)$_t$—NR⁵—(CR⁴₂)$_t$]$_u$—U—(CR⁴₂)$_t$—O—(CR⁴₂)$_t$—R⁸, wherein, U is selected from the group consisting of —C(O)—, —C(S)— and —S(O)₂—, each R⁴, R⁵ and R⁷ is independently selected from the group consisting of hydrogen, C₁ to C₈ alkyl, C₁ to C₈ heteroalkyl, cycloalkyl, heterocycle, aryl, heteroaryl and aralkyl, R⁸ is selected from the group consisting of hydrogen, C₁ to C₈ alkyl, C₁ to C₈ heteroalkyl, cycloalkyl, heterocycle, aryl, heteroaryl, aralkyl, —C(O)—R⁸¹, —C(S)—R⁸¹, —C(O)—O—R⁸¹, —C(O)—N—R⁸¹₂, —S(O)₂—R⁸¹ and —S(O)₂—N—R⁸¹₂, wherein each R⁸¹ is independently chosen from the group consisting of hydrogen, C₁ to C₈ alkyl, C₁ to C₈ heteroalkyl, cycloalkyl, heterocycle, aryl, heteroaryl and aralkyl, optionally, R⁷ and R⁸ together form a 4-7 membered ring, each t is independently 0, 1, 2, 3, or 4, and u is 0, 1, or 2.

The compounds of the present invention include pharmaceutically acceptable salts of I as well as an optically pure enantiomer, racemate or diastereomeric mixtures thereof.

In a first embodiment of the first aspect, A' is selected from the group consisting of a single bond, —(CR$_2$)$_n$—O—(CR$_2$)$_p$—, —(CR$_2$)$_n$—N(R$^N$)—(CR$_2$)$_p$—, —(CR$_2$)$_n$—C(O)—N(R$^N$)—(CR$_2$)$_p$—, —(CR$_2$)$_n$—N(R$^N$)—C(O)—N(R$^N$)—(CR$_2$)$_p$— and —(CR$_2$)$_n$—N(R$^N$)—C(O)—O—(CR$_2$)$_p$— and a heteroaryl group selected from the group consisting of

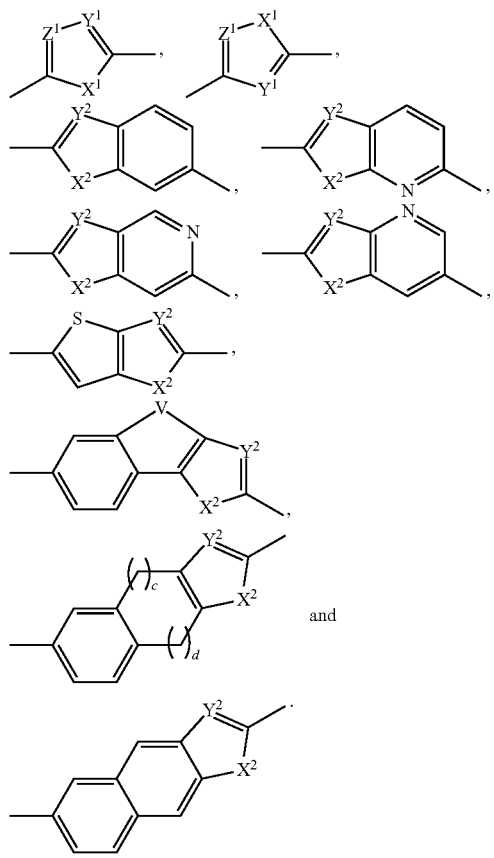

and

In a second embodiment of the first aspect, A' is selected from the group consisting of a single bond,

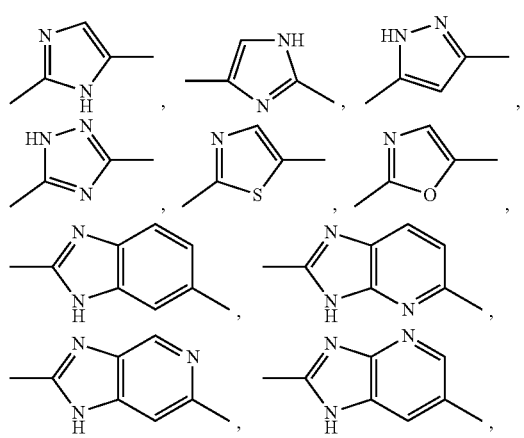

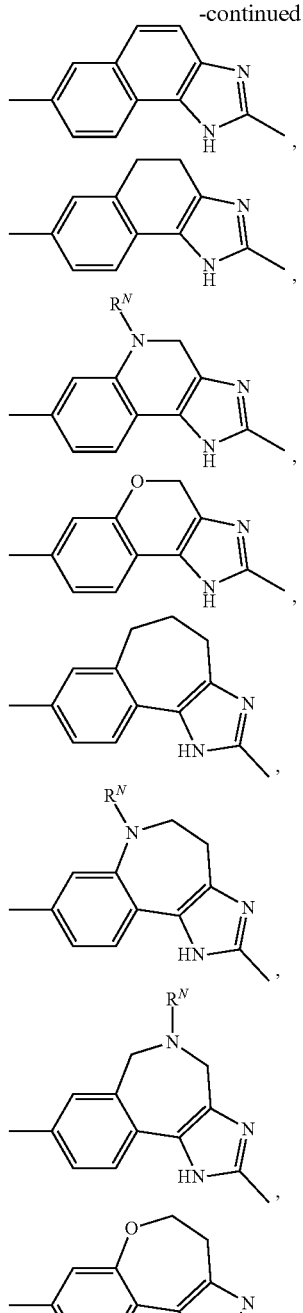

In a third embodiment of the first aspect, R$^c$, R$^d$, R$^e$ and R$^f$ are each independently selected from the group consisting of: hydrogen, C$_1$ to C$_8$ alkyl and C$_1$ to C$_8$ heteroalkyl, wherein, each hetero atom, if present, is independently N, O or S, R$^c$ and R$^d$ are optionally joined to form a 4- to 8-membered heterocycle which is optionally fused to another 3- to 6-membered heterocycle, and R$^e$ and R$^f$ are optionally joined to form a 4- to 8-membered heterocycle which is optionally fused to another 3- to 6-membered heterocycle.

In a fourth embodiment of the first aspect, $R^c$ and $R^d$ or $R^e$ and $R^f$ are optionally joined to form a 4- to 8-membered heterocycle which is optionally fused to another 3- to 6-membered heterocycle.

In a fifth embodiment of the first aspect, $R^c$ and $R^d$ are joined and form a heterocyclic fused ring system selected from the group consisting of:

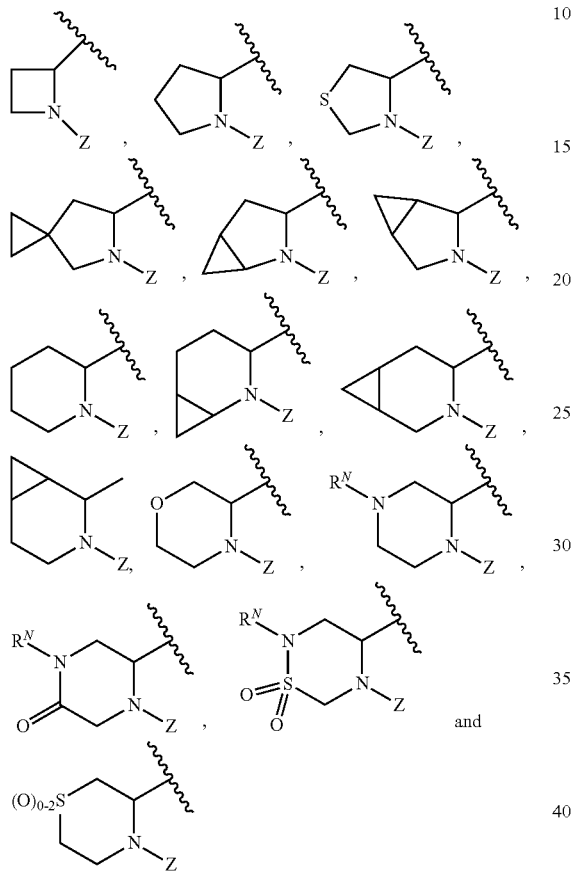

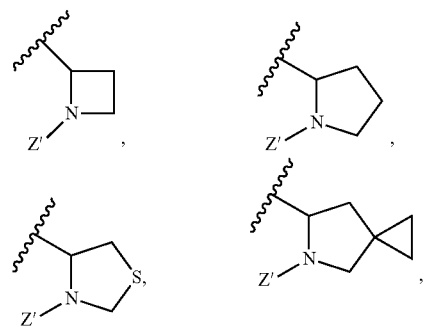

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a sixth embodiment of the first aspect, $R^e$ and $R^f$ are joined and form a heterocyclic fused ring system selected from the group consisting of:

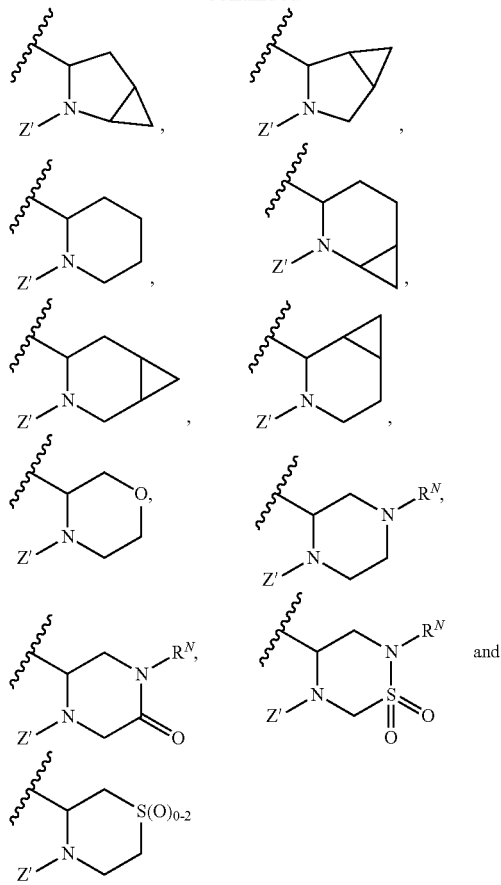

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a seventh embodiment of the first aspect, B and B' together is selected from the group consisting of

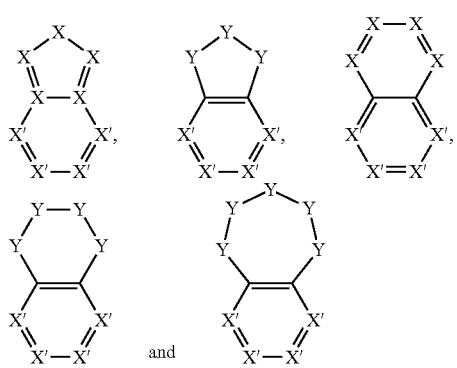

wherein
  each X is independently N or C and if C, may include a hydrogen as necessary to complete the valence shell;
  each X' is independently —N— or —CH—, with the proviso that no more than two X' are —N—;
  each Y is independently selected from —CH$_2$—, —NH—, —O—, —S—, —C(O)$_2$—, or —S(O)$_{1-2}$—; and B and B' attach to the remainder of the compound at any available attachment point on the molecule.

In an eighth embodiment of the first aspect, B and B' together is

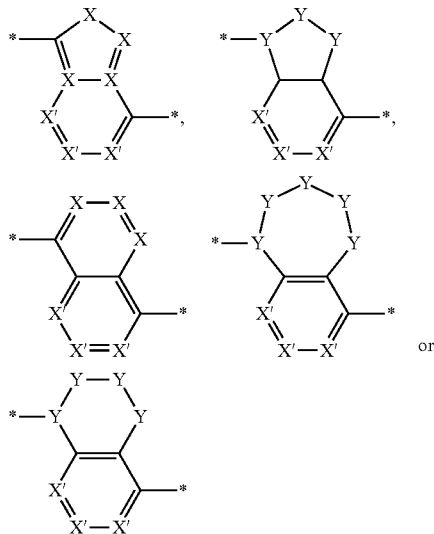

wherein * indicates attachment points to the remainder of the compound.

In a ninth embodiment of the first aspect, B and B' together is

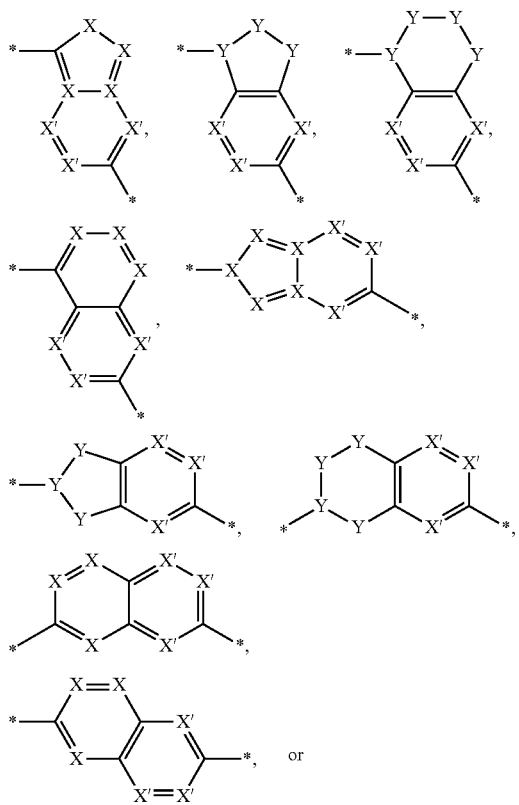

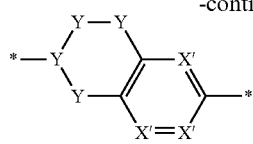

wherein * indicates attachment points to the remainder of the compound.

In a tenth embodiment of the first aspect, B and B' together is

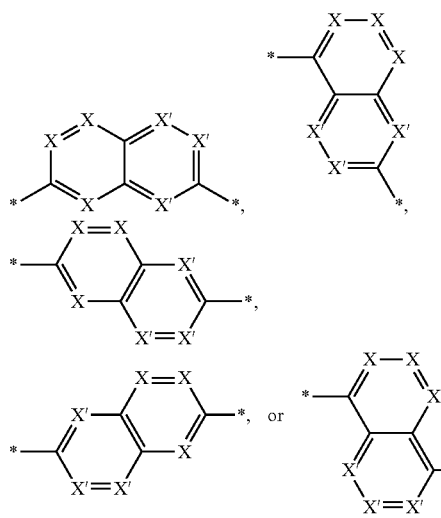

wherein * indicates attachment points to the remainder of the compound wherein no more than 2 of X are nitrogen.

In an eleventh embodiment of the first aspect, B and B' together is

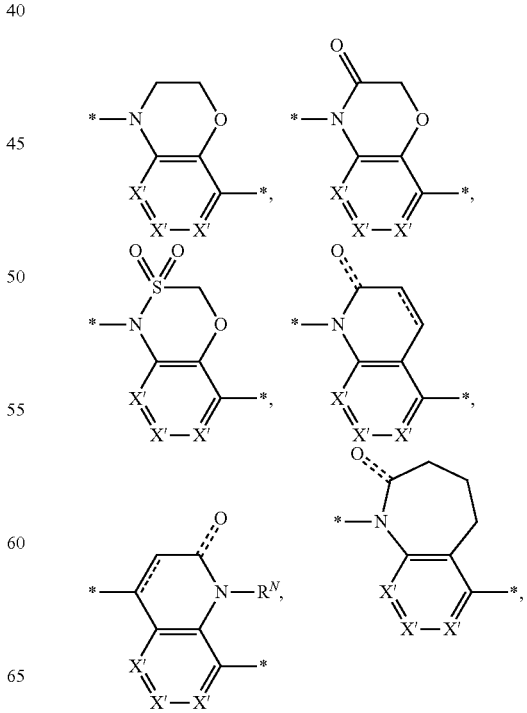

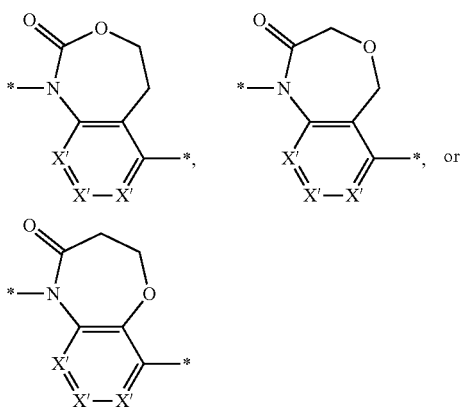

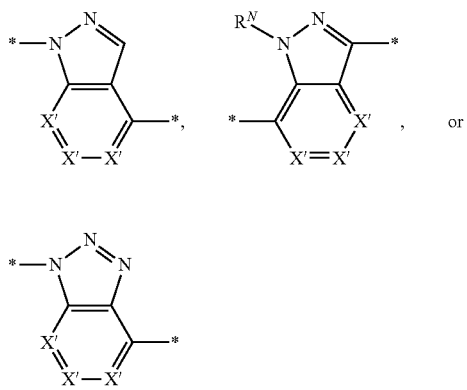

wherein * indicates attachment points to the remainder of the compound and $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a twelfth embodiment of the first aspect, B and B' together is

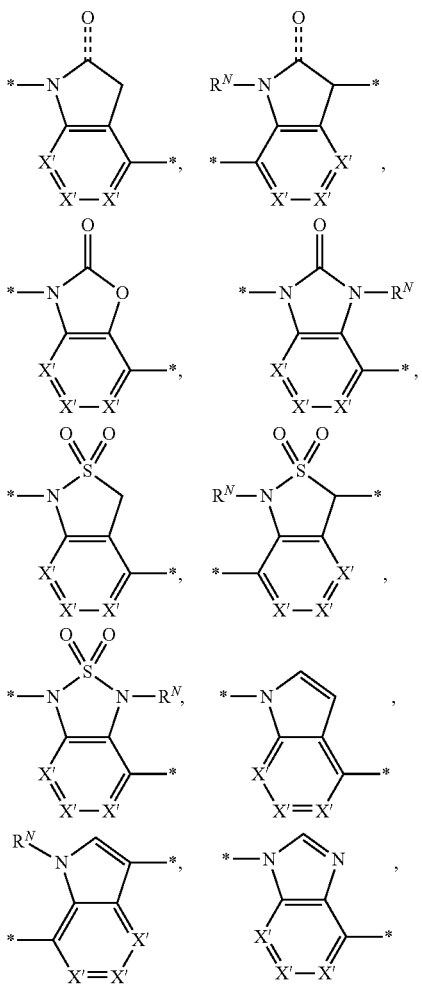

wherein * indicates attachment points to the remainder of the compound and $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a thirteenth embodiment of the first aspect, B and B' together is

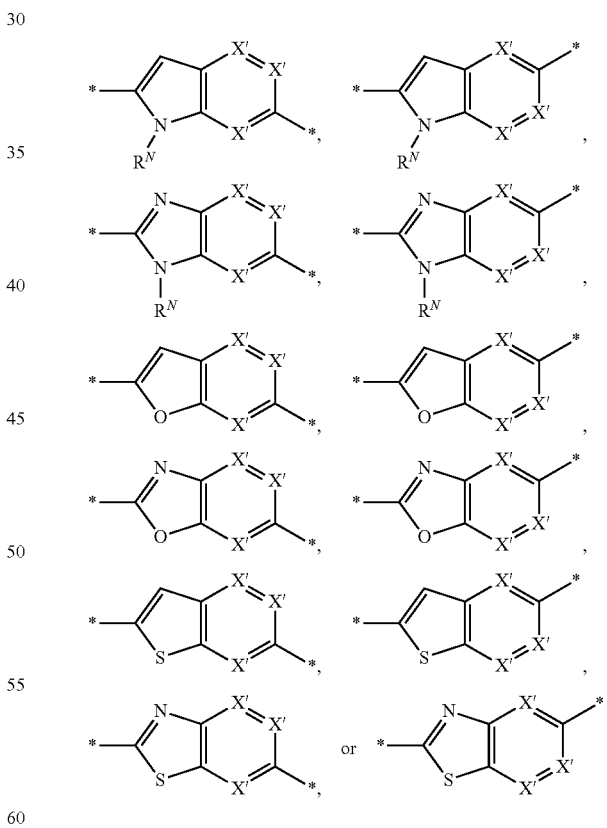

wherein * indicates attachment points to the remainder of the compound and $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a fourteenth embodiment of the first aspect, B and B' together is

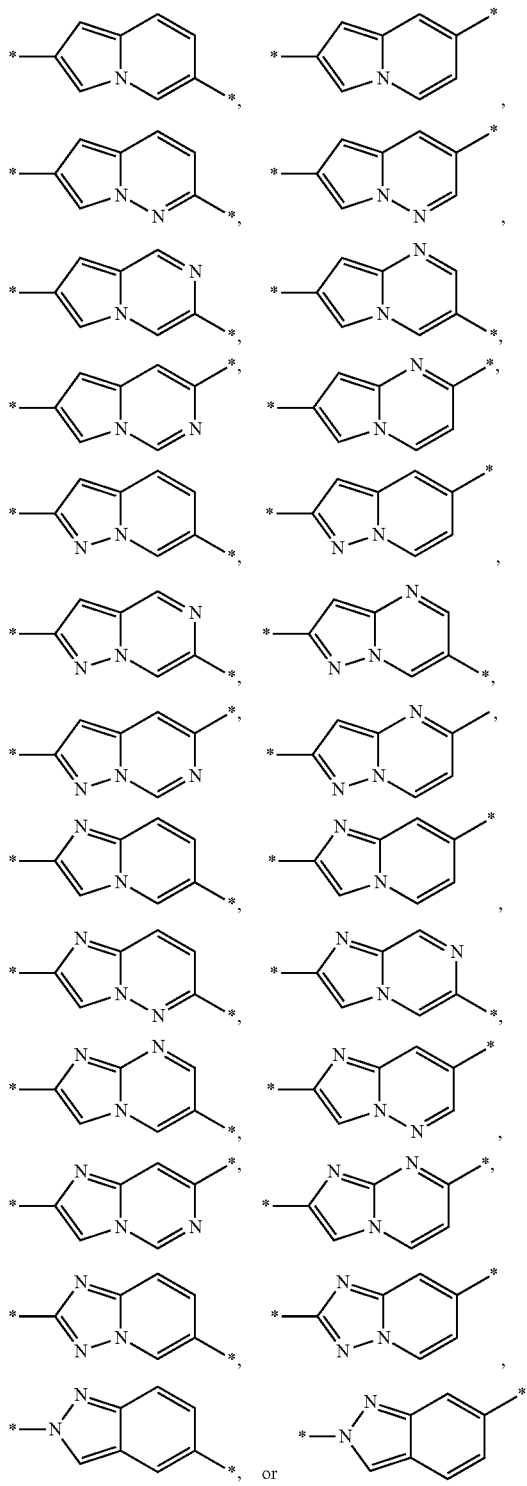

wherein * indicates attachment points to the remainder of the compound and the six-membered ring optionally contains one or two additional nitrogens as heteroatoms with the proviso that the total number of nitrogens in the six-membered ring does not exceed two.

In a fifteenth embodiment of the first aspect, B and B' together is

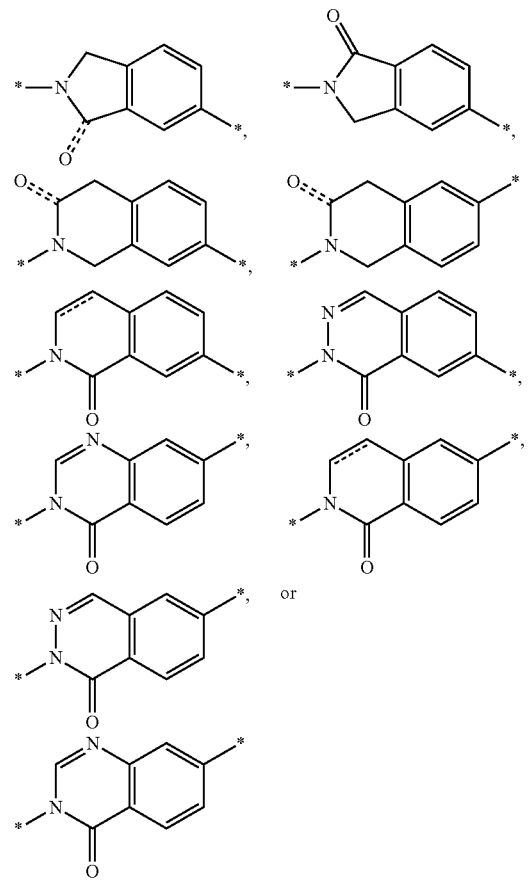

wherein * indicates attachment points to the remainder of the compound and the phenyl moiety optionally contains one or two nitrogens as heteroatoms.

In a sixteenth embodiment of the first aspect, B and B' together is

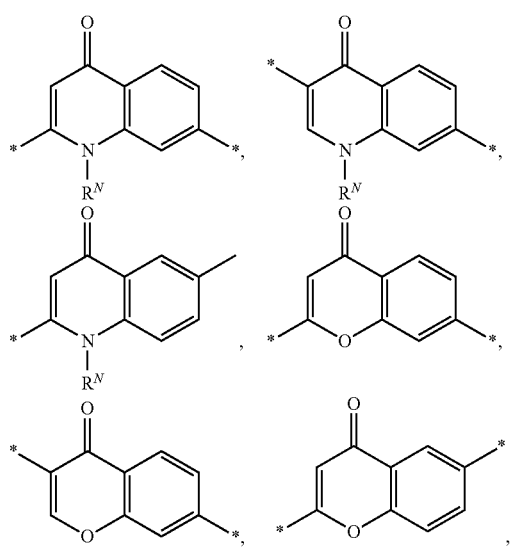

-continued

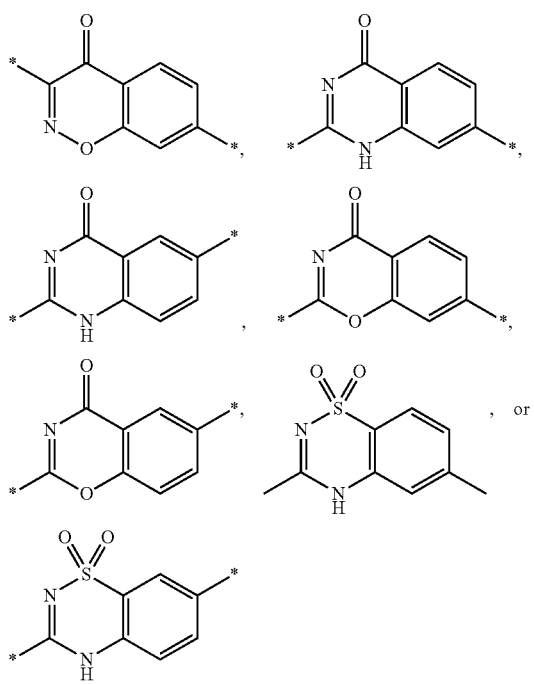

wherein * indicates attachment points to the remainder of the compound; the phenyl moiety optionally contains one or two nitrogens as heteroatoms; and $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a second aspect of the invention, compounds have formula II:

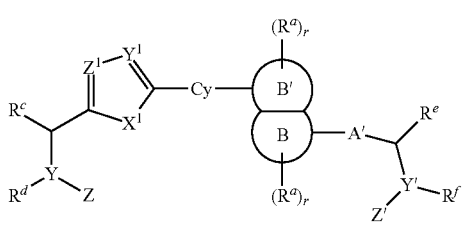

wherein A' is selected from the group consisting of a single bond,

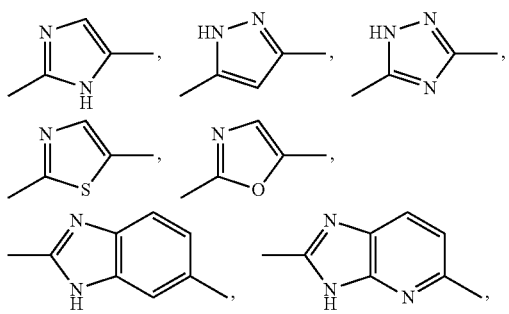

-continued

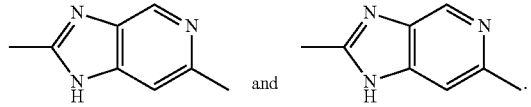

In a first embodiment of the second aspect, compounds have formula II wherein A' is

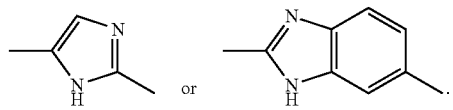

In a second embodiment of the second aspect, compounds have formula IIa:

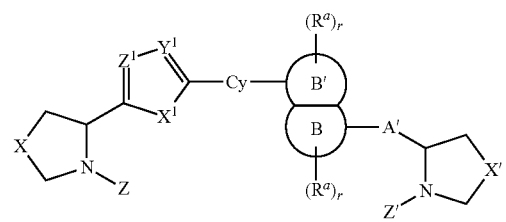

wherein X and X' are each independently selected from the group consisting of a bond, —$CH_2$—, —$CH_2$—$CH_2$—, —CH=CH—, —O—, —S—, —$S(O)_{1-2}$—, —$CH_2O$—, —$CH_2S$—, —$CH_2S(O)_{1-2}$— and —$CH_2N(R^1)$—, wherein $R^1$ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIa as well as an optically pure enantiomer, racemate or diastereomeric mixtures thereof.

In a third embodiment of the second aspect, compounds have formula IIa wherein A' is

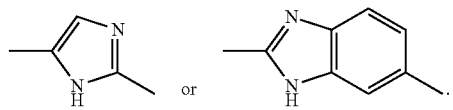

In a fourth embodiment of the second aspect, compounds have formula IIb:

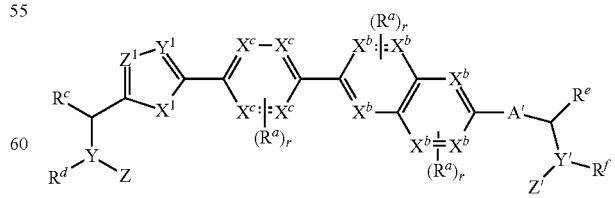

wherein each $X^b$ and $X^c$ is independently C or N.

The compounds of the present invention include pharmaceutically acceptable salts of IIb as well as an optically pure enantiomer, racemate or diastereomeric mixtures thereof.

In a fifth embodiment of the second aspect, compounds have formula IIb wherein A' is

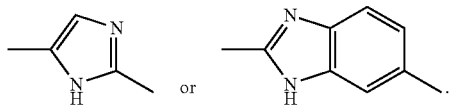

In a sixth embodiment of the second aspect, compounds have formula IIc:

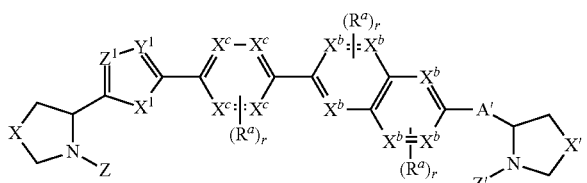

wherein X and X' are each independently selected from the group consisting of a bond, —CH$_2$—, —CH$_2$—CH$_2$, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIc as well as an optically pure enantiomer, racemate or diastereomeric mixtures thereof.

In a seventh embodiment of the second aspect, compounds have formula IIc wherein A' is

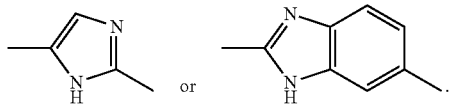

In an eighth embodiment of the second aspect, compounds have formula IId:

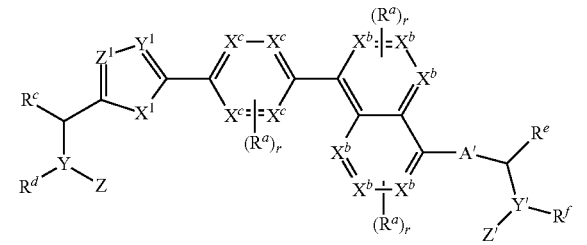

wherein each X$^b$ and X$^c$ is independently C or N.

The compounds of the present invention include pharmaceutically acceptable salts of IId as well as an optically pure enantiomer, racemate or diastereomeric mixtures thereof.

In a ninth embodiment of the second aspect, compounds have formula IId wherein A' is

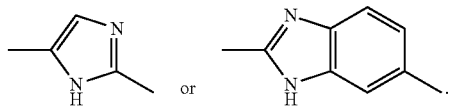

In a tenth embodiment of the second aspect, compounds have formula IIe:

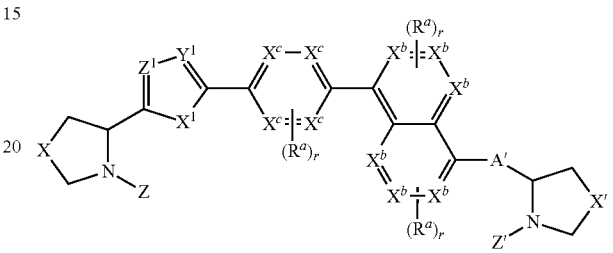

wherein X and X' are each independently selected from the group consisting of a bond, —CH$_2$—, —CH$_2$—CH$_2$, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIe as well as an optically pure enantiomer, racemate or diastereomeric mixtures thereof.

In an eleventh embodiment of the second aspect, compounds have formula IIe wherein A' is

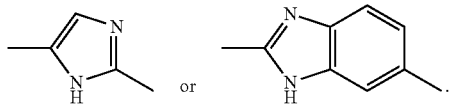

In a twelfth embodiment of the second aspect, compounds have formula IIf:

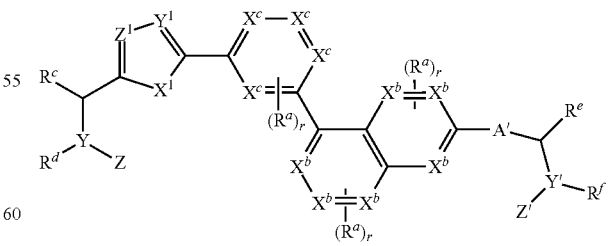

wherein each X$^b$ and X$^c$ is independently C or N.

The compounds of the present invention include pharmaceutically acceptable salts of IIf as well as an optically pure enantiomer, racemate or diastereomeric mixtures thereof.

In a thirteenth embodiment of the second aspect, compounds have formula IIf wherein A' is

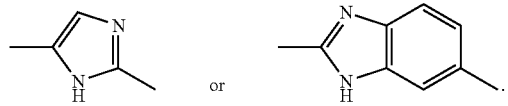

In a fourteenth embodiment of the second aspect, compounds have formula IIg:

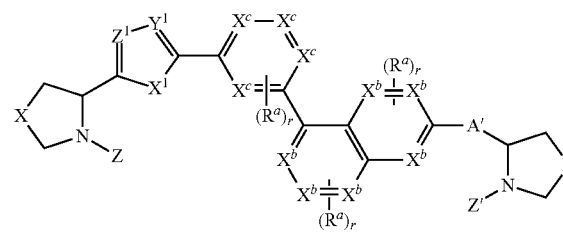

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIg as well as an optically pure enantiomer, racemate or diastereomeric mixtures thereof.

In a fifteenth embodiment of the second aspect, compounds have formula IIg wherein A' is

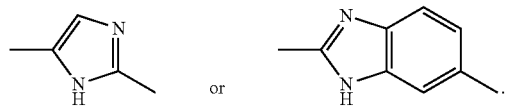

In a sixteenth embodiment of the second aspect, compounds have formula IIh:

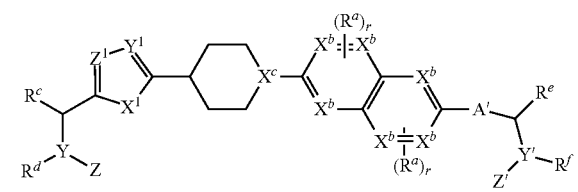

wherein X$^c$ and each X$^b$ is independently C or N.

The compounds of the present invention include pharmaceutically acceptable salts of IIh as well as an optically pure enantiomer, racemate or diastereomeric mixtures thereof.

In a seventeenth embodiment of the second aspect, compounds have formula IIh wherein A' is

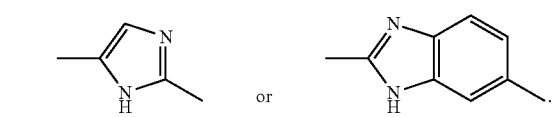

In an eighteenth embodiment of the second aspect, compounds have formula IIi:

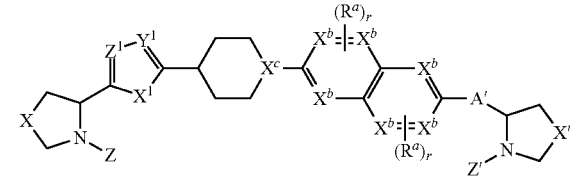

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIi as well as an optically pure enantiomer, racemate or diastereomeric mixtures thereof.

In a nineteenth embodiment of the second aspect, compounds have formula IIi wherein A' is

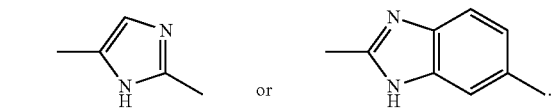

In a twentieth embodiment of the second aspect, compounds have formula IIh or IIi wherein X$^c$ is C.

In an twenty-first embodiment of the second aspect, compounds have formula IIh or IIi wherein X$^c$ is N.

In a twenty-second embodiment of the second aspect, compounds have formula IIj:

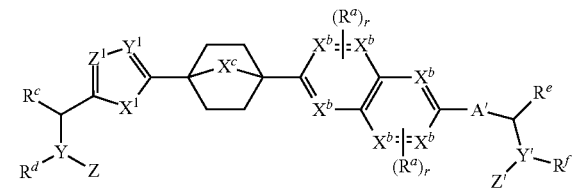

wherein
X$^c$ is —CH$_2$—, —NH— or —CH$_2$—CH$_2$—, and
each X$^b$ is independently C or N.

The compounds of the present invention include pharmaceutically acceptable salts of IIj as well as an optically pure enantiomer, racemate or diastereomeric mixtures thereof.

In a twenty-third embodiment of the second aspect, compounds have formula IIj wherein A' is In a twenty-fourth embodiment of the second aspect, compounds have formula IIk:

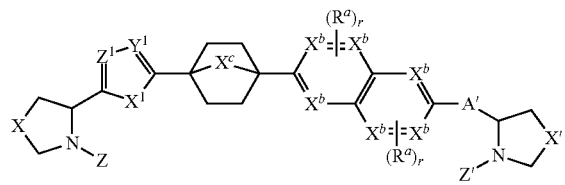

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIk as well as an optically pure enantiomer, racemate or diastereomeric mixtures thereof.

In a twenty-fifth embodiment of the second aspect, compounds have formula IIk wherein A' is

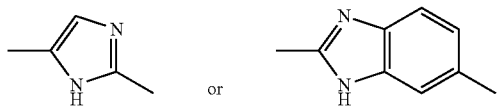

In a twenty-sixth embodiment of the second aspect, compounds have formula Il1:

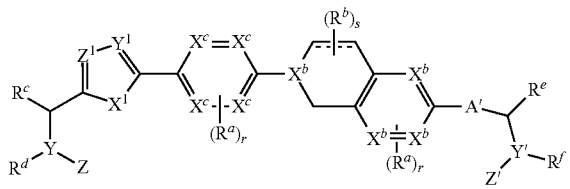

wherein:
each X$^b$ and X$^c$ is independently C or N;
each R$^b$ is selected from the group consisting of oxo, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and
s is 0, 1, 2, or 3.

The compounds of the present invention include pharmaceutically acceptable salts of Il1 as well as an optically pure enantiomer, racemate or diastereomeric mixtures thereof.

In a twenty-seventh embodiment of the second aspect, compounds have formula Il1 wherein A' is

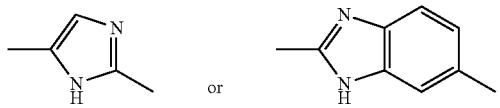

In a twenty-eighth embodiment of the second aspect, compounds have formula IIm:

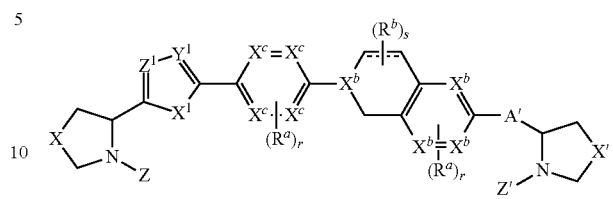

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of III as well as an optically pure enantiomer, racemate or diastereomeric mixtures thereof.

In a twenty-ninth embodiment of the second aspect, compounds have formula IIm wherein A' is

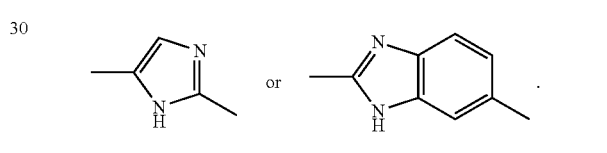

In a thirtieth embodiment of the second aspect, compounds have formula IIn:

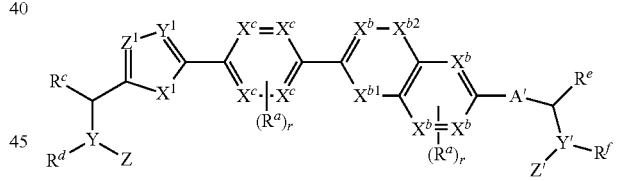

wherein:
each X$^b$ and X$^c$ is independently C or N;
X$^{b1}$ is N or O; and
X$^{b2}$ is S(O)$_2$ or C(O).

The compounds of the present invention include pharmaceutically acceptable salts of IIn as well as an optically pure enantiomer, racemate or diastereomeric mixtures thereof.

In a thirty-first embodiment of the second aspect, compounds have formula IIn wherein A' is

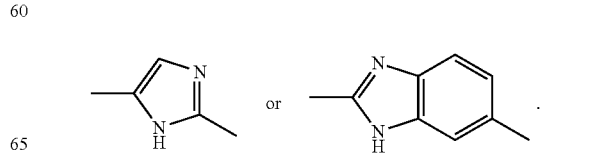

In a thirty-second embodiment of the second aspect, compounds have formula IIo:

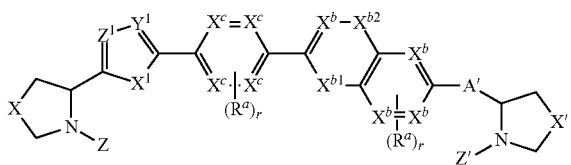

wherein X and X' are each independently selected from the group consisting of a bond, —$CH_2$—, —$CH_2$—$CH_2$—, —CH=CH—, —O—, —S—, —$S(O)_{1-2}$—, —$CH_2O$—, —$CH_2S$—, —$CH_2S(O)_{1-2}$— and —$CH_2N(R^1)$—, wherein $R^1$ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIo as well as an optically pure enantiomer, racemate or diastereomeric mixtures thereof.

In a thirty-third embodiment of the second aspect, compounds have formula IIo wherein A' is

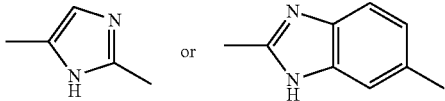

In an thirty-fourth embodiment of the second aspect, compounds have formula IIp:

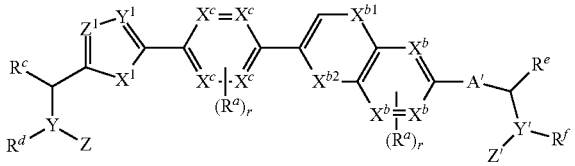

wherein:
each $X^b$ and $X^c$ is independently C or N;
$X^{b1}$ is N or O; and
$X^{b2}$ is $S(O)_2$ or C(O).

The compounds of the present invention include pharmaceutically acceptable salts of IIp as well as an optically pure enantiomer, racemate or diastereomeric mixtures thereof.

In a thirty-fifth embodiment of the second aspect, compounds have formula IIp wherein A' is

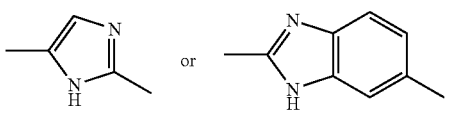

In a thirty-sixth embodiment of the second aspect, compounds have formula IIq:

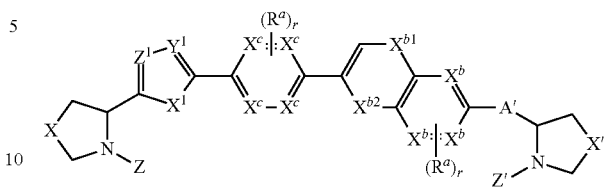

wherein X and X' are each independently selected from the group consisting of a bond, —$CH_2$—, —$CH_2$—$CH_2$—, —CH=CH—, —O—, —S—, —$S(O)_{1-2}$—, —$CH_2O$—, —$CH_2S$—, —$CH_2S(O)_{1-2}$— and —$CH_2N(R^1)$—, wherein $R^1$ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIq as well as an optically pure enantiomer, racemate or diastereomeric mixtures thereof.

In a thirty-seventh embodiment of the second aspect, compounds have formula IIq wherein A' is

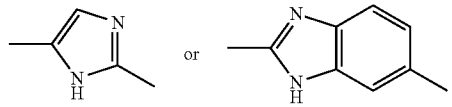

In a third aspect of the invention, compounds have formula III:

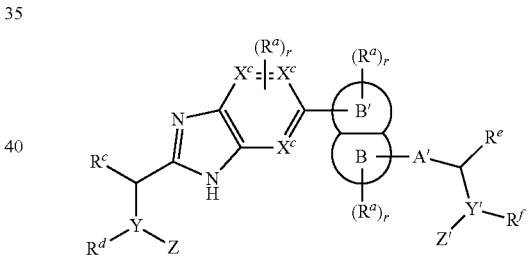

wherein
A' is selected from the group consisting of a single bond,

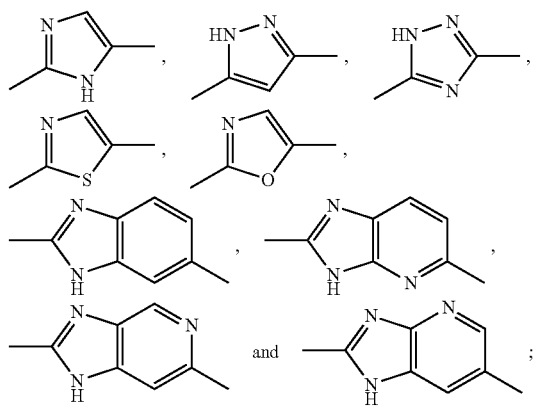

and
each $X^c$ is independently C or N.

The compounds of the present invention include pharmaceutically acceptable salts of III as well as an optically pure enantiomer, racemate or diastereomeric mixtures thereof.

In a first embodiment of the third aspect, compounds have formula III wherein A' is

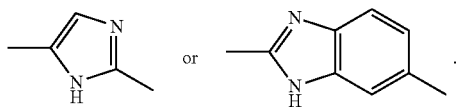

In a second embodiment of the third aspect, compounds have formula IIa:

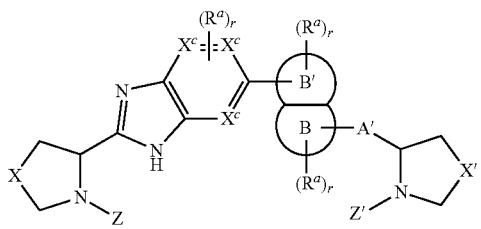

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIa as well as an optically pure enantiomer, racemate or diastereomeric mixtures thereof.

In a third embodiment of the third aspect, compounds have formula IIa wherein A' is

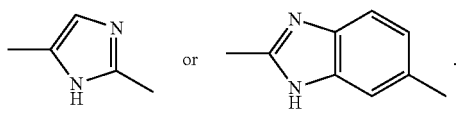

In a fourth embodiment of the third aspect, compounds have formula IIIb:

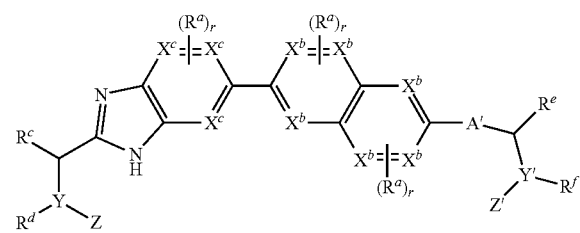

wherein each
X$^b$ is independently C or N.

The compounds of the present invention include pharmaceutically acceptable salts of IIb as well as an optically pure enantiomer, racemate or diastereomeric mixtures thereof.

In a fifth embodiment of the third aspect, compounds have formula IIIb wherein A' is

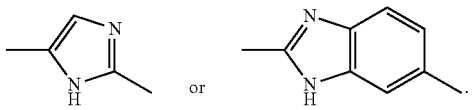

In a sixth embodiment of the third aspect, compounds have formula IIIc:

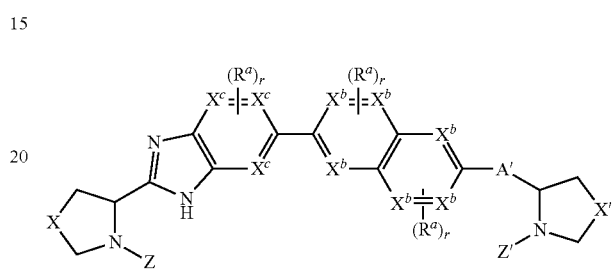

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIIc as well as an optically pure enantiomer, racemate or diastereomeric mixtures thereof.

In a seventh embodiment of the third aspect, compounds have formula IIIc wherein A' is

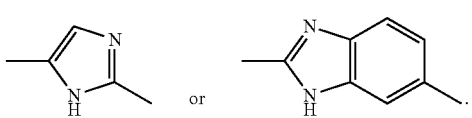

In an eighth embodiment of the third aspect, compounds have formula IIId:

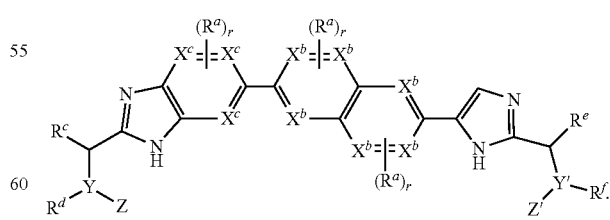

The compounds of the present invention include pharmaceutically acceptable salts of IIId as well as an optically pure enantiomer, racemate or diastereomeric mixtures thereof.

In a ninth embodiment of the third aspect, compounds have formula IIIe:

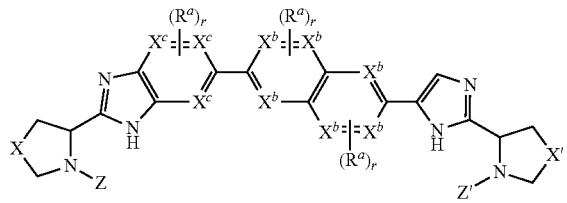

wherein X and X' are each independently selected from the group consisting of a bond, —CH$_2$—, —CH$_2$—CH$_2$—, —CH═CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIIe as well as an optically pure enantiomer, racemate or diastereomeric mixtures thereof.

In a tenth embodiment of the third aspect, compounds have formula IIIf:

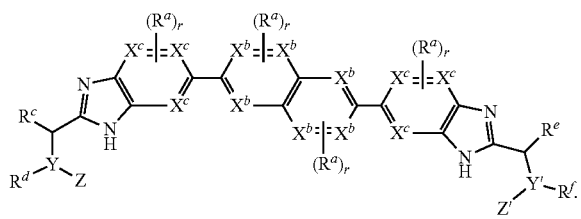

The compounds of the present invention include pharmaceutically acceptable salts of IIIf as well as an optically pure enantiomer, racemate or diastereomeric mixtures thereof.

In an eleventh embodiment of the third aspect, compounds have formula IIIg:

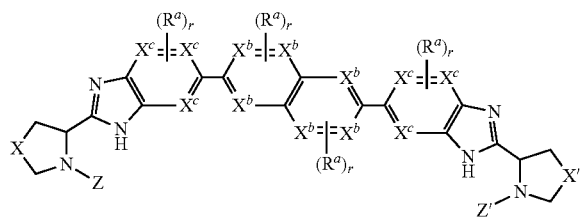

wherein X and X' are each independently selected from the group consisting of a bond, —CH$_2$—, —CH$_2$—CH$_2$—, —CH═CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIIg as well as an optically pure enantiomer, racemate or diastereomeric mixtures thereof.

In a twelfth embodiment of the third aspect, compounds have formula IIIh:

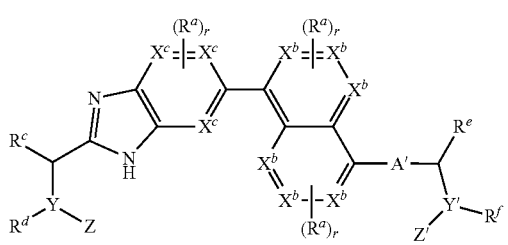

wherein each X$^b$ is independently C or N.

The compounds of the present invention include pharmaceutically acceptable salts of IIIh as well as an optically pure enantiomer, racemate or diastereomeric mixtures thereof.

In a thirteenth embodiment of the third aspect, compounds have formula IIIh wherein A' is

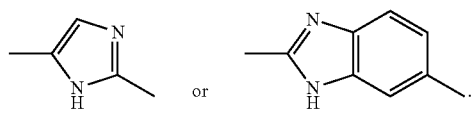

In a fourteenth embodiment of the third aspect, compounds have formula IIIi:

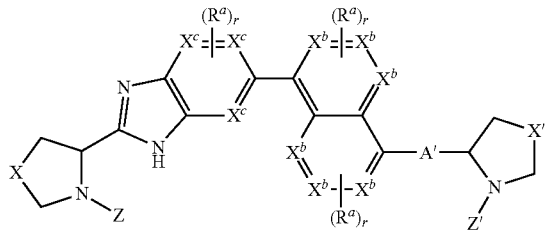

wherein X and X' are each independently selected from the group consisting of a bond, —CH$_2$—, —CH$_2$—CH$_2$—, —CH═CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIIi as well as an optically pure enantiomer, racemate or diastereomeric mixtures thereof.

In a fifteenth embodiment of the third aspect, compounds have formula IIIi wherein A' is

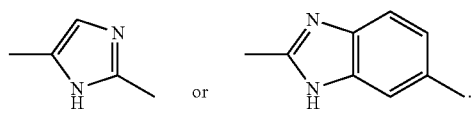

In a sixteenth embodiment of the third aspect, compounds have formula IIIj:

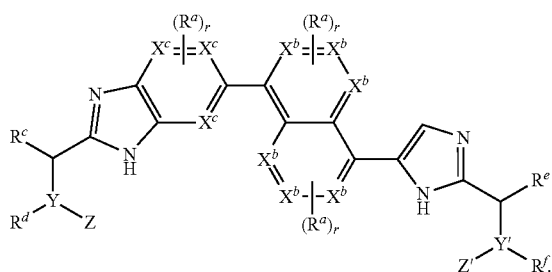

The compounds of the present invention include pharmaceutically acceptable salts of IIIj as well as an optically pure enantiomer, racemate or diastereomeric mixtures thereof.

In a seventeenth embodiment of the third aspect, compounds have formula IIIk:

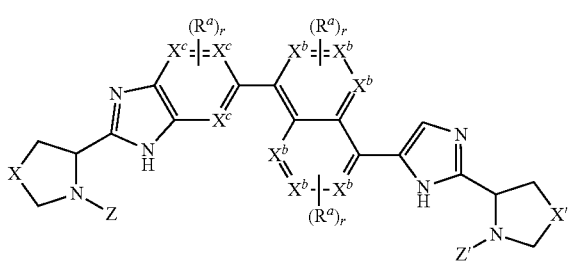

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIIk as well as an optically pure enantiomer, racemate or diastereomeric mixtures thereof.

In an eighteenth embodiment of the third aspect, compounds have formula IIIl:

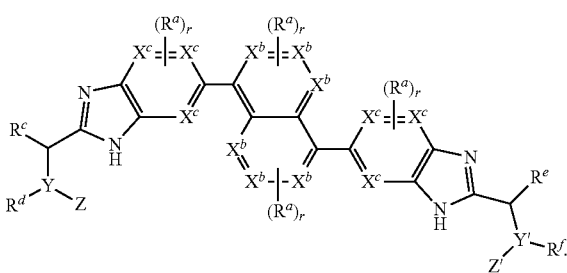

The compounds of the present invention include pharmaceutically acceptable salts of IIIl as well as an optically pure enantiomer, racemate or diastereomeric mixtures thereof.

In a nineteenth embodiment of the third aspect, compounds have formula IIIm:

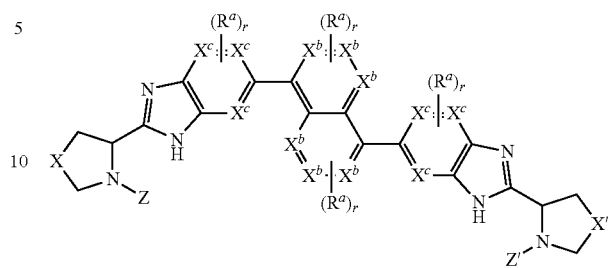

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIIm as well as an optically pure enantiomer, racemate or diastereomeric mixtures thereof.

In a twentieth embodiment of the third aspect, compounds have formula IIIn:

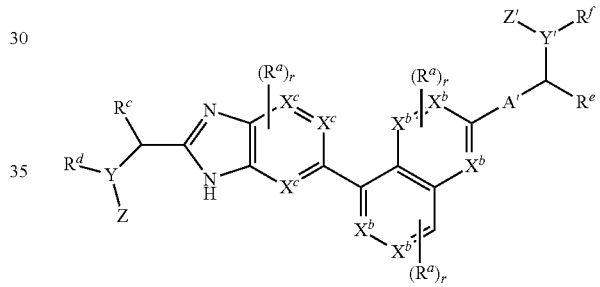

wherein each X$^b$ is independently C or N.

The compounds of the present invention include pharmaceutically acceptable salts of IIIn as well as an optically pure enantiomer, racemate or diastereomeric mixtures thereof.

In a twenty-first embodiment of the third aspect, compounds have formula IIIn wherein A' is

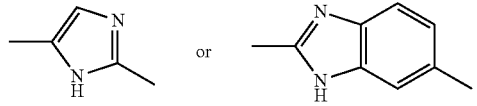

In a twenty-second embodiment of the third aspect, compounds have formula IIIo:

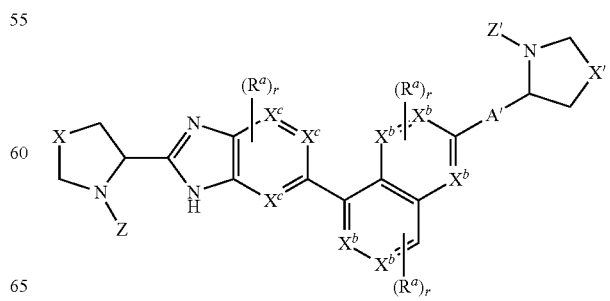

wherein X and X' are each independently selected from the group consisting of a bond, —CH₂—, —CH₂—CH₂—, —CH═CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIIo as well as an optically pure enantiomer, racemate or diastereomeric mixtures thereof.

In a twenty-third embodiment of the third aspect, compounds have formula IIIo wherein A' is

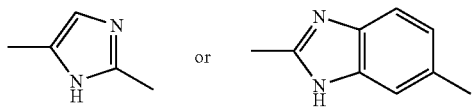

In a twenty-fourth embodiment of the third aspect, compounds have formula IIIp:

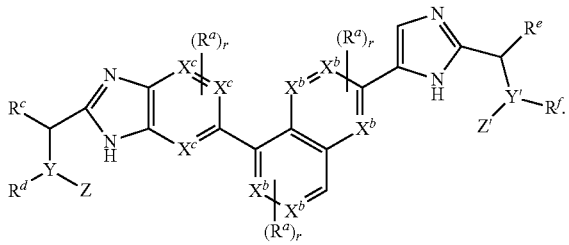

The compounds of the present invention include pharmaceutically acceptable salts of IIIp as well as an optically pure enantiomer, racemate or diastereomeric mixtures thereof.

In a twenty-fifth embodiment of the third aspect, compounds have formula IIIq:

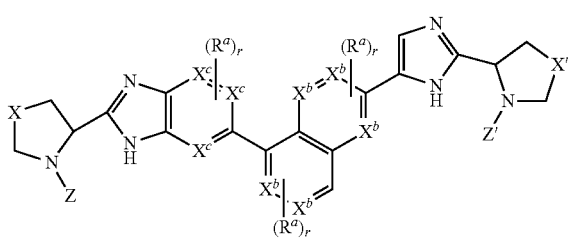

wherein X and X' are each independently selected from the group consisting of a bond, —CH₂—, —CH₂—CH₂—, —CH═CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIIq as well as an optically pure enantiomer, racemate or diastereomeric mixtures thereof.

In a fourth aspect of the invention, compounds have formula IV:

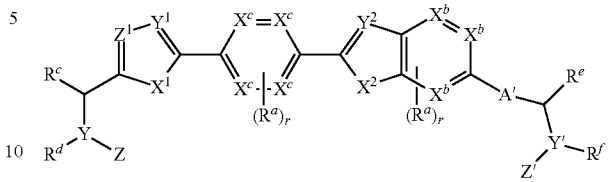

wherein:
A' is selected from the group consisting of a single bond,

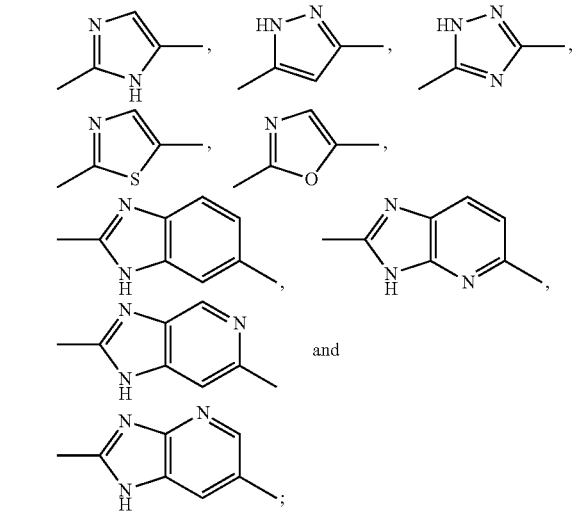

and
each $X^b$ and $X^c$ is independently C or N.

The compounds of the present invention include pharmaceutically acceptable salts of IV as well as an optically pure enantiomer, racemate or diastereomeric mixtures thereof.

In a first embodiment of the fourth aspect, compounds have formula IV wherein A' is

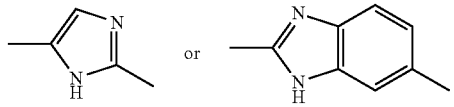

In a second embodiment of the fourth aspect, compounds have formula IVa:

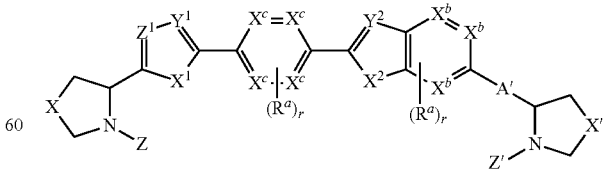

wherein X and X' are each independently selected from the group consisting of a bond, —CH₂—, —CH₂—CH₂—, —CH═CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IVa as well as an optically pure enantiomer, racemate or diastereomeric mixtures thereof.

In a third embodiment of the fourth aspect, compounds have formula IVa wherein A' is

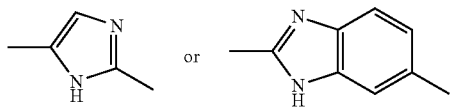

In a fifth aspect of the invention, compounds have formula V:

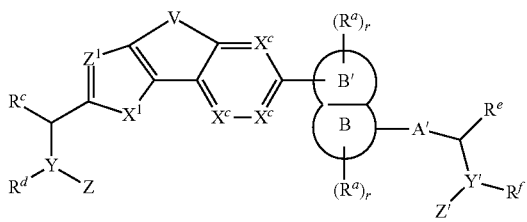

wherein:

A' is selected from the group consisting of a single bond,

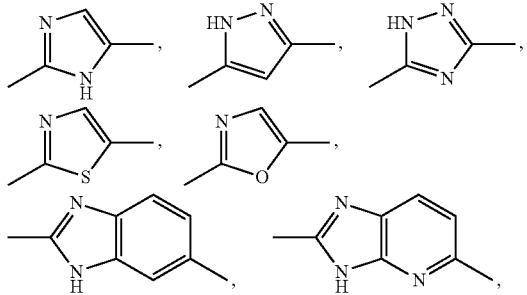

and

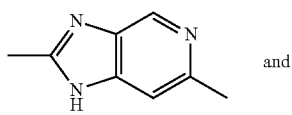

and
  each $X^c$ is independently C or N with the proviso that no more than two $X^c$ are N.

The compounds of the present invention include pharmaceutically acceptable salts of V as well as an optically pure enantiomer, racemate or diastereomeric mixtures thereof.

In a first embodiment of the fifth aspect, compounds have formula V wherein A' is

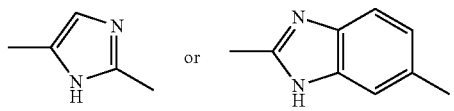

In a second embodiment of the fifth aspect, compounds have formula Va:

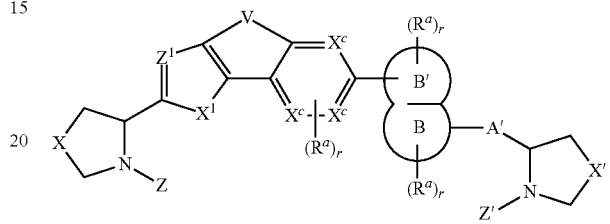

wherein X and X' are each independently selected from the group consisting of a bond, $-CH_2-$, $-CH_2-CH_2-$, $-CH=CH-$, $-O-$, $-S-$, $-S(O)_{1-2}-$, $-CH_2O-$, $-CH_2S-$, $-CH_2S(O)_{1-2}-$ and $-CH_2N(R^1)-$, wherein $R^1$ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of Va as well as an optically pure enantiomer, racemate or diastereomeric mixtures thereof.

In a third embodiment of the fifth aspect, compounds have formula Va wherein A' is

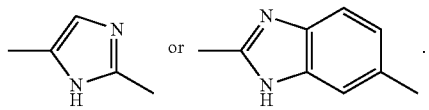

In a fourth embodiment of the fifth aspect, compounds have formula Vb:

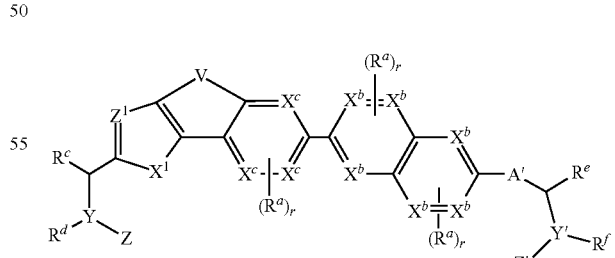

wherein
  each $X^b$ is independently C or N.

The compounds of the present invention include pharmaceutically acceptable salts of Vb as well as an optically pure enantiomer, racemate or diastereomeric mixtures thereof.

In a fifth embodiment of the fifth aspect, compounds have formula Vb wherein A' is

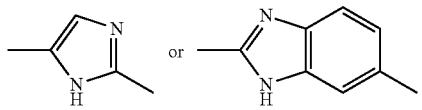

In a sixth embodiment of the fifth aspect, compounds have formula Vc:

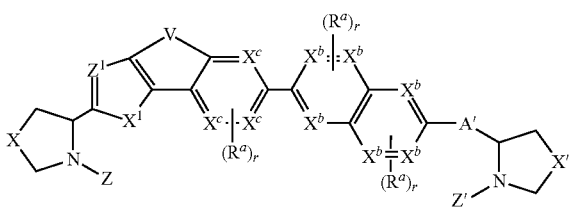

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of Vc as well as an optically pure enantiomer, racemate or diastereomeric mixtures thereof.

In a seventh embodiment of the fifth aspect, compounds have formula Vc wherein A' is

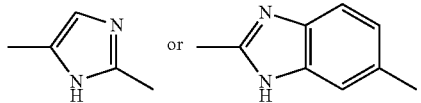

In an eighth embodiment of the fifth aspect, compounds have formula Vd:

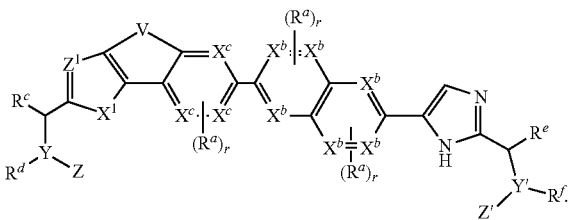

The compounds of the present invention include pharmaceutically acceptable salts of Vd as well as an optically pure enantiomer, racemate or diastereomeric mixtures thereof.

In a ninth embodiment of the fifth aspect, compounds have formula Ve:

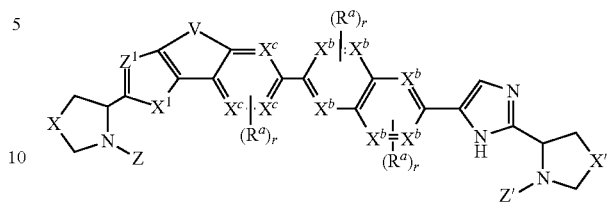

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of Ve as well as an optically pure enantiomer, racemate or diastereomeric mixtures thereof.

In a sixth aspect of the invention, in any compound of any of the second through fifth aspects, R$^c$, R$^d$, R$^e$ and R$^f$ are each independently selected from the group consisting of: hydrogen, C$_1$ to C$_8$ alkyl and C$_1$ to C$_8$ heteroalkyl, wherein,
each hetero atom, if present, is independently N, O or S,
R$^c$ and R$^d$ are optionally joined to form a 4- to 8-membered heterocycle which is optionally fused to another 3- to 6-membered heterocycle, and
R$^e$ and R$^f$ are optionally joined to form a 4- to 8-membered heterocycle which is optionally fused to another 3- to 6-membered heterocycle.

In a first embodiment of the sixth aspect, R$^c$ and R$^d$ or R$^e$ and R$^f$ are joined to form a 4- to 8-membered heterocycle which is optionally fused to another 3- to 6-membered heterocycle.

In a second embodiment of the sixth aspect, both of R$^c$ and R$^d$ and R$^e$ and R$^f$ are joined to form a 4- to 8-membered heterocycle which is optionally fused to another 3- to 6-membered heterocycle.

In a seventh aspect of the invention, each R$^a$, if present in any of the other aspects of the invention, is independently —CN, —OCHF$_2$, —OCF$_3$, —CF$_3$, or —F.

In an eighth aspect of the invention, if present in any compound of any of the other aspects, one of Y and Y' is N.

In a first embodiment of the eighth aspect, both Y and Y' are N.

In a ninth aspect of the invention, Z and Z' in any of the previous aspects are each 1-3 amino acids.

In a first embodiment of the ninth aspect, the amino acids are in the D configuration.

In a tenth aspect of the invention, Z and Z' in any of the previous aspects are each independently selected from the group consisting of —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$, —U—(CR$^4_2$)$_t$—R$^8$ and —[U—(CR$^4_2$)$_t$—NR$^5$—(CR$^4_2$)$_t$]$_u$—U—(CR$^4_2$)$_t$—O—(CR$^4_2$)$_t$—R$^8$.

In a first embodiment of the tenth aspect, both of Z and Z' are —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$.

In a second embodiment of the tenth aspect, one or both of Z and Z' are —U—(CR$^4_2$)$_t$—NR$^5$—(CR$^4_2$)$_t$—U—(CR$^4_2$)—NR$^7$—(CR$^4_2$)$_t$—R$^8$.

In a third embodiment of the tenth aspect, one or both of Z and Z' are —U—(CR$^4_2$)$_t$—NR$^7$—(CR$^4_2$)$_t$—R$^8$.

In a fourth embodiment of the tenth aspect, one or both of Z and Z' are —[C(O)—(CR$^4$A—NR$^5$—(CR$^4_2$)$_t$]$_u$—U—(CR$^4$A—NR$^7$—(CR$^4_2$)$_t$—R$^8$.

In a fifth embodiment of the tenth aspect, one or both of Z and Z' are —C(O)—(CR$^4_2$)$_t$—NR$^5$—(CR$^4_2$)$_t$—U—(CR$^4_2$)—NR$^7$—(CR$^4_2$)$_t$—R$^8$.

In a sixth embodiment of the tenth aspect, one or both of Z and Z' are —[C(O)—(CR$^4_2$)$_t$—NR$^5$—(CR$^4_2$)$_t$]$_u$—C(O)—(CR$^4_2$)$_t$—NR$^7$—(CR$^4_2$)$_t$—R$^8$.

In a seventh embodiment of the tenth aspect, one or both of Z and Z' are —C(O)—(CR$^4_2$)$_t$—NR$^5$—(CR$^4_2$)$_t$—C(O)—(CR$^4_2$)$_t$—NR$^7$—(CR$^4_2$)$_t$—R$^8$.

In an eighth embodiment of the tenth aspect, one or both of Z and Z' are —C(O)—(CR$^4_2$)$_t$—NR$^7$—(CR$^4_2$)$_t$—R$^8$.

In a ninth embodiment of the tenth aspect, one or both of Z and Z' are —C(O)—(CR$^4_2$)$_n$—NR$^7$—(CR$^4_2$)$_n$—C(O)—R$^{81}$.

In a tenth embodiment of the tenth aspect, one or both of Z and Z' are —C(O)—(CR$^4_2$)$_n$—NR$^7$—C(O)—R$^{81}$.

In an eleventh embodiment of the tenth aspect, one or both of Z and Z' are —C(O)—(CR$^4_2$)$_n$—NR$^7$—(CR$^4_2$)$_n$—C(O)—O—R$^{81}$.

In a twelfth embodiment of the tenth aspect, one or both of Z and Z' are —C(O)—(CR$^4_2$)$_n$—NR$^7$—C(O)—O—R$^{81}$.

In a thirteenth embodiment of the tenth aspect, one or both of Z and Z' are —U—(CR$^4_2$)$_t$—R$^8$.

In a fourteenth embodiment of the tenth aspect, one or both of Z and Z' are —C(O)—(CR$^4_2$)$_t$—R$^8$.

In a fifteenth embodiment of the tenth aspect, one or both of Z and Z' are —[U—(CR$^4_2$)$_t$—NR$^5$—(CR$^4_2$)$_t$]$_u$—U—(CR$^4_2$)$_t$—O—(CR$^4_2$)$_t$—R$^8$.

In a sixteenth embodiment of the tenth aspect, one or both of Z and Z' are —U—(CR$^4_2$)$_t$—NR$^5$—(CR$^4_2$)$_t$—U—(CR$^4_2$)$_t$—O—(CR$^4_2$)$_t$—R$^8$.

In a seventeenth embodiment of the tenth aspect, one or both of Z and Z' are —C(O)—(CR$^4_2$)$_t$—NR$^5$—(CR$^4_2$)$_t$—C(O)—(CR$^4_2$)$_t$—O—(CR$^4_2$)$_t$—R$^8$.

In an eighteenth embodiment of the tenth aspect, one or both of Z and Z' are —U—(CR$^4_2$)$_t$—O—(CR$^4_2$)$_t$—R$^8$.

General Synthesis

The following schemes exemplify some of the synthetic routes that are used for the preparations of compounds and their analogs included in this invention. These skilled in the art will understand that alternative routes may also be used to reach the same and similarly functionalized intermediates and target molecules. Alternative reagents for a given transformation are also possible.

The following abbreviations are used throughout this application:

ACN Acetonitrile
aq Aqueous
Bn Benzyl
BnOH Benzyl alcohol
Boc t-butoxycarbonyl
DCE Dichloroethane
DCM Dichloromethane
DIEA(DIPEA) Diisopropylethylamine
DMA N,N-Dimethylacetamide
DME 1,2-Dimethoxyethane
DMF N,N-Dimethylformamide
DMSO Dimethylsulfoxide
DMTMM 4-(4,6-Dimethoxy-1,3,5-triazin-2-yl)-4-methylmorpholinium chloride
DPPA Diphenylphosphoryl azide
DTT Dithiothreitol
EDC Ethylcarbodiimide hydrochloride
EDCl 1-Ethyl-3-[3-(dimethylamino)propyl]carbodiimide hydrochloride
EDTA Ethylene diamine tetraacetic acid
ESI Electrospray Ionization
Et$_3$N, TEA Triethylamine
EtOAc, EtAc Ethyl acetate
EtOH Ethanol
g Gram(s)
h Hour(s)
HBTU O-Benzotriazol-1-yl-N,N,N',N'-tetramethyluronium hexafluorophosphate
HOBt 1-Hydroxybenzotriazole
IC$_{50}$ The concentration of an inhibitor that causes a 50% reduction in a measured activity
LAH Lithium aluminum hydride
LDA Lithium diisopropylamide
LCMS Liquid Chramatography Mass Spectrometry
MeI Methyl Iodide
MeOH Methanol
min Minute(s)
mmol Millimole(s)
NMM 4-Methylmorpholine
NMP N-methylpyrrolidinone
PG Protective Group
PTT Phenyl trimethyl tribromide
Py Pyridine
rt Room temperature
TEA Triethylamine
Tf Trifluoromethanesulfonate
TFA Trifluoroacetic acid
TFAA Trifluoroacetic anhydride
THF Tetrahydrofuran
TLC Thin Layer Chromatography Reagents and solvents used below can be obtained from commercial sources such as Aldrich Chemical Co. (Milwaukee, Wis., USA). 1H-NMR spectra were recorded on a Bruker 400 MHz or 500 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Electrospray spray ionization (ESI) mass spectrometry analysis was conducted on a Hewlett-Packard 1100 MSD electrospray mass spectrometer using the HP1 100 HPLC for sample delivery. Mass spectrometry results are reported as the ratio of mass over charge, followed by the relative abundance of each ion (in parentheses) or a single m/z value for the M+H (or, as noted, M−H) ion containing the most common atomic isotopes. Isotope patterns correspond to the expected formula in all cases. Normally the analyte was dissolved in methanol at 0.1 mg/mL and 5 microliter was infused with the delivery solvent into the mass spectrometer, which scanned from 100 to 1500 daltons. All compounds could be analyzed in the positive ESI mode, using an acetonitrile/H$_2$O gradient (10%-90%) acetonitrile in H$_2$O with 0.1% formic acid as delivery solvent. The compounds provided below could also be analyzed in the negative ESI mode, using 2 mM NH$_4$OAc in acetonitrile/H$_2$O as delivery solvent. Enantiomeric purity was determined using a Hewlett-Packard Series 1050 system equipped with a chiral HLPC column (ChiralPak AD, 4.6 mm×150 mm) and isocratic elution using 5:95 isopropanolhexane as a mobile phase.

The compounds were named using ChemDraw program from Cambridge Soft Inc.

Scheme 1-1
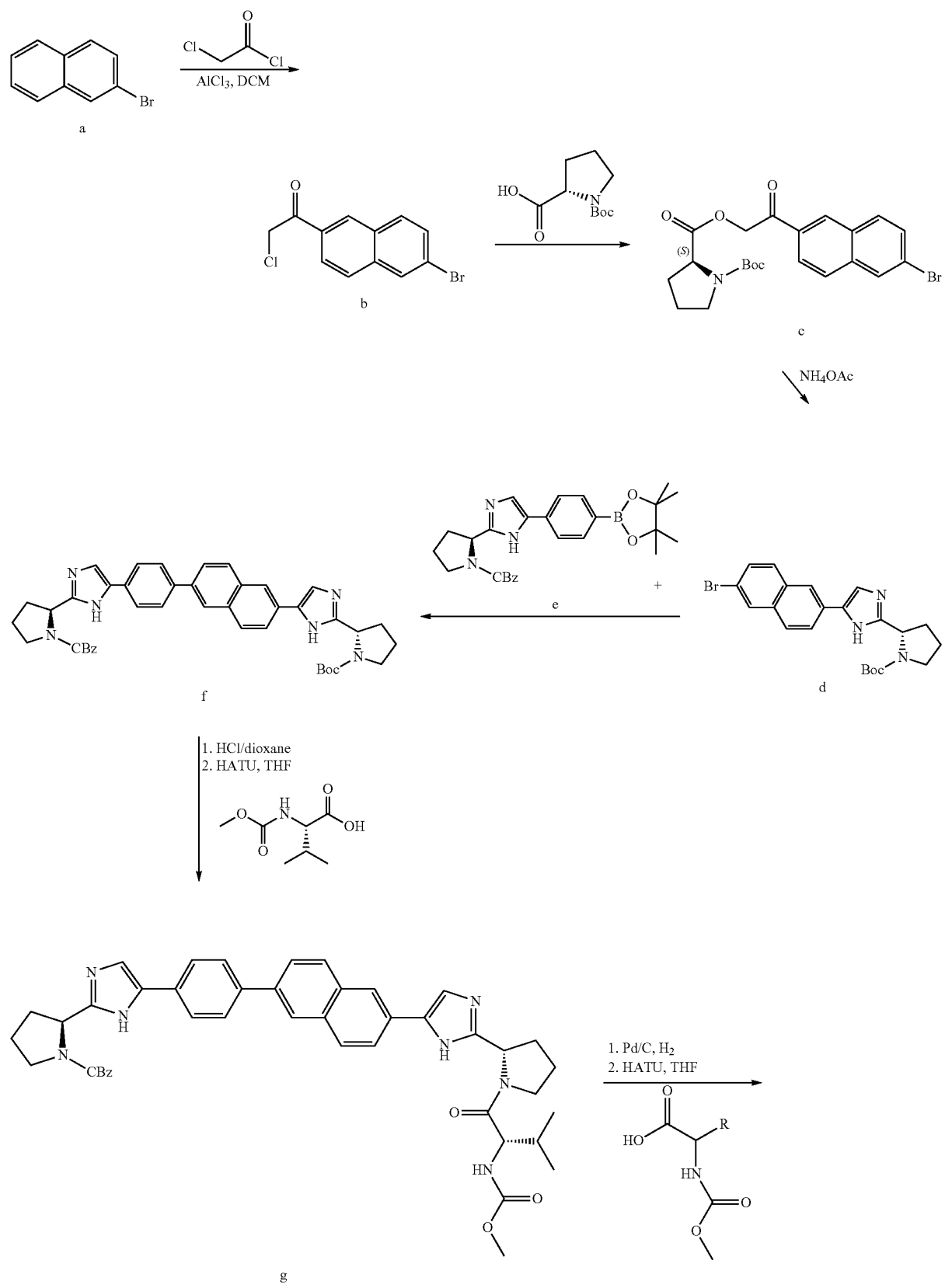

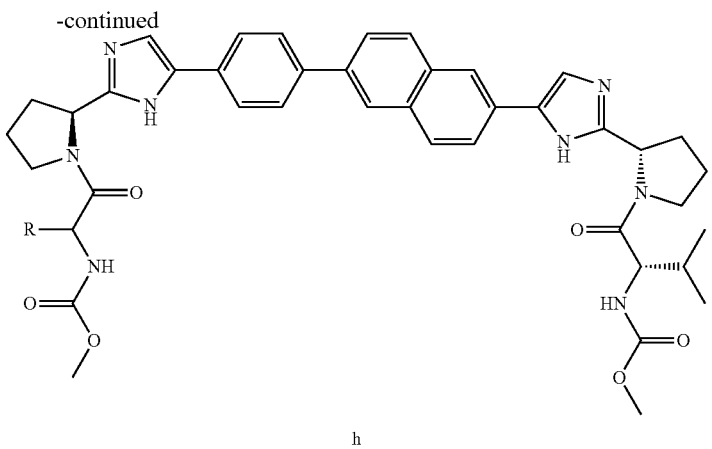

h

Example 1

Synthesis of Compounds of Formula IIc

Scheme 1-1 describes preparation of target molecules and their analogs with symmetrical and non-symmetrical functionalized ends.

Step a. To a solution of 2-bromonaphthane a (62.0 g, 300 mmol) in DCM (1 L) was added $AlCl_3$ (44.0 g, 330 mmol) and 2-chloroacetyl chloride (34.0 g, 330 mmol) at 0° C. The reaction mixture was stirred at 0° C. for 1 h and then $H_2O$ added (500 mL) and extracted. The organic layer was washed with $H_2O$, dried over anhydrous $Na_2SO_4$, evaporated under reduced pressure to give 80 g crude product, which was purified by re-crystallization from 10% EtOAc-hexane (v/v) to yield b (28 g, 36% yield) as a white solid: $^1$H NMR (500 MHz, $CDCl_3$) δ 8.44 (s, 1H), 8.07 (s, 1H), 8.04 (d, J=11.0 Hz, 1H), 7.84 (d, J=8.5 Hz, 2H), 7.66 (d, J=8.5 Hz, 1H), 4.81 (s, 2H) ppm; LCMS (ESI) m/z 282.9 $(M+H)^+$.

Step b. To a solution of b (28.0 g, 100 mmol) in DCM (500 mL) was added N-Boc-L-Pro-OH (24.7 g, 115 mmol) and $Et_3N$ (70.0 mL, 500 mmol) and the mixture was stirred at rt for 2 h. The mixture was concentrated under reduced pressure to afford crude c which was used for the next step without further purification. LC-MS (ESI) m/z 462.1 $(M+H)^+$.

Step c. To a solution of c (46.0 g, 100 mmol) in toluene (500 mL) was added $NH_4OAc$ (77 g, 1.0 mol) and the mixture was stirred at 110° C. overnight, and concentrated under reduced pressure. The resulting residue was purified by silica gel column chromatography (petroleum ether/EtOAc 1:1(v/v)) to afford d (30 g, 68% yield) as a yellow solid: LC-MS (ESI) m/z 442.1 $(M+H)^+$.

Step d. To a solution of d (10.0 g, 23.0 mmol) in anhydrous DME (200 mL) and equal molar of boronate e was added $PPh_3$ (1.2 g, 4.6 mmol), $Pd(PPh_3)_4$ (1.6 g, 2.3 mmol), and 2.0 M $Na_2CO_3$ solution. The mixture was refluxed under argon overnight. The organic solvent was removed under reduced pressure and the residue was treated with $H_2O$, extracted with EtOAc (2×200 mL). The combined organic phase was dried, filtered, and concentrated in vacuo to give a residue, which was purified by silica gel column chromatography (petroleum ether/EtOAc 3:1(v/v)) to afford f (10 g, 96% yield) as a yellow solid. LC-MS (ESI): m/z 709.3 $(M+H)^+$.

Step e. To a stirred solution of f (150 mg, 0.29 mmol) in dioxane (3 mL) was added 4.0 N HCl in dioxane (3 mL) dropwise. The mixture was stirred at rt for 4 h, and then concentrated to yield a yellowish solid (134 mg), which was used directly for the next step. The residue (134 mg, 0.290 mmol) was suspended in THF (5 mL) and DIPEA (0.32 mL) was added and followed by addition of N-methoxycarbonyl-L-Val-OH (151 mg, 0.860 mmol). After stirring for 15 min, HATU (328 mg, 0.860 mmol) was added and the mixture was stirred at rt for another 2 h and then concentrated. The residue was purified by prep-HPLC to obtain g (40 mg, 19% yield).

Scheme 1-2

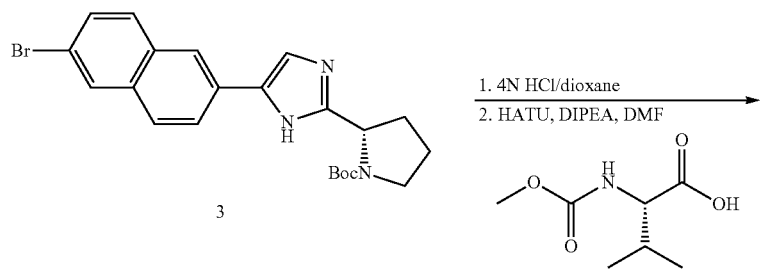

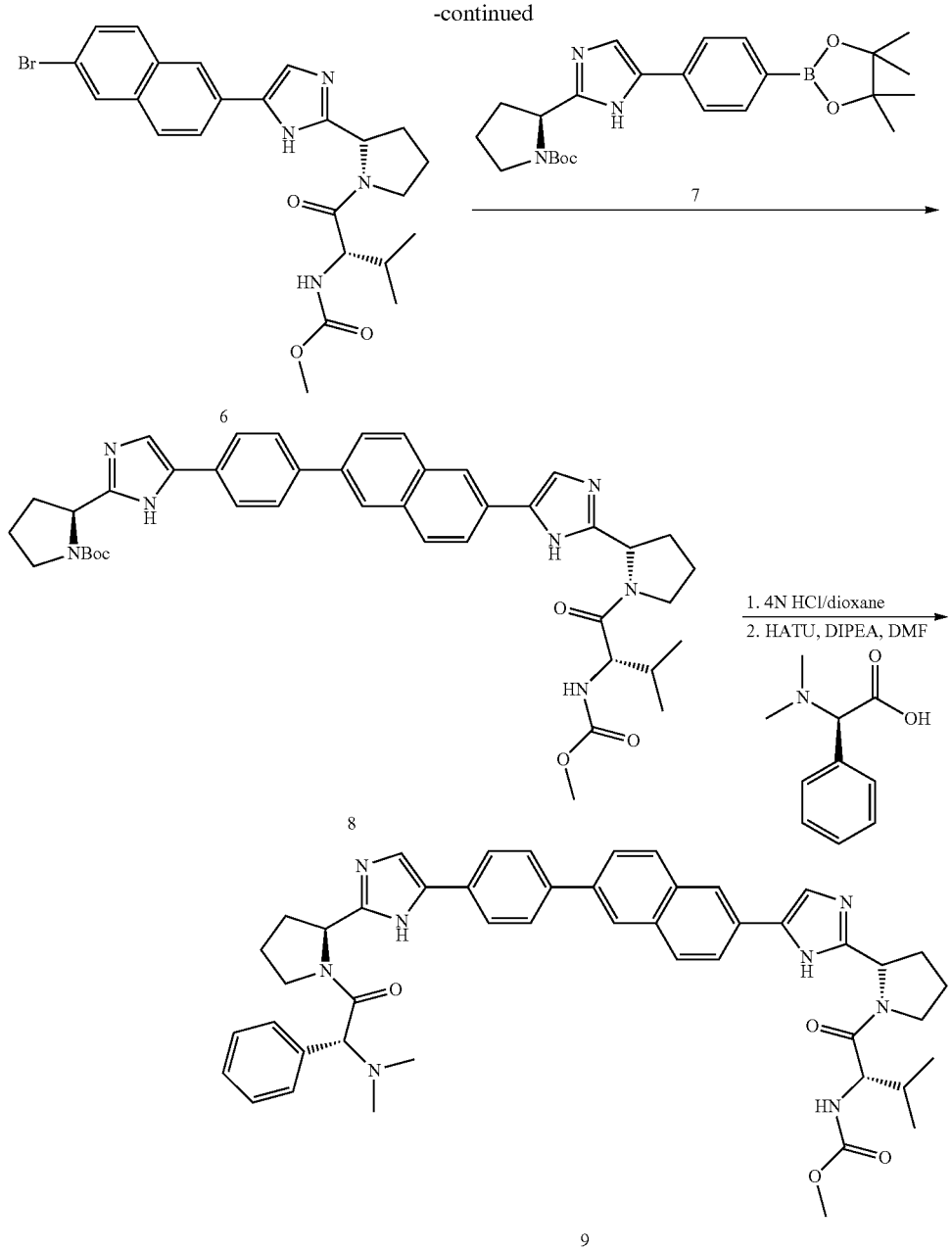

Step a. Referring to Scheme 1-2, to a solution of compound 3 (2.0 g, 4.5 mmol) in dioxane (25 mL) was added 4.0 N HCl in dioxane (25 mL). After stirring at rt for 4 h, the reaction mixture was concentrated and the residue was dried in vacuo to give a yellowish solid (2.1 g), which was used directly for the next step without further purification.

Step b. To the residue of step a (4.5 mmol) was added DMF (25 mL), followed by adding DIPEA (3.7 mL, 22.5 mmol) and N-methyl carbamate-L-valine (945 mg, 5.4 mmol). After stirring at rt for 15 min, the reaction mixture was added slowly to H$_2$O (400 mL). A white solid precipitated was filtered and dried to give compound 6 (2.2 g, 98% yield). LC-MS (ESI): m/z 499.1 (M+H)$^+$.

Step c. To a mixture of compound 6 (800 mg, 1.6 mmol), compound 7 (718 mg, 1.6 mmol), and NaHCO$_3$ (480 mg, 5.7 mmol) in 1,2-dimethoxyethane (15 mL) and H$_2$O (5 mL) was added Pd(dppf)Cl$_2$ (59 mg, 0.08 mmol). After stirring at 80° C. overnight under an atmosphere of N$_2$, the reaction mixture was concentrated. The residue was partitioned between 20% methanol/CHCl$_3$ (100 mL) and H$_2$O (100 mL). The organic phase was separated and the aqueous phase was extracted with 20% methanol/CHCl$_3$ (100 mL) again. The combined organic phase was consequently washed with brine, dried with anhydrous Na$_2$SO$_4$, filtered, and concentrated. The residue was purified by silica gel column chromatography (Petroleum ether/EtOAc=15:1(v/v)) to give compound 8 (1.0 g, 85% yield) as a yellow solid. LC-MS (ESI): m/z 732.4 (M+H)$^+$.

Step d. To a solution of compound 8 (200 mg, 0.27 mmol) in dioxane (3.0 mL) was added 4 N HCl in dioxane (3.0 mL). After stirring at rt for 2 h, the reaction mixture was concentrated and the residue was dried in vacuo to give an HCl salt in quantitative yield, which was used directly for the next step without further purification.

Step e. To a solution of the salt (0.27 mmol) in DMF (5.0 mL) was added DIPEA (0.47 mL, 2.7 mmol), followed by adding N,N-dimethyl-D-phenyl glycine (59 mg, 0.33 mmol) and HATU (125 mg, 0.33 mmol). After stirring at rt for 1 h, the reaction mixture was partitioned between H$_2$O and DCM. The organic phase was washed successively with H$_2$O and brine, dried with anhydrous Na$_2$SO$_4$, filtered, and concentrated. The residue was purified by prep-HPLC to give compound 9. LC-MS (ESI): m/z 793.4 (M+H)$^+$.

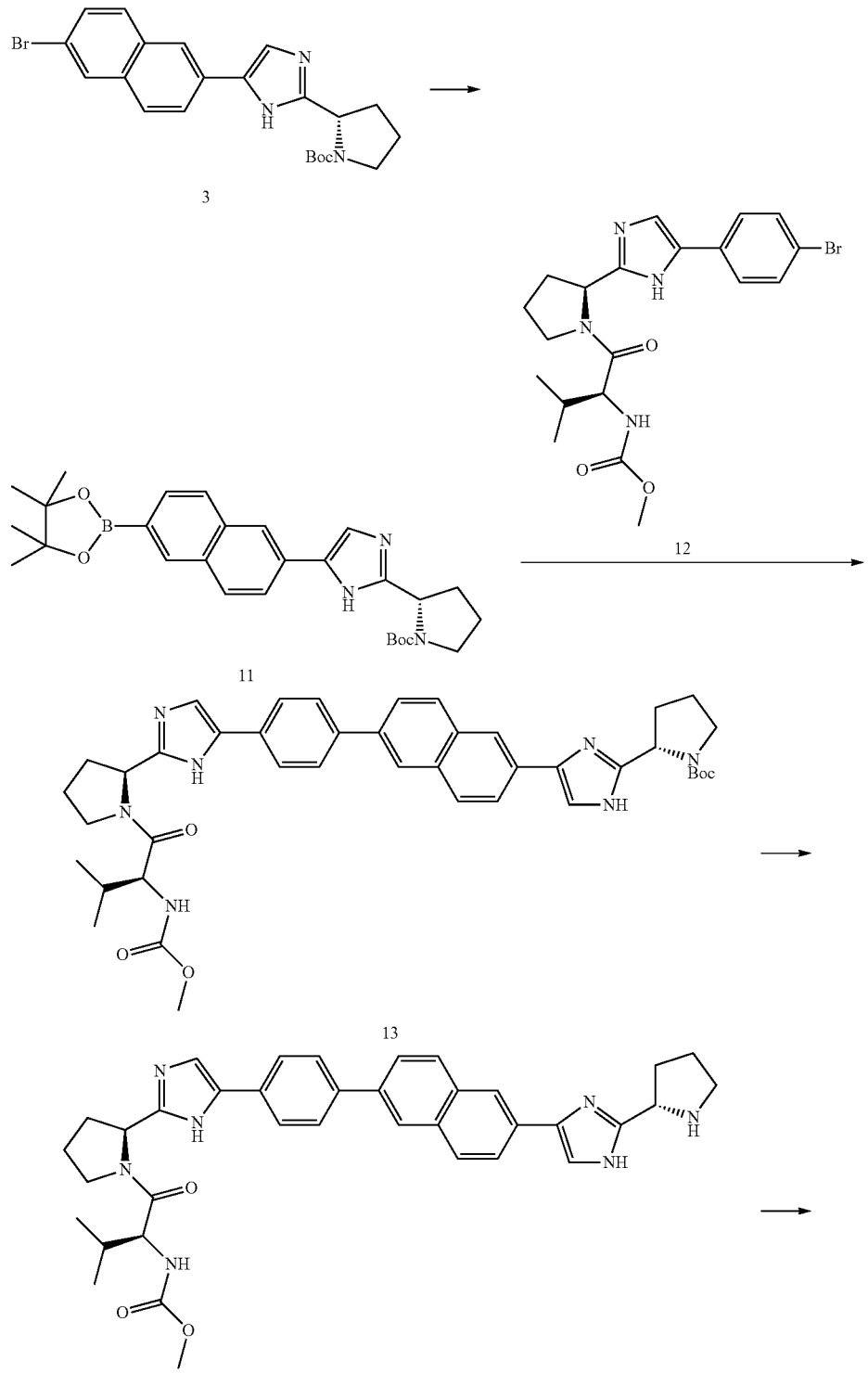

-continued

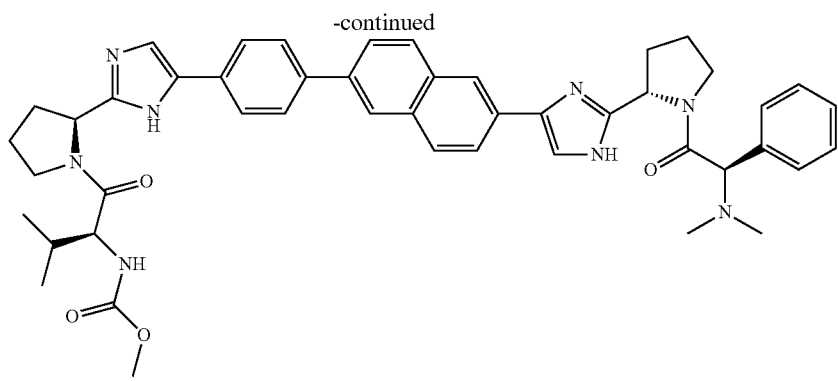

15

Step a. To a mixture of compound 3 (3.2 g, 7.2 mmol), bis(pinacolato)diboron (3.86 g, 15.2 mmol), and KOAc (1.85 g, 18.8 mmol) in 1,4-dioxane (100 mL) was added Pd(dppf)Cl$_2$ (440 mg, 0.6 mmol). After stirring at 80° C. for 3 h under an atmosphere of N$_2$, the reaction mixture was concentrated. The residue was purified with silica gel column chromatography (Petroleum ether/EtOAc=2/1(v/v)) to give compound 11 (2.8 g, 80% yield) as a white solid. LC-MS (ESI): m/z 490.3 (M+H)$^+$.

Step b. To a mixture of compound 11 (626 mg, 1.27 mmol), compound 12 (570 mg, 1.27 mmol), and NaHCO$_3$ (420 mg, 4.99 mmol) in 1,2-dimethoxyethane (30 mL) and H$_2$O (10 mL) was added Pd(dppf)Cl$_2$ (139 mg, 0.19 mmol). After stirring at 80° C. overnight under an atmosphere of N$_2$, the reaction mixture was concentrated. The residue was partitioned between 20% methanol/CHCl$_3$ (100 mL) and H$_2$O (100 mL). The aqueous phase was extracted with 20% methanol/CHCl$_3$ (100 mL) again. The combined organic phase was consequently washed with brine, dried with anhydrous Na$_2$SO$_4$, filtered, and concentrated. The residue was purified by silica gel column chromatography (Petroleum ether/EtOAc=2/1(v/v)) to give compound 13 (635 mg, 68% yield) as a yellow solid. LC-MS (ESI): m/z 732.4 (M+H)$^+$.

Step c. To a solution of compound 13 (200 mg, 0.27 mmol) in dioxane (3.0 mL) was added 4 N HCl in dioxane (3.0 mL). After stirring at rt for 2 h, the reaction mixture was concentrated and the residue was dried in vacuo to yield the HCl salt of compound 14 in quantitative yield, which was used directly for the next step without further purification.

Step d. To a solution of the salt (0.27 mmol) in DMF (5.0 mL) was added DIPEA (0.47 mL, 2.7 mmol), followed by adding N,N-dimethyl-D-phenyl glycine (59 mg, 0.33 mmol) and HATU (125 mg, 0.33 mmol). After stirring at rt for 1 h, the reaction mixture was partitioned between H$_2$O and DCM. The organic phase was consequently washed with H$_2$O and brine, dried with anhydrous Na$_2$SO$_4$, filtered, and concentrated. The residue was purified by prep-HPLC to give compound 15. LC-MS (ESI): m/z 793.4 (M+H)$^+$.

Scheme 2-1

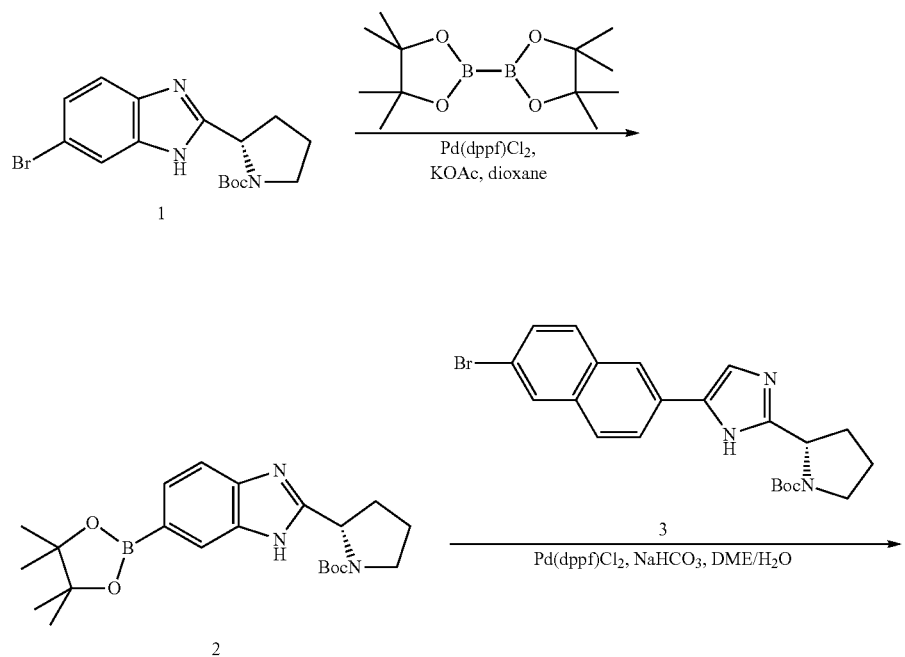

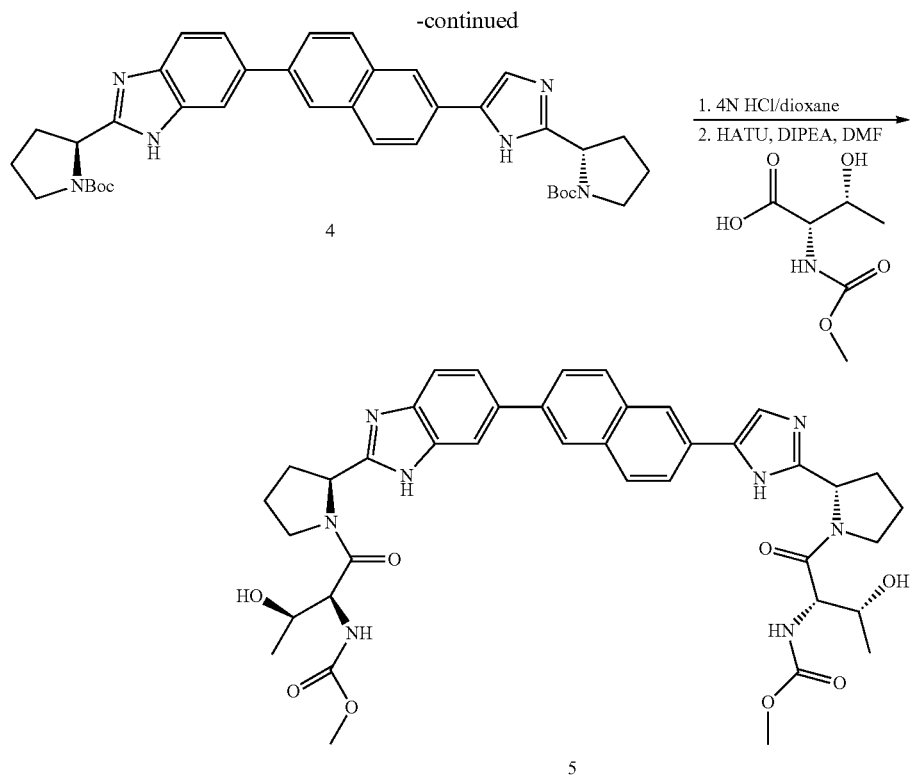

Example 2

Synthesis of Compounds of Formula IIIe

Step a. Referring to Scheme 2-1, to a mixture of compound 1 (5.05 g, 13.8 mmol), bis(pinacolato)diboron (7.1 g, 27.9 mmol), and KOAc (3.2 g, 32.5 mmol) in 1,4-dioxane (100 mL) was added Pd(dppf)Cl$_2$ (400 mg, 0.5 mmol). After stirring at 80° C. for 3 h under an atmosphere of N$_2$, the reaction mixture was concentrated. The residue was purified by silica gel column chromatography (Petroleum ether/EtOAc=2/1(v/v)) to give compound 2 (3.0 g, 53% yield) as a gray solid. LC-MS (ESI): m/z 414.2 (M+H)$^+$.

Step b. To a mixture of compound 2 (522 mg, 1.26 mmol), compound 3 (500 mg, 1.13 mmol), and NaHCO$_3$ (333 mg, 3.96 mmol) in 1,2-dimethoxyethane (30 mL) and H$_2$O (10 mL) was added Pd(dppf)Cl$_2$ (74 mg, 0.1 mmol). After stirring at 80° C. overnight under an atmosphere of N$_2$, the reaction mixture was concentrated. The residue was partitioned between 20% methanol/CHCl$_3$ (100 mL) and H$_2$O (100 mL). The organic phase was separated and the aqueous phase was extracted with 20% methanol/CHCl$_3$ (100 mL) again. The combined organic phase was consequently washed with brine, dried with anhydrous Na$_2$SO$_4$, filtered, and concentrated. The residue was purified by silica gel column chromatography (DCM/MeOH=50:1 (v/v)) to give compound 4 (450 mg, 55% yield) as a yellow solid. LC-MS (ESI): m/z 649.3 (M+H)$^+$.

Step c. To a stirred solution of compound 4 (160 mg, 0.25 mmol) in dioxane (2.0 mL) was added 4N HCl in dioxane (2.0 mL). After stirring at rt for 3 h, the reaction mixture was concentrated and the residue was dried in vacuo to give an HCl salt in quantitative yield, which was used directly for the next step without further purification.

Step d. To a solution of above salt (0.25 mmol) in DMF (4.0 mL) was added DIPEA (0.44 mL, 2.5 mmol), followed by adding N-methyl carbamate-L-Threonine (110 mg, 0.62 mmol) and HATU (240 mg, 0.63 mmol). After stirring at rt for 1 h, the reaction mixture was partitioned between H$_2$O and DCM. The organic phase was consequently washed with H$_2$O and brine, dried with anhydrous Na$_2$SO$_4$, filtrated, and concentrated. The residue was purified by prep-HPLC to give compound 5 as a white powder. LC-MS (ESI): m/z 767.3 (M+H)$^+$.

Scheme 2-1-1 provides an alternative synthetic pathway to the compounds disclosed herein.

Scheme 2-1-1

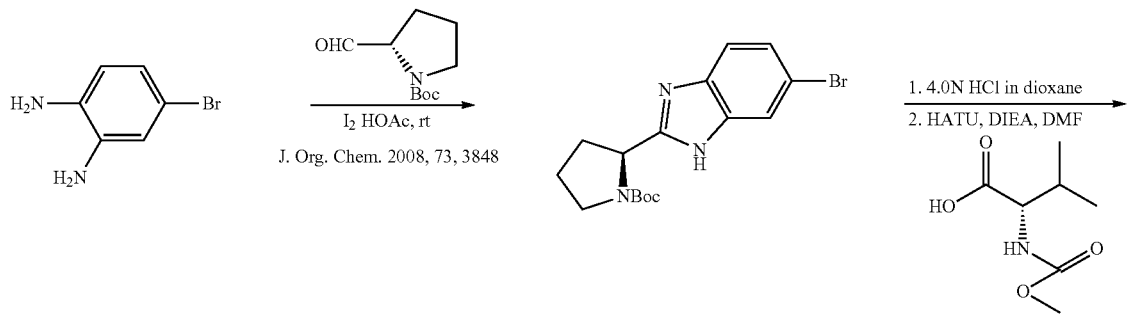

-continued
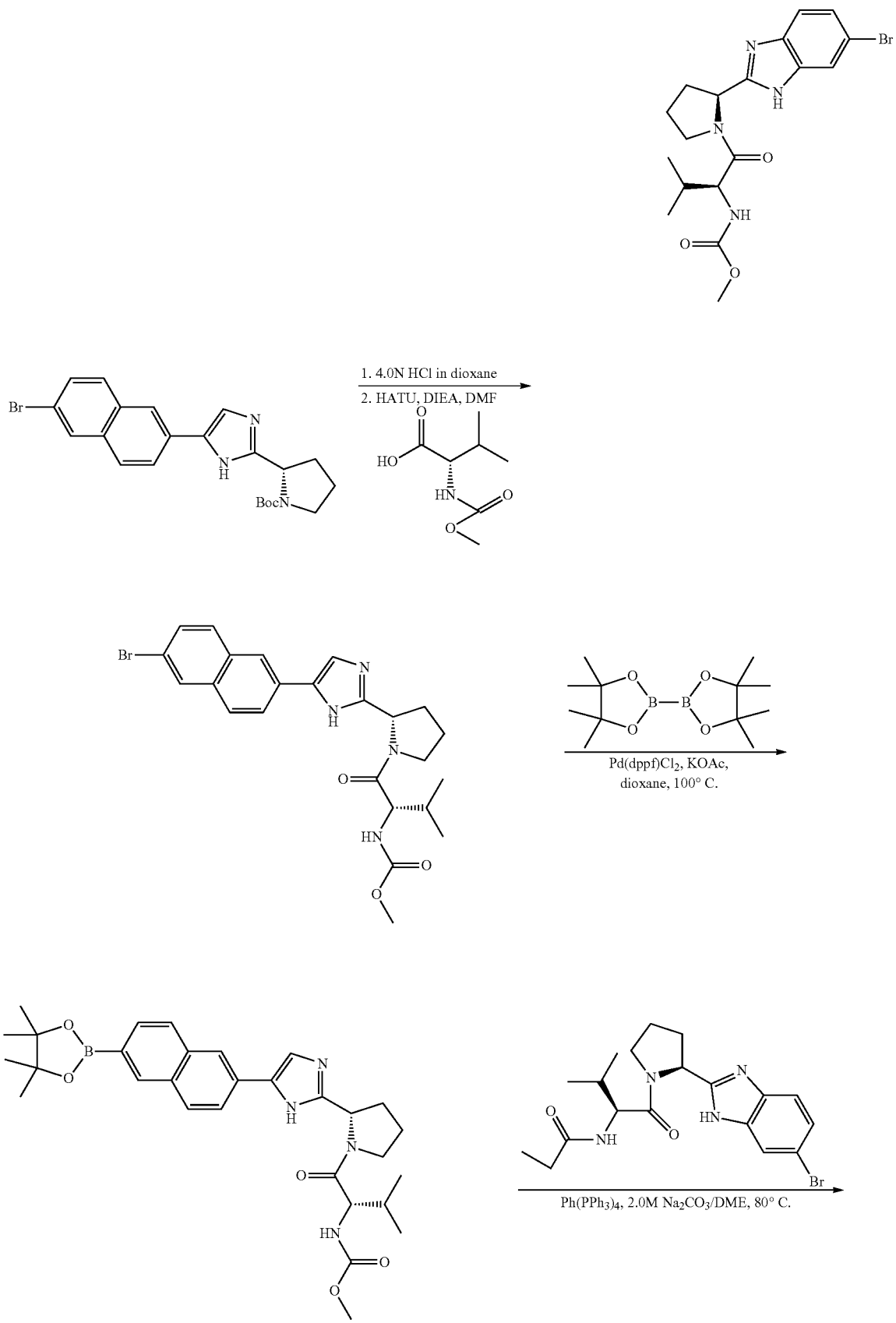

-continued
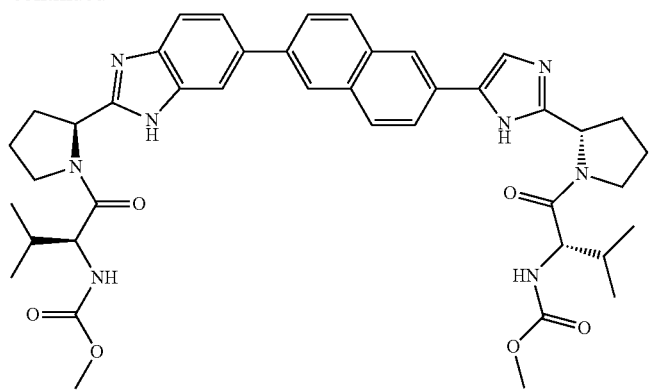
Scheme 2-2
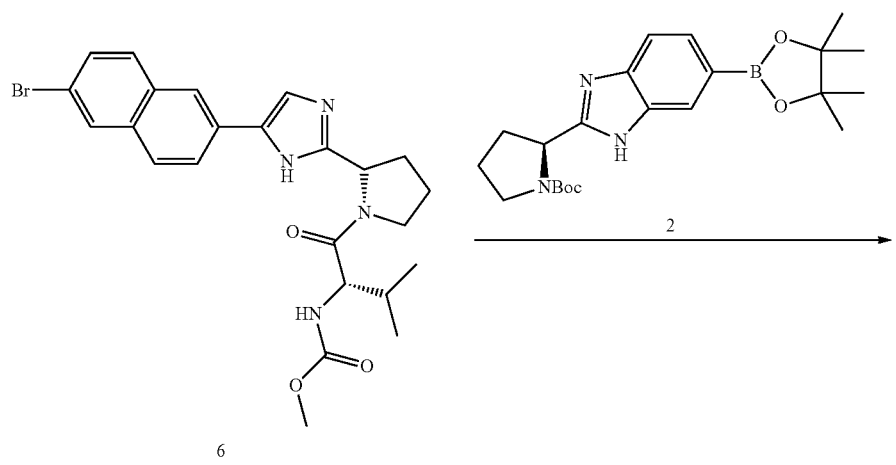
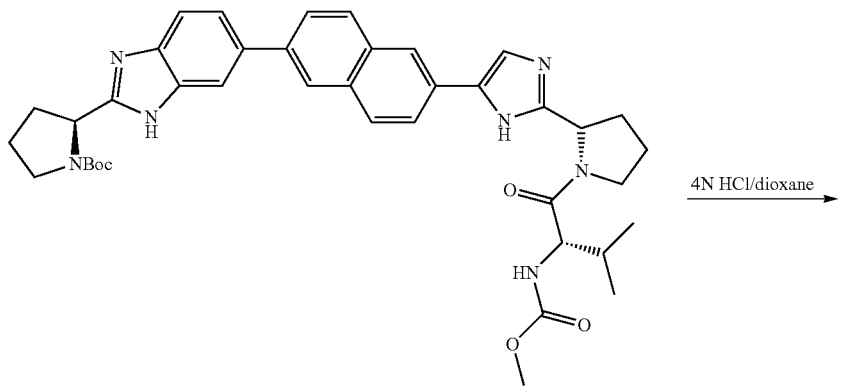

-continued

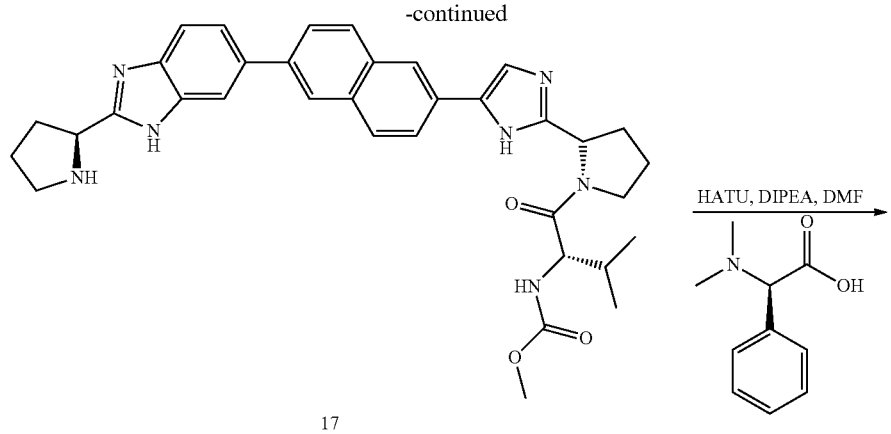

17

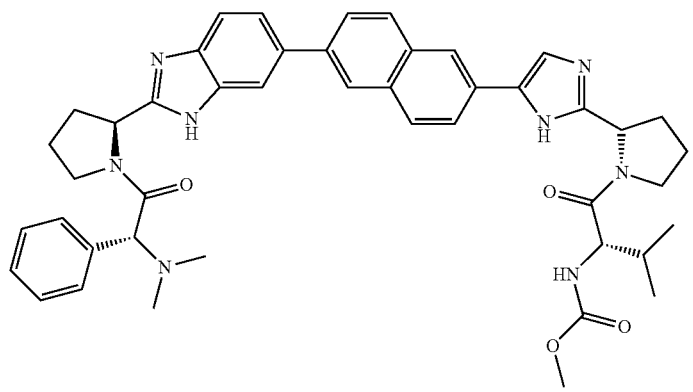

18

Step a. Referring to Scheme 2-2, to a mixture of compound 2 (1.16 g, 2.32 mmol), compound 6 (1.40 g, 3.39 mmol), and NaHCO$_3$ (823 mg, 9.8 mmol) in 1,2-dimethoxyethane (30 mL) and H$_2$O (10 mL) was added Pd(dppf)Cl$_2$ (103 mg, 0.14 mmol). After stirring at 80° C. over night under an atmosphere of N$_2$, the reaction mixture was concentrated. The residue was partitioned between 20% methanol/CHCl$_3$ (150 mL) and H$_2$O (150 mL). The aqueous phase was extracted with 20% methanol/CHCl$_3$ (150 mL) again. The combined organic phase was consequently washed with brine, dried with anhydrous Na$_2$SO$_4$, filtered, and concentrated. The residue was purified by silica gel column chromatography (Petroleum ether/acetone=1.5/1 (v/v)) to give compound 16 (1.32 g, 80% yield) as a yellow solid. LC-MS (ESI): m/z 706.4 (M+H)$^+$.

Step b. To a solution of compound 16 (200 mg, 0.28 mmol) in dioxane (3.0 mL) was added 4 N HCl in dioxane (3.0 mL). After stirring at rt for 2 h, the reaction mixture was concentrated and the residue was dried in vacuo to give the HCl salt of compound 17 in quantitative yield, which was used directly for the next step.

Step c. To a solution of the salt (0.28 mmol) in DMF (5.0 mL) was added DIPEA (0.49 mL, 2.8 mmol), followed by adding N,N-dimethyl-D-phenyl glycine (61 mg, 0.34 mmol) and HATU (129 mg, 0.34 mmol). After stirring for 1 h at rt, the reaction mixture was partitioned between H$_2$O and DCM. The organic phase was consequently washed with H$_2$O and brine, dried with anhydrous Na$_2$SO$_4$, filtered, and concentrated. The residue was purified by prep-HPLC to give compound 18. LC-MS (ESI): m/z 767.4 (M+H)$^+$.

Scheme 2-3

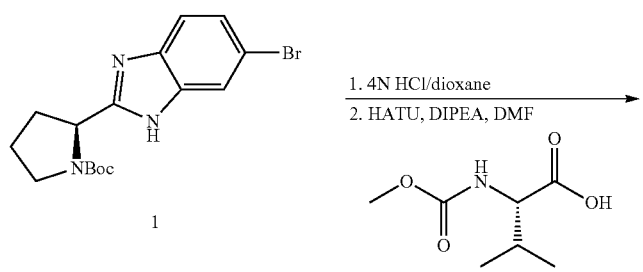

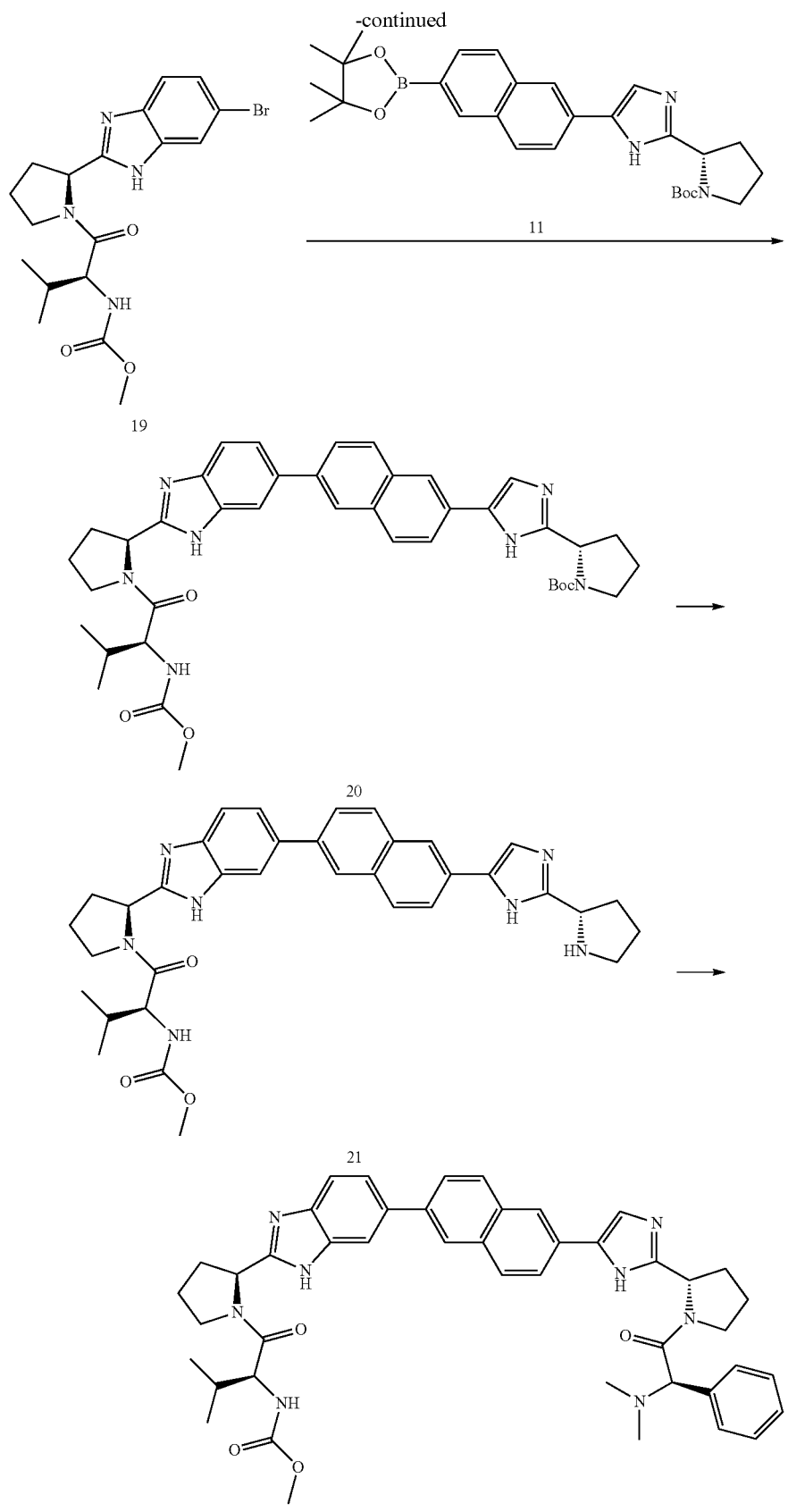

Step a. Referring to Scheme 2-3, to a solution of compound 1 (4.0 g, 10.9 mmol) in dioxane (40 mL) was added 4 N HCl in dioxane (40 mL). After stirring at rt overnight, the reaction mixture was concentrated. The residue was washed with DCM, filtered, and dried in vacuo to afford a hydrochloride salt in quantitative yield, which was used for the next step without further purification.

Step b. To a solution of the salt (10.9 mmol) in DMF (30 mL) was added DIPEA (5.8 mL, 33.0 mmol), followed by adding N-methoxycarbonyl-L-valine (2.1 g, 12.1 mmol) and HATU (4.6 g, 12.1 mmol). After stirring at rt for 1 h, the reaction mixture was partitioned between $H_2O$ and DCM. The organic phase was consequently washed with $H_2O$ and brine, dried with anhydrous $Na_2SO_4$, filtered, and concentrated. The residue was purified by silica gel column chromatography (DCM/Petroleum ether=4/1 (v/v)) to give compound 19 (3.0 g, 65% yield). LC-MS (ESI): m/z 423.1 $(M+H)^+$.

Step c. To a mixture of compound 11 (800 mg, 1.9 mmol), compound 19 (700 mg, 1.7 mmol), and $NaHCO_3$ (561 mg, 6.6 mmol) in 1,2-dimethoxyethane (60 mL) and $H_2O$ (20 mL) was added $Pd(dppf)Cl_2$ (183 mg, 0.25 mmol). After stirring at 80° C. overnight under an atmosphere of $N_2$, the reaction mixture was concentrated. The residue was then partitioned between 20% methanol/$CHCl_3$ (100 mL) and $H_2O$ (100 mL). The aqueous phase was extracted with 20% methanol/$CHCl_3$ (100 mL) again. The combined organic phase was consequently washed with brine, dried with $Na_2SO_4$, filtered, and concentrated. The residue was purified by silica gel column chromatography (Petroleum ether/EtOAc=2/1(v/v)) to give compound 20 (600 mg, 52% yield) as a yellow solid. LC-MS (ESI): m/z 706.4 $(M+H)^+$.

Step d. To a solution of compound 20 (200 mg, 0.28 mmol) in dioxane (3.0 mL) was added 4N HCl in dioxane (3.0 mL). After stirring at rt for 2 h, the reaction mixture was concentrated and the residue was dried in vacuo to yield the HCl salt of compound 21 in quantitative yield, which was used directly for the next step without further purification.

Step e. To a solution of compound 21 (0.28 mmol) in DMF (5.0 mL) was added DIPEA (0.49 mL, 2.8 mmol), followed by N,N-dimethyl-D-phenyl glycine (64 mg, 0.36 mmol) and HATU (129 mg, 0.34 mmol). After stirring at rt for 1 h, the reaction mixture was partitioned between $H_2O$ and DCM. The organic phase was washed successively with $H_2O$ and brine, dried with anhydrous $Na_2SO_4$, filtered, and concentrated. The residue was purified by prep-HPLC to give compound 22. LC-MS (ESI): m/z 767.4 $(M+H)^+$.

Scheme 2-4

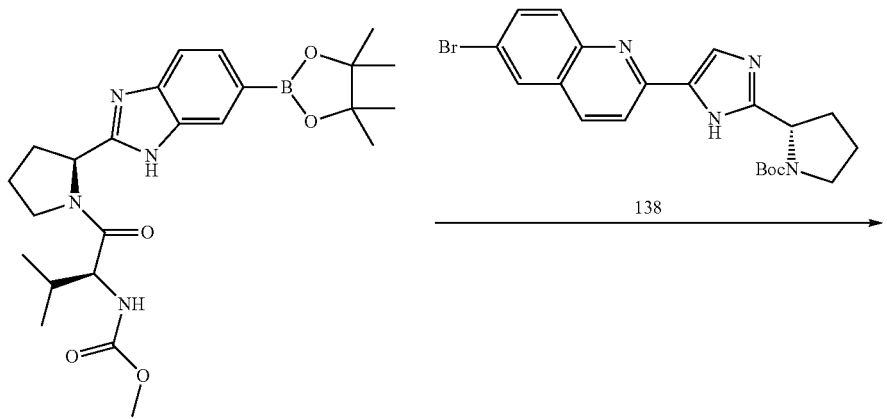

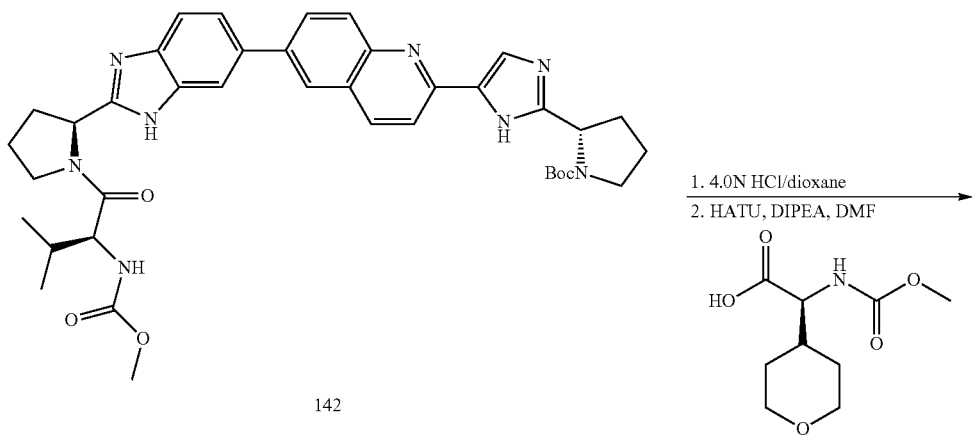

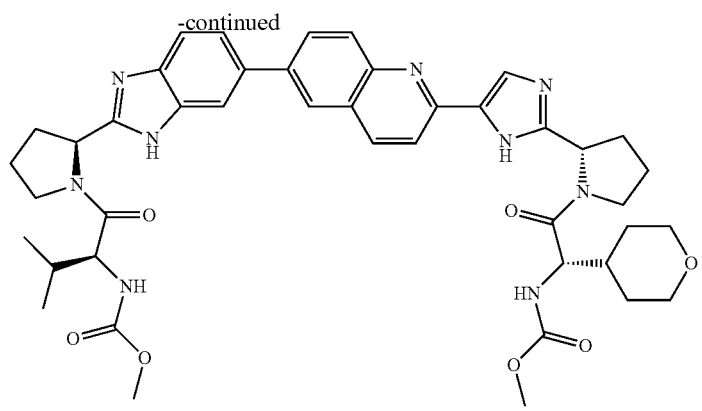

143

Step a. To a mixture of compound 74 (510 mg, 1.09 mmol), compound 138 (300 mg, 0.68 mmol), NaHCO$_3$ (228 mg, 2.72 mmol) in 1,2-dimethoxyethane (20 mL) and H$_2$O (5 mL) was added Pd(dppf)Cl$_2$.CH$_2$Cl$_2$ (111 mg, 0.140 mmol) at rt under an atmosphere of N$_2$. After stirring at 80° C. overnight under an atmosphere of N$_2$, the reaction mixture was concentrated and the residue was diluted with EtOAc (100 mL) and H$_2$O (25 mL). The organic phase was washed with brine and dried with anhydrous Na$_2$SO$_4$. The solvent was removed and the residue was purified by silica gel column chromatography (Petroleum ether/EtOAc=1/2 (v/v)) to give compound 142 (360 mg, 75% yield) as a yellow solid. LC-MS (ESI): m/z 707.4 (M+H)$^+$.

Step b. To a solution of compound 142 (115 mg, 0.16 mmol) in dioxane (2.0 mL) was added 4 N HCl in dioxane (2.0 mL) at rt. After stirring at rt overnight, the reaction mixture was concentrated and the residue was dried in vacuo to give an HCl salt, which was used for the next step without further purification. LC-MS (ESI) m/z 607.3 (M+H)$^+$.

Step c. Subsequently, the HCl salt was dissolved in DMF (2 mL) and the resulting mixture was added DIEA (0.28 mL, 1.6 mmol), N-Moc-L-(tetrahydro-2H-pyran-4-yl)glycine (41 mg, 0.19 mmol), and HATU (73 mg, 0.19 mmol). After stirring at rt for 15 min, the reaction mixture was concentrated and the residue was purified by preparative HPLC to give compound 143. LC-MS: (ESI) m/z 806.4 (M+H)$^+$.

Example 3

Synthesis of Additional Compounds of Formula IIc

Scheme 3-1

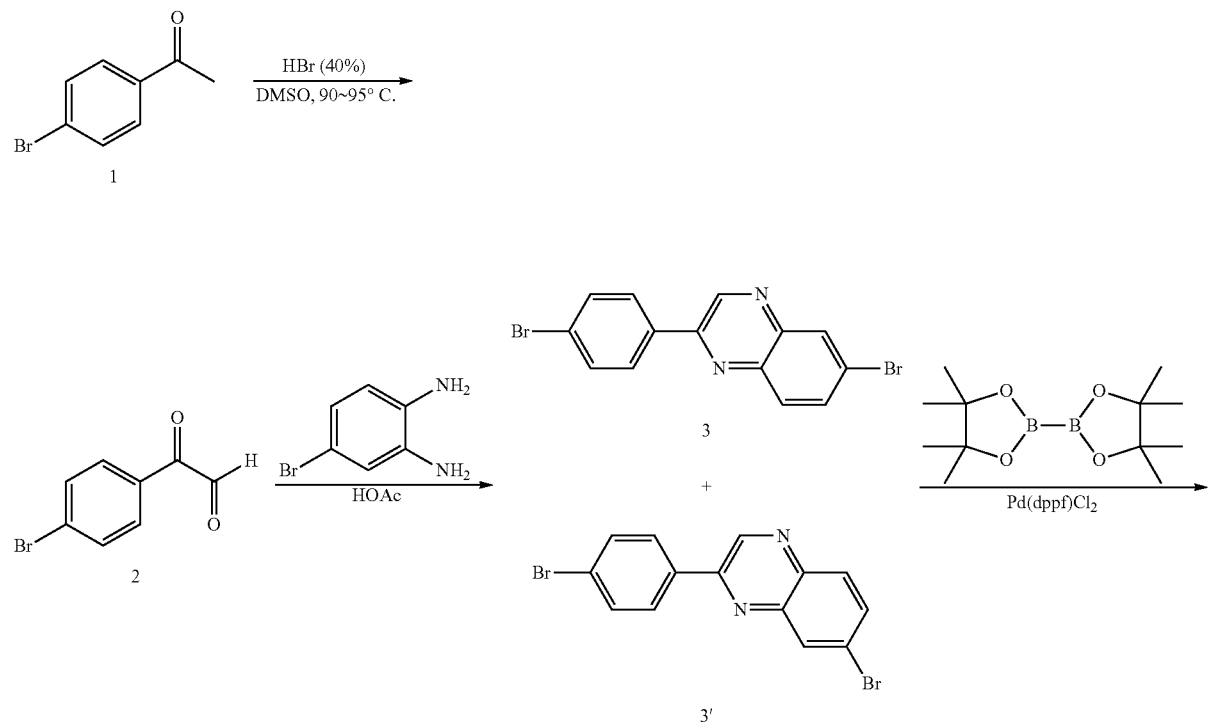

-continued

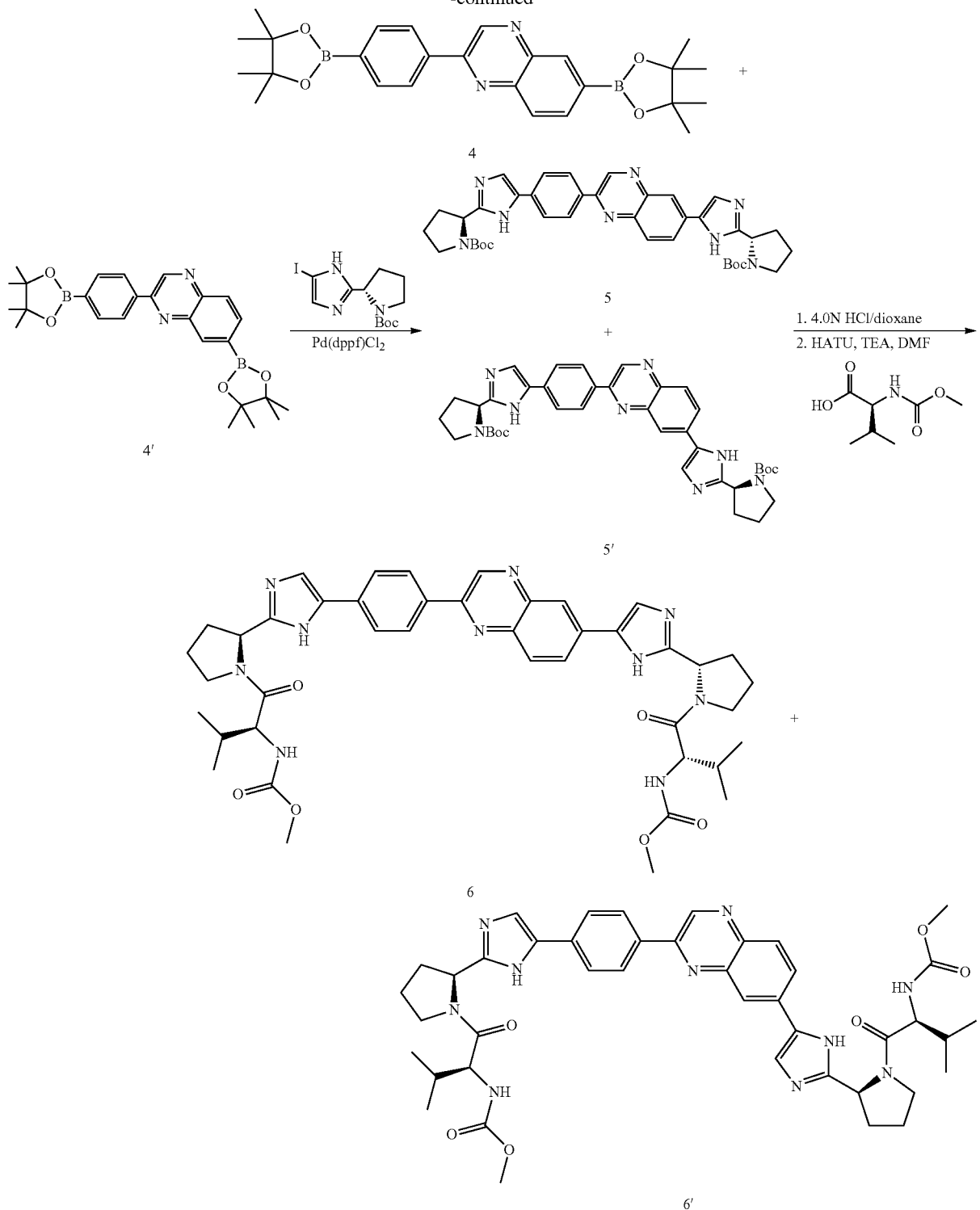

Step a. Referring to Scheme 3-1, to a solution of compound 1 (49.7 g, 0.25 mol) in DMSO was added 40% aq. HBr (0.50 mol) drop wise at rt. After stirring at 90° C. for 3 h, the reaction mixture was poured into H₂O and the resulting mixture was kept at 50~60° C. The yellow solid was collected by filtration and re-crystallized in acetone/H₂O (1/19 (v/v) two times to give compound 2 (50 g, 87% yield). LC-MS (ESI): m/z 212.9 (M+H)⁺.

Step b. A mixture of 2 (19.0 g, 80.0 mmol) and 4-bromobenzene-1,2-diamine (15.0 g, 80.0 mmol) in HOAc (180 mL) was refluxed overnight. Subsequently, the reaction mixture was poured into ice H₂O. The solid was collected by filtration and purified by silica gel column chromatography to give compounds 3 and 3' (2.8 g, 10% yield) as a pair of regioisomers. LC-MS (ESI): m/z 362.9 (M+H)⁺.

Step c. A mixture of compound 3 (4.8 g, 5.4 mmol), bis(pinacolato)diboron (9.6 g, 38 mmol), potassium acetate (3.8 g, 38 mmol), and Pd(dppf)Cl$_2$.CH$_2$Cl$_2$ (524 mg, 0.54 mmol) in dioxane (100 mL) was stirred at 80° C. for 17 h under an atmosphere of Ar. Subsequently, the reaction mixture was filtered. The filtered cake was washed with EtOAc (50 mL×3) several times. The filtrate was washed with H$_2$O and dried with anhydrous Na$_2$SO$_4$. The solvent was removed and the residue was purified by silica gel column chromatography (PE/acetone=10:1 (v/v)) to give compounds 4 and 4' (2.2 g, 89% yield) as a pair of regio-isomers. LC-MS (ESI): m/z 459.3 (M+H)$^+$. (The corresponding boronic acid was also isolated and used as an active intermediate for the next step).

Step d. A mixture of compounds 4 and 4' (1.0 g, 2.2 mmol), (S)-tert-butyl 2-(5-iodo-1H-imidazol-2-yl)pyrrolidine-1-carboxylate (2.0 g, 5.4 mmol), sodium bicarbonate (1.5 g, 18 mmol), and Pd(dppf)Cl$_2$.CH$_2$Cl$_2$ (427 mg, 0.44 mmol) in DME/H$_2$O (3/1 (v/v) (80 mL) was stirred at 80° C. for 17 h under an atmosphere of Ar. Subsequently, the reaction mixture was concentrated and the residue was diluted with EtOAc (100 mL). The organic layer was washed with brine and dried with anhydrous Na$_2$SO$_4$. The solvent was removed and the residue was purified by silica gel column chromatography (PE/acetone=10:1 (v/v)) to give compounds 5 and 5' (590 mg, 40% yield) as a pair of regio-isomers. LC-MS (ESI): m/z 677.3 (M+H)$^+$.

Step e. A mixture of compounds 5 and 5' (200 mg, 0.3 mmol) in 4.0 N HCl in dioxane (10 mL) was stirred at rt overnight. The solvent was removed and the residue was dried in vacuo to give an HCl salt, which was used for the next step without further purification. LC-MS (ESI): m/z 477.2 (M+H)$^+$.

Step f. Subsequently, the HCl salt was dissolved in DMF (3 mL) and the resulting mixture was sequentially added Et$_3$N (304 mg, 3.0 mmol), N-Moc-L-Val-OH (116 mg, 0.66 mmol) and HATU (251 mg, 0.66 mmol). After stirring at rt for 2 h, the reaction mixture was poured into H$_2$O (50 mL) and the resulting suspension was extracted with DCM several times (20 mL×3). The extracts were combined, washed with brine, and dried with anhydrous MgSO$_4$. The solvent was removed and the residue was purified by preparative HPLC and to give compounds 6 and 6' as a pair of regio-isomers. LC-MS (ESI): m/z 791.4 (M+H)$^+$.

Scheme 3-2

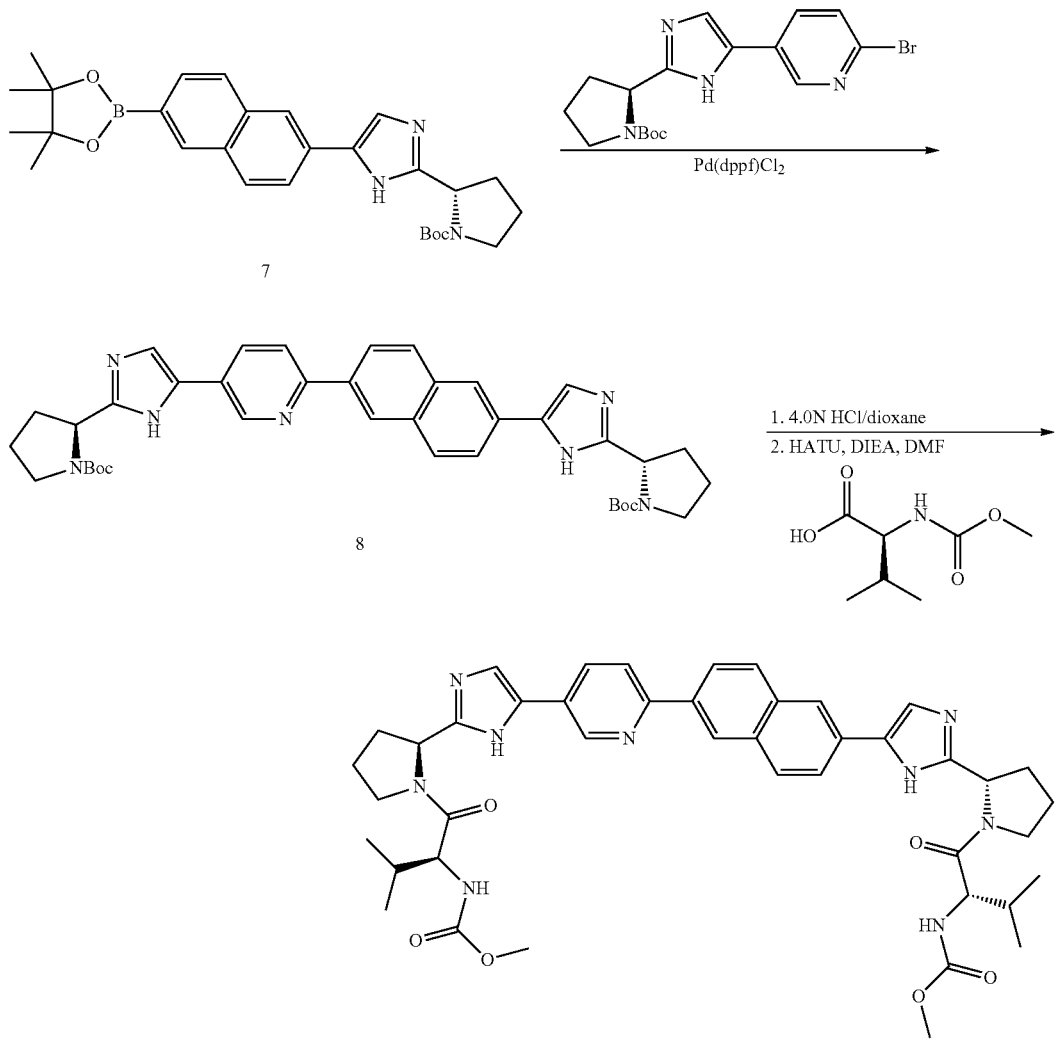

Step a. Referring to Scheme 3-2, to a solution of compound 7 (909 mg, 1.86 mmol), (S)-tert-butyl-2-(5-(6-bromopyridin-3-yl)pyrrolidine-1-carboxylate (800 mg, 2.04 mmol), and NaHCO$_3$ (625 mg, 7.44 mmol) in 1,2-dimethoxyethane (100 mL) and H$_2$O (30 mL) was added Pd(dppf)Cl$_2$ (152 mg, 0.186 mmol) at rt under an atmosphere of Ar. After stirring at 80° C. overnight under an atmosphere of Ar, the reaction mixture was concentrated. The residue was diluted with CH$_2$Cl$_2$ (200 mL). The organic layer was washed with H$_2$O and dried with anhydrous Na$_2$SO$_4$. The solvent was removed and the residue was purified by silica gel column chromatography (DCM/MeOH=50:1 (v/v)) to give compound 8 (700 mg, 55% yield). LC-MS (ESI) m/z: 676.4 (M+H)$^+$.

Step b. To a stirred solution of compound 8 (200 mg, 0.296 mmol) in dioxane (3 mL) was added 4 N HCl in dioxane (3 mL). After stirring at rt for 4 h, the reaction mixture was concentrated and the residue was dried in vacuo to give an HCl salt, which was used for the next step without further purification. LC-MS (ESI) m/z: 476.2 (M+H)$^+$.

Step c. Subsequently, the HCl salt was dissolved in DMF (3 mL) and the resulting mixture was sequentially added DIEA (388 mg, 3.0 mmol), N-Moc-L-Val-OH (116 mg, 0.66 mmol) and HATU (251 mg, 0.66 mmol). After stirring at rt for 2 h, the reaction mixture was poured into H$_2$O (50 mL) and the resulting suspension was extracted with DCM several times (20 mL×3). The extracts were combined, washed with brine, and dried with anhydrous MgSO$_4$. The solvent was removed and the residue was purified by preparative HPLC and to give compound 9. $^1$H NMR (500 MHz, CDCl$_3$) δ 9.09 (s, 1H), 8.67 (s, 1H), 8.31-8.34 (m, 3H), 8.27-8.29 (m, 1H), 8.17-8.19 (m, 1H), 8.11-8.13 (m, 1H), 8.07 (s, 1H), 8.04 (s, 1H), 7.90-7.91 (m, 1H), 5.29-5.31 (m, 2H), 4.26-4.27 (m, 2H), 4.13 (s, 2H), 3.93-3.95 (m, 2H), 3.68 (s, 6H), 2.60-2.62 (m, 3H), 2.32-2.33 (m, 2H), 2.15-2.28 (m, 5H), 2.10-2.11 (m, 3H), 1.00-1.02 (m, 2H), 0.96-0.98 (m, 6H), 0.92-0.93 (m, 6H) ppm. LC-MS (ESI): m/z 790.4 (M+H)$^+$.

Scheme 3-3

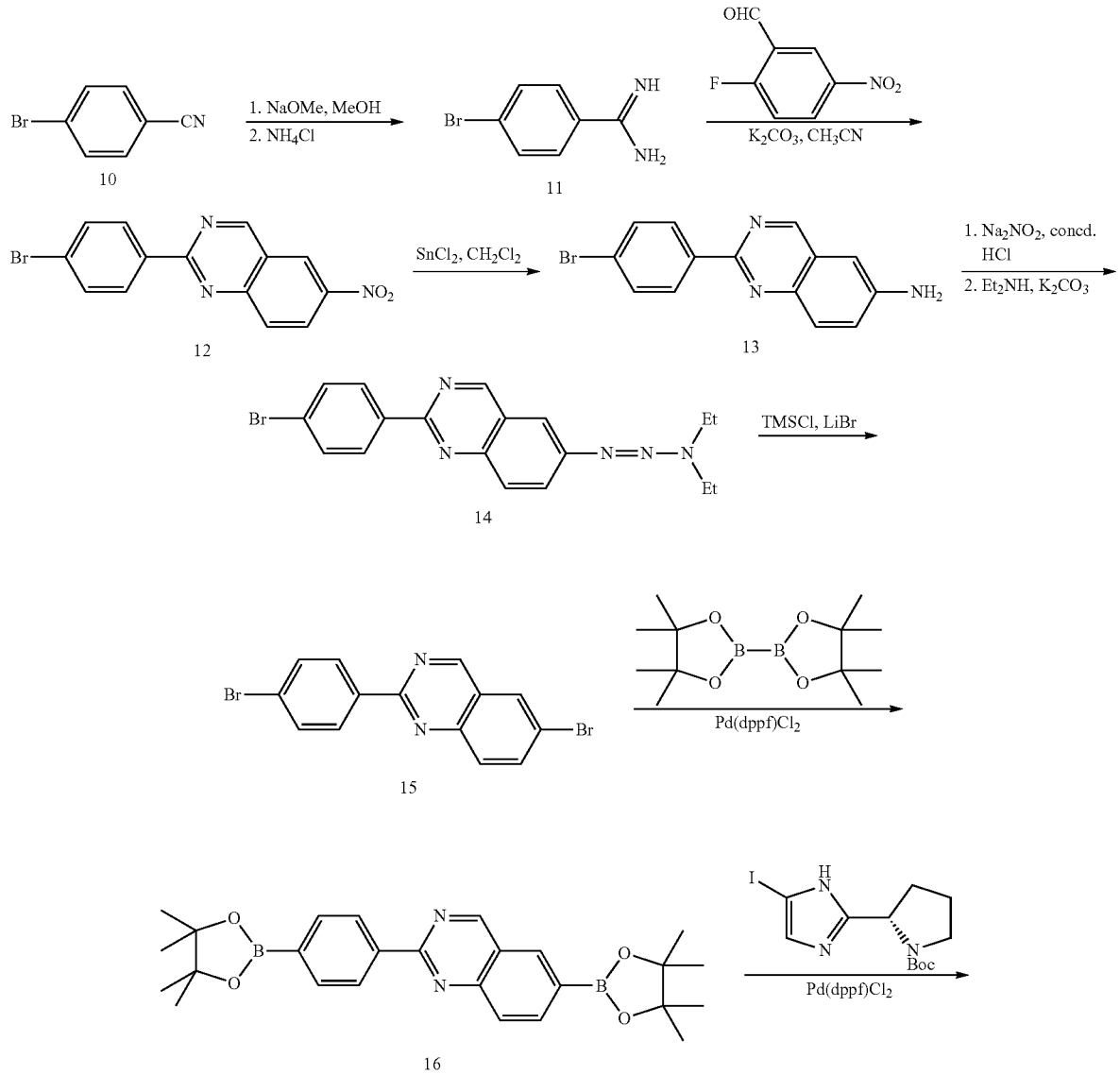

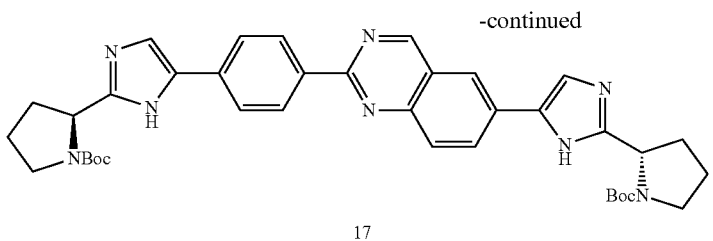

17

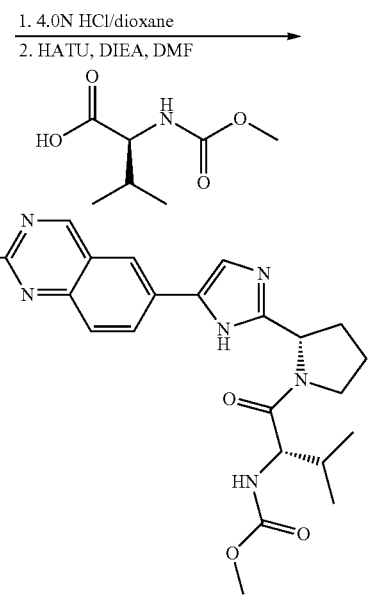

18

Step a. Referring to Scheme 3-3, to a solution of 10 (45.0 g, 247 mmol) in MeOH (500 mL) was added NaOMe (1.4 g, 25 mmol) at rt. After stirring at rt for 48 h, the reaction mixture was added NH$_4$Cl (13.4 g, 250 mmol) and the resulting mixture was stirred from another 24 h. The solvent was removed and the residue was dried in vacuo to give compound 11, which was used for the next step without further purification. LC-MS: (ESI) m/z=199.0 (M+H)$^+$.

Step b. To a solution of 11 (15 g, 75 mmol) in CH$_3$CN (500 mL) was added K$_2$CO$_3$ (11.4 g, 83.0 mmol), followed by 2-fluoro-5-nitrobenzaldehyde (12.7 g, 75.0 mmol). After refluxing for 12 h, the reaction mixture was concentrated and the residue was washed with MeOH to give crude compound 12 (12 g), which was used for the next step without further purification. LC-MS: (ESI) m/z=330.0 (M+H)$^+$.

Step c. A solution of 12 (5.0 g, 15 mmol) in MeOH (500 mL) was added tin (II) chloride (14.3 g, 75.0 mmol) and concentrated hydrochloric acid (17 mL). After stirring at rt for 3.5 h, the reaction mixture was carefully added saturated aqueous NaHCO$_3$ solution (470 mL). The resulting mixture was extracted with ethyl acetate (100 mL×3). The extracts were combined and washed with brine and dried with anhydrous Na$_2$SO$_4$. The solvent was removed and the residue was dried in vacuo to give crude compound 13 (2.5 g). LC-MS: (ESI) m/z=300.0 (M+H)$^+$.

Step d. To a solution of 13 (300 mg, 1.0 mmol) in concentrated HCl (0.25 mL) was added a solution of NaNO$_2$ (76 mg, 1.1 mmol) in H$_2$O (1 mL) drop wise at 0° C. After stirring at 0° C. for 30 min, the reaction mixture was added to a solution of K$_2$CO$_3$ (207 mg, 1.5 mmol) and Et$_2$NH (0.11 g, 1.5 mmol) in ice H$_2$O (1 mL). Subsequently, ether (100 mL) was added to the mixture. The organic layer was separated, washed with H$_2$O (15 mL) and dried with anhydrous Na$_2$SO$_4$. The solvent was removed and the residue was dried in vacuo to give crude compound 14 (350 mg), which was used for the next step without further purification. LC-MS (ESI): m/z 384.1 (M+H)$^+$.

Step e. To a solution of compound 14 (1.8 g, 4.7 mmol) and LiBr (834 mg, 9.6 mmol) in acetonitrile (10 mL) was added TMSCl (782 mg, 7.2 mmol) at rt. After stirring at 60° C. for 15 min, the reaction mixture was cooled to rt and treated with 5% aqueous NaHCO$_3$ solution (30 mL). The mixture was concentrated and the residue was extracted with CH$_2$Cl$_2$ (50 mL×3). The extracts were combined, washed with brine, and dried with anhydrous Na$_2$SO$_4$. The solvent was removed and the residue was purified by silica gel column chromatography (Pentane/ether=1/19 (v/v)) to give compound 15 (1.0 g, 59% yield). LC-MS: (ESI) m/z=362.9 (M+H)$^+$.

Step f. To a solution of 15 (300 mg, 0.82 mmol) in dioxane (20 mL) was sequentially added bis(pinacolato)diboron (915 mg, 3.63 mmol), potassium acetate (403 mg, 4.12 mmol), and Pd(dppf)Cl$_2$ (134 mg, 0.160 mmol) at rt under an atmosphere of Ar. After stirring at 80° C. for 17 h under an atmosphere of Ar, the reaction mixture was diluted with EtOAc (100 mL). The resulting mixture was washed with H$_2$O and dried with anhydrous Na$_2$SO$_4$. The solvent was removed and the residue was purified by silica gel column chromatography (PE/acetone=3/1 (v/v)) to give compound 16 (227 mg, 60% yield) LC-MS (ESI): m/z 459.3 (M+H)$^+$. (The corresponding boronic acid was also isolated and used as an active intermediate for the next step).

Step g. A solution of 16 (300 mg, 0.65 mmol) in DME/H$_2$O (3/1(v/v); 30 mL) was sequentially added (S)-tert-butyl 2-(5-iodo-1H-imidazol-2-yl)pyrrolidine-1-carboxylate (595 mg, 1.64 mmol), NaHCO$_3$ (443 mg, 5.28 mmol), and Pd(dppf)Cl$_2$.CH$_2$Cl$_2$ (126 mg, 0.13 mmol) at rt under an atmosphere of Ar. After stirring at 80° C. for 17 h under an atmosphere of Ar, the reaction mixture was diluted with EtOAc (150 mL). The organic layer was isolated, washed with brine, and dried with anhydrous Na$_2$SO$_4$. The solvent was removed and the residue was purified by silica gel column chromatography (PE/acetone=2/1(v/v)) to give compound 17 (151 mg, 34% yield) as a yellowish solid. LC-MS (ESI): m/z 677.3 (M+H)$^+$.

Step h. To a solution of compound 17 (100 mg, 0.15 mmol) in dioxane (2 mL) was added 4 N HCl in dioxane (2 mL) at rt.

After stirring at rt overnight, the solvent was removed and the residue was dried in vacuo to give an HCl salt, which was used for the next step without further purification. LC-MS (ESI): m/z 477.2 (M+H)$^+$.

J=8.5), 5.30-5.26 (m, 2H), 4.25 (d, 2H, J=6.5), 4.12 (s, 2H), 3.91 (s, 2H), 3.67 (s, 6H), 2.61-2.60 (m, 2H), 2.31-2.17 (m, 6H), 2.08-2.05 (m, 2H), 1.02-0.91 (m, 12H) ppm; LC-MS (ESI) m/z: 791.4 (M+H)$^+$.

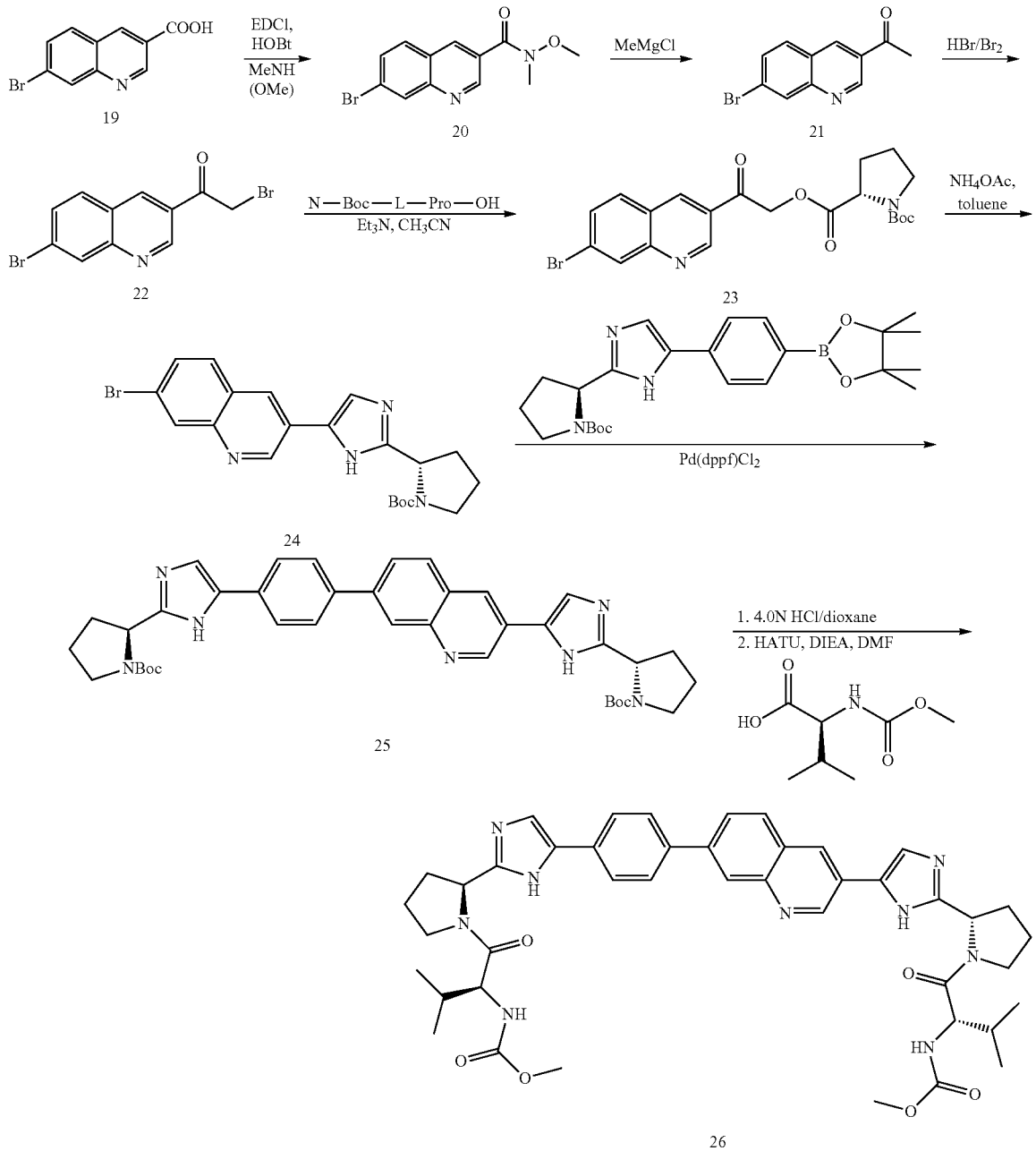

Scheme 3-4

Step i. To a solution of the HCl salt in DMF (2 mL) was added DIPEA (0.24 mL, 1.5 mmol), followed by N-Moc-L-Val-OH (65 mg, 0.37 mmol), and HATU (141 mg, 0.37 mmol). After stirring at rt for 30 min, the reaction solution was poured into H$_2$O (50 mL). The suspension was filtered and the solid was purified by preparative HPLC to give compound 18. $^1$H NMR (500 MHz, CD$_3$OD) δ 9.69 (s, 1H), 8.80 (d, 2H, J=7.5), 8.49 (s, 1H), 8.35 (d, 2H, J=8.0), 8.24 (d, 2H, J=8.5), 8.15 (s, 1H), 8.12 (s, 1H), 8.01 (s, 2H), 7.93 (d, 2H, Step a. Referring to Scheme 3-4, a solution of 19 (5.00 g, 19.8 mmol) in CH$_3$CN (200 mL) was respectively added EDCI (9.10 g, 47.6 mmol), HOBt (1.34 g, 5.95 mmol), MeNH(OMe).HCl (2.93 g, 30 mmol), and Et$_3$N (6.6 g, 65.3 mmol) at rt. After stirring at rt for 3 h, the reaction mixture was concentrated and the residue was purified by silica gel column chromatography (Petroleum ether/EtOAc=5/1 (v/v)) to give compound 20 (5.1 g, 87% yield) as a white solid. LC-MS (ESI): m/z 295.0 (M+H)$^+$.

Step b. To a solution of compound 20 (2.0 g, 6.8 mmol) in THF (200 mL) was slowly added 3M MeMgCl in THF (4.5 mL) at 0° C. under an atmosphere of $N_2$. After stirring at 0° C. for 1 h and then at rt for 1 h, the reaction was quenched by adding several drops of aqueous $NH_4Cl$. The reaction mixture was concentrated and the residue was diluted with aqueous $NaHCO_3$ (5 mL) and EtOAc (100 mL). The organic phase was washed with brine and dried with anhydrous $Na_2SO_4$. The solvent was removed and the residue was purified by silica gel column chromatography (Petroleum ether/AcOEt=10:1(v/v)) to give compound 21 (1.0 g, 59%) as a white solid. LC-MS (ESI): m/z 250.0 $(M+H)^+$.

Step c. A solution of compound 21 (500 mg, 2.0 mmol) in HOAc (20 mL) and 48% aqueous HBr (0.5 mL) was slowly added $Br_2$ (320 mg, 2.0 mmol) in 48% aqueous HBr (0.5 mL) at rt. After stirring at rt for 2 h, the reaction mixture was concentrated and the residue was diluted with $H_2O$ (100 mL). The mixture was extracted with EtOAc (100 mL×3). The extracts were combined and washed with saturated $NaHCO_3$ (30 mL×3) and dried with anhydrous $Na_2SO_4$. The solvent was removed and the residue was dried in vacuo to give crude compound 22 (440 mg) as a white solid, which was used for the next step without further purification. LC-MS (ESI): m/z 327.9 $(M+H)^+$.

Step d. A solution of compound 22 (415 mg, 1.26 mmol) in $CH_3CN$ (15 mL) was respectively added N-Boc-L-Pro-OH (300 mg, 1.36 mol) and $Et_3N$ (382 mg, 3.78 mmol) at rt. After stirring at rt for 2 h, the reaction mixture was concentrated and the residue was dried in vacuo to give crude compound 23 (580 mg), which was used for the next step without further purification; LC-MS (ESI): m/z 463.1 $(M+H)^+$.

Step e. A mixture of compound 23 (580 mg, 1.25 mmol) and $NH_4OAc$ (962 mg, 12.5 mmol) in toluene (25 mL) was stirred at 110° C. overnight. The reaction mixture was concentrated and the residue was purified by silica gel column chromatography (Petroleum ether/EtOAc=9/1(v/v)) to give compound 24 (400 mg, 72%) as a white solid. LC-MS (ESI): m/z 443.1 $(M+H)^+$.

Step f. To a mixture of compound 24 (380 mg, 0.86 mmol), (S)-tert-butyl 2-(5-(4-(4,4,5,5-tetramethyl-1,3,2-dioxaborolan-2-yl)-1H-imidazol-2-yl)pyrrolidine-1-carboxylate (378 mg, 0.860 mmol), and $NaHCO_3$ (253 mg, 3.01 mmol) in 1,2-dimethoxyethane (15 mL) and $H_2O$ (5 mL) was added $Pd(dppf)Cl_2$ (35 mg, 0.04 mmol) under an atmosphere of $N_2$. After stirring at 80° C. overnight under an atmosphere of $N_2$, the reaction mixture was concentrated. The residue was diluted with $H_2O$ (50 mL) and extracted with EtOAc (50 mL×3). The extracts were combined and washed with brine and dried with anhydrous $Na_2SO_4$. The solvent was removed and the residue was purified by silica gel column chromatography (Petroleum ether/EtOAc=5/2 (v/v)) to give compound 25 (550 mg, 95% yield) as a yellow solid. LC-MS (ESI): m/z 676.4 $(M+H)^+$.

Step g. To a solution of compound 26 (150 mg, 0.22 mmol) in dioxane (2 mL) was added 4N HCl in dioxane (2 mL) at rt. After stirring at rt overnight, the solvent was removed and the residue was dried in vacuo to give an HCl salt, which was used for the next step without further purification. LC-MS (ESI): m/z 476.2 $(M+H)^+$.

Step h. To a mixture of the HCl salt in DMF (2 mL) was added DIPEA (0.37 mL, 2.3 mmol), followed by N-Moc-L-Val-OH (101 mg, 0.58 mmol) and HATU (218 mg, 0.58 mmol). After stirring at rt for 30 min, the reaction mixture was concentrated and the residue was purified by preparative HPLC to give compound 26. $^1$H NMR (500 MHz, $CD_3OD$) δ 7.96 (d, 2H, J=11.5), 7.83-7.78 (m, 4H), 7.72 (d, 2H, J=8.0), 5.56 (m, 1H), 5.38-5.32 (m, 2H), 4.46-4.42 (m, 1H), 4.27-4.26 (m, 1H), 4.21-4.13 (m, 2H), 3.97-3.94 (m, 1H), 3.66 (s, 6H), 2.89-2.86 (m, 1H), 2.64-2.62 (m, 2H), 2.34-2.25 (m, 3H), 2.01-1.96 (m, 2H), 0.94-0.87 (m, 12H) ppm; LC-MS (ESI): m/z 790.4 $(M+H)^+$.

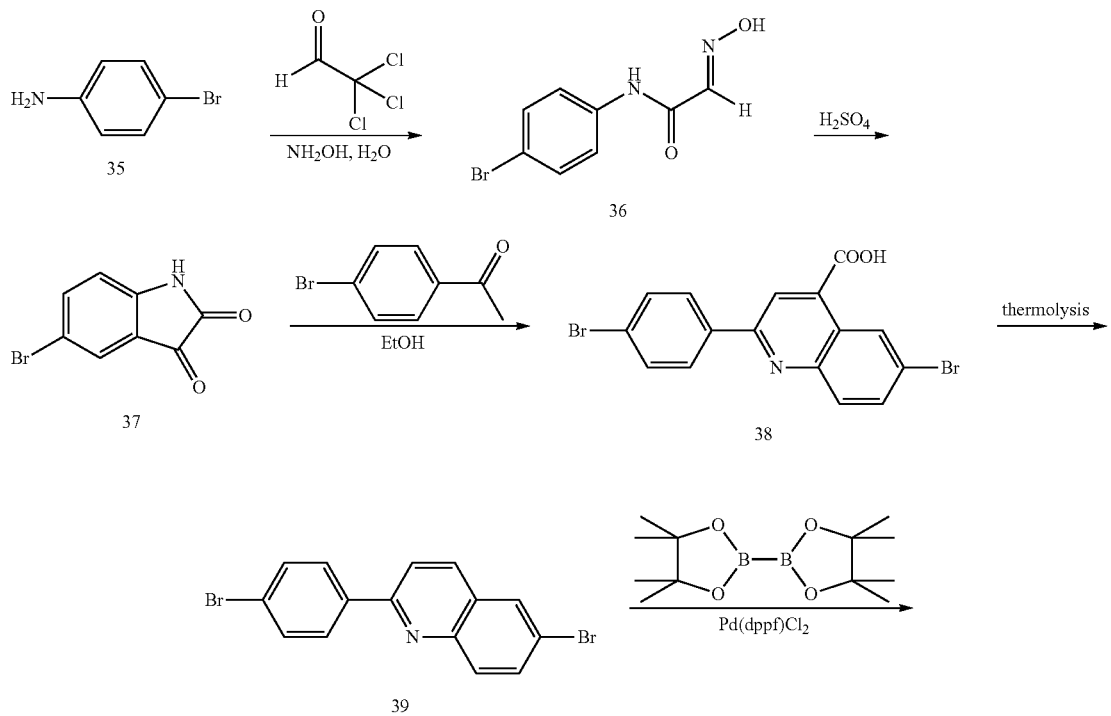

Scheme 3-5

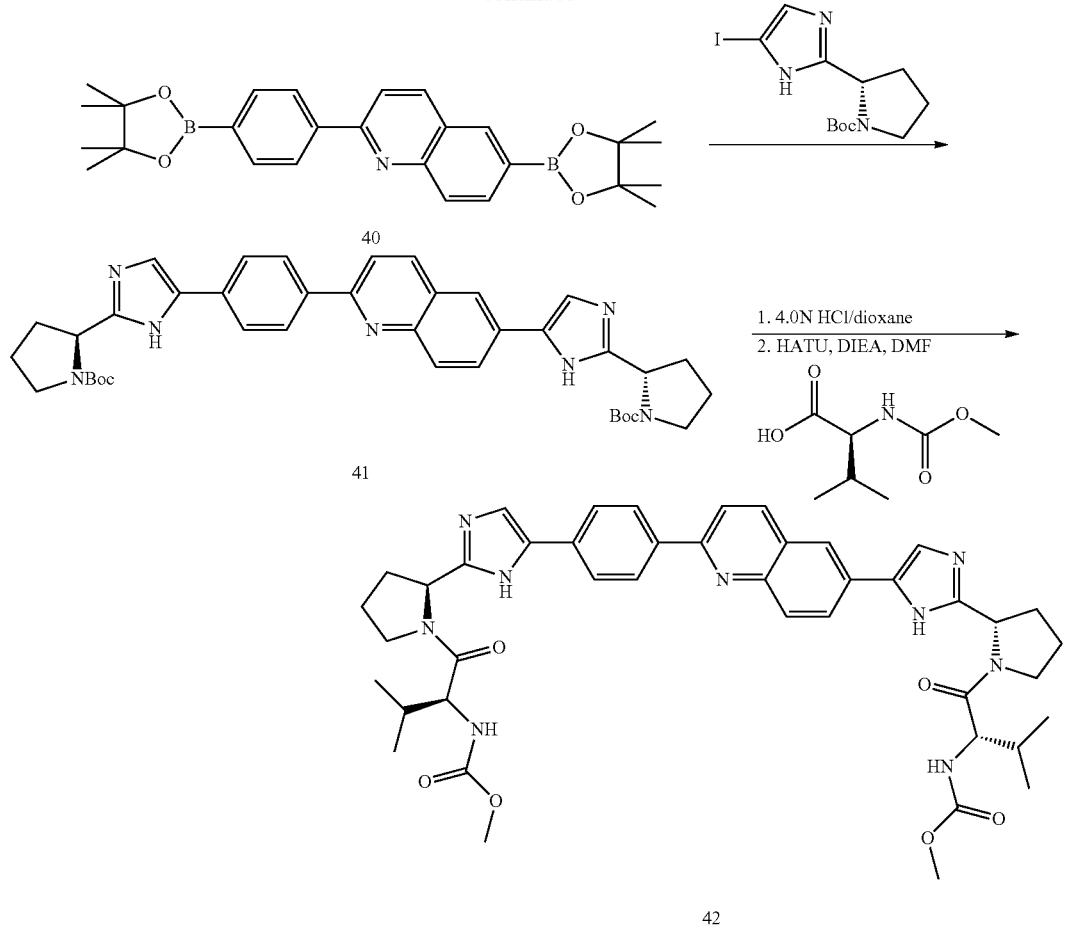

Step a. Referring to Scheme 3-5, a mixture of trichloroacetealdehyde (7.2 g, 48 mmol) in water (120 mL) was added $Na_2SO_4$ (104 g), followed by 4-bromobenzenamine (35) in concd. aq. HCl (10 mL) and $NH_2OH \cdot HCl$ (8.8 g, 0.13 mol) in $H_2O$ (100 mL). After refluxing for 1 h, the reaction mixture was cooled to rt. The solid was collected by filtration and dried in vacuo to give compound 36 (8.0 g, 91%) as a yellow solid. LC-MS (ESI) m/z: 243.0 $(M+H)^+$.

Step b. To a round-bottomed flask was charged with 20 mL of $H_2SO_4$ (98%) and the solution was warmed to 50° C. Subsequently, compound 36 (4.8 g, 20 mmol) was added at such a rate as to keep the temperature between 60 and 70° C. After the completion of adding compound 36, the resulting mixture was warmed to 80° C. and stirred for another 10 min. The mixture was cooled to rt and poured into ice (200 g). The solid was collected by filtration, washed with water for several times, and dried in vacuo to give compound 37 (3.6 g, 80% yield) as an orange solid. LC-MS (ESI) m/z: 225.9 $(M+H)^+$.

Step c. A mixture of compound 37 (1.35 g, 6.0 mmol), 1-(4-bromophenyl)ethanone (1.14 g, 5.7 mmol), and potassium hydroxide (1.02 g, 18.3 mmol) in ethanol (50 mL) was refluxed overnight. The reaction mixture was concentrated and the residue was diluted with petroleum ether (100 mL) and water (200 mL). The aqueous phase was isolated, acidified by adding 1N HCl, and then extracted with ethyl acetate (50 mL×3). The extracts were combined, washed with brine, and dried with anhydrous $Na_2SO_4$. The solvent was removed and the residue was dried in vacuo to give crude compound 38 (1.2 g) as a red solid, which was used for the next step without further purification. LC-MS (ESI) m/z: 405.9 $(M+H)^+$.

Step d. A flask that charged with compound 5 (1.2 g, 2.95 mmol) was heated to 300° C. for 30 min under an atmosphere of Ar. The solid was then purified by silica gel column chromatography (Petroleum ether/EtOAc=19:1 (v/v)) to give compound 39 (160 mg, 15% yield) as a yellow solid. LC-MS (ESI) m/z: 361.9 $(M+H)^+$.

Step e. A mixture of compound 39 (0.11 g, 0.30 mmol), bis(pinacolato)diboron (0.34 g, 1.3 mmol), potassium acetate (0.15 g, 1.5 mmol), and $Pd(dppf)Cl_2$ (50 mg, 0.06 mmol) and dioxane (20 mL) was stirred at 80° C. overnight under an atmosphere of Ar. Subsequently, the reaction mixture was diluted with EtOAc (100 mL). The resulting mixture was washed with $H_2O$ (50 mL) and dried with anhydrous $Na_2SO_4$. The solvent was removed and the residue was purified by silica gel column chromatography (Petroleum ether/acetone=10/1 (v/v)) to give compound 40 (0.12 g, 86% yield). LC-MS (ESI) m/z: 458.3 $(M+H)^+$. (The corresponding boronic acid was also isolated and used as an active intermediate for the next step).

Step f. A solution of compound 40 (120 mg, 0.26 mmol) in $DME/H_2O$ (3/1(v/v); 24 mL) was sequentially added (S)-tert-butyl 2-(5-iodo-1H-imidazol-2-yl)pyrrolidine-1-carboxylate (290 mg, 0.80 mmol), $NaHCO_3$ (220 mg, 2.6 mmol), and $Pd(dppf)Cl_2 \cdot CH_2Cl_2$ (62 mg, 0.064 mmol) at rt under an atmosphere of Ar. After stirring at 80° C. overnight under an atmosphere of Ar, the reaction mixture was diluted with EtOAc (100 mL). The organic layer was isolated, washed with brine, and dried with anhydrous $Na_2SO_4$. The solvent was removed and the residue was purified by silica gel column chromatography (PE/acetone=2/1 (v/v)) to give compound 17 (151 mg, 86% yield) as a yellow solid. LC-MS (ESI): m/z 676.4 (M+H)$^+$.

Step g. To a stirred solution of compound 41 (120 mg, 0.18 mmol) in dioxane (2 mL) was added 4N HO/dioxane (2 mL). After stirring at rt overnight, the reaction mixture was concentrated and the residue was dried in vacuo to give an HCl salt, which was used for the next step without further purification. LC-MS (ESI): m/z 476.2 (M+H)$^+$.

Step h. To a mixture of the HCl salt in DMF (2 mL) was added DIPEA (0.3 mL, 1.8 mmol), followed by N-Moc-L-Val-OH (79 mg, 0.45 mmol) and HATU (169 mg, 0.45 mmol). After stirring at rt for 30 min, the reaction mixture was slowly poured into $H_2O$. The solid was collected by filtration and purified by preparative HPLC to give compound 42. $^1$H NMR (500 MHz, $CD_3OD$) δ 8.96 (d, 2H, J=9.5 Hz), 8.63 (s, 1H), 8.53 (d, 2H, J=10.0 Hz), 8.40-8.39 (m, 3H), 8.18 (s, 1H), 8.08 (d, 2H, J=13 Hz), 5.29-5.28 (m, 2H), 4.26-4.24 (m, 2H), 4.11-4.10 (m, 2H), 3.99-3.97 (m, 2H), 3.66 (s, 6H), 2.60 (m, 2H), 2.30-2.24 (m, 3H), 2.21-2.19 (m, 3H), 2.14-2.09 (m, 2H), 1.00-0.83 (m, 12H) ppm; LC-MS (ESI) m/z: 790.4 (M+H)$^+$.

Scheme 3-6

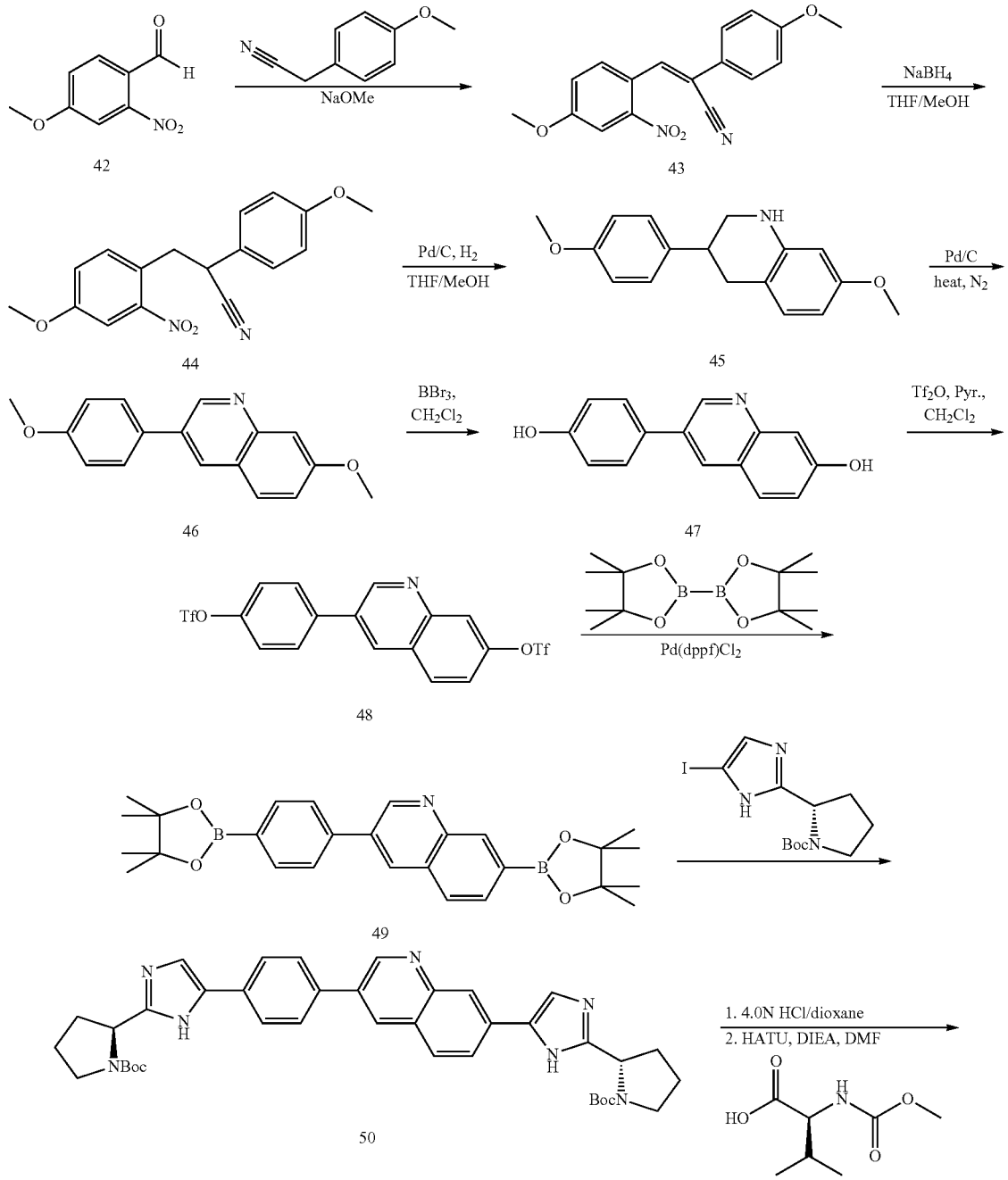

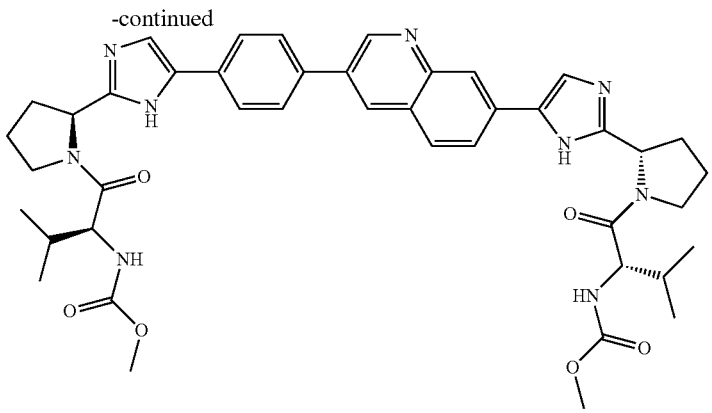

Step a. Referring to Scheme 3-6, a mixture of 4-methoxy-2-nitrobenzaldehyde (42) (1.4 g, 7.7 mmol) and 4-methoxyphenyl acetonitrile (1.13 g, 7.7 mmol) was added to a solution of sodium methylate (0.4 g, 7.7 mmol) in methanol (10 mL) at rt. After stirring at rt for 5 h, the reaction mixture was filtered. The solid was washed with water and 95% ethanol, respectively, and dried in vacuo to give compound 43 (1.82 g, 77% yield) as a yellow powder. $^1$H NMR (500 MHz, CDCl$_3$) δ 7.90 (d, J=8.5 Hz, 1H), 7.85 (s, 1H), 7.70 (d, J=2.0 Hz, 1H), 7.63 (d, J=9.0 Hz, 2H), 7.28 (m, 1H), 6.98 (d, J=9.0 Hz, 2H), 3.94 (s, 3H), 3.87 (s, 3H) ppm. LC-MS (ESI): m/z 311.1 (M+H)$^+$.

Step b. A solution of compound 43 (15.5 g, 50 mmol) in THF/methanol (5/1 (v/v), 240 mL) was added NaBH$_4$ (2.8 g, 75 mmol) at rt. After stirring at rt for 4 h, the reaction mixture was poured into ice water and treated with 1 N aq. HCl. The resulting mixture was extracted with EtOAc (50 mL×2). The extracts were combined, washed with brine, and dried with anhydrous Na$_2$SO$_4$. The solvent was removed and the residue was dried in vacuo to give crude compound 44 (9.8 g), which was used for the next step without further purification. LC-MS (ESI): m/z 335.1 (M+Na)$^+$.

Step c. A mixture of compound 44 (9.0 g, 29 mmol) and 10% Pd/C (4.5 g) in THF (240 mL) and MeOH (60 mL) was stirred at 45° C. for 48 h under an atmosphere of H$_2$. The resulting mixture was filtered through CELITE™ 545; the filtered cake was washed with MeOH (50 mL×3). The filtrate was concentrated and the residue was purified by silica gel column chromatography (Petroleum ether/Ethyl acetate 9:1) to give compound 45 (5.5 g, 71% yield) as a white solid. $^1$H NMR (500 MHz, CDCl$_3$) δ 7.16 (d, J=8.5 Hz, 2H), 6.91-6.87 (m, 3H), 6.25 (d, J=8.5 Hz, 1H), 6.12 (s, 1H), 3.80 (s, 3H), 3.75 (s, 3H), 3.41 (d, J=11.0 Hz, 1H), 3.27 (t, J=11.0 Hz, 1H), 3.11-3.05 (m, 1H), 2.90 (d, J=8.0 Hz, 2H) ppm; LC-MS (ESI): m/z 270.1 (M+H)$^+$.

Step d. A mixture of compound 45 (2.7 g, 10 mmol) and 10% Pd/C (1.4 g) was stirred at 270~280° C. for 30 min under an atmosphere of Ar. The mixture was purified by silica gel column chromatography (Petroleum ether/EtOAc=6/1 (v/v)) to give compound 46 (1.8 g, 68%) as a white solid. LC-MS (ESI): m/z 266.1 (M+H)$^+$.

Step e. To a solution of compound 46 (0.80 g, 3.0 mmol) in CH$_2$Cl$_2$ (30 mL) was added 4 N BBr$_3$/CH$_2$Cl$_2$ (4.5 mL, 18 mmol) at −40° C. After stirring at rt overnight, the reaction mixture was diluted with water (30 mL). The resulting mixture was treated with 1 N aq. NaOH solution to adjust the pH to 8, and extracted with EtOAc (60 mL×2). The extracts were combined, washed with brine, and dried with anhydrous Na$_2$SO$_4$. The solvent was removed and the residue was purified by silica gel chromatography (Petroleum ether/EtOAc=2/1 (v/v)) to give compound 47 (0.7 g, 99%) as a white solid. LC-MS (ESI): m/z 238.1 (M+H)$^+$.

Step f. To a solution of compound 47 (0.82 g, 3.5 mmol) and pyridine (1.3 g, 16 mmol) in CH$_2$Cl$_2$ (45 mL) was added and Tf$_2$O (3.6 g, 13 mmol) at 0° C. After stirring at rt for 30 min, the reaction mixture was concentrated and the residue was purified by silica gel chromatography (Petroleum ether/EtOAc=10/1 (v/v)) to give compound 48 (0.40 g, 23%) as a yellow solid. LC-MS (ESI): m/z 502.1 (M+H)$^+$.

Step g. A mixture of compound 48 (0.40 g, 0.80 mmol), bis(pinacolato)diboron (1.0 g, 4.0 mmol), potassium acetate (0.55 g, 5.6 mmol), and Pd(dppf)Cl$_2$ (200 mg, 0.24 mmol) and dioxane (20 mL) was stirred at 80° C. overnight under an atmosphere of Ar. Subsequently, the reaction mixture was diluted with EtOAc (100 mL). The resulting mixture was washed with H$_2$O (50 mL) and dried with anhydrous Na$_2$SO$_4$. The solvent was removed and the residue was purified by silica gel column chromatography (Petroleum ether/acetone=10/1 (v/v)) to give compound 49 (0.20 g, 54% yield). LC-MS (ESI) m/z: 458.3 (M+H)$^+$. (The corresponding boronic acid was also isolated and used as an active intermediate for the next step).

Step h. A solution of compound 49 (160 mg, 0.35 mmol) in DME/H$_2$O (3/1(v/v); 40 mL) was sequentially added (S)-tert-butyl 2-(5-iodo-1H-imidazol-2-yl)pyrrolidine-1-carboxylate (388 mg, 1.07 mmol), NaHCO$_3$ (289 mg, 3.44 mmol), and Pd(dppf)Cl$_2$.CH$_2$Cl$_2$ (71 mg, 0.090 mmol) at rt under an atmosphere of Ar. After stirring at 80° C. overnight under an atmosphere of Ar, the reaction mixture was diluted with EtOAc (100 mL). The organic layer was isolated, washed with brine, and dried with anhydrous Na$_2$SO$_4$. The solvent was removed and the residue was purified by silica gel column chromatography (Petroleum ether/acetone=2/1 (v/v)) to give compound 50 (151 mg, 64% yield) as a yellow solid. LC-MS (ESI): m/z 676.4 (M+H)$^+$.

Step i. To a stirred solution of compound 50 (140 mg, 0.21 mmol) in dioxane (2 mL) was added 4N HCl in dioxane (2 mL) at rt. After stirring at rt overnight, the reaction mixture was concentrated and the residue was dried in vacuo to give an HCl salt, which was used for the next step without further purification. LC-MS (ESI): m/z 476.2 (M+H)$^+$.

Step j. To a mixture of the HCl salt in DMF (2 mL) was added DIPEA (0.35 mL, 2.1 mmol), followed by N-Boc-L-Val-OH (92 mg, 0.53 mmol), and HATU (200 mg, 0.530 mmol). After stirring at rt for 30 min, the reaction mixture was poured into water. The solid was collected by filtration and purified by preparative HPLC to give compound 51. $^1$H NMR (500 MHz, CD$_3$OD) δ 9.29 (br, 1H), 8.67-8.63 (m, 1H), 8.44-8.41 (m, 1H), 8.29-8.21 (m, 2H), 8.13 (s, 2H), 8.01 (s, 2H), 5.31-5.25 (m, 2H), 4.26-4.23 (m, 2H), 4.12 (s, 2H), 4.05-3.91 (m, 2H), 3.66 (s, 3H), 3.62 (s, 3H), 2.60 (m, 2H), 2.31-1.95 (m, 7H), 1.01-0.86 (m, 12H) ppm; LC-MS (ESI): m/z 790.4 (M+H)$^+$.
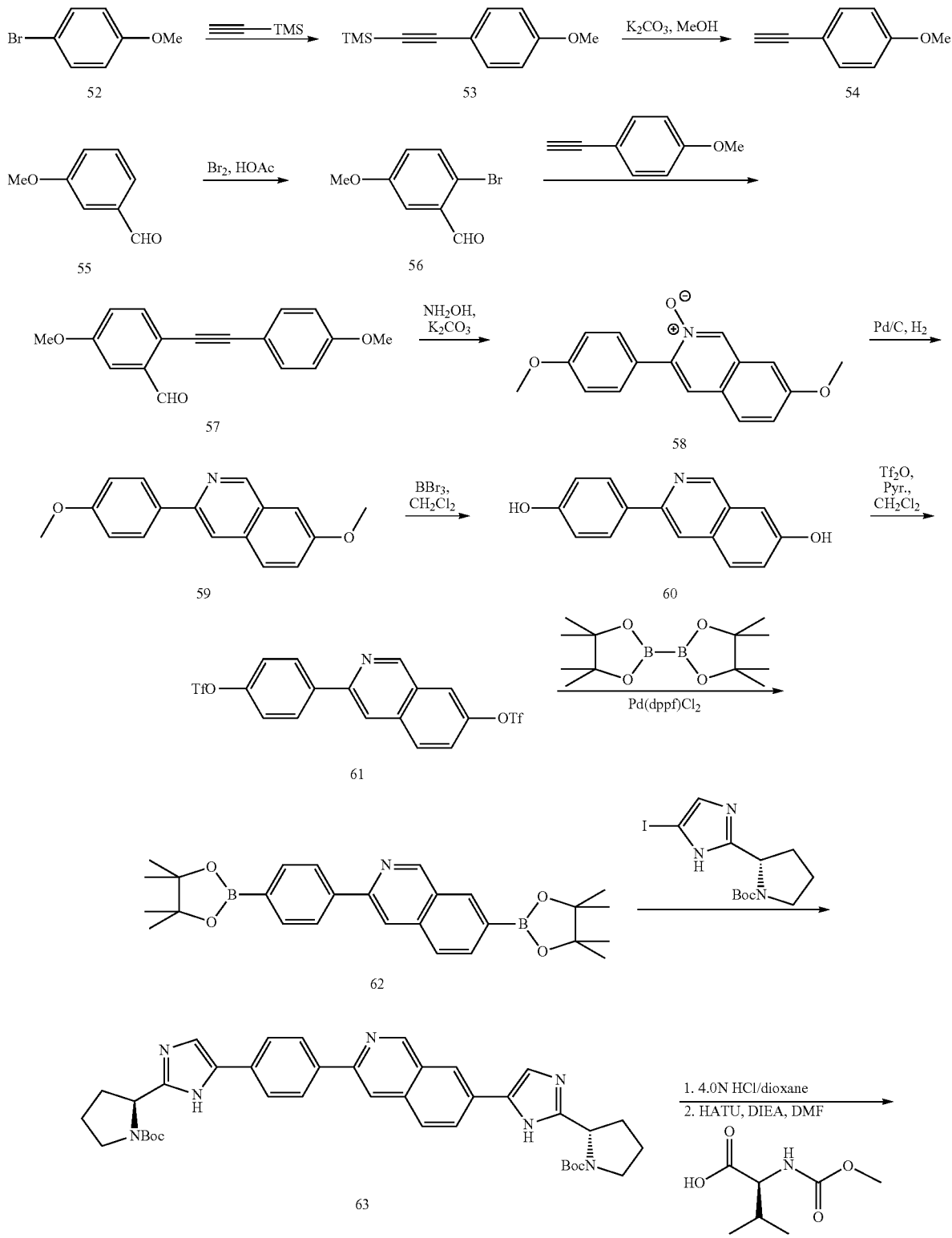

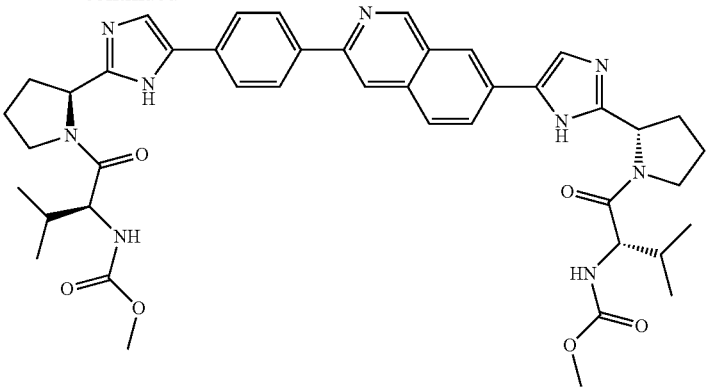

64

Step a. Referring to Scheme 3-7, a mixture of compound 52 (9.35 g, 50 mmol), TMS-acetylene (7.35 g, 75 mmol), DIEA (21.0 mL, 150 mmol), CuI (475 mg, 2.50 mmol), Pd(PPh$_3$)$_2$Cl$_2$ (3.51 g, 5.0 mmol), and PPh$_3$ (2.62 g, 10.0 mmol) in anhydrous THF (100 mL) was refluxed overnight under an atmosphere of Ar. The reaction mixture was concentrated and the residue was diluted with water (50 mL) and EtOAc (150 mL). The organic layer was washed with brine and dried with anhydrous Na$_2$SO$_4$. The solvent was removed and the residue was purified by silica gel column chromatography (Petroleum ether/EtOAc=10/1 (v/v)) to give compound 53 (10.0 g, 98%) as a yellow oil. LC-MS (ESI): m/z 205.1 (M+H)$^+$.

Step b. A mixture of compound 53 (2.4 g, 11.7 mmol) and K$_2$CO$_3$ (4.9 g, 35.3 mmol) in THF (20 mL) and MeOH (20 mL) was stirred at rt for 3 h. The solvent was removed and the residue was diluted with EtOAc (150 mL), washed with brine, and dried with anhydrous Na$_2$SO$_4$. The solvent was removed and the residue was purified by silica gel column chromatography (Petroleum ether/acetone=10/1 (v/v)) to give compound 54 (1.3 g, 84%) as a yellow oil. LC-MS (ESI): m/z 133.1 (M+H)$^+$.

Step c. To a solution of compound 55 (25.0 g, 184 mmol) in AcOH (125 mL) was added Br$_2$ (11.0 mL, 220 mmol). After stirring at rt for 4 h, the reaction mixture was filtered. The solid was washed with H$_2$O and dried in vacuo to give compound 56 (38 g, 96%) as a white solid. LC-MS (ESI): m/z 215.0 (M+H)$^+$.

Step d. A mixture of compound 54 (17.9 g, 83.3 mmol), compound 56 (11.0 g, 83.3 mmol), CuI (1.59 g, 0.25 mmol), Et$_3$N (23.00 mL, 166.6 mmol), Pd(PPh$_3$)$_2$Cl$_2$ (2.95 g, 4.20 mmol), and PPh$_3$ (4.40 g, 16.7 mmol) in DMF (100 mL) was stirred at 40° C. overnight under an atmosphere of N$_2$. The reaction mixture was concentrated and the residue was diluted with EtOAc (500 mL). The resulting mixture was washed with brine and dried with anhydrous Na$_2$SO$_4$. The solvent was removed and the residue was purified by silica gel column chromatography (Petroleum ether/EtOAc=10/1 (v/v)) to give compound 57 (9.8 g, 45%). LC-MS (ESI): m/z 267.1 (M+H)$^+$.

Step e. A solution of compound 57 (5.5 g, 21 mmol) in EtOH (100 mL) was added hydroxylamine hydrochloride (1.73 g, 25.0 mmol) and NaOAc (2.05 g, 25.0 mmol), respectively. After stirring at 60° C. for 2 h, the reaction mixture was added K$_2$CO$_3$ (4.3 g, 31 mmol) and H$_2$O (15 mL). The resulting mixture was refluxed for 12 h and then concentrated. The residue was dissolved in EtOAc and the resulting mixture was washed with brine and dried with anhydrous Na$_2$SO$_4$. The solvent was removed and the residue was dried in vacuo to give crude compound 58 (5.8 g). LC-MS (ESI): m/z 282.1 (M+H)$^+$.

Step f. A mixture of compound 58 (100 mg, 0.36 mmol) and 5% Pd/C (75 mg) in EtOH (25 mL) was stirred at rt overnight under an atmosphere of H$_2$. The reaction mixture was filtered through CELITE™545. The filtered cake was washed MeOH (25 mL×3). The filtrate was concentrated and the residue was purified by silica gel column chromatography to give compound 59 (50 mg, 53%). LC-MS (ESI): m/z 266.1 (M+H)$^+$.

Step g. To a solution of compound 59 (2.0 g, 7.5 mmol) in CH$_2$Cl$_2$ (75 mL) was added 4N BBr$_3$ in CH$_2$Cl$_2$ (12 mL, 45 mmol) at −40° C. under an atmosphere of N$_2$. After stirring at rt overnight, the reaction was quenched by adding water (10 mL). Subsequently, the mixture was treated with saturated aqueous NaHCO$_3$ to adjust the pH value to 8. The organic layer was washed with brine and dried with anhydrous Na$_2$SO$_4$. The solvent was removed and the residue was purified by silica gel column chromatography (Petroleum ether/EtOAc=2/1 (v/v)) to give compound 60 (1.36 g, 76%) as a white solid. LC-MS (ESI): m/z 238.1 (M+H)$^+$.

Step h. To a solution of substrate 7 (1.36 g, 5.7 mmol) and pyridine (2.03 g, 25.7 mmol) in CH$_2$Cl$_2$ (120 mL) was added Tf$_2$O (5.84 g, 20.7 mmol) in CH$_2$Cl$_2$ (30 mL) at 0° C. After stirring at 0° C. for 30 min, the reaction mixture was concentrated and the residue was purified by silica gel column chromatography (Petroleum ether/EtOAc=10/1 (v/v)) to give compound 61 (2.4 g, 84%) as a yellow solid. LC-MS (ESI): m/z 502.0 (M+H)$^+$.

Step i. A mixture of compound 61 (2.0 g, 4.0 mmol), bis(pinacolato)diboron (5.1 g, 20 mmol), potassium acetate (2.7 g, 28 mmol), and Pd(dppf)Cl$_2$ (0.98 g, 1.2 mmol) and dioxane (80 mL) was stirred at 80° C. overnight under an atmosphere of Ar. Subsequently, the reaction mixture was diluted with EtOAc (100 mL). The resulting mixture was washed with H$_2$O (50 mL) and dried with anhydrous Na$_2$SO$_4$. The solvent was removed and the residue was purified by silica gel column chromatography (Petroleum ether/acetone=10/1 (v/v)) to give compound 62 (986 mg, 54% yield). LC-MS (ESI) m/z: 458.3 (M+H)$^+$. (The corresponding boronic acid was also isolated and used as an active intermediate for the next step).

Step j. A solution of compound 62 (1.7 g, 3.7 mmol) in DME/H$_2$O (3/1(v/v); 40 mL) was sequentially added (S)-tert-butyl 2-(5-iodo-1H-imidazol-2-yl)pyrrolidine-1-carboxylate (3.70 g, 10.0 mmol), NaHCO$_3$ (2.7 g, 32 mmol), and Pd(dppf)

Cl$_2$ (0.65 mg, 0.80 mmol) at rt under an atmosphere of Ar. After stirring at 80° C. overnight under an atmosphere of Ar, the reaction mixture was diluted with EtOAc (150 mL). The organic layer was isolated, washed with brine, and dried with anhydrous Na$_2$SO$_4$. The solvent was removed and the residue was purified by silica gel column chromatography (Petroleum ether/acetone=2/1(v/v)) to give compound 63 (650 mg, 26%) as a yellow solid. LC-MS (ESI): m/z 676.4 (M+H)$^+$.

Step k. To a stirred solution of compound 63 (200 mg, 0.3 mmol) in dioxane (3 mL) was added 4N HCl in dioxane (3 mL) at rt. After stirring at rt overnight, the reaction mixture was concentrated and the residue was dried in vacuo to give an HCl salt, which was used for the next without further purification. LC-MS (ESI): m/z 476.2 (M+H)$^+$.

Step l. Subsequently, a mixture of the HCl salt in DMF (3 mL) was added DIPEA (0.5 mL, 3.0 mmol), followed by N-Moc-L-Val-OH (130 mg, 0.740 mmol), and HATU (281 mg, 0.740 mmol). After stirring at rt for 30 min, the reaction mixture was poured into H$_2$O. The solid was collected by filtration and purified by preparative HPLC to give compound 64. $^1$H NMR (500 MHz, CD$_3$OD) δ ppm 9.80 (s, 1H), 8.87-8.71 (m, 2H), 8.41-8.18 (m, 6H), 8.05-7.80 (m, 3H), 5.30-5.27 (m, 2H), 4.25 (s, 2H), 4.12 (s, 2H), 4.03-3.90 (m, 2H), 3.66 (s, 6H), 2.61 (s, 2H), 2.31-2.08 (m, 8H), 1.09-0.90 (m, 12H); LCMS (ESI): m/z 790.4 (M+H)$^+$.

Scheme 3-8

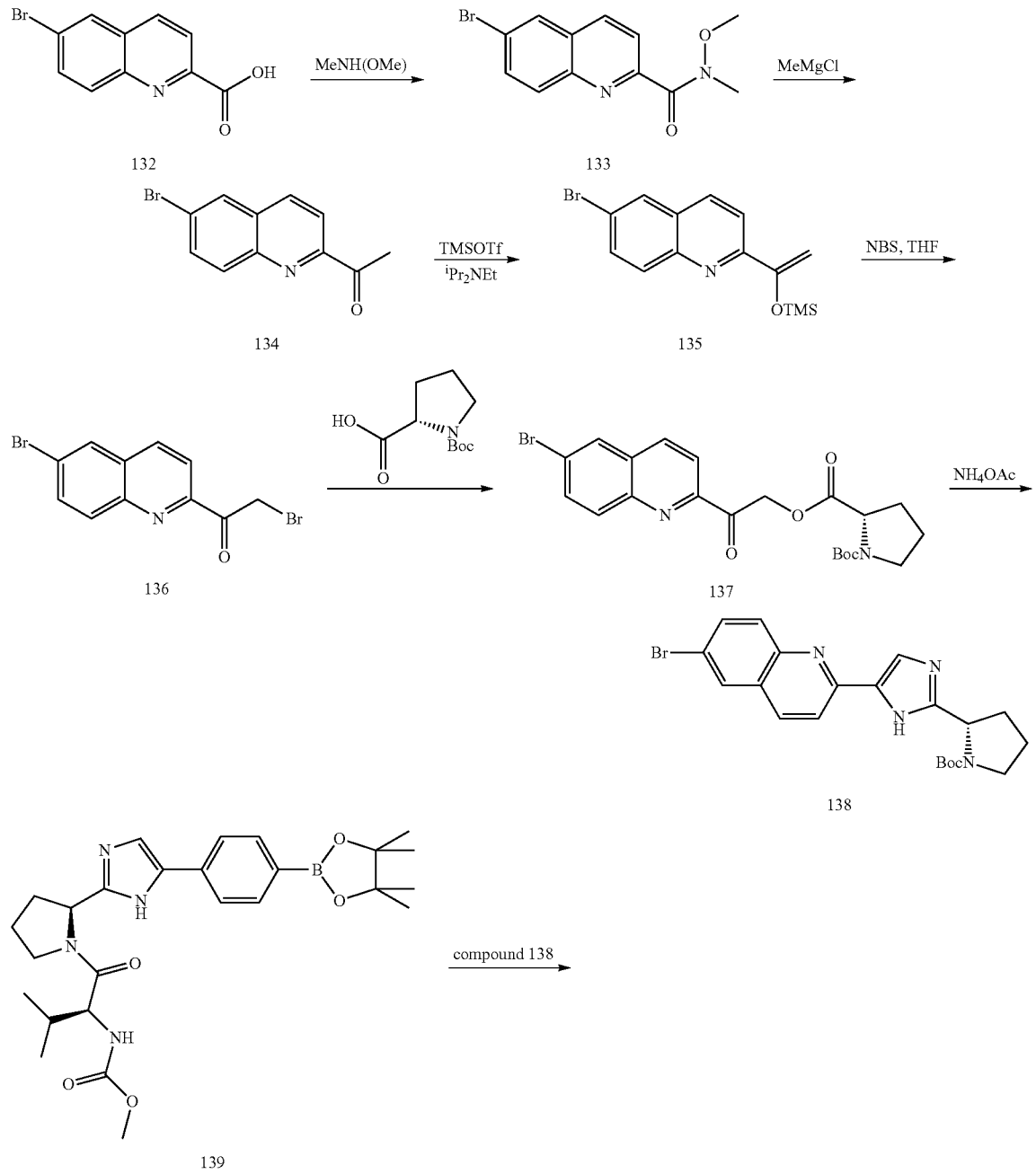

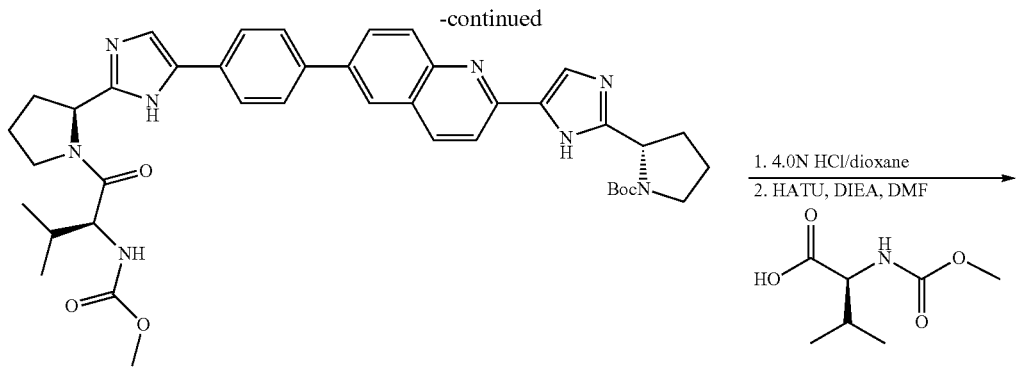

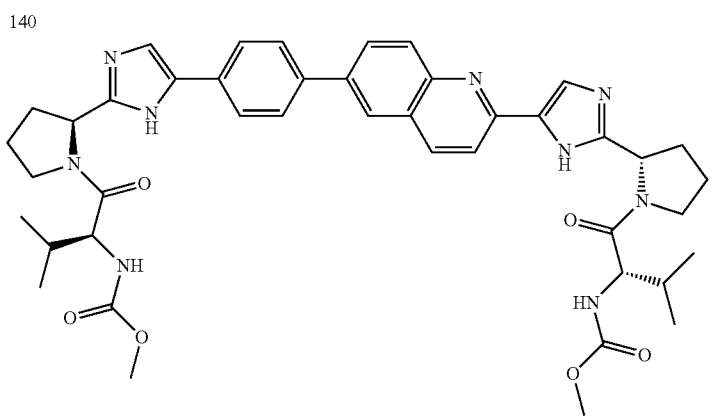

140

141

Step a. Referring to Scheme 3-8, to a solution of 132 (3.70 g, 14.7 mmol) in DMF (50 mL) at rt, N,O-Dimethylhydroxylamine hydrochloride (1.46 g, 15.0 mmol), HATU (6.15 g, 16.2 mmol), and Et₃N (2.22 g, 22.0 mmol) were added. After stirring at rt for 24 h, the reaction mixture was concentrated and the residue was diluted with DCM (150 mL). The mixture was washed with saturated aqueous NH₄Cl and brine, respectively, and dried with anhydrous Na₂SO₄. The solvent was removed and the residue was purified by silica gel column chromatography (Petroleum ether/EtOAc=4/1 (v/v)) to give compound 133 (3.78 g, 87% yield) as a yellow solid. LC-MS (ESI): m/z 295.0 (M+H)⁺.

Step b. To a solution of compound 133 (3.53 g, 12.0 mmol) in THF (80 mL) was slowly added 3M MeMgCl in THF (6 mL) at 0° C. After stirring at 0° C. for 1 h and then at rt for another 1 h, the reaction was quenched by adding saturated aqueous NH₄Cl. The reaction mixture was concentrated and the residue was added saturated aqueous NaHCO₃ (25 mL) and EtOAc (100 mL). The organic phase was washed with brine and dried with anhydrous Na₂SO₄. The solvent was removed and the residue was dried in vacuo to give compound 134 (3.0 g, 100%) as a white solid. LC-MS (ESI): m/z 250.0 (M+H)⁺.

Step c. To a solution of compound 134 (2.80 g, 11.2 mmol) in DCM (80 mL) was added ⁱPr₂NEt (5.79 g, 44.8 mmol). The mixture was cooled to 0° C. and TMSOTf (7.47 g, 33.6 mmol) was drop-wisely added. After stirring at 0° C. for 30 min and then at rt for another 1 h, the reaction mixture was washed with saturated aqueous NaHCO₃ and brine, respectively, and dried with anhydrous Na₂SO₄. The solvent was removed and the residue was dried in vacuo to give crude compound 135 (3.6 g), which was used for the next step without further purification. LC-MS (ESI): m/z 322.0 (M+H)⁺.

Step d. To a solution of compound 135 (3.60 g, 11.2 mmol) in THF (60 mL) was drop-wisely added solution of NBS (1.79 g, 10.1 mmol) in THF (20 mL) at 0° C. After stirring at 10° C. for 1 h, the reaction mixture was concentrated and the residue was diluted with DCM (150 mL). The mixture was washed with brine and dried with anhydrous Na₂SO₄. The solvent was removed and the residue was dried in vacuo to give crude compound 136 (3.6 g), which was used of the next step without further purification. LC-MS (ESI): m/z 327.9 (M+H)⁺.

Step e. To a solution of compound 136 (3.6 g, 10.9 mmol) in EtOAc (100 mL) at rt, (S)—N-Boc-Pro-OH (2.47 g, 11.5 mmol) and Et₃N (3.31 g, 32.7 mmol) were added. After stirring at rt for 5 h, the reaction mixture was washed with saturated aqueous NaHCO₃ and brine, respectively, and dried with anhydrous Na₂SO₄. The solvent was removed and the residue was dried in vacuo to give crude compound 137 (5.0 g), which was used for the next step without further purification. LC-MS (ESI): m/z 463.1 (M+H)⁺.

Step f. A mixture of crude compound 137 (5.0 g) and NH₄OAc (8.39 g, 109 mmol) in toluene (100 mL) was stirred at 115° C. overnight. The solvent was removed and the residue was diluted with EtOAc (200 mL). The mixture was washed with water and dried with anhydrous Na₂SO₄. The solvent was removed and the residue was purified by silica gel column chromatography (Petroleum ether/EtOAc=3/1 (v/v)) to give compound 138 (1.2 g, 25%) as a white solid. LC-MS (ESI): m/z 443.1 (M+H)⁺.

Step g. To a mixture of compound 138 (442 mg, 1.00 mmol), compound 139 (546 mg, 1.10 mmol), and NaHCO₃ (336 mg, 4.00 mmol) in 1,2-dimethoxyethane (8 mL) and H₂O (2 mL) was added Pd(dppf)Cl₂·CH₂Cl₂ (163 mg, 0.20 mmol) under an atmosphere of N₂. After stirring at 80° C.

overnight, the reaction mixture was concentrated and the residue was diluted with EtOAc (50 mL) and H₂O (10 mL). The organic phase was washed with brine and dried with anhydrous Na₂SO₄. The solvent was removed and the residue was purified by silica gel column chromatography (Petroleum ether/EtOAc=1/2 (v/v)) to give compound 140 (500 mg, 68% yield) as a yellow solid. LC-MS (ESI): m/z 733.4 (M+H)⁺.

Step h. To a solution of compound 140 (139 mg, 0.19 mmol) in dioxane (2 mL) was added 4N HCl in dioxane (2.0 mL). After stirring at rt for 2 h, the reaction mixture was concentrated and the residue was dissolved in water (5 mL) and added saturated aqueous NaHCO₃ to adjust pH value to 8. The resulting mixture was saturated with NaCl and extracted with DCM (15 mL×5). The extracts were combined and dried with dried with anhydrous Na₂SO₄. The solvent was removed and the residue was dried in vacuo to give a free base, which was used for the next step without further purification. LC-MS (ESI): m/z 633.3 (M+H)⁺.

Step i. Subsequently, the free base was dissolved in DCM (5 mL) and the mixture was added N-Moc-L-Val-OH (40 mg, 0.23 mmol) and DIC (29 mg, 0.23 mmol). After stirring at rt for 20 min, the reaction mixture was concentrated and the residue was purified by preparative HPLC to give compound 141. LC-MS (ESI): m/z 790.4 (M+H)⁺.

Scheme 4-1

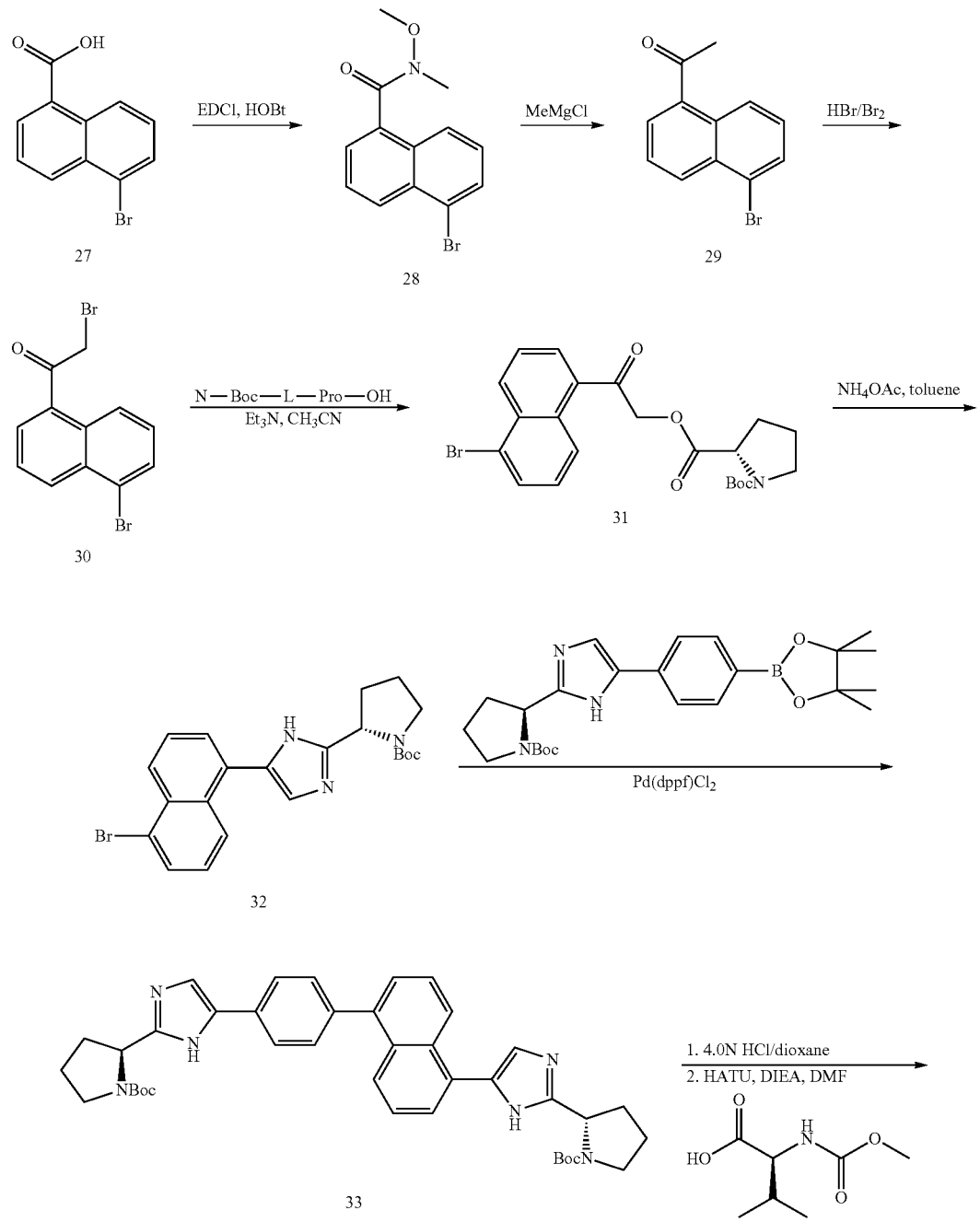

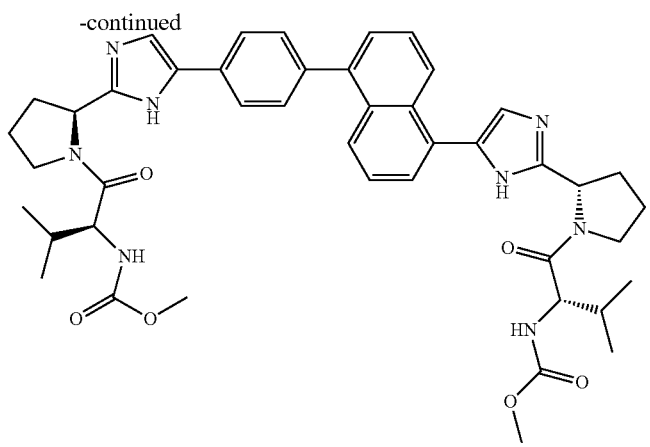

34

Example 4

Synthesis of Compounds of Formula IIe

Step a. Referring to Scheme 4-1, a solution of compound 27 (5.0 g, 20 mmol) in $CH_3CN$ (200 mL) was added EDCI (5.8 g, 30 mmol), HOBt (675 mg, 30 mmol), MeNH(OMe).HCl (2.93 g, 30 mmol), and $Et_3N$ (6.1 g, 60 mmol) at rt. After stirring at rt for 3 h, the reaction mixture was concentrated and the residue was purified by silica gel column chromatography (Petroleum ether/EtOAc=5/1 (v/v)) to give compound 28 (5.4 g, 92% yield) as a white solid. LC-MS (ESI): m/z 294.0 $(M+H)^+$.

Step b. To a solution of compound 28 (2.9 g, 10 mmol) in THF (100 mL) was slowly added 3M MeMgCl in THF (20 mmol) at 0° C. under an atmosphere of $N_2$. After stirring at 0° C. for 1 h and then at rt for 1 h, the reaction was quenched by adding several drops of aq. $NH_4Cl$. The reaction mixture was concentrated and the residue was diluted with EtOAc (100 mL). The organic phase was washed with sat. aq. $NaHCO_3$ and dried with anhydrous $Na_2SO_4$. The solvent was removed and the residue was purified by silica gel column chromatography (Petroleum ether/AcOEt=10:1(v/v)) to give compound 29 (2.3 g, 92% yield). LC-MS (ESI): m/z 249.0 $(M+H)^+$.

Step c. To a solution of 29 (1.84 g, 7.4 mmol) in DCM (100 mL) was drop-wisely added $Br_2$ (18.8 g, 14.7 mmol) at 0° C. After stirring at 0° C. for 30 min, the reaction mixture was warmed to rt with stirring for another 2 h. Subsequently, the reaction mixture was respectively washed with water, and saturated aqueous $NaHCO_3$, and the organic phase was dried with anhydrous $Na_2SO_4$. The solvent was removed and the residue was dried in vacuo to give crude compound 30 (2.0 g) as a yellow solid, which was used for the next step without further purification. LC-MS (ESI): m/z 326.9 $(M+H)^+$.

Step d. A solution of compound 30 (1.95 g, 5.9 mmol) in DCM (50 mL) was added N-Boc-L-Pro-OH (1.6 g, 7.3 mmol) and $Et_3N$ (1.7 mL, 12.2 mmol) at rt. After stirring st rt for 2 h, the reaction mixture was washed with saturated $NH_4Cl$, and brine, respectively; the organic phase was dried with anhydrous $Na_2SO_4$. The solvent was removed and the residue was dried in vacuo to give crude compound 31 (2.4 g), which was used for the next step without further purification. LC-MS (ESI): m/z 462.1 $(M+H)^+$.

Step e. A mixture of compound 31 (2.4 g, 5.2 mmol) and $NH_4OAc$ (4.0 g, 52 mmol) in toluene (52 mL) stirred at 110° C. overnight. Subsequently, the reaction mixture was cooled to rt and diluted with EtOAc (100 mL). The mixture was washed with saturated aqueous $Na_2CO_3$ (50 mL×2), and brine, respectively; the organic phase was dried with anhydrous $Na_2SO_4$. The solvent was removed and the residue was purified by silica gel column chromatography (Petroleum ether/EtOAc=1/1 (v/v)) to give compound 32 (1.4 g, 62%) as a yellow solid. LC-MS (ESI): m/z 442.1 $(M+H)^+$.

Step f. To a mixture of compound 32 (1.0 g, 2.3 mmol), (S)-tert-butyl 2-(5-(4-(4,4,5,5-tetramethyl-1,3,2-dioxaborolan-2-yl)-1H-imidazol-2-yl)pyrrolidine-1-carboxylate (1.0 g, 2.3 mmol), and $NaHCO_3$ (0.76 g, 9.0 mmol) in 1,2-dimethoxyethane (30 mL) and $H_2O$ (10 mL) was added $Pd(dppf)Cl_2$ (277 mg, 0.34 mmol) under an atmosphere of $N_2$. After stirring at 80° C. overnight under an atmosphere of $N_2$, the reaction mixture was concentrated. The residue was diluted with $H_2O$ (50 mL) and the aqueous phase was extracted with EtOAc (50 mL×3). The extracts were combined and washed with brine and dried with anhydrous $Na_2SO_4$. The solvent was removed and the residue was purified by silica gel column chromatography (Petroleum ether/EtOAc=5/2 (v/v)) to give compound 33 (1.0 g, 78% yield) as a yellow solid. LC-MS (ESI): m/z 675.4 $(M+H)^+$.

Step g. To a stirred solution of compound 33 (250 mg, 0.37 mmol) in dioxane (3 mL) was drop-wisely added 4.0N HCl in dioxane (3 mL) at rt. After stirring at rt for 4 h, the reaction mixture was concentrated and the residue was dried in vacuo to give an HCl salt, which was used for the next step without further purification. LC-MS (ESI): m/z 475.3 $(M+H)^+$.

Step h. Subsequently, the HCl salt was suspended in THF (5 mL) and DIPEA (0.35 mL) and N-Moc-L-Val-OH (130 mg, 0.74 mmol) at rt. After stirring at rt for 15 min, HATU (340 mg, 0.89 mmol) was added and the resulting reaction mixture was stirred at rt for another 2 h. The solvent was removed and the residue was purified by preparative HPLC to give compound 34. $^1H$ NMR (500 MHz, $CDCl_3$) δ 8.04-8.06 (m, 1H), 7.96-7.99 (m, 2H), 7.91-7.92 (m, 2H), 7.79 (s, 1H), 7.70-7.71 (m, 2H), 7.66-7.67 (m, 2H), 7.60-7.61 (m, 2H), 5.29-5.31 (m, 2H), 4.27 (s, 2H), 4.13 (s, 2H), 3.92 (s, 2H), 3.68 (s, 6H), 2.63 (s, 2H), 2.17-2.32 (m, 6H), 2.12 (s, 2H), 0.93-0.97 (m, 12H) ppm; LC-MS (ESI): m/z 789.4 $(M+H)^+$.

Example 5

Synthesis of Compounds of Formula IIl1

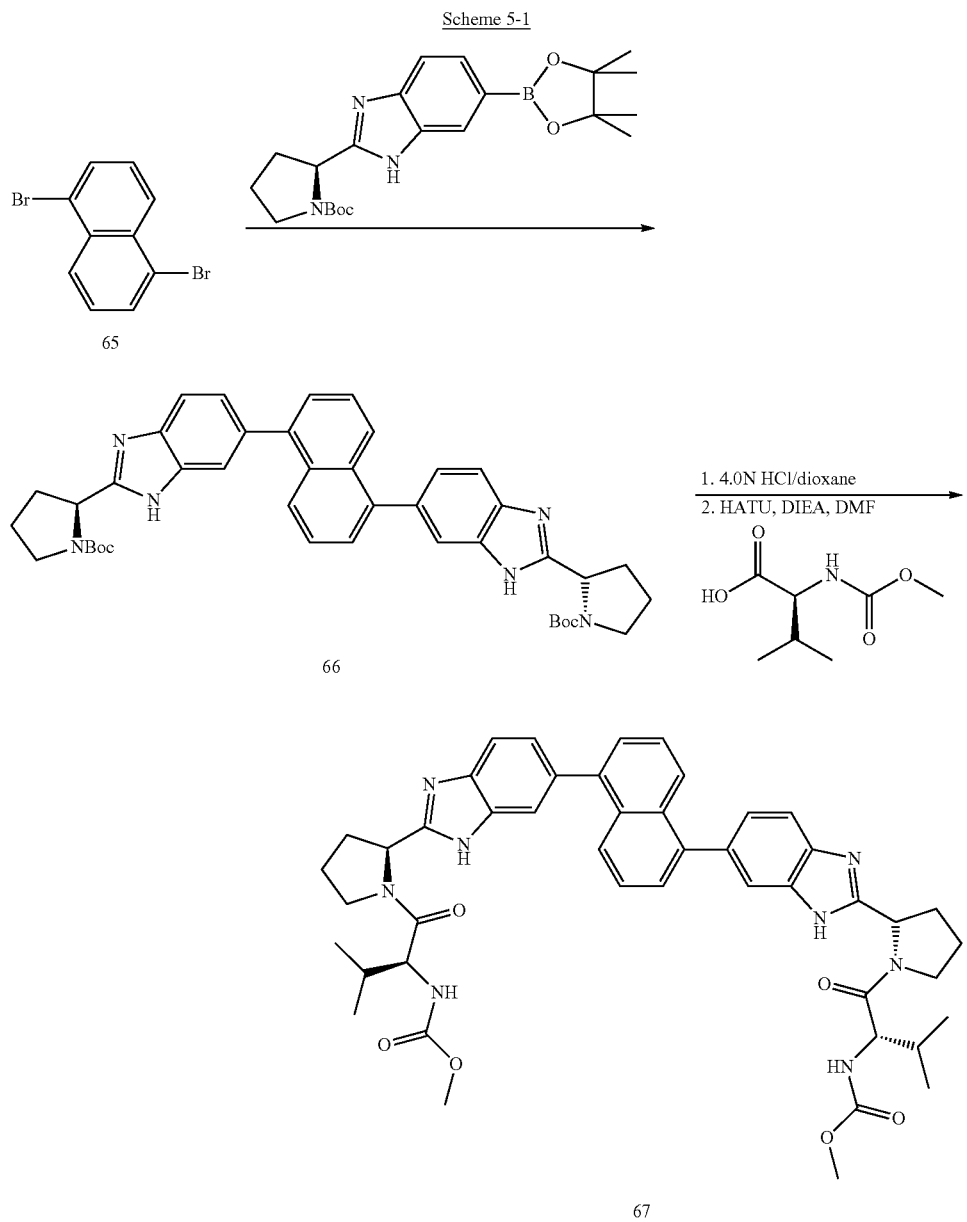

Step a. Referring to Scheme 5-1, a mixture of compound 65 (300 mg, 1.05 mmol), (S)-tert-butyl 2-(6-(4,4,5,5-tetramethyl-1,3,2-dioxaborolan-2-yl)-1H-benzo[d]imidazol-2-yl)pyrrolidine-1-carboxylate (1.14 g, 2.75 mmol), and NaHCO$_3$ (740 mg, 8.80 mmol) in 1,2-dimethoxyethane (30 mL) and water (10 mL) were added Pd(dppf)Cl$_2$ (179 mg, 0.220 mmol) at rt under an atmosphere of N$_2$. After stirring at 80° C. overnight, the reaction mixture was concentrated. The residue was diluted with DCM (100 mL) and water (25 mL). The organic layer was washed with brine and dried with anhydrous Na$_2$SO$_4$. The solvent was removed and the residue was purified by silica gel column chromatography (Petroleum ether/acetone=2/1 (v/v)) to give compound 66 (650 mg, 86%). LC-MS (ESI): m/z 699.4 (M+H)$^+$.

Step b. To a solution of compound 66 (110 mg, 0.16 mmol) in dioxane (2 mL) was added 4.0 N HCl in dioxane (2 mL) at rt. After stirring at rt for 3 h, the reaction mixture was concentrated and the residue was dried in vacuo to give an HCl salt, which was used directly for the next step without further purification. LC-MS (ESI): m/z 499.3 (M+H)$^+$.

Step c. Subsequently, the HCl salt was dissolved in DMF (2 mL), followed by adding DIPEA (207 mg, 16 mmol), N-Moc-L-Val-OH (68 mg, 0.39 mmol), and HATU (148 mg, 0.39 mmol) at rt. After stirring at rt for 15 min, the reaction mixture was added into water. The solid was collected by filtration and purified by preparative HPLC to give compound 67. LC-MS (ESI) m/z 813.4 (M+H)$^+$.

Example 6
Synthesis of Compounds of Formula IIId
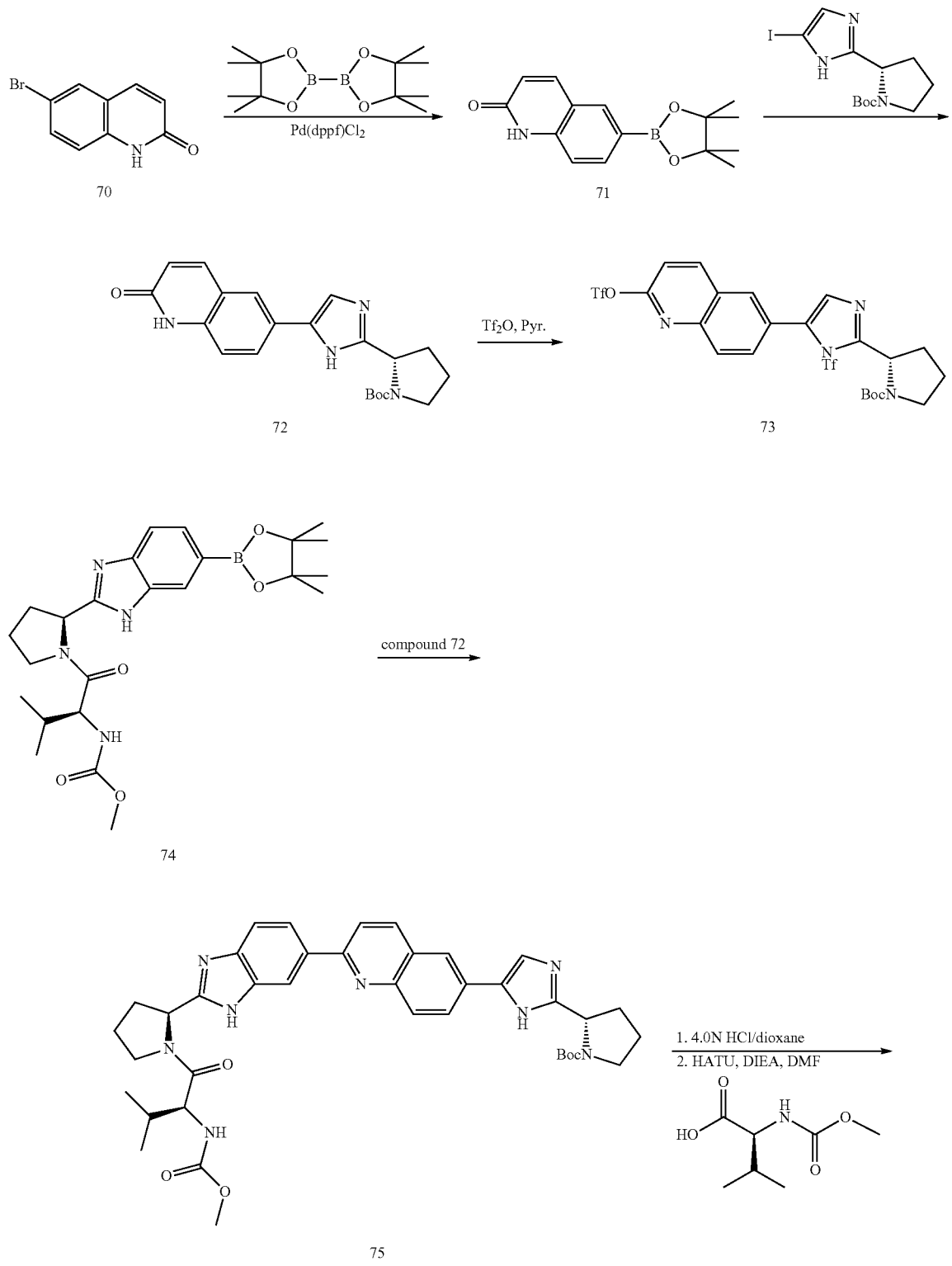
Scheme 6-1

-continued

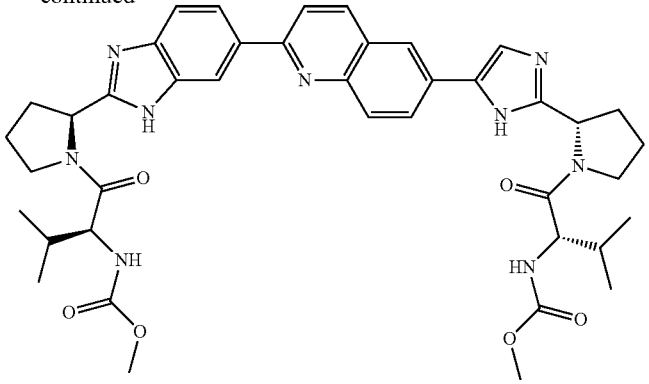

76

Step a. Referring to Scheme 6-1, a mixture of compound 70 (8.00 g, 35.7 mmol, purchased from Aldrich Chemicals, Milwaukee, Wis., USA), bis(pinacolato)diboron (10.9 g, 42.8 mmol), $K_2CO_3$ (10.50 g, 107.1 mmol) in 1,4-dioxane (600 mL) was added Pd(dppf)$Cl_2$ (2.9 g, 3.6 mmol) at rt under an atmosphere of $N_2$. After stirring at 80° C. for 3 h under an atmosphere of $N_2$, the reaction mixture was cooled to rt and filtered through Celiirt®545. The filtered cake was washed with EtOAct (100 mL×3). The filtrate was concentrated and the residue was diluted with EtOAc (500 mL). The resulting mixture was washed with brine and dried with anhydrous $Na_2SO_4$. The solvent was removed and the residue was purified by silica gel column chromatography (Petroleum ether/Acetone=1/1 (v/v)) to give compound 71 (8.28 g, 86% yield) as a light brown solid. LC-MS (ESI) m/z 272.1 (M+H)$^+$.

Step b. To a mixture of compound 71 (5.90 g, 21.8 mmol), (S)-tert-butyl 2-(5-iodo-1H-imidazol-2-yl)pyrrolidine-1-carboxylate (9.50 g, 26.2 mmol), $NaHCO_3$ (7.30 g, 87.2 mmol) in 1,2-dimethoxyethane (500 mL) and water (150 mL) was added Pd(dppf)$Cl_2$ (3.6 g, 4.4 mmol) under an atmosphere of $N_2$. After stirring at 80° C. overnight, the reaction mixture was concentrated and the residue was diluted with EtOAc (250 mL) and water (50 mL). The organic layer was washed with brine and dried with anhydrous $Na_2SO_4$. The solvent was removed and the residue was purified by silica gel column chromatography (DCM/MeOH=5/1 (v/v)) to give compound 72 (5.30 g, 64% yield) as a yellow solid. LC-MS (ESI) m/z 381.2 (M+H)$^+$.

Step c. To a solution of compound 72 (2.0 g, 5.26 mmol) in 40 mL pyridine was drop-wisely added $Tf_2O$ (3.71 g, 13.1 mmol) at 0° C. After stirring at 0° C. for 1 h and at rt for 3 h, the reaction mixture was concentrated. The residue was purified by silica gel column chromatography (Petroleum ether/acetone=4/1 (v/v)) to give compound 73 (2.04 g, 60% yield) as a yellow solid. LC-MS (ESI) m/z 645.1 (M+H)$^+$.

Step d. To a mixture of compound 73 (500 mg, 0.78 mmol), methyl (S)-3-methyl-1-oxo-1-((S)-2-(6-(4,4,5,5-tertamethyl-1,3,2-dioxaborolan-2-yl)-1H-benzo[d]imidazol-2-yl)butan-2-ylcarbamate (74) (419 mg, 0.89 mmol), and $NaHCO_3$ (299 g, 3.56 mmol) in 1,2-dimethoxyethane (60 mL) and water (20 mL) was added Pd(dppf)$Cl_2$ (147 mg, 0.18 mmol) at rt under an atmosphere of $N_2$. After stirring at 80° C. overnight under an atmosphere of $N_2$, the reaction mixture was concentrated. The residue was diluted with EtOAc (100 mL) and water (25 mL). The organic layer was washed with brine and dried with anhydrous $Na_2SO_4$. The solvent was removed and the residue was purified by silica gel column chromatography (Petroleum ether/acetone=1:1 (v/v)) to give compound 75 (0.40 g, 64% yield) as a yellow solid. LC-MS (ESI) m/z 707.4 (M+H)$^+$.

Step e. To a solution of compound 75 (114 mg, 0.161 mmol) in dioxane (2 mL) was added 4N HCl in dioxane (2 mL) at rt. After stirring at rt for 3 h, the reaction mixture was concentrated and the residue was dried in vacuo to give an HCl salt, which was used for the next step without further purification. LC-MS (ESI) m/z 607.3 (M+H)$^+$.

Step f. Subsequently, the HCl salt was dissolved in DMF (2 mL), followed by adding $Et_3N$ (0.11 mL, 0.81 mmol), N-Moc-L-Val-OH (32 mg, 0.18 mmol), and HATU (69 mg, 0.18 mmol) at rt. After stirring at rt for 1 h, the reaction mixture was concentrated and the residue was purified by preparative HPLC to give compound 76. LC-MS (ESI): m/z 764.4 (M+H)$^+$.

Scheme 6-2

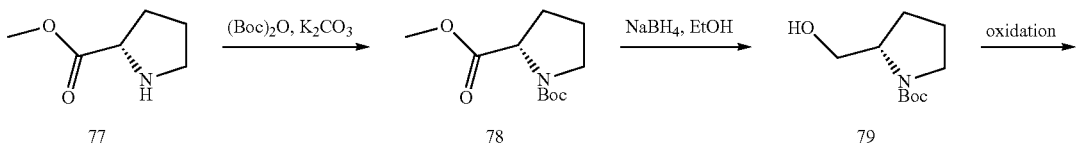

-continued
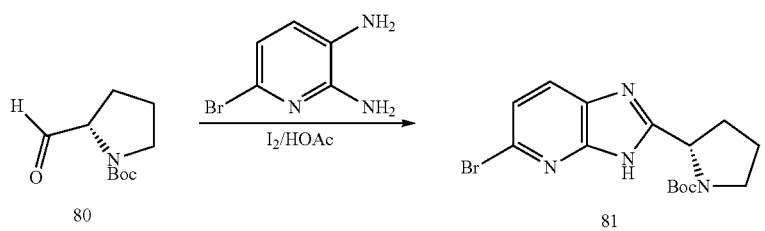
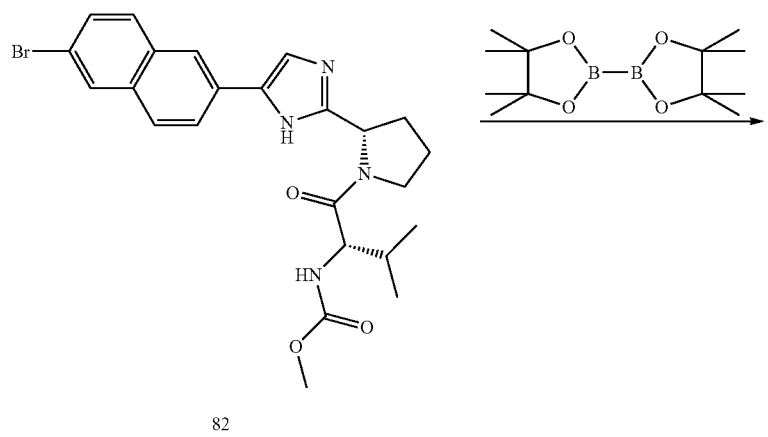
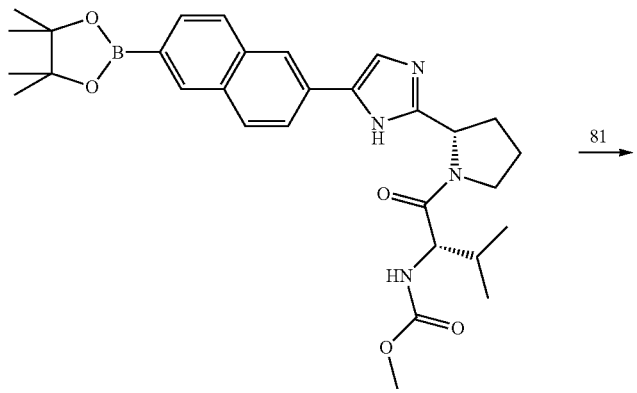
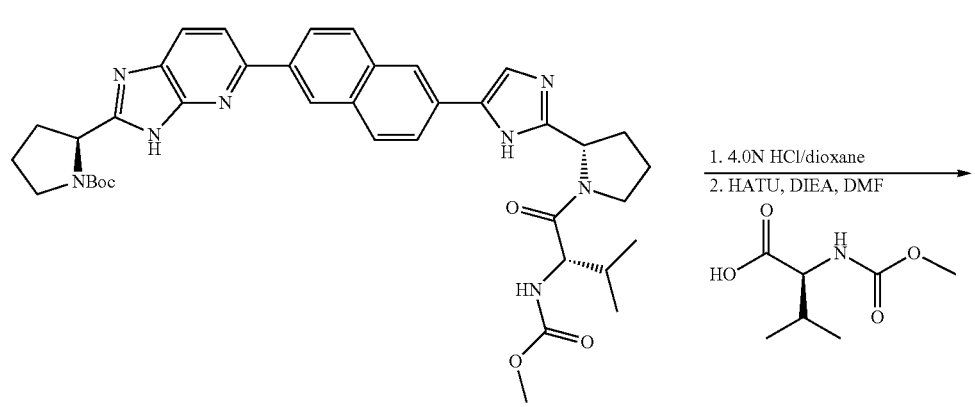

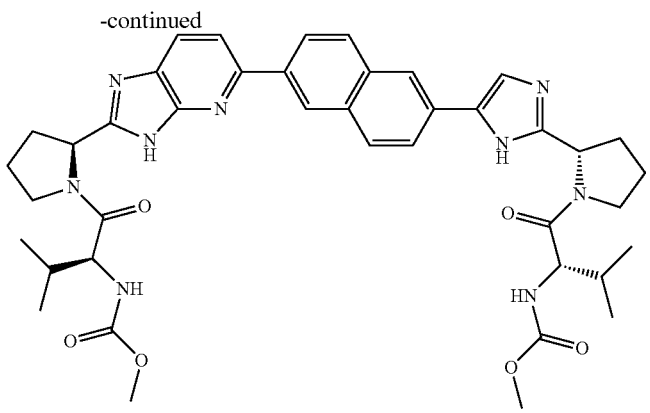

85

Step a. Referring to Scheme 6-2, a solution of compound 78 (50.0 g, 0.30 mol) in THF (500 mL) and H$_2$O (500 mL) was added K$_2$CO$_3$ (83 g, 0.60 mol) and (Boc)$_2$O (73.0 g, 0.330 mol). After stirring at rt overnight, the reaction mixture was concentrated and the residue was extracted with EtOAc (250 mL×3). The extracts were combined, washed with brine, and dried with anhydrous Na$_2$SO$_4$. The solvent was removed and the residue was dried in vacuo to give crude compound 78 (62 g), which was used for the next step without further purification. LC-MS (ESI) m/z 230.1 (M+H)$^+$.

Step b. To a solution of compound 78 (60.0 g, 260 mmol) in EtOH (1 L) was slowly added NaBH$_4$ (50.0 g, 1.30 mol) at rt. After stirring at rt overnight, the reaction was quenched by adding acetone (10 mL). The resulting mixture was concentrated and the residue was diluted with EtOAc (500 mL). The mixture was washed with brined and dried in vacuo. The solvent was removed and the residue was purified by silica gel column chromatography (Petroleum ether/EtOAc=1/1 (v/v)) to give compound 79 (42.0 g, 80% yield) as a white solid. LC-MS (ESI) m/z 202.1 (M+H)$^+$.

Step c. To a solution of compound 79 (30.0 g, 150 mmol) and DMSO (35.0 g, 450 mmol) in DCM (1 L) was added oxalyl chloride (28.0 g, 220 mmol) at −78° C. After stirring at −78° C. for 4 h, the reaction mixture was added Et$_3$N (60.0 g, 600 mol) and the resulting mixture was stirred for another 1 h at −78° C. Subsequently, the reaction was quenched by adding H$_2$O. The organic layer was separated and the aqueous layer was extracted with DCM (200 mL×2). The extracts were combined, washed with brine, and dried with Na$_2$SO$_4$. The solvent was removed and the residue was dried in vacuo to give crude compound 80 (22.0 g) as a colorless oil, which was used immediately without further purification. LC-MS (ESI) m/z 200.1 (M+H)$^+$.

Step d. A mixture of compound 80 (7.7 g, 38.5 mmol), 6-bromopyridine-2,3-diamine (8.0 g, 42.8 mmol) (PCT Intl. Appl. WO 2008021851), and iodine (1.08 g, 4.28 mmol) in AcOH (30 mL) was stirred at rt overnight. The reaction mixture was neutralized by adding saturated aqueous NaHCO$_3$. The resulting mixture was extracted with EtOAc (200 mL×3). The extracts were combined, washed with brine, and dried with anhydrous Na$_2$SO$_4$. The solvent was removed and the residue was purified by silica gel column chromatography (DCM/MeOH=80/1 (v/v)) to give compound 81 (7.8 g, 55% yield). LC-MS (ESI) m/z 367.1 (M+H)$^+$.

Step e. A mixture of compound 82 (10.0 g, 20.1 mmol), bis(pinacolato)diboron (7.65 g, 30.1 mmol), potassium acetate (6.89 g, 70.3 mmol), and Pd(dppf)Cl$_2$.CH$_2$Cl$_2$ (886 mg, 1.0 mmol) in 1,4-dioxane (200 mL) was stirred at 80° C. for 3 h under an atmosphere of N$_2$. The reaction mixture was filtered through CELITE™545 and the filtered cake was washed with EtOAc (200 mL×3). The filtrate was washed with brine and dried with anhydrous Na$_2$SO$_4$. The solvent was removed and the residue was purified by silica gel column chromatography (DCM/MeOH=50/1 (v/v)) to give compound 83 (9.8 g, 89% yield) as a white solid: LC-MS (ESI) m/z 547.3 (M+H)$^+$.

Step f. A mixture of compound 81 (2.0 g, 5.4 mmol), compound 83 (2.9 g, 5.4 mmol), NaHCO$_3$ (1.60 g, 18.9 mmol), and Pd(dppf)Cl$_2$.CH$_2$Cl$_2$ (239 mg, 0.27 mmol) in 1,2-dimethoxyethane (90 mL) and water (30 mL) was stirred at 80° C. overnight under an atmosphere of N$_2$. The reaction mixture was concentrated and the residue was added DCM (200 mL) and water (50 mL). The organic phase was washed with brine and dried with anhydrous Na$_2$SO$_4$. The solvent was removed and the residue was purified by silica gel column chromatography (DCM/MeOH=80/1 (v/v)) to give compound 84 (1.5 g, 40% yield) as a yellow solid. LC-MS (ESI) m/z 707.4 (M+H)$^+$.

Step g. To a solution of compound 84 (200 mg, 0.28 mmol) in 3 mL dioxane was added 4N HCl in dioxane (3 mL). After stirring at rt for 3 h, the reaction mixture was concentrated and the residue was dried in vacuo to give an HCl salt, which was used for the next step without further purification. LC-MS (ESI) m/z 607.3 (M+H)$^+$.

Step h. Subsequently, the HCl salt was dissolved in DMF (3 mL), and the resulting mixture was added Et$_3$N (0.20 mL, 1.4 mmol), N-Moc-L-Val-OH (55 mg, 0.31 mmol), and HATU (118 mg, 0.31 mmol). After stirring at rt for 1 h, the reaction mixture was concentrated and the residue was purified by preparative HPLC to give compound 85. LC-MS (ESI): m/z 764.4 (M+H)$^+$.

Scheme 6-3
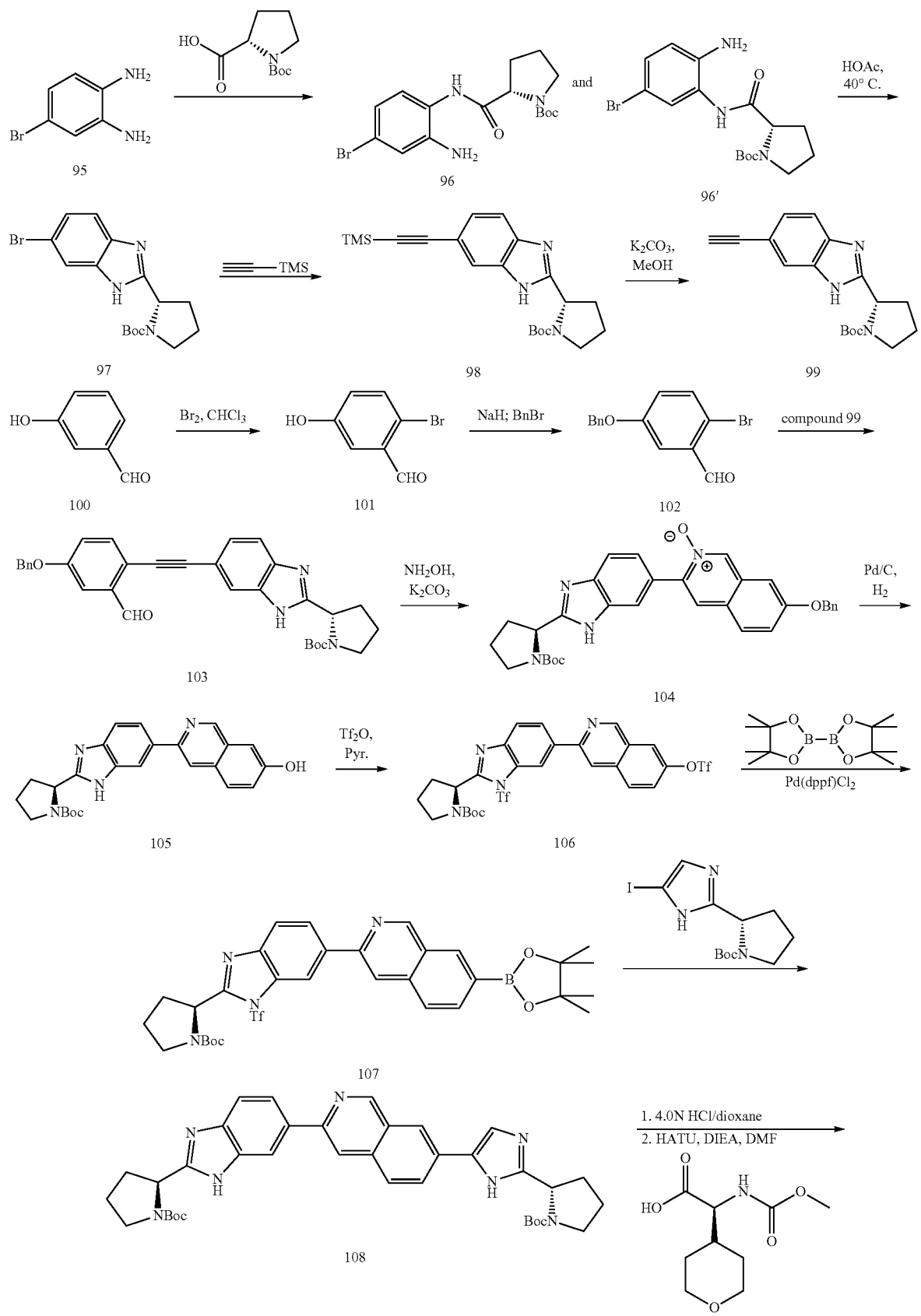

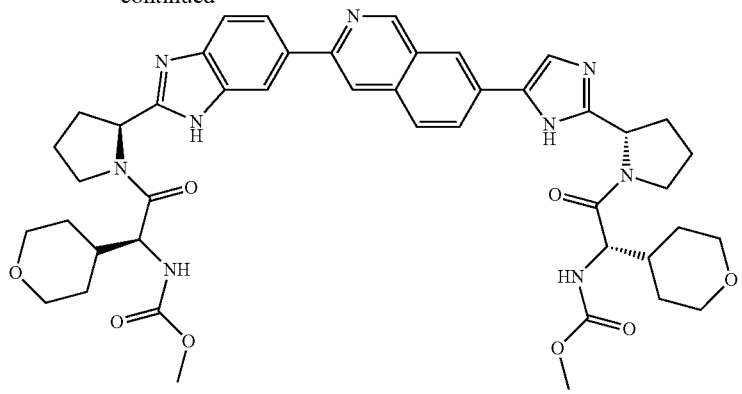

109

Step a. Referring to Scheme 6-3, to a solution of N-Boc-L-Pro-OH (29 g, 135 mmol) and DIPEA (29 g, 225 mmol) in THF (500 mL) was added HATU (51 g, 135 mmol) at rt. After stirring at rt for 10 min, 4-bromobenzene-1,2-diamine (95) (25 g, 135 mmol) was added and the resulting solution was stirred at rt for another several hours. Subsequently, the reaction mixture was concentrated and the residue was diluted with EtOAc (500 mL). The resulting mixture was washed with water for several times (100 mL×3) and dried with anhydrous Na$_2$SO$_4$. The solvent was removed and the residue was dried in vacuo to give a mixture of crude compounds 96 and 96', which were used for the next step without further purification. LC-MS (ESI): m/z 384.1 (M+H)$^+$.

Step b. A mixture of crude compounds 96 and 96' obtained from the reaction above in AcOH (1000 mL) was stirred at 40° C. for 12 h. Subsequently, the reaction mixture was carefully neutralized by adding saturated aqueous sodium bicarbonate solution to adjust the pH value to 8. The resulting mixture was extracted with EtOAc for several times (250 mL×3). The extracts were combined, washed with water, and dried with anhydrous Na$_2$SO$_4$. The solvent was removed and the residue was purified by silica gel chromatography (Petroleum ether/EtOAc=4/1 (v/v)) to give 97 (35 g, 71% yield, two steps from 95) as a yellow solid. LC-MS (ESI): m/z 366.1 (M+H)$^+$.

Step c. A mixture of compound 97 (10.0 g, 27.3 mmol), trimethylsilylacetylene (4.0 g, 41.0 mmol), DIPEA (3.5 g, 27.3 mmol), CuI (220 mg, 1.15 mmol), PPh$_3$ (1.2 g, 4.6 mmol), and Pd(PPh$_3$)$_2$Cl$_2$ (1.6 g, 2.3 mmol) in anhydrous THF (200 mL) was refluxed overnight under an atmosphere of N$_2$. The reaction mixture was concentrated and the residue was diluted with EtOAc (250 mL). The mixture was washed with brine and dried with anhydrous Na$_2$SO$_4$. The solvent was removed and the residue was purified by silica gel column chromatography (Petroleum ether/EtOAc=3/1 (v/v)) to compound 98 (7.8 g, 85% yield). LC-MS (ESI): m/z 384.2 (M+H)$^+$.

Step d. A mixture of compound 98 (7.7 g, 20 mmol) and K$_2$CO$_3$ (27.6 g, 0.2 mol) in THF (150 mL) and MeOH (150 mL) was stirred at rt for 3 h. The reaction mixture was filtered through CELITE™545 and the filtered cake was washed with EtOAc (100 mL×3). The filtrate was concentrated and the residue was diluted with DCM (250 mL). The mixture was washed with brined and dried with anhydrous Na$_2$SO$_4$. The solvent was removed and the residue was purified by silica gel column chromatography (Petroleum ether/acetone=2/1 (v/v)) to give compound 99 (4.7 g, 75% yield). LC-MS (ESI): m/z 312.2 (M+H)$^+$.

Step e. To a solution of m-hydroxybenzaldehyde (100) (30.0 g, 0.24 mol) in dry CHCl$_3$ (245 mL) was slowly added bromine (12.36 mL, 0.24 mol) over 40-45 min at rt. After completion of the addition, the reaction mixture was stirred at rt for 3 h. Subsequently, saturated aqueous NaHCO$_3$ was carefully added to neutralize the mixture. The organic layer was washed with brine and dried with Na$_2$SO$_4$. The solvent was removed and the residue was dried in vacuo to give crude compound 101 (37 g) as a brown solid. LC-MS (ESI): m/z 200.9 (M+H)$^+$.

Step f. To a solution of compound 101 (10 g, 49.8 mol) in anhydrous THF/DMF (5/1 (v/v), 120 mL) was added NaH (2.0 g, 51 mmol, 60% dispersion in mineral oil) at 0° C. under an atmosphere of N$_2$. After stirring at rt for 30 min, the mixture was added benzyl bromide (8.7 mL, 73 mmol) over 20-25 min. The resulting mixture was stirred at rt overnight and the reaction was quenched by adding saturated aqueous NH$_4$Cl (50 mL). The reaction mixture was concentrated and the residue was diluted with EtOAc (150 mL) and water (50 mL). The organic phase was washed with brine and dried with anhydrous Na$_2$SO$_4$. The solvent was removed and the residue was purified by silica gel column chromatography (Petroleum ether/EtOAc=10/1 (v/v)) to give compound 102 (11 g, 77% yield). LC-MS (ESI): m/z 291.0 (M+H)$^+$.

Step g. A mixture of compound 99 (2.80 g, 9.0 mmol), compound 102 (2.6 g, 9.0 mmol), Pd(PPh$_3$)$_2$Cl$_2$ (6.3 g, 0.9 mmol), CuI (2.55 g, 1.34 mmol), Et$_3$N (2.5 mL, 18 mmol), and PPh$_3$ (4.7 g, 1.8 mmol) in DMF (100 mL) was stirred at 60° C. for 12 h. Subsequently, the reaction mixture was concentrated. The residue was diluted with EtOAc (150 mL) and water (50 mL). The organic phase was washed with brined and dried with anhydrous Na$_2$SO$_4$. The solvent was removed and the residue was purified by silica gel column chromatography (Petroleum ether/EtOAc=10/1 (v/v)) to give compound 103 (4.0 g, 86% yield). LC-MS (ESI): m/z 522.2 (M+H)$^+$.

Step h. A solution of compound 103 (4.1 g, 7.9 mmol) in EtOH (100 mL) was added hydroxylamine hydrochloride (650 mg, 9.4 mmol) and NaOAc (770 mg, 9.4 mmol), respectively, at rt. After stirring at 60° C. for 2 h, the reaction mixture was added K$_2$CO$_3$ (1.64 g, 11.85 mmol) and water (20 mL). The resulting mixture was refluxed for 12 h. Subsequently, the reaction mixture was concentrated and the residue was diluted with EtOAc (200 mL) and water (20 mL). The organic phase was washed with brine and dried with anhydrous Na$_2$SO$_4$. The solvent was removed and the residue was purified by silica gel column chromatography (Petroleum ether/

Acetone=5/1 (v/v) to DCM/MeOH=5/1 (v/v)) to give compound 104 (1.5 g, 36% yield). LC-MS (ESI): m/z 537.2 (M+H)+.

Step i. A mixture of compound 104 and 10% Pd/C (1.5 g) in MeOH (50 mL) was stirred at rt overnight under an atmosphere of $H_2$. Subsequently, the reaction mixture was filtered through CELITE™545 and the filtered cake was washed with MeOH (50 mL×3). The filtrate was concentrated and the residue was purified by silica gel column chromatography to give compound 105 (670 mg, 56% yield). LC-MS (ESI): m/z 431.2 (M+H)+.

Step j. To a solution of compound 105 (650 mg, 1.5 mmol) in anhydrous pyridine (711 mg, 9.0 mmol) was added $Tf_2O$ (1.07 g, 3.8 mmol) at 0° C. After stirring at rt overnight, the reaction mixture was concentrated and the residue was diluted with EtOAc (100 mL). The mixture was washed with brine and dried with anhydrous $Na_2SO_4$. The solvent was removed and the residue was purified by silica gel column chromatography (Petroleum ether/EtOAc=5/1 (v/v)) to give compound 106 (720 mg, 69% yield). LC-MS (ESI): m/z 695.1 (M+H)+.

Step k. A mixture of compound 106 (410 mg, 0.6 mmol), bis(pinacolato)diboron (227 mg, 0.9 mmol), $PdCl_2$(dppf).$CH_2Cl_2$ (100 mg, 0.12 mmol), and KOAc (235 mg, 2.4 mmol) in dioxane (15 mL) was stirred at 80° C. for 1 h under an atmosphere of $N_2$. The reaction mixture was used for the next step without any work-up. LC-MS (ESI): m/z 673.2 (M+H)+.

Step l. To the above reaction mixture was added (S)-tert-butyl 2-(5-iodo-1H-imidazol-2-yl)pyrrolidine-1-carboxylate (370 mg, 1.02 mmol), followed by $NaHCO_3$ (201 mg, 2.4 mmol), 1,2-dimethoxyethane (4 mL), water (2 mL), and Pd(dppf)$Cl_2$.$CH_2Cl_2$ (100 mg, 0.12 mmol) under an atmosphere of $N_2$. After stirring at 80° C. for 2 h under an atmosphere of $N_2$, the reaction mixture was added $K_2CO_3$ (691 mg, 5 mmol) and MeOH (20 mL). After stirring at rt for 30 min, the mixture was concentrated. The residue was diluted with EtOAc (150 mL) and water (50 mL). The organic layer was washed with brine and dried with anhydrous $Na_2SO_4$. The solvent was removed and the residue was purified by silica gel column chromatography (Petroleum ether/EtOAc=5/1 (v/v)) to give compound 108 (140 mg, 36% yield; two steps from compound 107). LC-MS (ESI) m/z 650.3 (M+H)+.

Step m. To a solution of compound 108 (135 mg, 0.2 mmol) in dioxane (2 mL) was added 4 N HCl in dioxane (2 mL) at rt. After stirring at rt overnight, the reaction mixture was concentrated and the residue was dried in vacuo to give an HCl salt, which was used for the next step without further purification. LCMS (ESI): m/z 450.2 (M+H)+.

Step n. Subsequently, the HCl salt was dissolved in DMF (2 mL) and the resulting mixture was added DIPEA (0.33 mL, 2.0 mmol), N-THPoc-L-Val-OH (108 mg, 0.50 mmol), and HATU (190 mg, 0.50 mmol). After stirring at rt for 15 min, the reaction mixture was added into ice water. The solid was collected by filtration and purified by preparative HPLC to give compound 109. LC-MS (ESI): m/z 848.4 (M+H)+.

Scheme 6-4

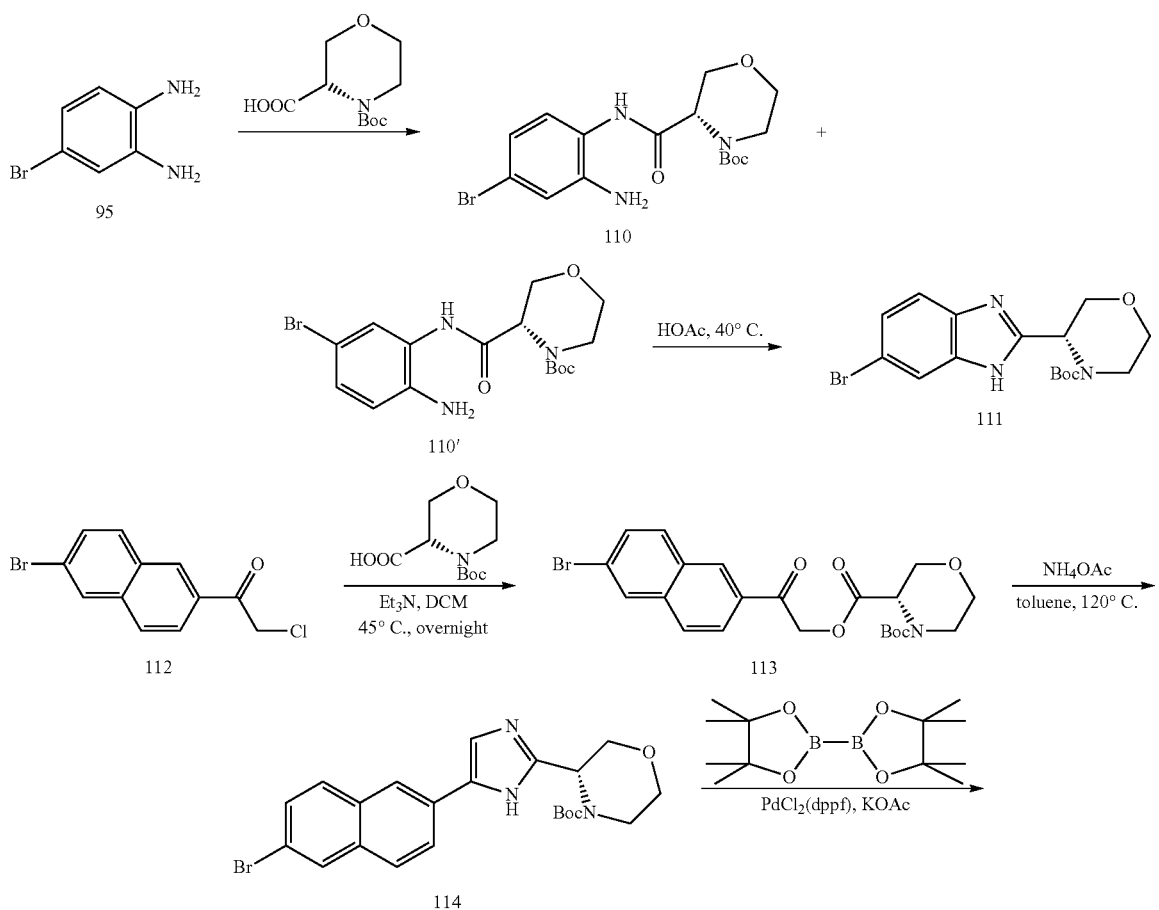

-continued

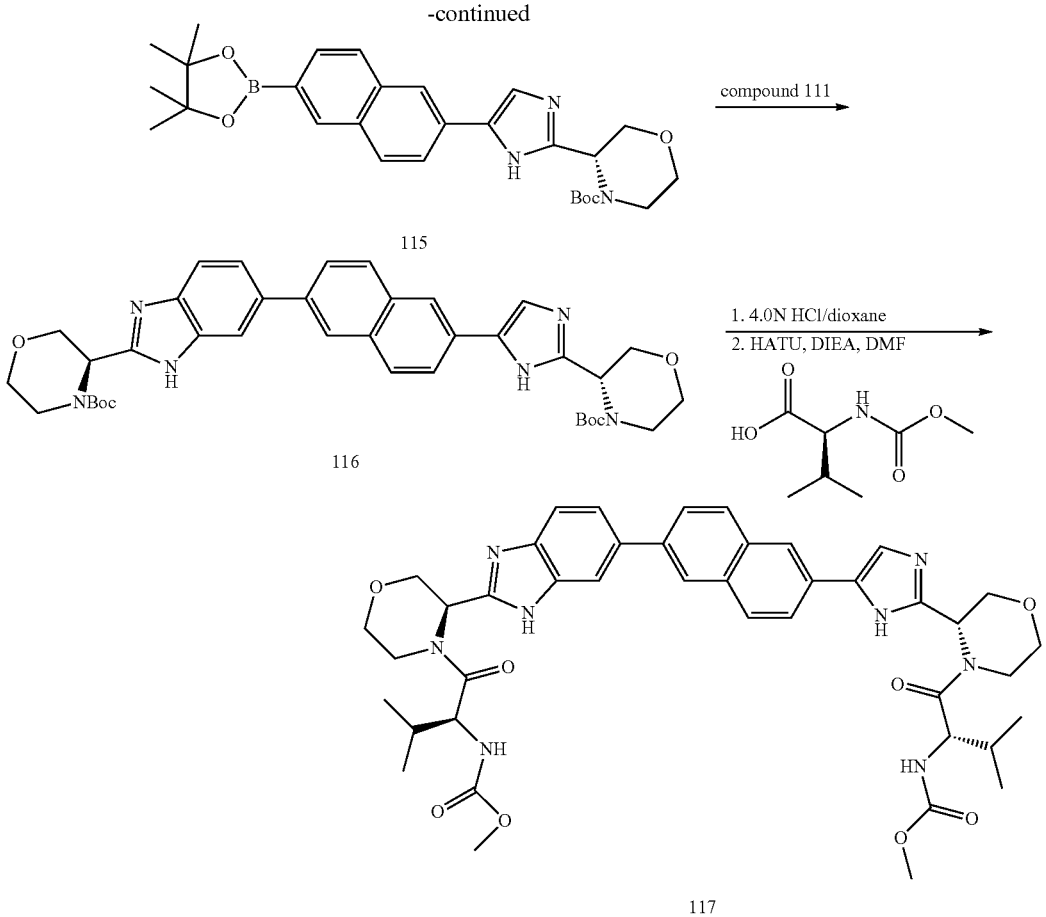

Step a. Referring to Scheme 6-4, to a solution of (S)-4-(tert-butoxycarbonyl)morphine-3-carboxylic acid (4.1 g, 22.0 mmol) and DIPEA (4.3 g, 33.0 mmol) in THF (100 mL) was added compound 95 (4.6 g, 20.0 mmol) at rt. After stirring for 5 min, the reaction mixture was added HATU (7.6 g, 20.0 mmol) was added and the resulting mixture was stirred at rt for 2 h. The reaction mixture was concentrated and the residue was diluted with EtOAc (200 mL) and water (50 mL). The organic phase was washed with brine and dried with anhydrous $Na_2SO_4$. The solvent was removed and the residue was dried in vacuo to give a crude mixture of compounds 110 and 110' (10 g), which was used for the next step without further purification. LC-MS (ESI) m/z 400.1 (M+H)$^+$.

Step b. A mixture of compounds 110 and 110' (10 g) in AcOH (50 mL) was stirred at 40° C. for 16 h. Subsequently, the reaction mixture was added into ice water (200 mL) and neutralized by adding saturated aqueous $Na_2CO_3$ to adjust pH value to pH 8. The resulting mixture was extracted with EtOAc (100 mL×3) and the extracts were combined, washed with brine, and dried with anhydrous $Na_2SO_4$. The solvent was removed and the residue was purified by silica gel column chromatography (Petroleum ether/EtOAc=1/3 (v/v)) to give compound 111 (4.5 g, 60% yield; two steps from 95) as a yellow solid. LC-MS (ESI) m/z 382.1 (M+H)$^+$.

Step c. A solution of 1-(6-bromonaphthalen-2-yl)-2-chloroethanone (112) (27.0 g, 95.2 mmol) in DCM (200 mL) was added (S)-4-(tert-butoxycarbonyl)morphine-3-carboxylic acid (20.0 g, 86.6 mmol) and $Et_3N$ (60.0 mL, 433 mmol), respectively. After stirring at 45° C. overnight, the reaction mixture was washed with saturated aqueous $NaHCO_3$ (50 mL), saturated aqueous $NH_4Cl$ (50 mL), and brine, respectively, and dried with anhydrous $Na_2SO_4$. The solvent was removed and the residue was dried in vacuo to give crude compound 113 (41.4 g), which was used for next step without further purification. LC-MS (ESI) m/z 478.1 (M+H)$^+$.

Step d. A mixture of crude compound 113 (41.4 g) and $NH_4OAc$ (100 g, 1.30 mol) in toluene (300 mL) was stirred at 120° C. overnight. The reaction mixture was concentrated and the residue was diluted with EyOAc (500 mL). The mixture was washed with water and dried with anhydrous Na2SO4. The solvent was removed and the residue was purified by silica gel column chromatography (Petroleum ether/acetone=6/1 tot/1 (v/v)) to give compound 114 (24 g, 61% yield; two steps from 112) as a yellow solid. LC-MS (ESI): m/z 458.1 (M+H)$^+$.

Step e. A mixture of compound 114 (3 g, 6.55 mmol), bis(pinacolato)diboron (1.83 g, 7.2 mmol), and $K_2CO_3$ (1.67 g, 17.03 mmol) in 1,4-dioxane (100 mL) was added Pd(dppf)$Cl_2$.DCM (0.8 g, 0.98 mmol) under an atmosphere of $N_2$. After stirring at 80° C. overnight under an atmosphere of $N_2$, the reaction mixture was filtered through CELITE™545 and the filtered cake was washed with EtOAc (100 mL×3). The filtrate was washed with brine and dried with anhydrous $Na_2SO_4$. The solvent was removed and the residue was purified by silica gel column chromatography (DCM/MeOH=50/1(v/v)) to give compound 115 (2.0 g, 61% yield). LC-MS (ESI): m/z 506.3 (M+H)$^+$.

Step f. To a mixture of compound III (500 mg, 1.3 mmol), compound 115 (900 mg, 1.78 mmol), and $NaHCO_3$ (328 mg, 3.9 mmol) in DME (15 mL) and water (5 mL) was added Pd(dppf)Cl$_2$.DCM (106 mg, 0.13 mmol) under an atmosphere of N$_2$. After stirring at 80° C. overnight under an atmosphere of N$_2$, the reaction mixture was concentrated and the residue was diluted with EtOAc (100 mL) and water (25 mL). The organic phase was washed with brined and dried with anhydrous Na$_2$SO$_4$. The solvent was removed and the residue was silica gel column chromatography (Petroleum ether/acetone=4/1 (v/v)) to give compound 116 (310 mg, 35% yield) as a yellow solid. LC-MS (ESI): m/z 703.3 (M+Na)$^+$.

Step g. To a stirred solution of compound 116 (150 mg, 0.31 mmol) in dioxane (3.0 mL) was added 4 N HCl in dioxane (3.0 mL) at rt. After stirring at rt for 3 h, the reaction mixture was concentrated and the residue was dried in vacuo to give an HCl salt, which was used for the next step without further purification.

Step h. Subsequently, the HCl salt was dissolved in DMF (3.0 mL) and the resulting mixture was added DIPEA (0.43 mL, 2.5 mmol), N-Moc-L-Val-OH (136 mg, 0.78 mmol), and HATU (353 mg, 0.93 mmol), respectively. After stirring at rt for 2 h, the reaction mixture was concentrated and the residue was purified by preparative HPLC to give compound 117. LC-MS (ESI): m/z 795.4 (M+H)$^+$.

Example 7

Synthesis of Compounds of Formula IIIg

Scheme 7-1

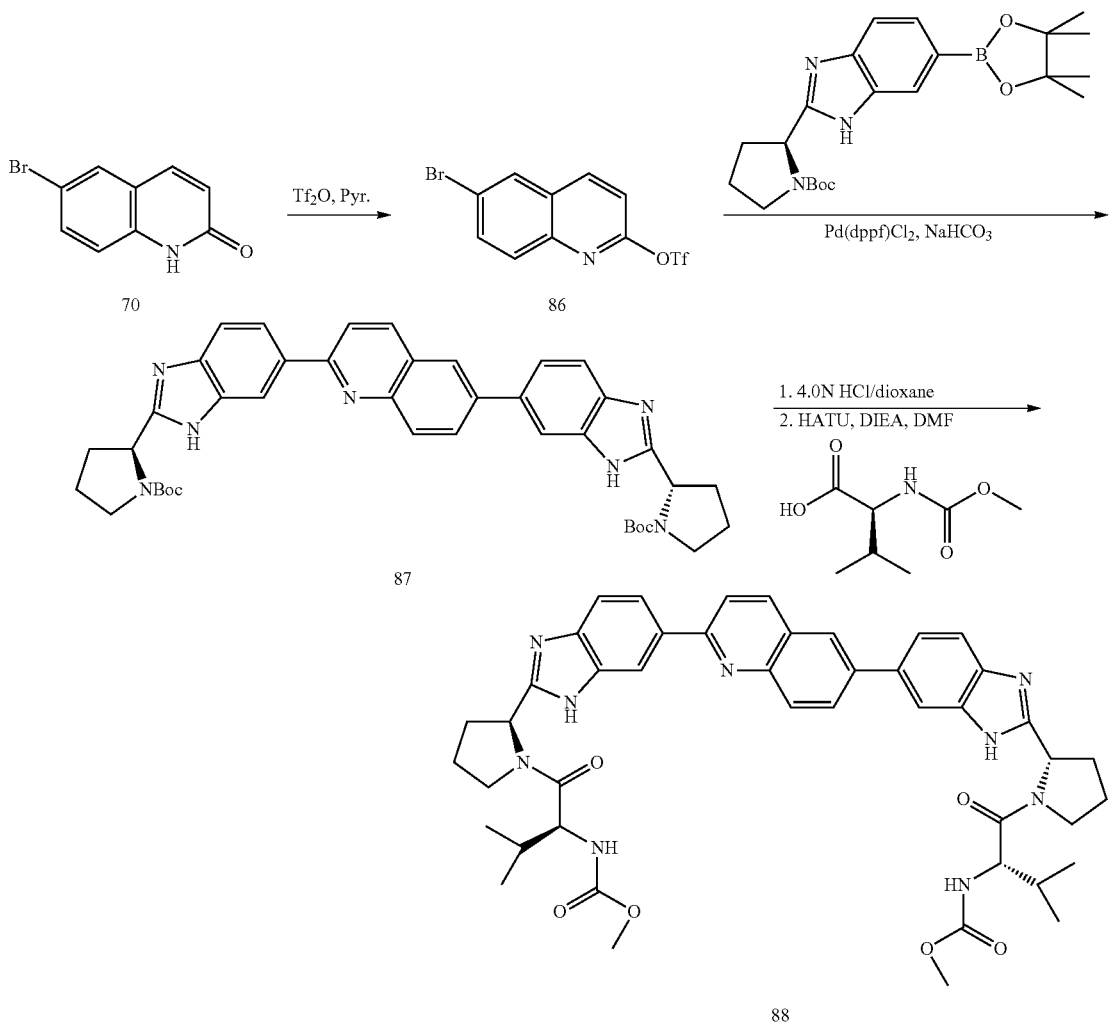

Step a. Referring to Scheme 7-1, to a solution of 6-bromoquinolin-2(1H)-one (70) (0.40 g, 1.8 mmol) in anhydrous pyridine (12 mL) was added drop-wisely with Tf$_2$O (0.81 g, 2.9 mmol) at 0° C. After stirring at 0° C. for 1 h and at rt for 3 h, the reaction mixture was concentrated. The residue was dissolved in DCM (100 mL); the resulting mixture was washed with water (25 mL×3) and dried with anhydrous Na2SO4. The solvent was removed and the residue was purified by silica gel column chromatography (Petroleum ether/acetone=2/1 (v/v)) to give compound 86 (0.54 g, 84% yield) as a yellow solid. LC-MS (ESI) m/z 355.9 (M+H)$^+$.

Step b. To a mixture of compound 86 (0.54 g, 1.5 mmol), (S)-tert-butyl 2-(6-(4,4,5,5-tetramethyl-1,3,2-dioxaborolan-2-yl)-1H-benzo[d]imidazol-2-yl)pyrrolidine-1-carboxylate (1.24 g, 3.0 mmol), and NaHCO$_3$ (1.01 g, 12.0 mmol) in 1,2-dimethoxyethane (30 mL) and water (10 mL) was added Pd(dppf)Cl$_2$·CH$_2$Cl$_2$ (0.27 g, 0.3 mmol) at rt under an atmosphere of N$_2$. After stirring at 80° C. overnight, the reaction mixture was concentrated. The residue was diluted with EtOAc (100 mL) and water (25 mL). The organic phase was isolated, washed with brine, and dried with anhydrous Na$_2$SO$_4$. The solvent was removed and the residue was purified by silica gel column chromatography (Petroleum ether/EtOAc=1/1 (v/v)) to give compound 87 (1.0 g, 95% yield) as a yellow solid. LC-MS (ESI) m/z 700.4 (M+H)$^+$.

Step c. To a solution of compound 87 (100 mg, 0.14 mmol) in dioxane (2 mL) was added 4N HCl in dioxane (2 mL) at rt. After stirring at rt for 4 h, the reaction mixture was concentrated and the residue was dried in vacuo to give an HCl salt, which was used directly for the next step without further purification. LC-MS (ESI) m/z 500.2 (M+H)$^+$.

Step d. Subsequently, the HCl salt was dissolved in DMF (2 mL) and the resulting mixture was added Et$_3$N (0.20 mL, 1.4 mmol), N-Moc-L-Val-OH (55 mg, 0.32 mmol), and HATU (122 mg, 0.32 mmol), respectively. After stirring at rt for 30 min, the reaction mixture was concentrated and the residue was purified by preparative HPLC to give compound 88. LC-MS (ESI): m/z 814.3 (M+H)$^+$.

Scheme 7-2

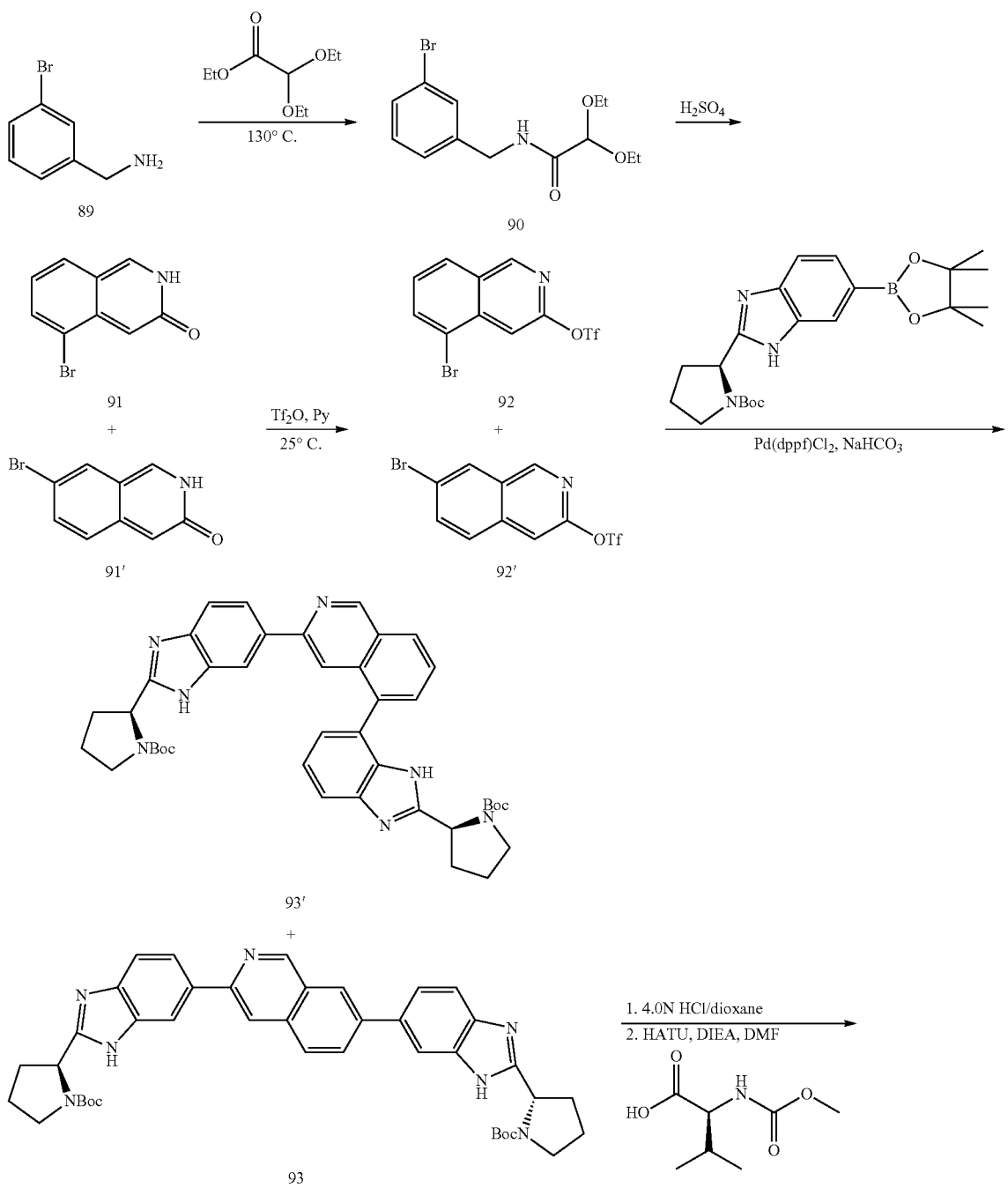

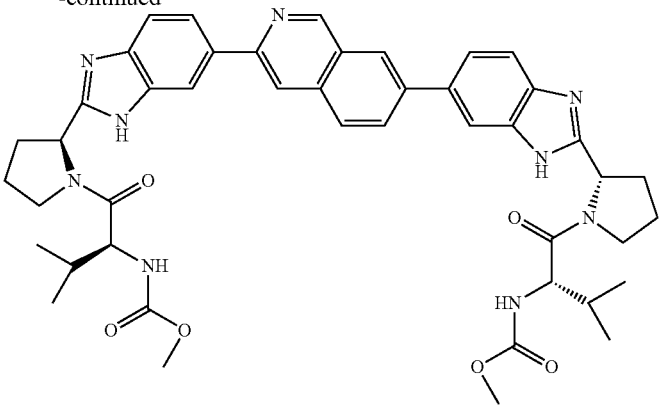

94

Step a. Referring to Scheme 7-2, a mixture of compound 89 (7.44 g, 40.0 mmol) and Ethyl 2,2-diethoxyacetate (9.15 g, 52.0 mmol) was stirred at 130° C. for 7 h. The reaction mixture was dissolved in petroleum ether (250 mL). The resulting mixture was washed with sat. aq. NH$_4$Cl and brine, respectively, and dried with anhydrous Na$_2$SO$_4$. The solvent was removed and the residue was dried in vacuo to give crude compound 90 (11.4 g) as a yellow oil, which was used for the next step without further purification. LC-MS (ESI) m/z 316.0 (M+H)$^+$.

Step b. A mixture of compound 90 (12.4 g, 40 mmol) in conc. H$_2$SO$_4$ (50 mL) was stirred at rt for 5 h. Subsequently, the reaction mixture was poured into ice-water. The suspension was filtered and the filtrate was neutralized with 10% NH$_4$OH. The solid was collected by filtration, washed with water, and dried in vacuo to give a mixture of compounds 91 and 91'. LCMS (ESI) m/z 224.0 (M+H)$^+$.

Step c. A mixture of compounds 92 and 92' (222 mg, 1.0 mmol) in anhydrous pyridine (5 mL) was added Tf$_2$O (0.5 mL) at 0° C. After stirring at rt for 8 h, the reaction mixture was concentrated and the residue was dissolved in DCM (50 mL). The mixture was washed with water (25 mL×3) and dried with anhydrous Na$_2$SO$_4$. The solvent was removed and the residue was purified with silica gel column chromatography (EtOAc/Petroleum ether=5/1 (v/v)) to give a mixture of compounds 92 and 92' (160 mg, 45% yield) as a yellow oil. LC-MS (ESI) m/z 355.9 (M+H)$^+$.

Step d. To a mixture of compounds 92 and 92' (160 mg, 0.45 mmol), (S)-tert-butyl 2-(6-(4,4,5,5-tetramethyl-1,3,2-dioxaborolan-2-yl)-1H-benzo[d]imidazol- 2-yl)pyrrolidine-1-carboxylate (463 mg, 1.12 mmol), and NaHCO$_3$ (227 mg, 2.7 mmol) in 1,2-dimethoxyethane (30 mL) and water (10 mL) was added Pd(dppf)Cl$_2$.CH$_2$Cl$_2$ (80 mg, 0.09 mmol) at rt under an atmosphere of N$_2$. After stirring at 80° C. overnight, the reaction mixture was concentrated and the residue was added EtOAc (100 mL) and water (20 mL). The organic phase was isolated, washed with brine, and dried with anhydrous Na$_2$SO$_4$. The solvent was removed and the residue was purified by silica gel column chromatography (Petroleum ether/EtOAc=1/1 (v/v)) to give compound 93 (180 mg, 57% yield) and compound 93' (60 mg, 19% yield). LC-MS (ESI) m/z 700.4 (M+H)$^+$.

Step e. To a solution of compound 93 (100 mg, 0.14 mmol) in dioxane (2 mL) was added 4N HCl in dioxane (2 mL). After stirring at rt for 3 h, the reaction mixture was concentrated and the residue was dried in vacuo to give an HCl salt, which was used for the next step without further purification. LC-MS (ESI) m/z 500.2 (M+H)$^+$.

Step f. Subsequently, the HCl salt was dissolved in DMF (2 mL) and the mixture was added Et$_3$N (0.2 mL, 1.4 mmol), N-Moc-L-Val-OH (55 mg, 0.32 mmol), and HATU (122 mg, 0.32 mmol), respectively. After stirring at rt for 1 hr, the reaction mixture was concentrated and the residue was purified by preparative HPLC to give compound 94. LC-MS (ESI): m/z 814.4 (M+H)$^+$.

Example 8

Synthesis of Compounds of Formula IIg

Scheme 8-1

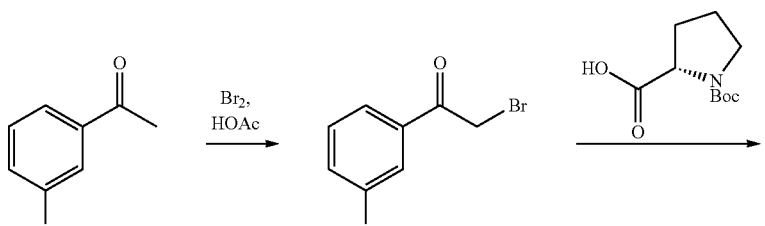

-continued
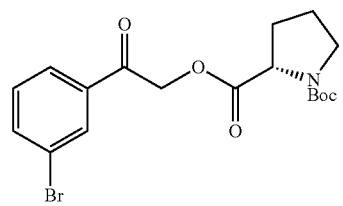
120
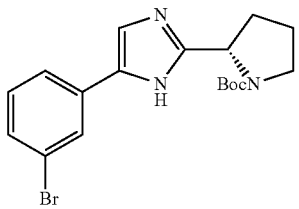
121
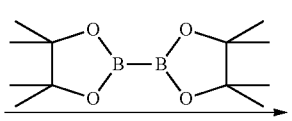
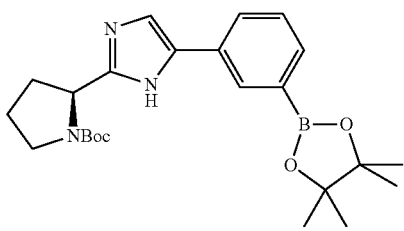
122
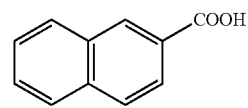
123
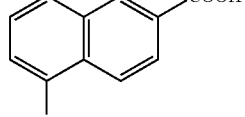
124
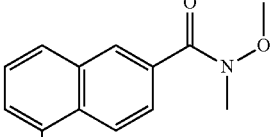
125
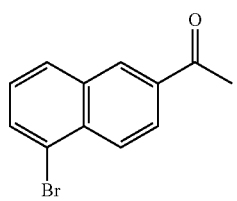
126
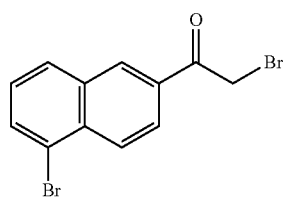
127
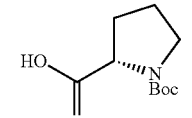
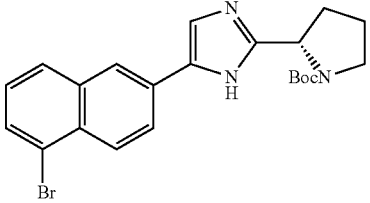
128
129
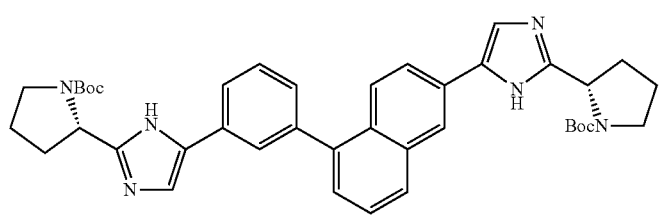
130
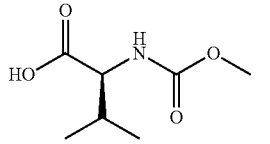

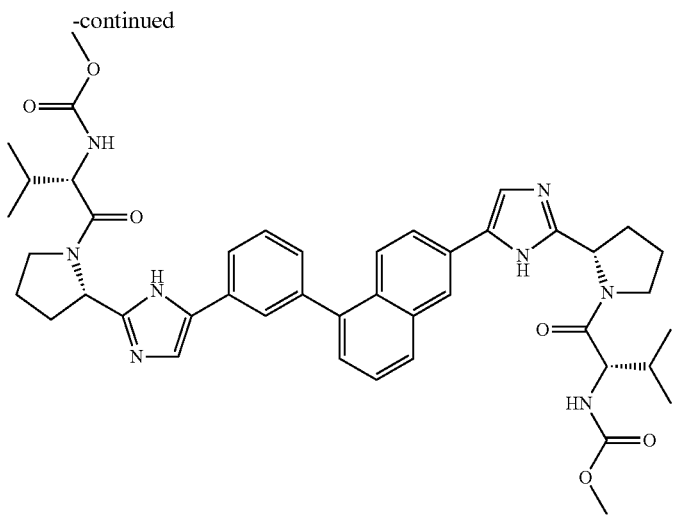

131

Step a. Referring to Scheme 8-1, to a solution of compound 118 (57.5 g, 290 mmol) in HOAc (100 mL) was slowly added Br₂ (49.0 g, 290 mmol) at rt. After stirring at rt for 2 h, the reaction mixture was slowly added saturated aqueous NaHCO₃. The organic phase was washed with brine and dried with anhydrous Na₂SO₄. The solvent was removed and the residue was dried in vacuo to give crude compound 119 (60 g), which was used for next step without further purification. LC-MS (ESI): m/z 276.9 (M+H)⁺.

Step b. To a solution of compound 119 (25.0 g, 89.9 mmol) in CH₃CN (100 mL) was added (S)—N-Boc-Pro-OH (19.4 g, 89.9 mmol), followed by Et₃N (37.35 mL, 269.7 mmol) at rt. After stirring at rt for 2 h, the reaction mixture was concentrated and the residue was diluted with DCM (250 mL). The mixture was washed with water and dried with anhydrous Na₂SO₄. The solvent was removed and the residue was dried in vacuo to give compound 120 (37 g), which was used for the next step without further purification. LC-MS (ESI): m/z 313.2 (M−100+H)⁺.

Step c. A mixture of crude compound 120 (37 g) and NH₄OAc (69.2 g, 899 mol) in xylene (100 mL) was stirred at 140° C. overnight. The reaction mixture was concentrated and the residue was diluted with DCM (500 mL). The mixture was washed with brine and dried with anhydrous Na2SO4. The solvent was removed and the residue was purified by silica gel column chromatography (Petroleum ether/acetone=10/1 (v/v)) to give compound 121 (12 g, 40% yield; three steps from compound 119) as a white solid. LC-MS (ESI): m/z 392.1 (M+H)⁺.

Step d. To a mixture of compound 121 (3 g, 7.65 mmol), bis(pinacolato)diboron (4.24 g, 16.8 mmol), KOAc (1.87 g, 19.1 mmol) in 1,4-dioxane (200 mL) was added Pd(dppf)Cl₂ (624 mg, 0.765 mmol) under an atmosphere of N₂. After stirring at 80° C. overnight under an atmosphere of N2, the reaction mixture was filtered through CELITE™545 and the filtered cake was washed with EtOAc (100 mL×3). The filtrate was washed with brine and dried with anhydrous Na₂SO₄. The solvent was removed and the residue was purified with silica gel column chromatography (Petroleum ether/acetone=8/1 (v/v)) to give compound 122 (2.9 g, 86% yield) as a gray solid. LC-MS (ESI) m/z 440.3 (M+H)⁺.

Step e. To a boiling solution of 2-naphthoic acid (123) (50.0 g, 290 mmol) in HOAc (100 mL) was slowly added a mixture of Br₂ (46.3 g, 290 mmol) and I₂ (1.25 g, 43.5 mmol). After completing the addition, the reaction mixture was refluxed for 30 min. The reaction mixture was cooled to rt and filtered. The solid was washed with HOAc and dried in vacuo to give crude compound 124 (50 g), which was used for the next step without further purification. LC-MS (ESI): m/z 251.0 (M+H)⁺.

Step f. A mixture of compound 124 (10.0 g, 39.8 mmol) in CH₃CN (200 mL) was added EDCI (18.3 g, 95.5 mmol), Et₃N (16.08 mL, 159.2 mmol), and N,O-Dimethylhydroxylamine hydrochloride (4.8 g, 50 mmol) at rt. After stirring at rt overnight, the reaction mixture was concentrated and the residue was diluted with DCM (250 mL). The mixture was washed with saturated aqueous NH₄Cl, saturated aqueous NaHCO₃, and brine, respectively and dried with anhydrous Na₂SO₄. The solvent was removed and the residue was purified by silica gel column chromatography (Petroleum ether/EtOAc=8/1 (v/v)) to give compound 125 (3.6 g, 31% yield) as a white solid. LC-MS (ESI): m/z 294.0 (M+H)⁺.

Step g. To a solution of compound 125 (3.60 g, 12.2 mmol) in THF (150 mL) was slowly added 3M MeMgCl in THF (8.31 mL) at 0° C. After stirring at 0° C. for 1 h and at rt for 1 h, the reaction was quenched by adding saturated aqueous NH₄Cl (5 mL). The solvent was removed and the residue was diluted with DCM. The mixture was washed with water and dried with anhydrous Na₂SO₄. The solvent was removed and the residue was purified by silica gel column chromatography (Petroleum ether/AcOEt=10/1 (v/v)) to give compound 126 (3.05 g, 100% yield) as a white solid. LC-MS (ESI): m/z 249.0 (M+H)⁺.

Step h. To a solution of compound 126 (3.05 g, 12.2 mmol) in DCM (100 mL) was slowly added Br₂ (1.93 g, 12.2 mmol) in DCM (10 mL) at rt. After stirring at rt for 2 h, the reaction was quenched by adding saturated aqueous NaHCO3 (10 mL). The organic layer was washed with brine and dried with anhydrous Na₂SO₄. The solvent was removed and the residue was dried in vacuo to give crude compound 127 (4.0 g), which was used for the next step without further purification. LC-MS (ESI): m/z 326.9 (M+H)⁺.

Step i. To a solution of crude compound 127 (4.0 g) in CH₃CN (15 mL) was added (S)—N-Boc-Pro-OH (3.14 g, 14.6 mmol) and Et₃N (3.70 g, 36.6 mmol). After stirring at rt for 2 h, the reaction mixture was concentrated and the residue was diluted with DCM (200 mL). Subsequently, the mixture was washed with saturated aqueous NH₄Cl and water respectively, and dried with anhydrous Na₂SO₄. The solvent was removed and the residue was dried in vacuo to give crude compound 128 (5.6 g), which was used for the next step without further purification. LC-MS (ESI): m/z 462.1 (M+H)⁺.

Step j. A mixture of crude compound 128 (5.6 g) and NH₄OAc (9.36 g, 122 mmol) in toluene (80 mL) was stirred at 110° C. overnight. The reaction mixture was concentrated and the residue was diluted with DCM (250 mL). The mixture was washed with water and dried with anhydrous Na₂SO₄. The solvent was removed and the residue was purified by silica gel column chromatography (Petroleum ether/EtOAc=5/1 (v/v)) to give compound 129 (3.0 g, 56 yield) as a white solid. LC-MS (ESI): m/z 442.1 (M+H)⁺.

Step k. To a mixture of compound 122 (633 mg, 1.44 mmol), compound 129 (500 mg, 1.31 mmol), and NaHCO₃ (330 mg, 3.01 mmol) in 1,2-dimethoxyethane (15 mL) and water (5 mL) was added Pd(dppf)Cl₂ (107 mg, 0.131 mmol) under an atmosphere of N₂. After stirring at 80° C. overnight, the reaction mixture was concentrated and the residue was diluted with EtOAc (50 mL) and water (20 mL). The organic phase was washed with brine and dried with anhydrous Na₂SO₄. The solvent was removed and the residue was purified by silica gel column chromatography (Petroleum ether/EtOAc=10/1 (v/v)) to give compound 130 (400 mg, 45% yield) as a yellow solid. LC-MS (ESI): m/z 675.4 (M+H)⁺.

Step l. To a solution of compound 130 (150 mg, 0.22 mmol) in dioxane (2.0 mL) was added 4N HCl in dioxane (2.0 mL) at rt. After stirring at rt for 3 h, the reaction mixture was concentrated and the residue was dried in vacuo to give an HCl salt, which was used for the next step without further purification. LC-MS (ESI): m/z 475.3 (M+H)⁺.

Step m. Subsequently, the HCl salt was dissolved in DMF (2.0 mL) and the mixture was added DIPEA (0.36 mL, 2.2 mmol), N-Moc-L-Val-OH (86 mg, 0.49 mmol), and HATU (202 mg, 0.49 mmol) at rt. After stirring at rt for 1 h, the reaction mixture was concentrated and the residue was purified by preparative HPLC to give compound 131. LC-MS (ESI): m/z 789.4 (M+H)⁺.

Example 9

Synthesis of Compounds of Formula IVa

Scheme 9-1

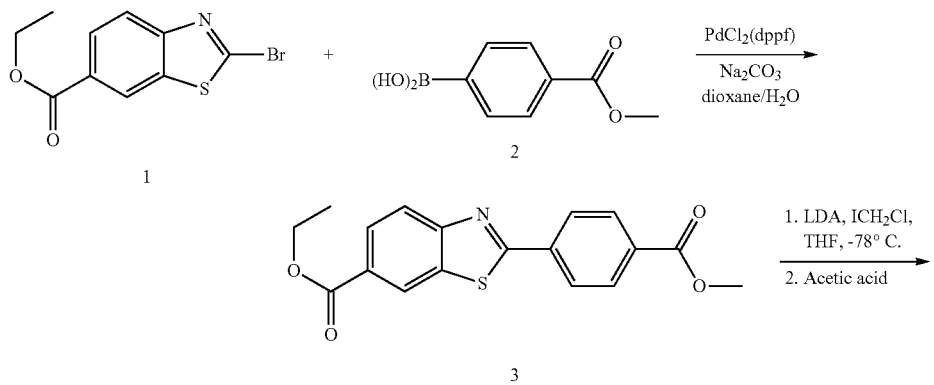

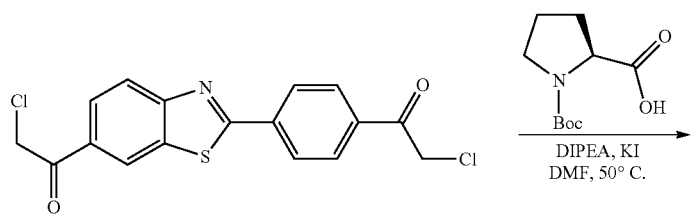

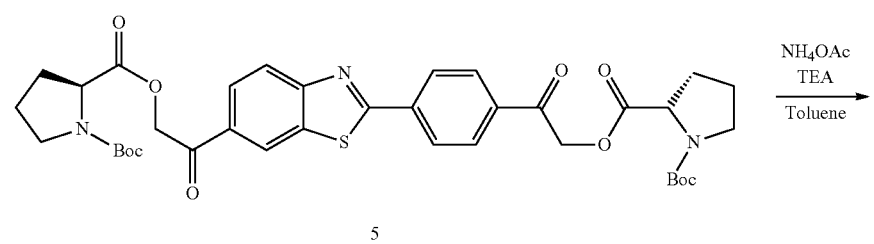

-continued

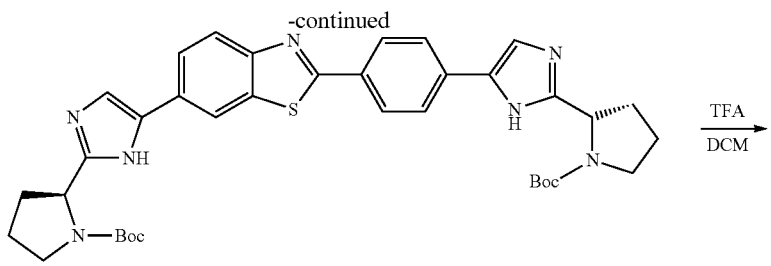

6

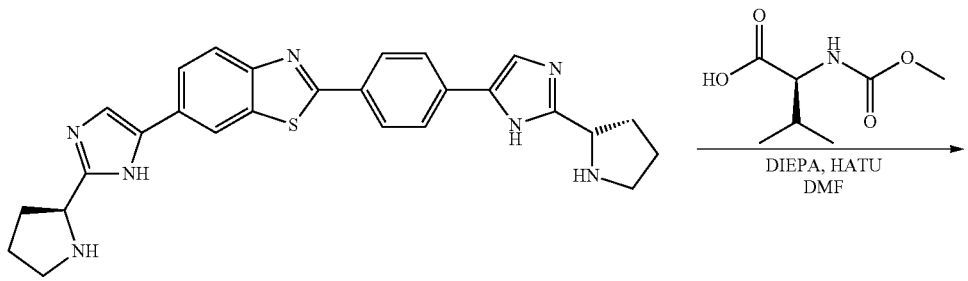

7

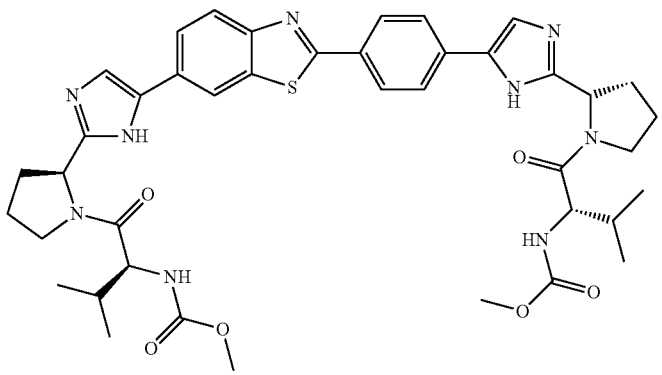

8

Step a. Referring to Scheme 9-1, a mixture of 2-bromobenzothiazole 1 (2.72 g, 9.5 mmol), 4-methoxycarbonylphenylboronic acid (2) (1.80 g, 10 mmol), Pd(dppf)Cl$_2$ (388 mg, 0.475 mmol) in 2 M Na$_2$CO$_3$ (10 mL) and dioxane (20 mL) was treated by a repeated process of degas-and-refilled-with-nitrogen three times. The reaction mixture was then stirred at 95° C. in nitrogen atmosphere for 4 h. After being cooled, the mixture was diluted with THF, and then filtered through a pad of CELITE™545. The filtrate was concentrated and the crude product was directly purified by flash chromatography (using methylene chloride as eluent) to give compound 3 (1.96 g, 60% yield) as a white solid.

Step b. A solution of n-butyllithium (2.5 M in hexane, 25.3 mL, 63.1 mmol) was slowly added into a solution of diisopropylamine (6.97 g, 68.8 mmol) in THF (20 mL) at −78° C. over 15 min. After addition, the solution was allowed to stir for 30 min at −78° C. and then warm up to 0° C. The LDA solution was cooled to −78° C. for next step.

Step c. A solution of 3 (1.96 g, 5.74 mmol) and chloroiodomethane (7.30 g, 41.2 mmol) in THF (15 mL) was cooled to −78° C. The LDA solution prepared above was slowly cannulated into this solution over 20 min. The resulting mixture was stirred for additional 1 h. The reaction was quenched by slowly adding a solution of acetic acid in THF (1/1 (v/v), 40 mL) at −78° C. The reaction mixture was warmed up to rt and then diluted with water and ethyl acetate. The aqueous layer was extracted with ethyl acetate. A combined organic layer was dried over anhydrous sodium sulfate, filtered and concentrated. The crude product 4 (1.80 g) was dried in vacuo and the residue was used directly for next condensation reaction.

Step d. A mixture of 4 (0.59 g, 1.61 mmol), N-Boc-L-Proline (0.83 g, 3.85 mmol), KI (0.64 g, 3.85 mmol) and diisopropylethylamine (0.64 g, 3.85 mmol) in DMF (40 mL) was stirred at 50° C. for 4 h. The solvent was evaporated and the residue was treated with water. The solid was collected by filtration and washed with water twice. After being dried in vacuum, the crude product was purified by flash chromatography (ethyl acetate/hexanes=1/9 to 1/5 (v/v)) to afford 5 (0.92 g, 67% yield) as a white solid.

Step e. A mixture of diester 5 (0.81 g, 1.12 mmol), ammonium acetate (2.59 g, 33.5 mmol) and triethylamine (3.39 g, 33.5 mmol) in toluene (100 mL) in a sealed tube was stirred at 140° C. for 90 min. After being cooled, the reaction mixture was transferred into a flask and concentrated to dryness. The residue was partitioned between chloroform and water, and the organic layer was washed with water and brine, and concentrated. The crude product was purified by flash chromatography (NH$_4$OH/acetone/ethyl acetate=1/2/100 (v/v/v)) to give compound 6 (0.51 g, 67% yield) as a white solid.

Step f. Trifluoroacetic acid (3 mL) was slowly added into a solution of 6 in methylene chloride (10 mL) at rt. The resulting mixture was stirred at the temperature for 1 h, and concentrated to dryness. The residue was dissolved in water, and the aqueous solution was basified to pH 11. The product was extracted with chloroform 5 times. After removal of the solvent, 7 (274 mg, 76%) was obtained as its TFA salt.

Step g. A mixture of N-methoxycarbonyl-L-valine (40 mg, 0.23 mmol), DIPEA (98 mg, 0.76 mmol) and HATU (87 mg, 0.23 mmol) in DMF was stirred at rt for 30 min. 7 (80 mg, 0.076 mmol) was added as solid. The reaction mixture was stirred at rt for 2 h, and then dropped into water. The precipitate was formed and collected by filtration. The crude product was purified by prep HPLC to afford compound 8 (16 mg). $^1$H NMR (CDCl$_3$, 300 MHz) δ 7.8-7.6 (4H, m), 7.5-7.3 (3H, m), 7.08 (2H, s), 5.5-5.4 (2H, d), 5.3-5.2 (2H, m), 5.05 (1H, s), 4.5-4.3 (2H, m), 4.2-4.1 (1H, m), 3.8-4.0 (4H, m), 3.74 (6H, s), 2.6-2.0 (10H, m), 1.10 (6H, d), 1.95 (6H, d) ppm. LC-MS (ESI): m/z 796.4 (M+H)$^+$.

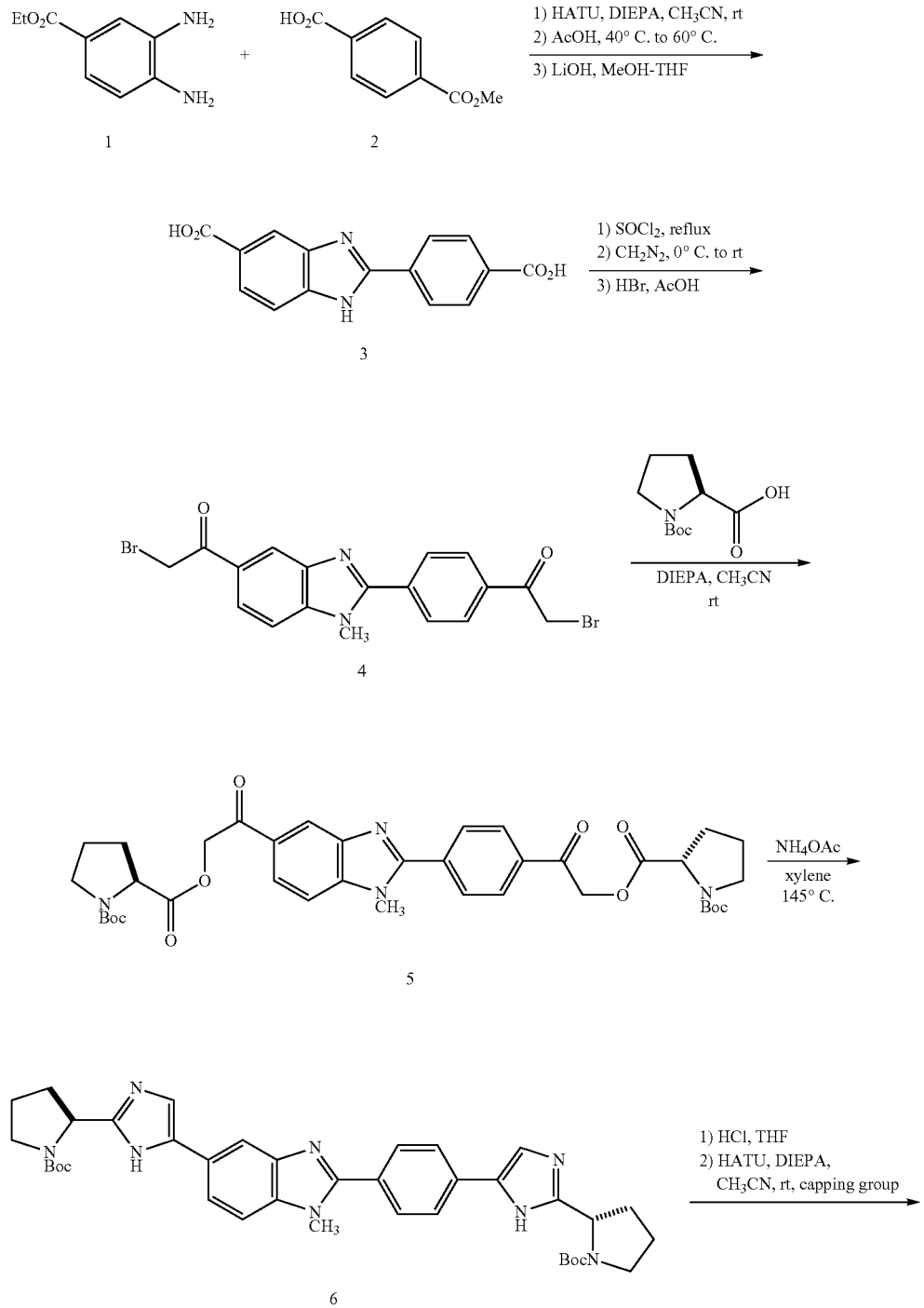

Scheme 9-2

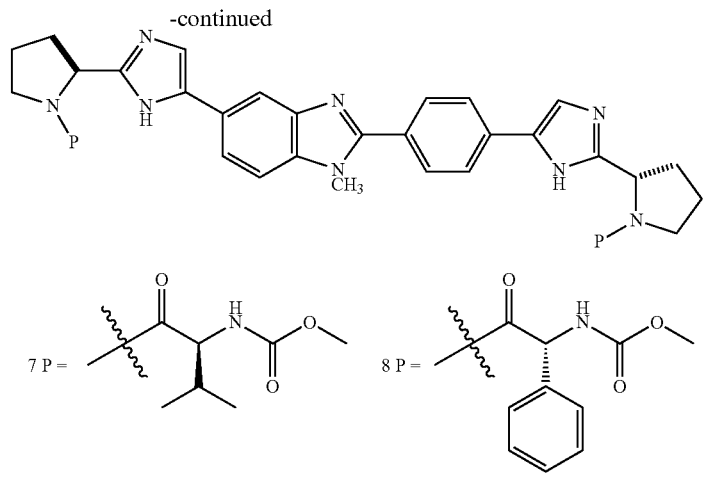

7 P = [structure with O, NH, O-methyl carbamate, isopropyl]

8 P = [structure with O, NH, O-methyl carbamate, phenyl]

Step a. Referring to Scheme 9-2, to a mixture of compound 2 (6.31 g, 35 mmol) and HATU (14.63 g, 38.5 mmol) in CH$_3$CN (150 mL) was added slowly DIEPA (9.05 g, 11.35 mL, 70 mmol). The resulting mixture was stirred at rt for 15 min. To the mixture was added 3,4-diamino-benzoic acid ethyl ester 1 (6.31 g, 35 mmol) at rt, and stir continued at rt for 17 h. The reaction was quenched with saturated NaHCO$_3$ solution, and extracted with EtOAc. (3×150 mL). Combined organic phases were washed with H$_2$O (2×200 mL) and brine (200 mL), dried over Na$_2$SO$_4$, filtered and concentrated on a rotary evaporator. The crude mixture was purified by column chromatography eluting hexane/EtOAc=3/1 to 2/1 (v/v) to give an amide (11.2 g, 94%) as yellow-brown solid. LC-MS (ESI): m/z (M+H)$^+$: 343, (M−H)$^-$: 341.

Step b. A mixture of the product (11.2 g, 33 mmol) from above reaction in AcOH (100 mL) was heated at 40° C. for 18 h. The temperature was allowed to warm to 60° C., and further heated the mixture for 24 h. All starting material was consumed based on LC-MS analysis. The excess solvent was removed on a rotary evaporator to give a crude mixture, which was subject to purification by column chromatography eluting with hexane/EtOAc=3/1 (v/v) to give a functionalized benzimidazole (10.2 g, 96% yield). LC-MS (ESI): m/z 325.1 (M+H)$^+$.

Step c. A mixture of the product (10.2 g, 31 mmol) from the above reaction and LiOH (7.54 g, 0.31 mol) in MeOH (200 mL) was heated under reflux condition for 60 h. The milky mixture was acidified with 10% HCl solution to adjust the pH 1 to give white precipitates. The precipitate was collected by filtration and then dried in vacuo to afford compound 3 (8.9 g, quantitative yield), which was used for the next step without further purification. LC-MS (ESI): m/z 283.1 (M+H)$^+$.

Step d. A mixture of 3 (8.9 g, 31 mmol) in thionyl chloride (60 mL) was refluxed for 3 h. The reaction mixture was concentrated and the residue was dried in vacuo to give acid chloride, which was mL suspended in a mixture of dried diethyl ether (200 mL)/THF (50 mL). To the suspension was added dropwise a flash generated diazomethane solution (approximately 166 mmol of diazomethane solution generated from 251 mmol of 4-N,N-trimethyl-benzenesulfonamide) at 0° C., and then stirred it at 0° C. to rt overnight (20 h). All volatile was removed on a rotary evaporator to give a residue. The residue was purified by column chromatography eluting hexanes/EtOAc=3/1 (v/v) to give a yellow solid (1.89 g, 17% yield).

Step e. To a mixture of 2-diazo-1-{2-[4-(2-diazo-acetyl)-phenyl]-1-methyl-1H-benzoimidazol-5-yl}-ethanone obtained from above (1.89 g, 5.49 mmol) in AcOH (50 mL) was added slowly HBr (48% in AcoH, 1.62 mL, 14.31 mmol) at rt. The resulting mixture was stirred at rt for 13 h, and then all volatile was removed on a rotary evaporator to give crude mixture. The crude mixture was further dried with toluene on a rotary evaporator (2×25 mL) to give compound 4 as yellow solid, which was used for the next step without further purification. LC-MS (ESI): m/z 448.9 (M+H)$^+$.

Step f. To a crude mixture of compound 4 (~5.49 mmol) in CH$_3$CN (50 mL) was added N-Boc-L-Proline (2.59 g, 12.01 mmol), followed by adding DIEPA (3.71 mL, 22.9 mmol) at rt. The resulting mixture was stirred at rt for 5 h, and quenched with H$_2$O. The mixture was extracted with EtOAc (3×50 mL). The combined organic phases were washed with H$_2$O (50 mL) and brined (50 mL), dried over Na$_2$SO$_4$, filtered, and concentrated on a rotary evaporator. The crude mixture was used for the next step without further purification. LC-MS (ESI): m/z 719.3 (M+H)$^+$.

Step g. To a crude solution of 5 (~5.72 mmol) in xylene (50 mL) was added NH$_4$OAc (6.61 g, 85.8 mmol). The resulting mixture was heated at 145° C. for 1.5 h, and then all solvent was removed on a rotary evaporator to give a crude mixture, which was subject to column chromatography eluting with hexane:EtOAc=1:3 to EtOAc only. Yellow-brown solid was obtained as compound 6 (717 mg). LC-MS (ESI): m/z 679.4 (M+H)$^+$.

Step h. To a crude solution of 6 (717 mg, 1.06 mmol) in THF (7.5 mL) was added HCl (4.0 M in dioxane, 10 mL) at rt. The resulting mixture was stirred at rt for 16 h, and then all volatile was removed on a rotary evaporator to give yellow solid. The yellow solid was washed with diethyl ether (2×10 mL) and then further dried on in vacuo to give an HCL salt, which was used for the next step without further purification. LC-MS (ESI): m/z 479.3. $^1$H NMR spectrum showed the crude product was a mixture of two regioisomers with a ratio of 1:1. (M+H)$^+$.

Step i. To a crude solution of the HCl salt (48 mg, ~0.1 mmol), N-Boc-L-Val-OH (35 mg, 0.2 mmol), and HATU (76 mg, 0.2 mmol) in CH$_3$CN (1.0 mL) was added DIEPA (65 μL, 0.4 mmol). The resulting mixture was stirred at rt for 2.5 h, and then all solvent was removed on a rotary evaporator to give crude mixture. The crude mixture was purified by prep-HPLC eluting H$_2$O to CH$_3$CN. Two regioisomers were obtained as 10.0 mg (yellow solid, 7) and 8.7 mg (yellow solid, 7'), respectively. Characterization of 7: $^1$H NMR (300 MHz, CDCl$_3$) δ 8.32 (br s, 1H), 7.19-7.92 (m, 8H), 5.39-5.86 (m, 2H), 5.21-5.34 (m, 2H), 4.30-4.42 (m, 2H), 3.60-3.78 (m, 12H), 2.76 (Br s, 1H), 2.20-2.44 (m, 4H), 1.98-2.18 (m, 4H), 0.89-1.12 (m, 12H) ppm. LC-MS (ESI): m/z (M+2)/2$^+$: 397, (M+1)$^+$: 794.

Characterization of compound 7'. $^1$H NMR (300 MHz, CDCl$_3$) δ 8.30 (Br s, 1H), 7.10-7.84 (m, 8H), 5.44-5.64 (m, 2H), 5.22-5.32 (m, 2H), 4.39 (t, J=6.6 Hz, 2H), 3.63-4.00 (m, 12H), 2.68 (br s, 1H), 2.21-2.38 (m, 4H), 2.00-2.16 (m, 4H), 0.87-1.07 (m, 12H). LC-MS (ESI): m/z 793.4 (M+H)$^+$.

The N-Moc-D-Phg-OHcapped analog 8 were obtained by following the same procedure as that used for synthesizing compounds 7 and 7' and using N-Moc-D-Phg-OH instead of N-Moc-L-Val-OH as an amide reagent. $^1$H NMR (300 MHz, CDCl$_3$) δ 8.32 (br s, 1H), 7.23-8.00 (m, 18H), 5.42-5.60 (m, 2H), 5.24-5.40 (m, 2H), 3.86 (br s, 4H), 3.56-3.74 (m, 6H), 2.64-2.86 (m, 2H), 2.00-2.36 (m, 4H), 1.91 (br s, 2H) ppm. LC-MS (ESI): m/z (M+2)/2$^+$: 431, (M+1)$^+$: 860.

Scheme 9-3

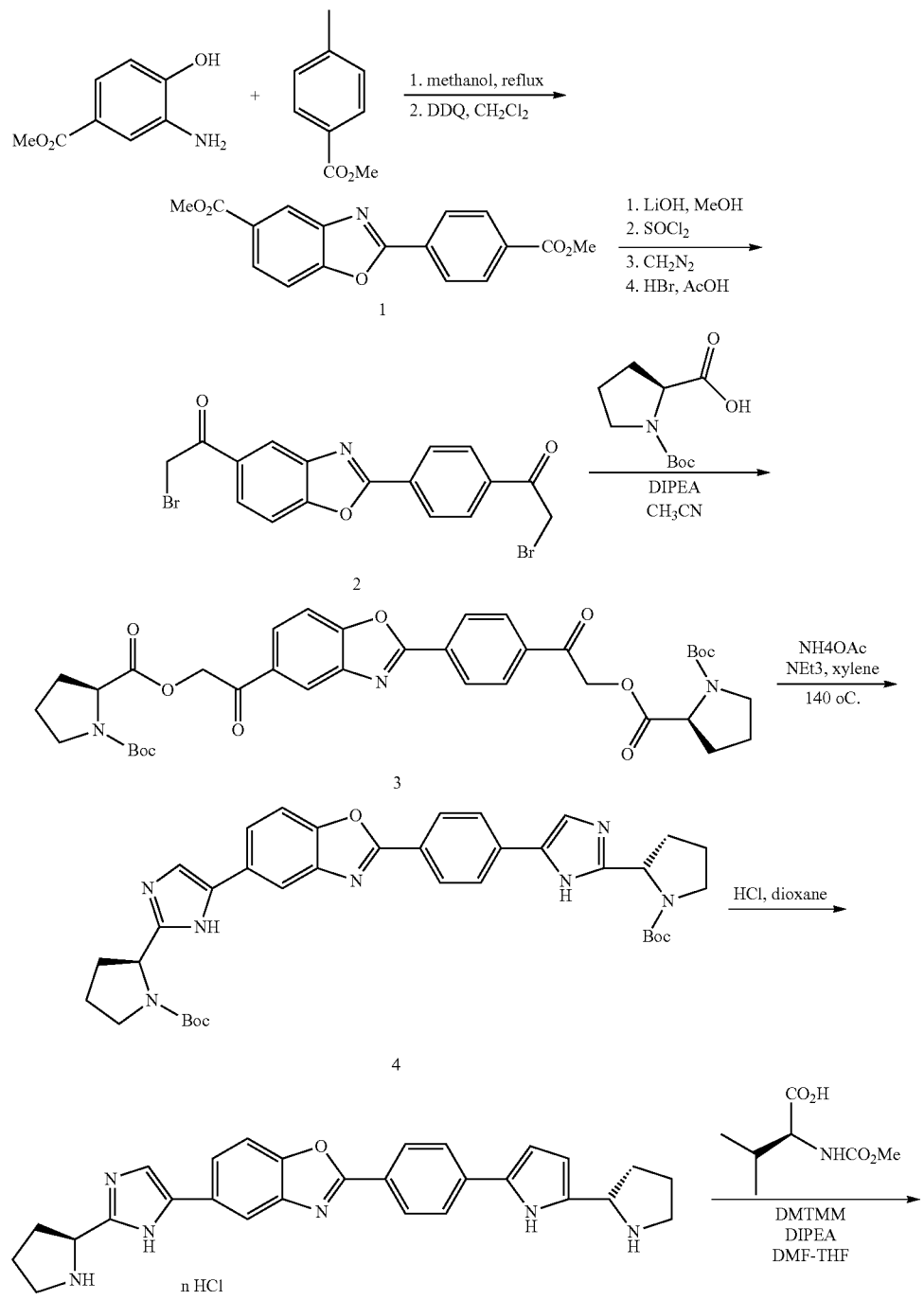

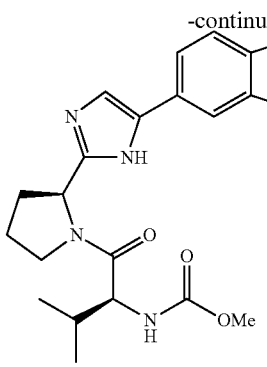
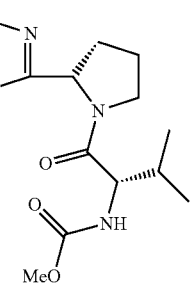

6

Step a. A mixture of methyl 3-amino-4-hydroxybenzoate (2.5 g, 15 mmol) and methyl 4-formylbenzoate (2.46 g, 15 mmol) in methanol (75 mL) was stirred at rt overnight. The solvent was evaporated under reduced pressure and the remaining residue was dissolved in dichloromethane (150 mL). DDQ (3.5 g, 15.4 mmol) was added and the reaction mixture was stirred at rt for 1 h. Saturated $NaHCO_3$ (200 mL) was added. The suspension was filtered off, the resulting solid was washed with saturated $NaHCO_3$ (50 mL), water (50 mL), and ethyl acetate (100 mL) and dried in vacuo to give compound 1 (4 g, 86% yield) as yellow solid.

Step b. A mixture of diester 1 (4 g, 12.8 mmol) and lithium hydroxide monohydrate (2.7 g, 64 mmol) in a solvent mixture of methanol and water (60 mL, methanol/water=1/5) was refluxed for 6 h. Methanol was evaporated and the remaining aqueous solution was neutralized by HCl (con). The resulting suspension solution was filtered off, the solid was washed with water (50 mL) and dried in vacuo to give the corresponding dicarboxylic acid (3.3 g, 95% yield) as yellow solid.

Step c. A sample of the dicarboxylic acid (2.88 g, 10.2 mmol) was suspended in thionyl chloride (30 mL), the mixture refluxed for 6 h. The reaction mixture was evaporated under reduced pressure and dried in vacuo to provide the corresponding diacyl chloride (3.25 g) as yellow solid.

Step d. A suspension of the diacyl chloride obtained (1.5 g, 4.7 mmol) in ether was treated with diazomethane (71 mL, 0.33 N in ether, 23 mmol) at 0° C. for 2 h. The solvent was evaporated under reduced pressure and dried in vacuo to give the corresponding diazoketone (1.55 g) as yellow solid. LC-MS (ESI): m/z 332.1 [M+H]+.

Step e. The diazoketone obtained (1.55 g, 4.7 mmol) was suspended in acetic acid (10 mL) and the mixture was dropwisely added 48% HBr in AcOH (3.93 g, 23.3 mmol) at 0° C. The reaction mixture was then warmed up to rt and stirred for 1 h. Saturated $Na_2CO_3$ was added slowly into the reaction mixture to neutralize the acid. The resulting suspension solution was filtered off and the solid was washed with water and dried in vacuo to give bromoketone 2 (1.38 g, 69% yield) as yellow solid.

Step f. A solution of bromoketone 2 (1.38 g, 3.2 mmol), N-Boc-LProline (2.7 g, 12.6 mmol) and DIPEA (2.2 mL, 12.6 mmol) in acetonitrile (3 mL) was stirred at rt overnight. Acetonitrile was evaporated and the remaining residue was partitioned between ethyl acetate (50 mL) and water (25 mL). The organic phase was then collected and dried over $Na_2SO_4$. After concentration under reduced pressure, the crude product was purified over silica gel (ethyl acetate/hexane=35/65) to give ester 3 (0.56 g, 25% yield) as yellow solid. LC-MS (ESI): m/z 706.3 [M+H]+.

Step g. A mixture of ester 3 (560 mg, 0.8 mmol) and ammonium acetate (1.84 g, 24 mmol) in degassed xylene (3.3 mL) in a sealed parr bottle was stirred at 140° C. for 90 min. Upon removal of volatile solvents the residual material was purified by silica gel chromotagraphy (ethyl acetate 100%, then ethyl acetate/methanol=90/10 (v/v)) to give bisimidazole 4 (474 mg, 89% yield) as yellow solid. LC-MS (ESI): m/z 666.3 [M+H]+.

Step h. To a solution of bisimidazole 4 (474 mg, 0.71 mmol) in THF (20 mL) was added 4N HCl in dioxane (3.6 mL, 14 mmol) at rt. The reaction mixture was stirred at rt for 2 h. The solvent was evaporated and the residue was dried in vacuo to give 5 (ca. 330 mg) as yellow HCL salt, which was used for the next step without further purification. LC-MS (ESI): m/z 465.2 [M+H]+.

Step i. To a solution of 5 (135 mg, 0.29 mmol), N-Moc_L-Val-OH (152.6 mg, 0.87 mmol) and DMTMM (240.5 mg, 0.87 mmol) in a solvent mixture of DMF-THF (2 mL, DMF/THF=1/3 (v/v)) was added DIPEA (0.5 mL, 2.9 mmol) at rt. The reaction mixture was stirred at rt for 2 h. THF was evaporated and the remaining reaction mixture was purified via prep-HPLC to provide compound 6 as white solid. $^1$H NMR (300 MHz, CD$_3$OD) δ 0.92 (m, 12H), 2.05 (m, 4H). 2.26 (m, 4H), 3.65 (s, 6H), 3.9 (m, 2H), 3.99 (m, 2H), 4.22 (m, 2H), 5.18 (m, 2H), 7.33 (s, 1H), 7.48 (s, 1H), 7.64 (d, J=8.7 Hz, 1H), 7.73 (d, J=8.1 Hz, 1H), 7.88 (d, J=8.1 Hz, 2H), 7.99 (s, 1H), 8.21 (d, J=8.7 Hz, 2H) ppm. LC-MS (ESI): m/z 780.4 (M+H)+.

Scheme 9-4

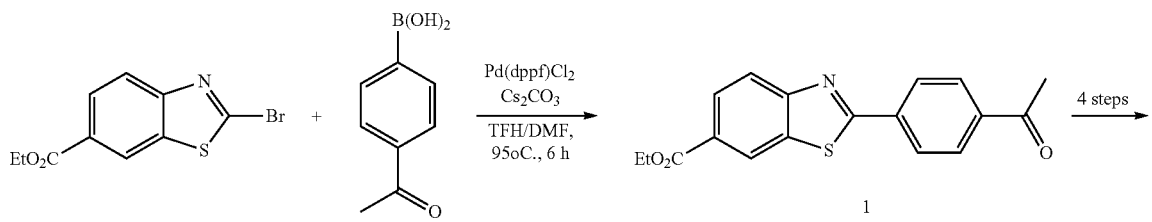

-continued
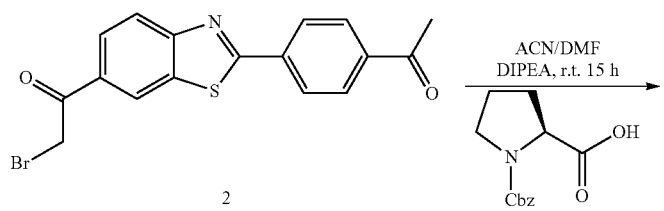
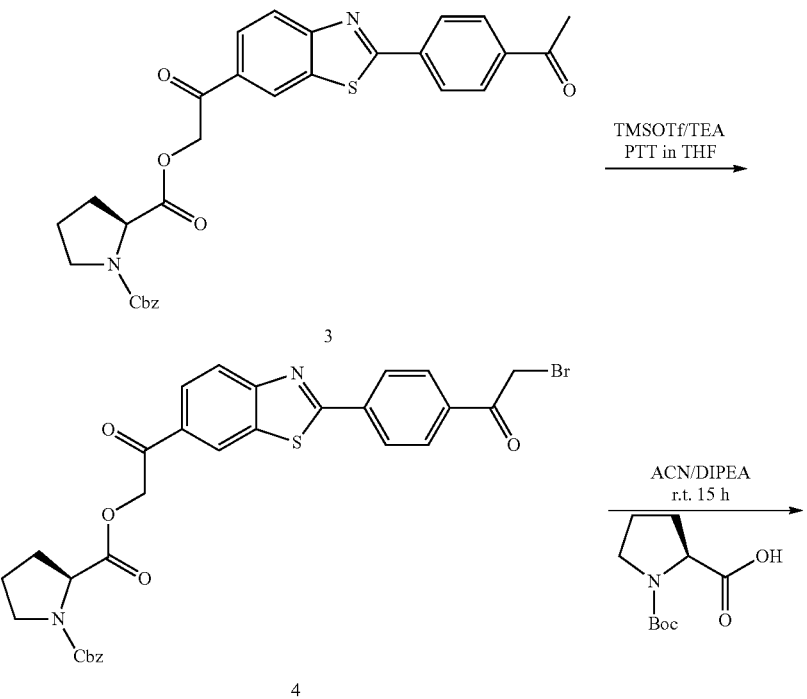
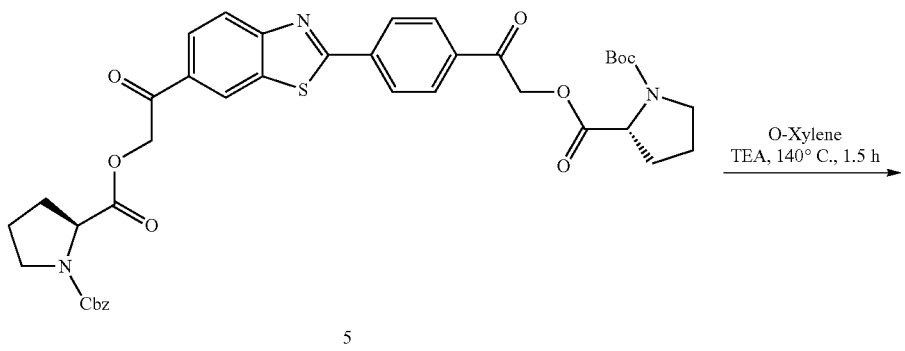
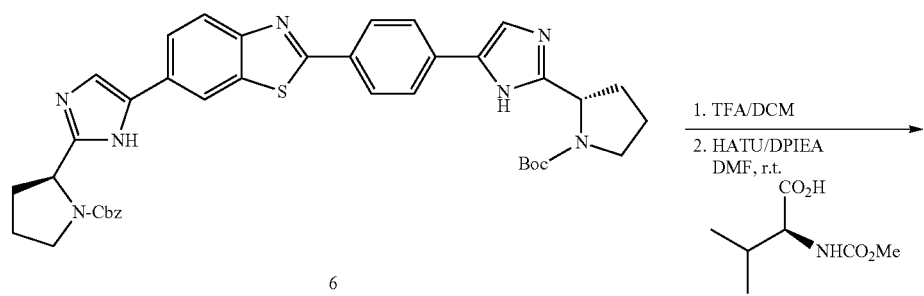

-continued

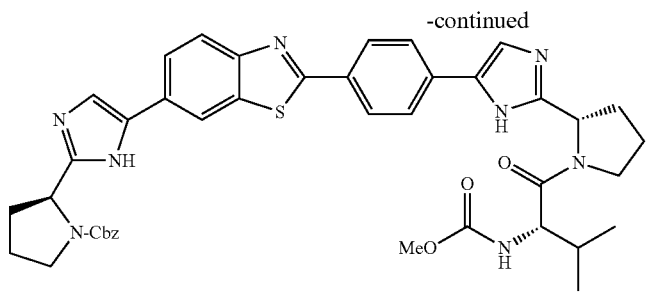

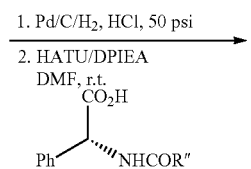

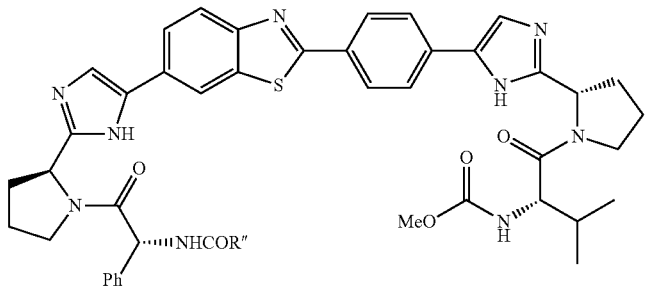

8 R' = OMe
9 R' = OBu-t
10 R' = NHMe

Step a. Referring to Scheme 9-4, ethyl 2-bromo-6-benothiazolecarboxylate (100 mg, 0.35 mmol), 4-acetylphenylboronic acid (69 mg, 0.42 mmol), Pd(dppf)Cl$_2$ (14 mg, 0.05 mmol) and Cs$_2$CO$_3$ (228 mg, 0.70 mmol) were dissolved in a mixed solvent (THF/DMF=3:2, 5 mL) in a Schlenk flask. The reaction mixture was degassed and refilled with nitrogen three times. The flask was heated to 95° C. under nitrogen 6 h, cooled to rt. The solvent was removed under reduced pressure and the residue was re-dissolved in dichloromethane (DCM). The DCM solution was washed with saturated NaHCO$_3$, brine and dried with Na$_2$SO$_4$, concentrated, purified by silica gel column (DCM/MeOH=9.8/0.2 (v/v)) to give 1 as slight yellow solid (70 mg, 62% yield). $^1$H NMR (300 MHz, CDCl$_3$) δ 8.65 (s, 1H), 8.17-8.21 (m, 3H), 8.06-8.13 (m, 3H), 4.43 (q, 2H), 2.66 (s, 3H), 1.44 (t, 3H) ppm. LC-MS (ESI): m/z 326.1 (M+H)$^+$.

Step b. To a suspension of 1 (4.0 g, 12.3 mmol) in the solvent mixture of THF/MeOH/H$_2$O (100 mL) was added LiOH.H$_2$O (2.58 g, 61.5 mmol). The reaction mixture was stirred at rt overnight. The volatile was removed, and water (50 mL) was added and the pH was adjusted to 1-2 with 2N HCl. The precipitate was filtered and dried to give a free acid (3.6 g, 100%) as white solid. LC-MS (ESI) m/z: 298.0 (M+H)$^+$.

Step c. A sample of the acid (3 g, 10 mmol) was suspended in thionyl chloride (50 mL), heated to refluxing for 2 h. The volatile was removed under reduced pressure and the residue (3.2 g) was dried in vacuo to give the corresponding acyl chloride.

Step d. To the suspension of the acyl chloride above (3 g, 9.5 mmol) in the mixed solvent of DCM/THF (7/3 (v/v), 100 mL) at 0° C. was added fresh-made diazomethane (5.0 equiv.) in diethyl ether. The reaction mixture was stirred from 0° C. to rt 1 h. LC-MS and $^1$H NMR showed reaction was completed. The solvent was removed to give crude product diazoketone. $^1$H NMR (300 MHz, CDCl$_3$) δ 8.43 (s, 1H), 8.20-8.23 (d, J=7.5, 2H), 8.08-8.15 (m, 3H), 7.86 (d, J=7.8, 1H), 6.0 (s, 1H), 2.68 (s, 3H) ppm.

Step e. The dizoketone was dissolved in acetic acid (50 mL) and HBr (1.1 equiv, 48% aq. solution) was added, stirred at rt for 1 h, concentrated to give compound 2 (4.5 g).

Step f. To a solution of the N-Cbz_L-Proline (3.59 g, 14.4 mmol) in acetonitrile (100 mL) and DMF (50 mL) was added diisopropylethylamine (6.0 mL, 36 mmol) and 2 (4.5 g, 12 mmol) in acetonitrile (50 mL). The reaction mixture was stirred at rt overnight. The solvent was removed and product was extracted with dichloromethane (3×), washed with NaHCO$_3$ (200 mL) and brine, dried over Na$_2$SO$_4$. After removal of the solvent, the crude product was purified on silica column (Hexane/EtOAc=1/1 (v/v)) to give 3 (1.2 g). LC-MS (ESI): m/z 543.2 (M+H)$^+$.

Step g. To a solution of 3 (1.2 g, 2.2 mmol) and TEA (2.18 mL, 13.2 mmol) in DCM was added TMS-OTf (0.8 mL, 4.4 mmol) at −78° C. After the reaction was stirred to r.t overnight, PTT (910 mg, 2.42 mmol) was added. The reaction was stirred at rt for 2 h and quenched with NaHCO$_3$ solution. The mixture was partitioned between water and CH$_2$Cl$_2$ (3×), and the organic phase was washed with brine, dried, filtered and concentrated in vacuo to give crude compound 4 (1.37 g).

Step h. To a solution of N-Boc-L-Proline (568 mg, 2.6 mmol) in acetonitrile (10 mL) was added DIPEA (0.54 mL, 3.3 mmol) and 4 (1.37 g, 2.2 mmol) in acetonitrile (10 mL). The reaction mixture was stirred at rt overnight. The solvent was removed and product was extracted with dichloromethane (3×), washed with NaHCO$_3$ (200 mL) and brine, dried with Na$_2$SO$_4$. After removal of the solvent, the crude product was purified on silica column (Hexanes/EtOAc=1/1 (v/v)) to give 5 (900 mg, 54% yield). LC-MS (ESI): m/z 756.3 (M+H)$^+$.

Step i. To a solution of 5 (900 mg, 1.19 mmol) in o-xylene (20 mL) in a pressure tube was added ammonium acetate (2.75 g, 35.7 mmol) and triethylamine (5 mL, 35.7 mmol). The tube was sealed and heated to 140° C. for 1.5 h, cooled to rt The volatile component was removed in vacuum, and the residue was partitioned between water and CH$_2$Cl$_2$, and the organic phase was dried, filtered and concentrated in vacuum. The resulting crude material was purified by a flash chromatography (Hex: EA: MeOH=5:5:1) to provide 6 as yellow residue (630 mg, 74% yield). LC-MS (ESI): m/z 716.3 (M+H)+.

Step j. To a solution of 6 (630 mg, 0.88 mmol) in DCM (20 mL) was added TFA (5 mL). The reaction mixture was stirred at rt for 2 h; TFA was removed to give a TFA salt, which was used for the next step without further purification.

Step k. To a solution of the TFA salt (550 mg, 0.88 mmol) in DMF (10 mL) was added N-Moc-L-Val-OH (308 mg, 1.76 mmol), HATU (502 mg, 1.32 mmol) and DIPEA (871 μL, 5.28 mmol). The reaction was stirred at rtrt overnight. The solvent was removed under reduced pressure. The crude product was purified on silica gel column ($CH_2Cl_2$/MeOH=9.8/0.2 (v/v)) to give 7 (500 mg, 74% yield). LC-MS (ESI): m/z 773.3 (M+H)+.

Step l. To a solution of 7 (500 mg, 0.647 mmol) in MeOH (20 mL) was added Pd/C (50 mg) and several drops of con. HCl, purged with $H_2$. The reaction mixture was shaken in the shaker under 60 psi for 48 h. The mixture was filtered on CELITE™ and concentrated; the residue was purified on silica gel column (DCM/MeOH=8/2 (v/v)) to give a free amine (300 mg).

Step m. To a solution of the free amine from Step 8a (100 mg, 0.16 mmol) in DMF (5 mL) was added N-Moc-D-Phg-OH (43 mg, 0.204 mmol), HATU (60 mg, 0.157 mmol) and DIPEA (155 μL, 0.942 mmol). The reaction was stirred at rtrt overnight. The solvent was removed under reduced pressure. The crude product was purified on preparative HPLC to give 8 (33 mg), in which R" is a methyl group. LC-MS (ESI): m/z 830.3 (M+H)+.

Additional Examples

Similarly taking a sample of the free amine from Step 8a and by substituting N-Boc-D-Phg-OH for N-Moc-D-Phg-OH in Step b above, the corresponding N-Boc analog 9 was obtained (75 mg). LC-MS (ESI) m/z: 872.4 (M+H)]+.

Taking a sample of 9 (70 mg, 0.08 mmol) in DCM (15 mL) and treated with TFA (4 mL). The corresponding de-Boc product was obtained as a TFA salt.

To a solution of the TFA salt in THF (10 mL) was added DIPEA (132 μL, 0.8 mmol) and CDI (39 mg, 0.24 mmol). The reaction was stirred at rtrt until the reaction completed (monitored by LC-MS). To the solution was added methyl amine hydrochloride (54 mg, 0.8 mmol). The reaction was stirred at rtrt overnight. The solvent was removed and the residue was purified by prep-HPLC to give compound 10 (12 mg) LC-MS (ESI): m/z 829.4 (M+H)+.

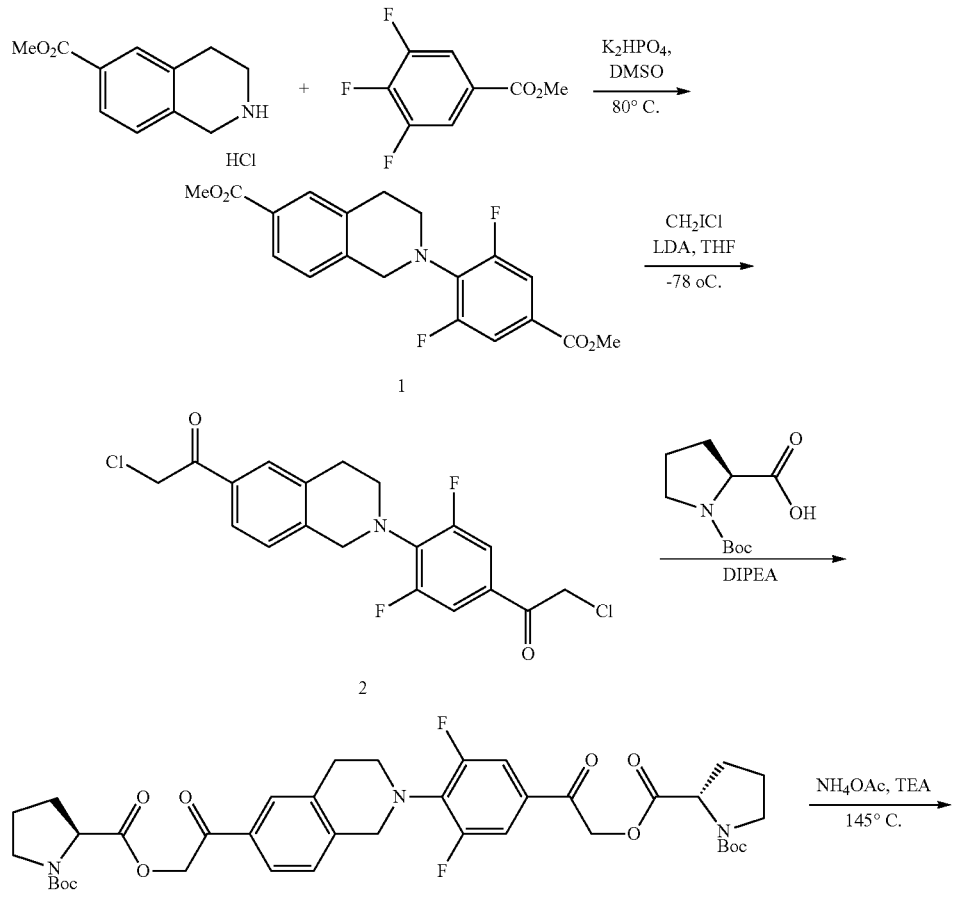

Scheme 10-1

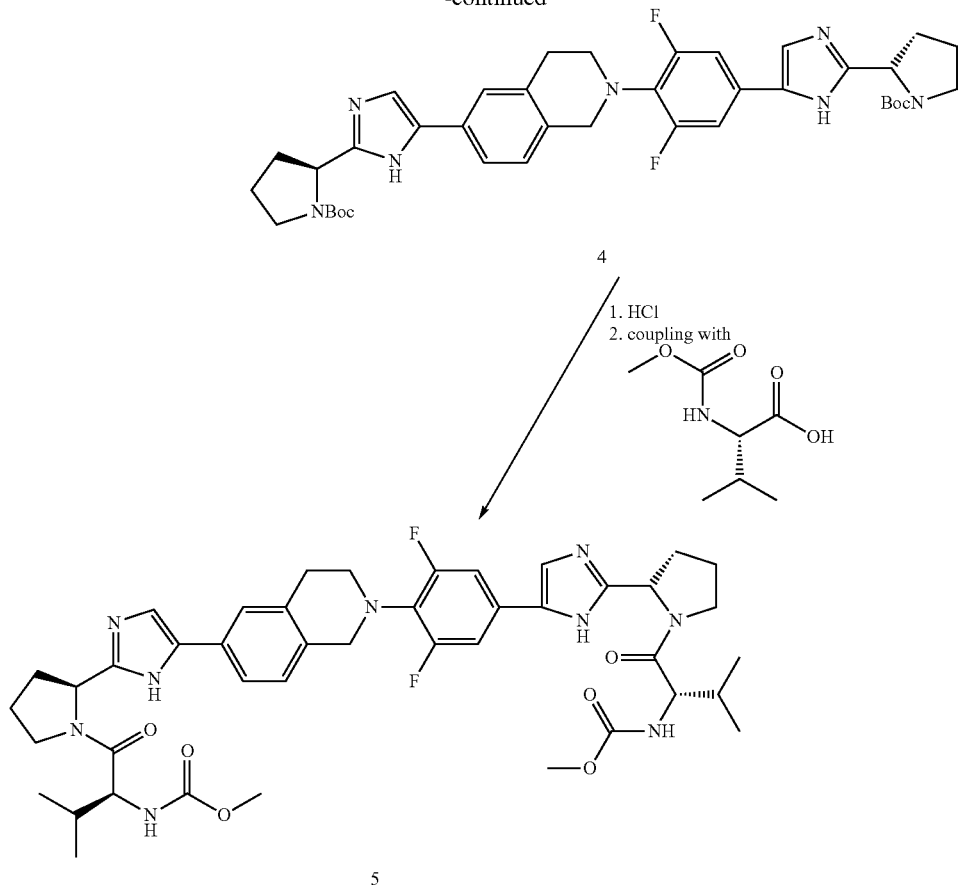

Example 10

Synthesis of Compounds of Formula IIm

Step a. Referring to Scheme 10-1, a mixture of methyl 1,2,3,4-tetrahydroisoquinoline-6-carboxylate hydrochloride (4.28 g, 18.8 mmol), 3,4,5-trifluorobenzoic acid methyl ester (3.8 g, 20 mmol) and $K_2HPO_4$ (17.0 g, 98 mmol) in 60 mL of DMSO was stirred at 80° C. for 8 hours. After cooling down, the resulting mixture was partitioned in 800 mL of EtOAc and 800 mL of $H_2O$. The organic layer was washed with $H_2O$ followed by brine and dried ($Na_2SO_4$). After concentration, the residue was purified by silica gel column chromatography (hexanes/ethyl acetate (v/v), 3/1 to 1/1) to afford compound 1 (4.1 g, 60% yield) as slightly yellow solid. $^1$H NMR (300 MHz, $CDCl_3$) δ 7.80-7.88 (m, 2H), 7.48-7.62 (m, 2H), 7.13 (d, 1H), 4.55 (s, 2H), 3.91 (s, 3H), 3.90 (s, 3H), 3.58 (t, 2H), 3.04 (t, 2H) ppm.

Step b. To a solution of 1 (2.0 g, 5.53 mmol) and chloroiodomethane (5.86 g, 33.2 mmol) in THF (40 mL) was added LDA (precooled to −78° C., freshly made from 10 mL diisoproylamine and 26.5 mL of 2.5 M n-BuLi in hexanes in 40 mL of THF) at −78° C. via cannula over 20 min. The reaction mixture was stirred for two hours at −78° C. before it was quenched by dropwise addition of 12 mL of AcOH/THF (v/v, 1/1). The resulting mixture was warmed up and partitioned in EtOAc and saturated $NaHCO_3$. The organic layer was washed with $H_2O$ and dried over $Na_2SO_4$. After concentration, the residue was purified by the flash column chromatography (silica, hexanes/ethyl acetate, v/v, 4/1) to afford compound 2 (1.19 g, 54% yield) as brown solid. $^1$H NMR (300 MHz, $CDCl_3$) δ 7.76-7.81 (m, 2H), 7.42-7.56 (m, 2H), 7.20 (d, 1H), 4.69 (s, 2H), 4.61 (s, 2H), 4.57 (s, 2H), 3.64 (t, 2H), 3.07 (t, 2H) ppm.

Step c. Compound 2 (1.19 g, 2.99 mmol), N-Boc-L-Proline (1.65 g, 7.64 mmol), KI (1.27 g, 7.65 mmol) and DIPEA (1.32 mL, 7.63 mmol) were dissolved in $CH_3CN$ (15.3 mL). The reaction mixture was then heated to 50° C. in an oil bath for 4 h and cooled to rt. The solvent was removed under vacuum, and the crude was partitioned in EtOAc (20 mL) and $H_2O$ (10 mL). The organic layer was separated and the aqueous layer was extracted with EtOAc (2×20 mL). The combined EtOAc layers were dried over $Na_2SO_4$, filtered and concentrated under vacuum. The crude material was purified by flash column chromatograph eluted with hexanes/ethyl acetate (2/1 to 1/1 (v/v)) to afford 3 as a yellow solid (1.1 g, 49% yield).

Step d. Compound 3 (1.0 g, 1.32 mmol), $NH_4OAc$ (2.89 g, 39.6 mmol), TEA (5.52 mL, 96.6 mL) were dissolved in xylene (6.6 mL). The reaction mixture in a sealed tube was then heated to 140° C. in an oil bath for 2 h and then cooled to rt. EtOAc and $H_2O$ were added and the organic layer was separated. The aqueous layer was extracted with EtOAc (3×50 mL). The combined EtOAc layers were dried over $Na_2SO_4$, filtered and concentrated under vacuum. The crude material was purified by flash column chromatograph eluted with hexanes/ethyl acetate (1/2 to 0/1 (v/v)) to afford 4 as yellow solid (0.7 g, 74% yield).

Step 5. A sample of compound 4 (0.50 g, 0.70 mmol), dissolved in dioxane (2 mL) with stirring, was treated with 4M HCl in dioxane (14.3 mL, 57.3 mmol). After stirring at rt for 2 h, the reaction mixture was concentrated and the residue was dried in vacuo to give an HCl salt, which was used for the next without further purification. rt The HCl salt (50 mg, 0.097 mmol) and N-Moc-L-Valine (34 mg, 0.194 mmol) were dissolved in DMF (2 mL). DIPEA (0.2 mL, 1.16 mmol) and DMTMM (53.6 mg, 0.19 mmol) were added to the mixture. After stirring at rt for overnight, the reaction mixture was concentrated and the residue was purified by preparative HPLC to give rt compound 5 (9.3 mg) as a light yellow solid $^1$H NMR (CD$_3$OD, 300 MHz) δ 8.18 (1H, s), 7.52-6.99 (7H, m), 5.35-5.27 (1H, m), 5.19-5.11 (2H, m), 4.33 (2H, s), 4.25-4.19 (2H, m), 4.03-3.95 (3H, m), 3.90-3.80 (2H, m), 3.70-3.65 (6H, s), 3.50-3.45 (2H, m), 3.00-2.95 (2H, m), 2.40-1.98 (12H, m), 0.99-0.88 (12H, m) ppm. LC-MS (ESI): m/z 830.4 (M+H)$^+$.

Scheme 11-1

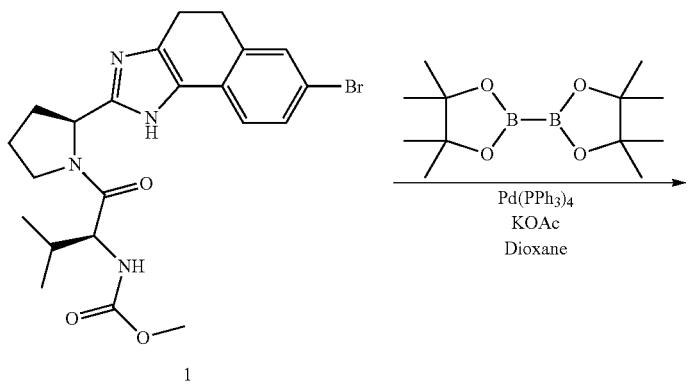

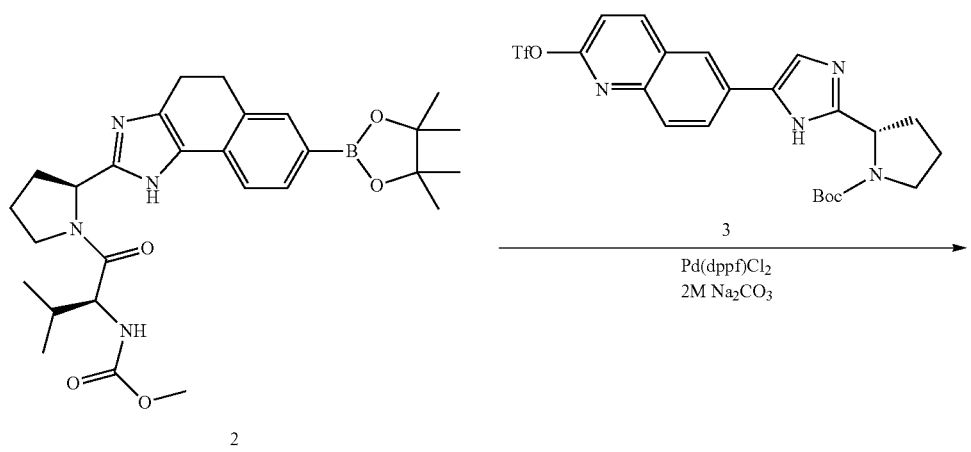

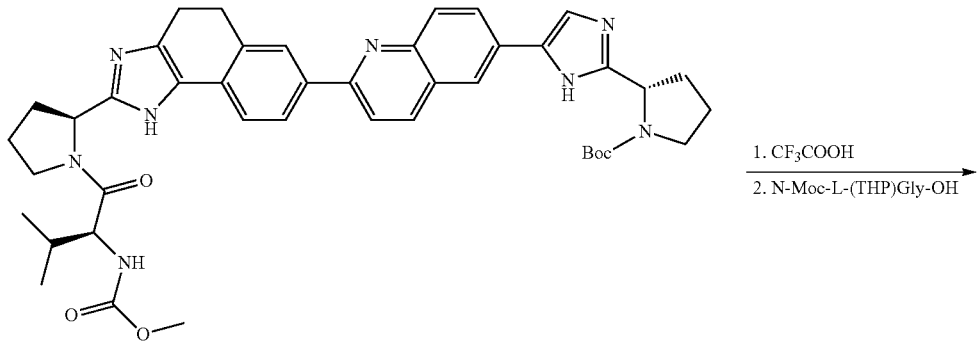

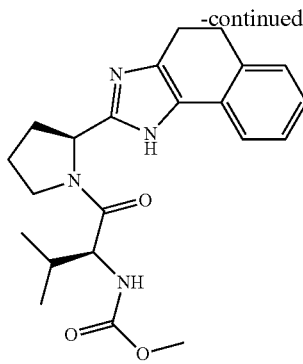
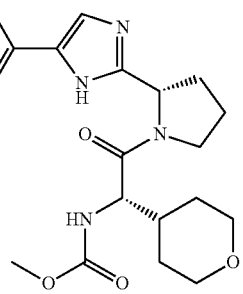

↓ DDQ

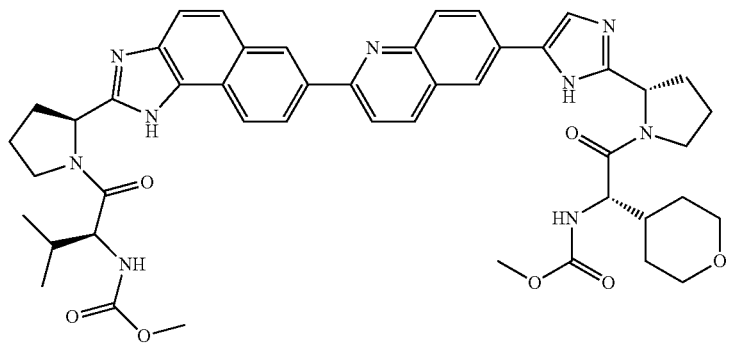

6

Example 11

Synthesis of Compounds of Formula Vc

Step a. Referring to Scheme 11-1, to a solution of the bromide 1 (2.0 g, 4.2 mmol, prepared according to published conditions) in dioxane (60 mL) was added bis(pinacolato) diboron (4.32 g, 17 mmol), Pd(PPh$_3$)$_4$ (0.49 g, 0.42 mmol) and potassium acetate (2.06 g, 21 mmol) under nitrogen atmosphere. The reaction mixture was stirred at 80° C. for 5 h, and then diluted with ethyl acetate (150 mL). The organic phase was washed with H$_2$O (20 mL), dried over sodium sulfate and concentrated in vacuo. The residue was further purified by silica gel column chromatography (hexanes/ethyl acetate=1/4 to 0/1 (v/v)) to give 2 (1.73 g, 79% yield). LC-MS (ESI): m/z 523.3 (M+H)$^+$.

Step b. A mixture of 2-quinolinol triflate 3 (0.72 g, 1.4 mmol), boronic ester 2 (0.73 g, 1.4 mmol), Pd(dppf)C$_{12}$-DCM (114 mg, 0.14 mmol) in 2 M Na$_2$CO$_3$ (2.8 mL) and dioxane (5.6 mL) was treated by a process of degas-and-refilled-with-nitrogen three times. The reaction mixture was then stirred at 90° C. under nitrogen atmosphere for 4 h. After being cooled, the mixture was diluted with THF, and then filtered through a pad of CELITE™. The filtrate was concentrated and the crude product was purified by flash chromatography (NH$_4$OH/acetonitrile/ethyl acetate, 1:8:100) affording a pure product 4 (0.80 g, 75% yield) as a white solid. LC-MS (ESI): m/z 759.4 (M+H)$^+$.

Step c. Trifluoroacetic acid (2.5 mL) was slowly added into a solution of 4 (0.80 g, 1.5 mmol) in CH$_2$Cl$_2$ (5.0 mL) at rtrt. The resulting mixture was stirred at rtrt for 2 h, and then concentrated to dryness. The crude product was dried in vacuo to give a TFA salt, which was used for the next step without further purification. LCMS (ESI): m/z 659.3 (M+H)$^+$.

Step d. To a mixture of the TFA salt (69.1 mg, 0.11 mmol) obtained from above reaction in DMF (3 mL) was added DIPEA (0.23 mL, 1.4 mmol), followed by L-N-methoxycarbonyl-(4-tetrahydro-2H-pyran-4-yl)glycine (30 mg, 0.14 mmol) and HATU (52 g, 0.14 mmol). After stirring at rt for 2 h, the reaction mixture was slowly dropped into H$_2$O while stirring. The resulting precipitate was collected by filtration. The crude product was purified by prep-HPLC to afford product 5 (34.5 mg). $^1$H NMR (CDCl$_3$, 300 MHz) δ 7.90 (m, 1H), 7.80-7.60 (m, 4H), 7.5 (m, 2H), 7.36 (d, 1H), 7.10 (broad s, 2H), 7.56 (d, 1H), 7.44 (d, 1H), 5.28 (m, 2H), 4.54 (t, 1H), 4.42 (t, 1H), 4.10-3.93 (m, 7H), 3.68 (m, 7H), 3.42 (m, 2H), 3.00-2.22 (m, 8H), 2.08 (m, 5H), 1.80-1.40 (4H), 1.10-0.90 (m, 6H) ppm LC-MS (ESI): m/z 858.4 (M+H)$^+$.

Step e. A solution of compound 5 (37.7 mg, 0.044 mmol), DDQ (10.0 mg, 0.044 mmol) in 6 mL of benzene was refluxed for 2.5 h. After removal of the solvent, the crude product was purified by prep-HPLC to afford 6 (23 mg) as yellow powder. ¹H NMR (CDCl₃, 300 MHz) δ 8.40-7.40 (m, 10H), 7.22 (s, 1H), 5.60-5.40 (m, 3H), 5.30 (m, 2H), 4.60-4.40 (m, 2H), 4.20-3.80 (m, 6H), 3.70 (m, 7H), 3.44 (m, 3H), 2.50-2.00 (m, 13H), 1.10-0.92 (m, 6H) ppm. LC-MS (ESI): m/z 856.4 (M+H)⁺.

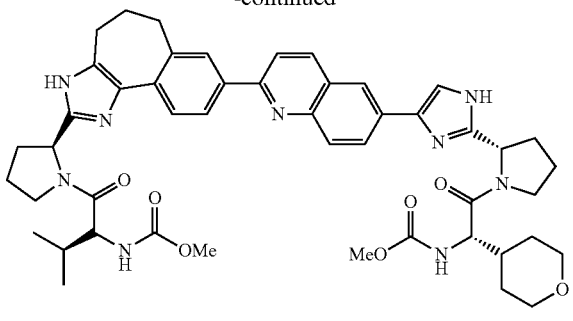

6a

Following procedures and conditions described in Scheme 11-1 and substituting compound 1a for compound 1, compound 6a was prepared. ¹H NMR (300 MHz, CD₃OD) δ 9.21-9.18 (m, 1H), 8.79 (s, 1H), 8.56-8.50 (m, 3H), 8.26-8.19 (m, 3H), 8.10-8.07 (m, 1H), 5.32-5.25 (m, 2H), 4.34-4.24 (m, 2H), 4.13-4.06 (m, 2H), 3.95-3.89 (m, 4H), 3.67 (s, 6H), 3.24-3.09 (m, 6H), 2.65-2.10 (m, 12H), 1.60-1.30 (m, 4H), 1.01-0.91 (m, 6H) ppm; LC-MS (ESI): m/z 872.4 (M+H)⁺.

Example 12

Additional Synthetic Schemes for Compounds of the Invention

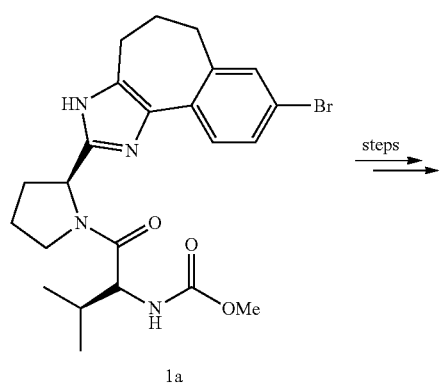

1a

Scheme 12-1

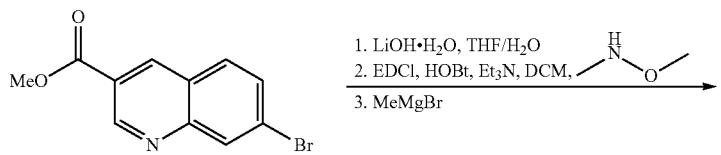

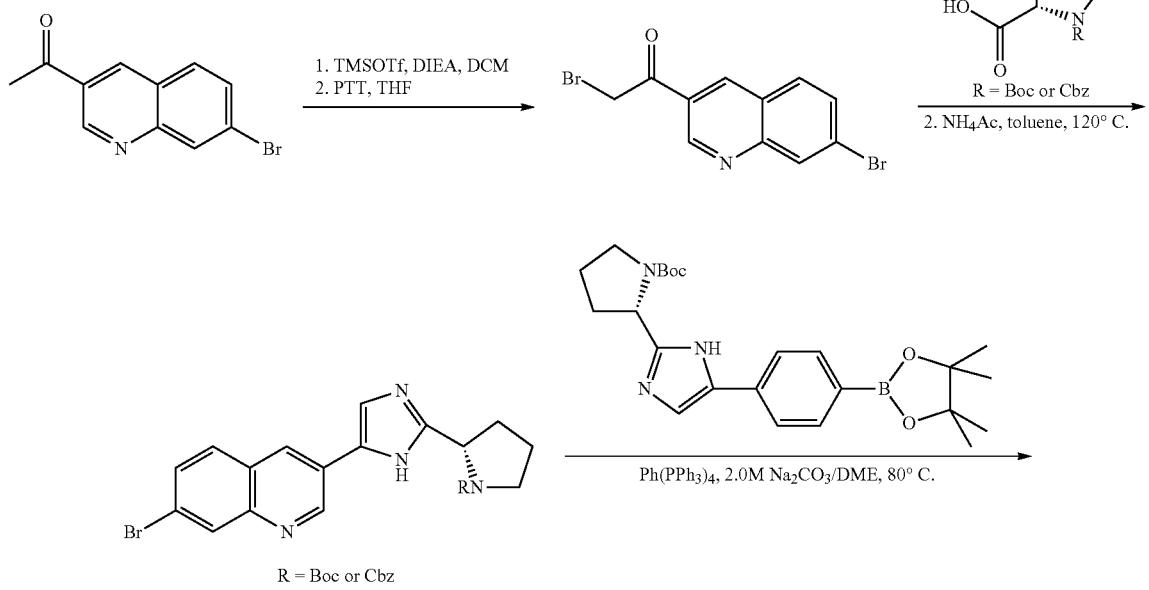

R = Boc or Cbz

-continued
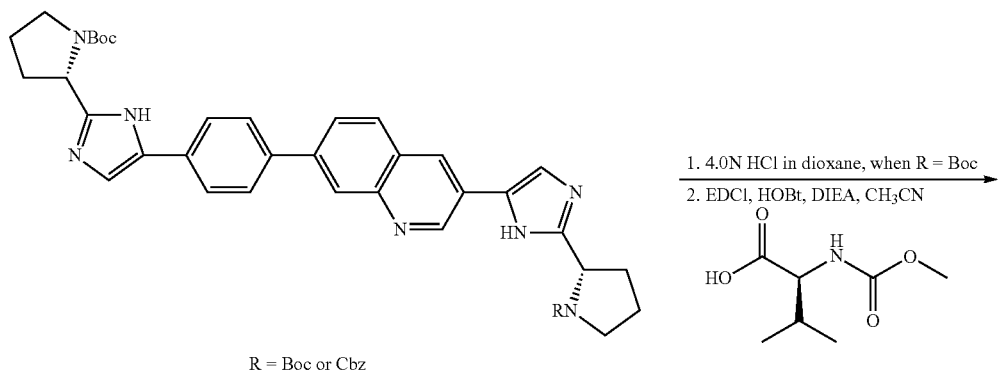
R = Boc or Cbz
1. 4.0N HCl in dioxane, when R = Boc
2. EDCl, HOBt, DIEA, CH$_3$CN
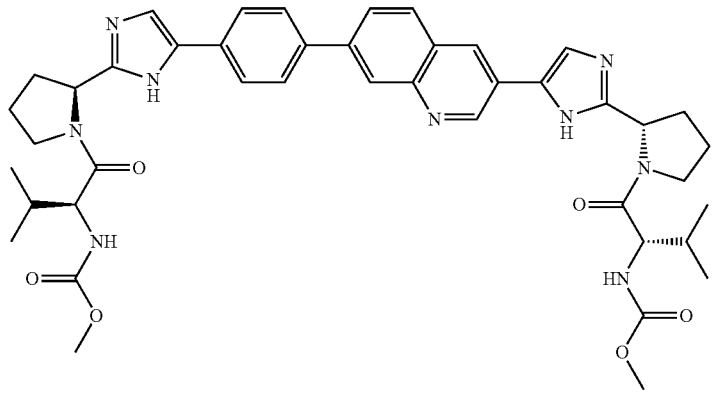
Scheme 12-2
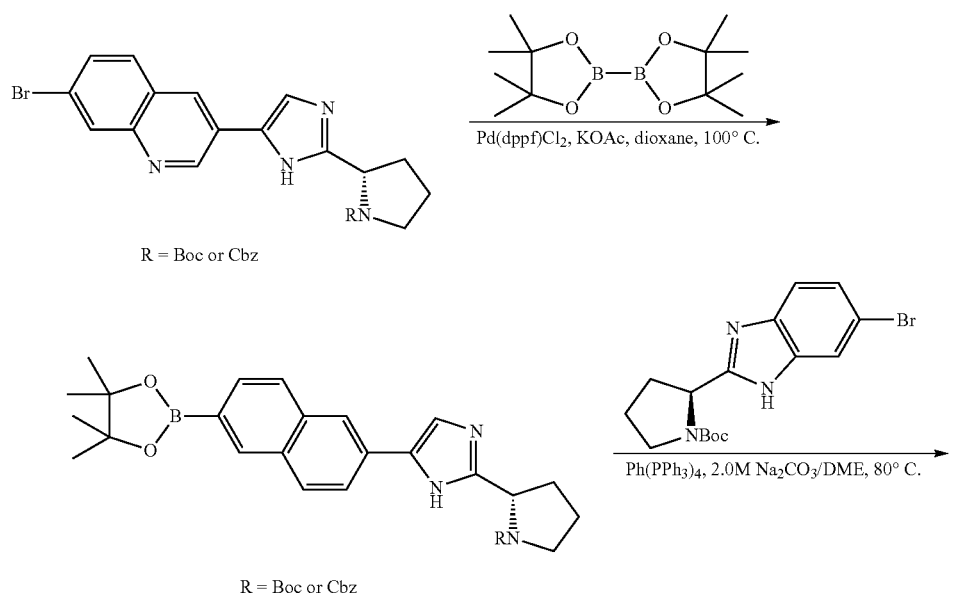
R = Boc or Cbz 191
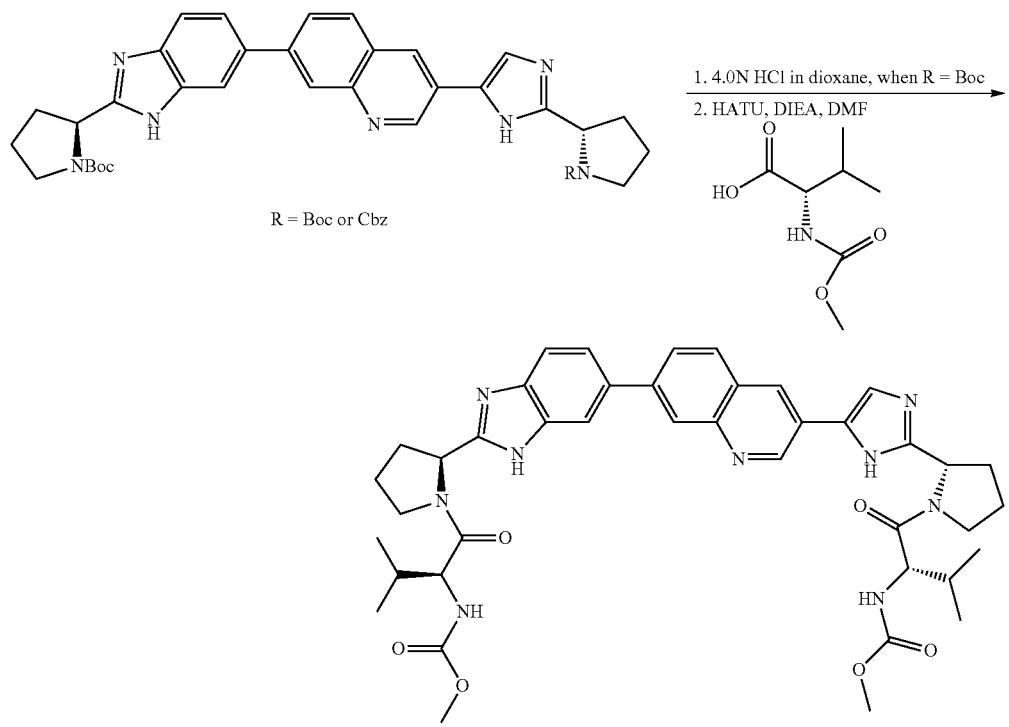
R = Boc or Cbz
192
Scheme 12-3
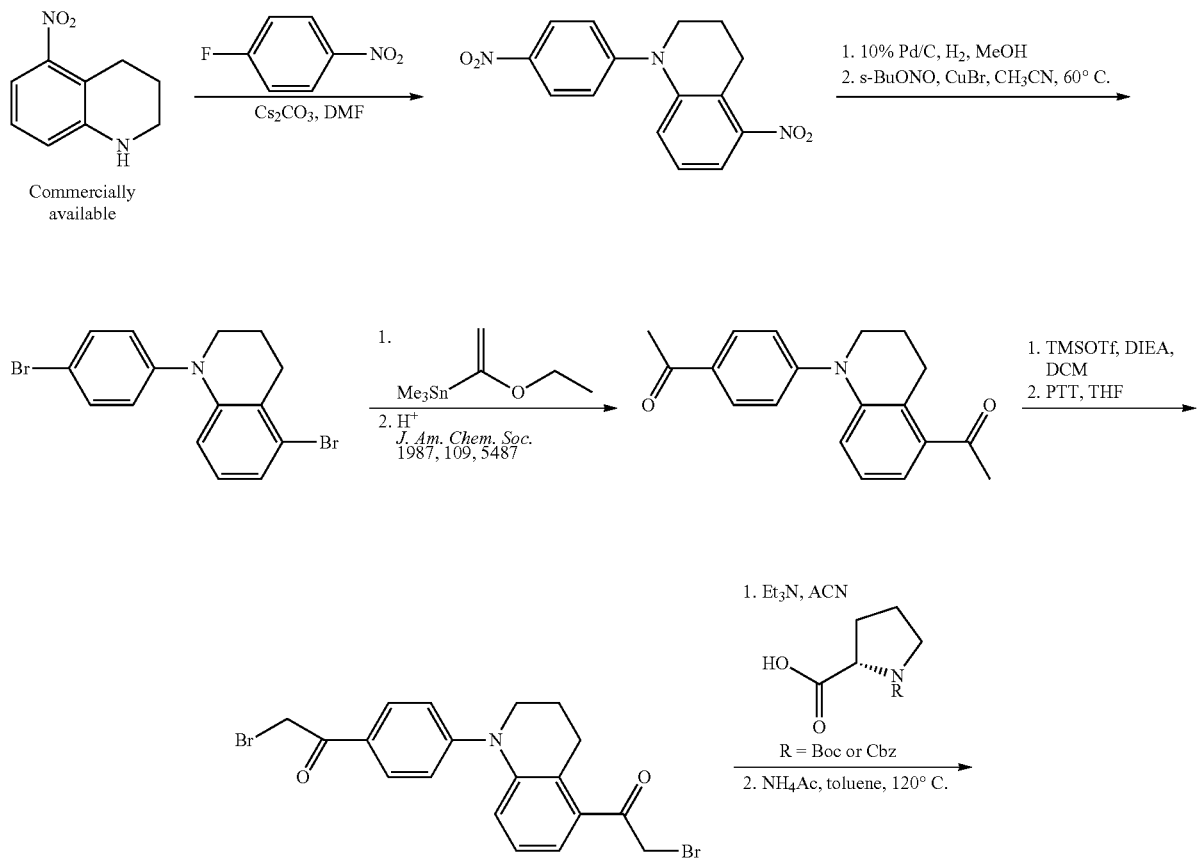

-continued
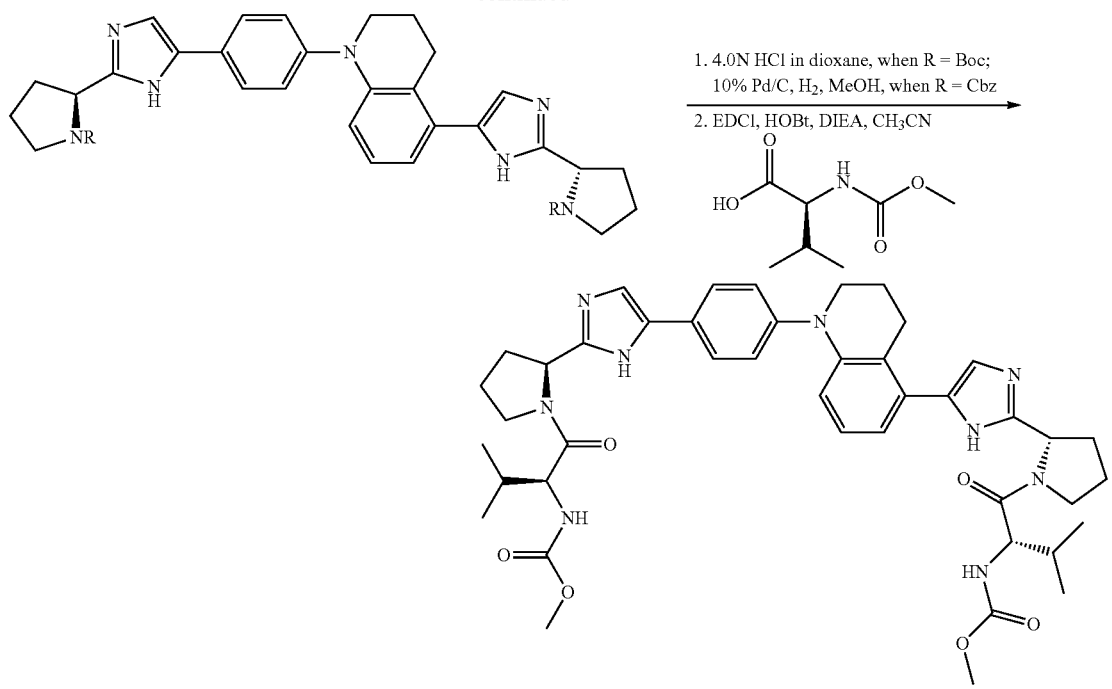
Scheme 12-4
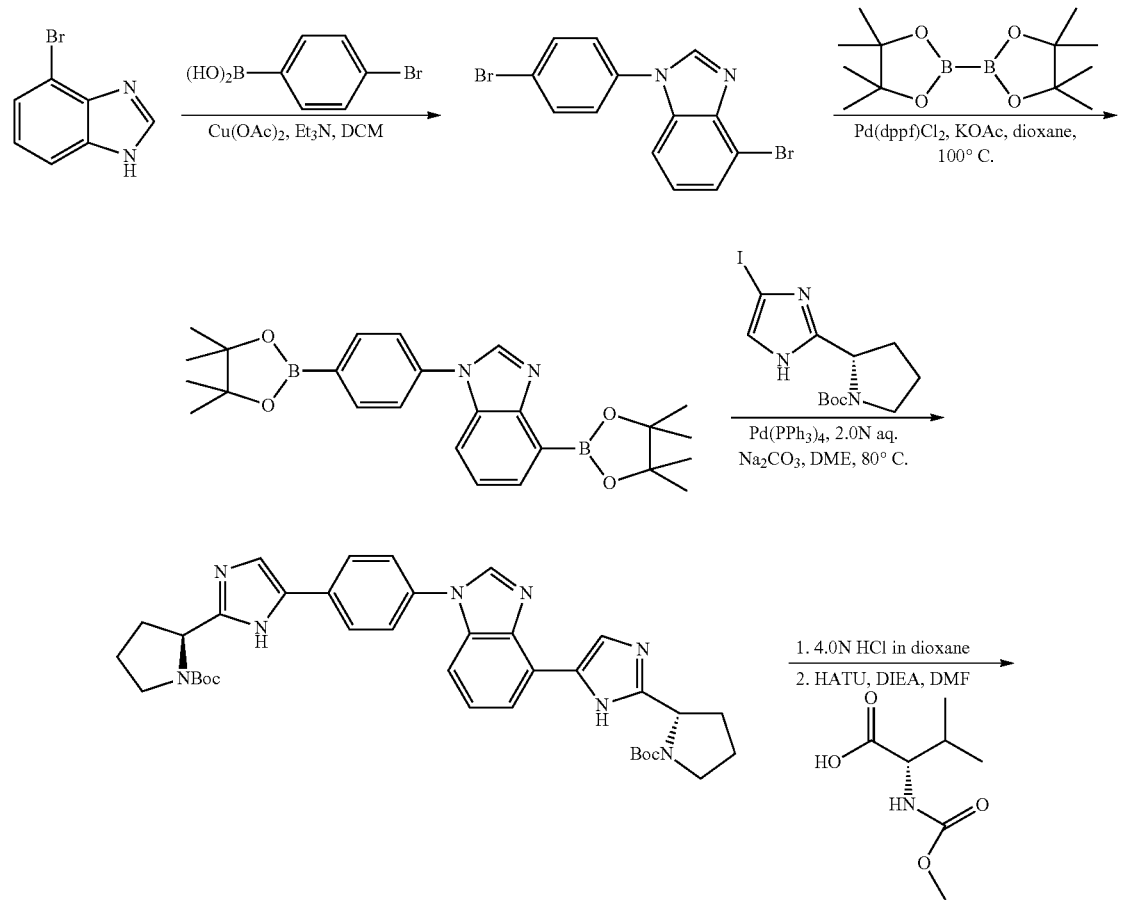

-continued
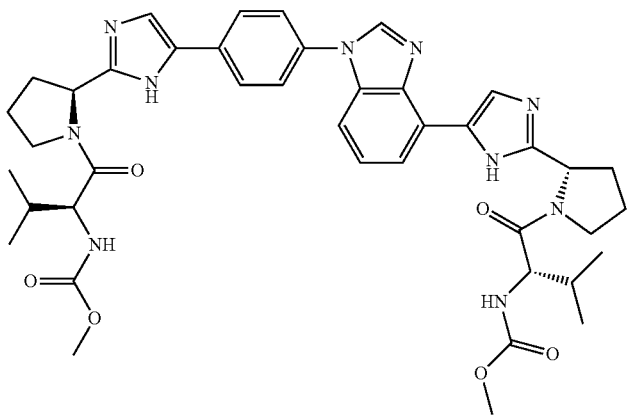
Scheme 12-5
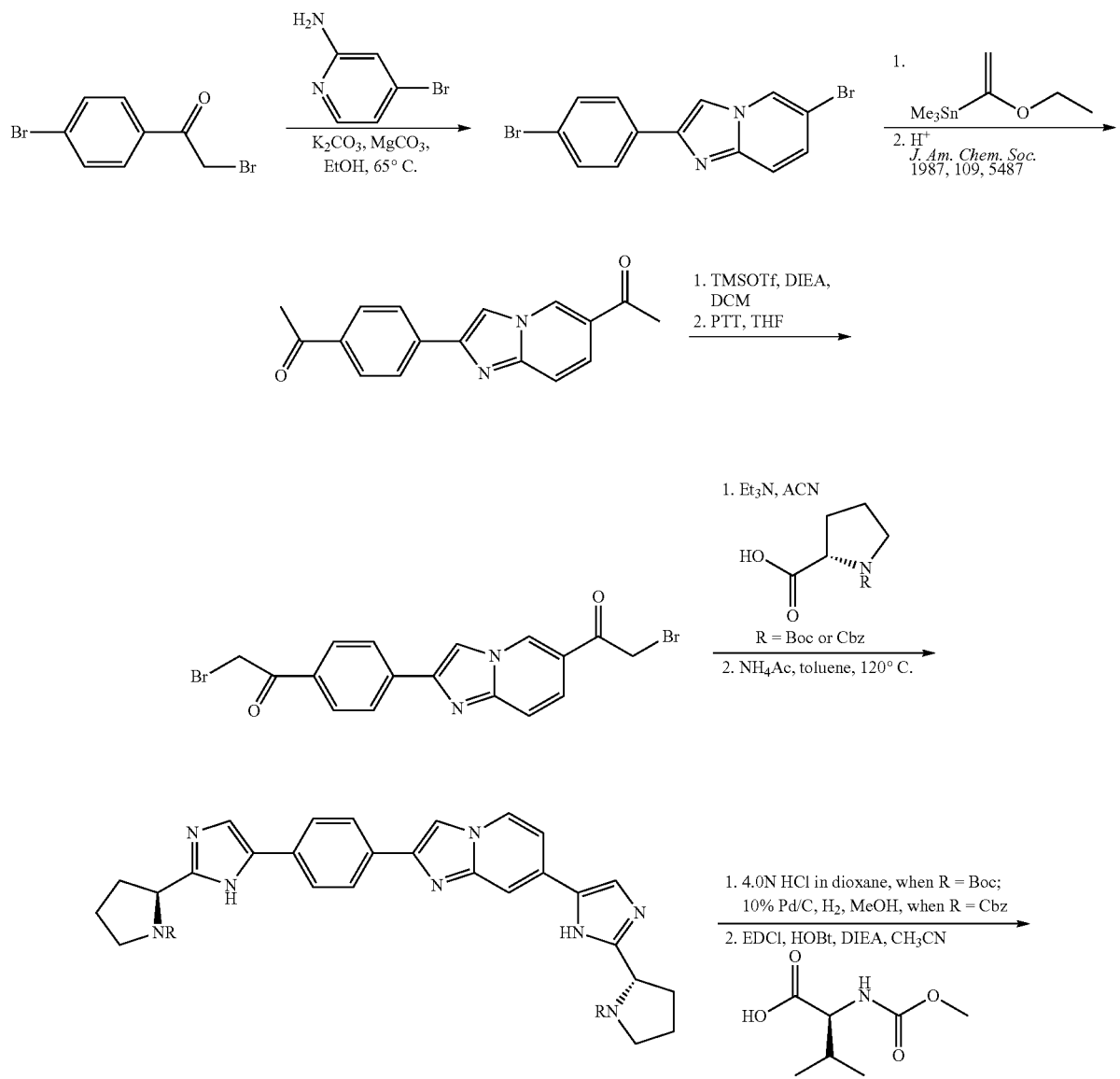

-continued
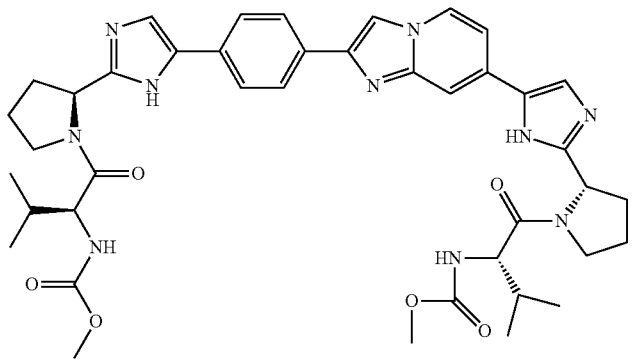
Scheme 12-6
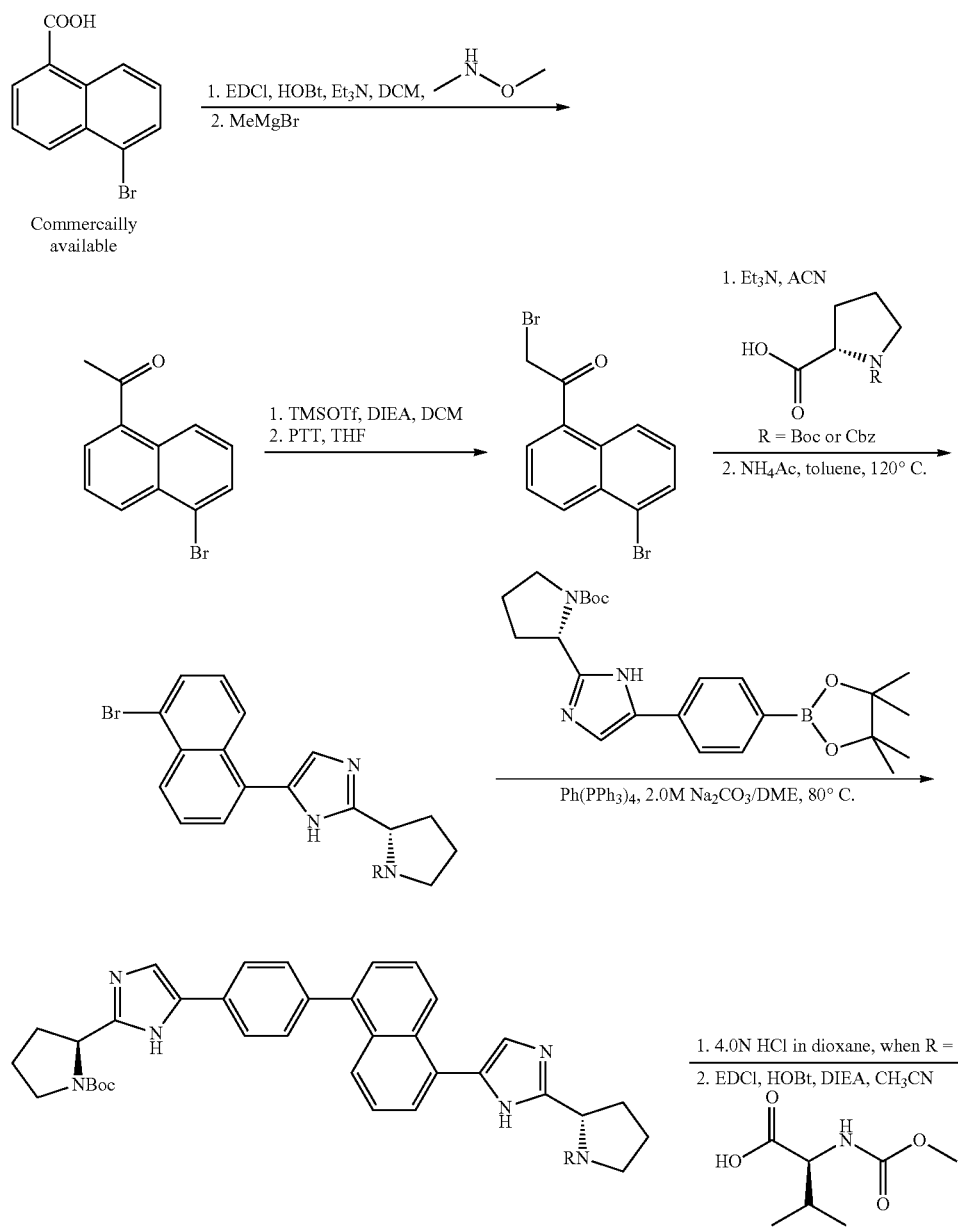

-continued
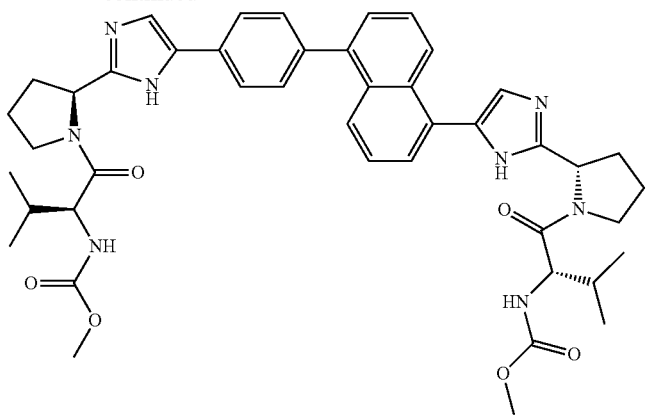
Scheme 12-7
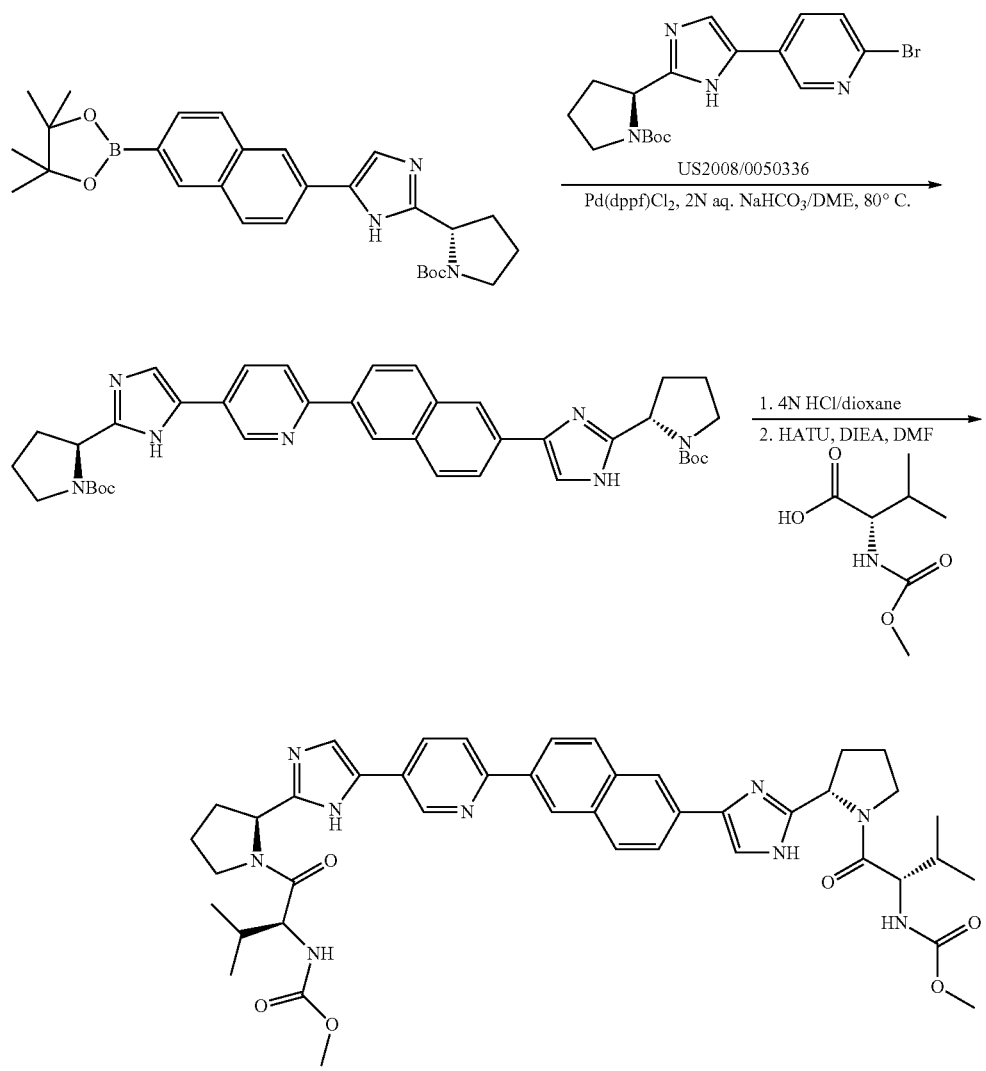

Scheme 12-8

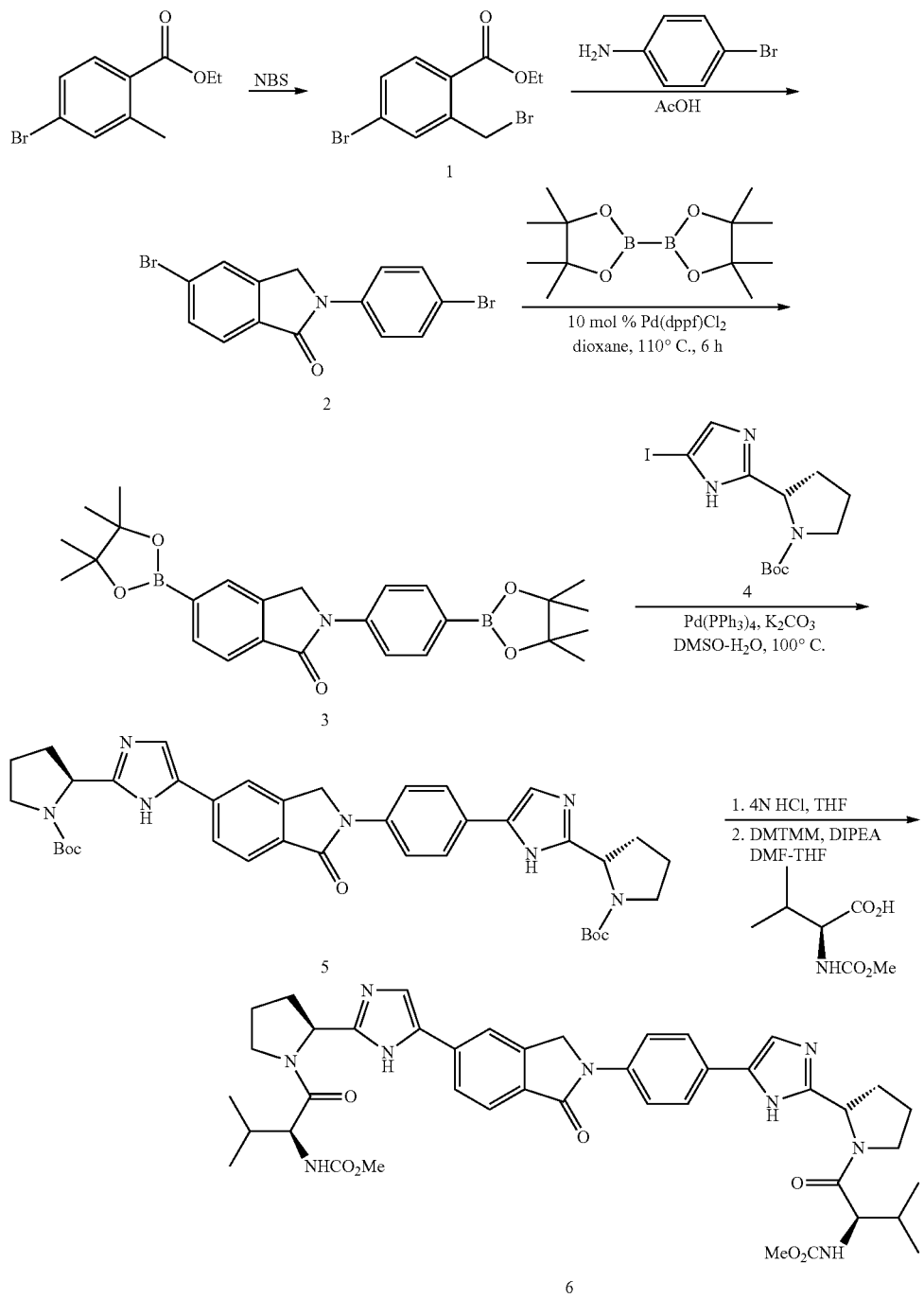

Step a. Referring to Scheme 12-8, a mixture of ethyl 4-bromo-2-methylbenzoate (1.0 g, 4.11 mmol) and NBS (1.15 g, 6.46 mmol) in CCl$_4$ (13.7 mL) was heated to reflux for 6 h. The white precipitate was filtered off and the filtrate was concentrated under reduced pressure to obtain yellow oil 1 (1.47 g) which contained approx. 25% of unreacted starting material by LC/MS. The crude material was used without further purification.

Step b. Crude ester 1 (4.11 mmol) was dissolved in glacial acetic acid (13.7 mL), and 4-bromoanaline (0.85 g, 4.93 mmol) was added to the solution. The reaction mixture was then heated to reflux for 12 h and cooled to rt. H$_2$O (150 mL) was added and neutralized with solid Na$_2$CO$_3$ to pH 7. The aqueous solution was extracted with ethyl acetate (3×100 mL), and the organic layers were dried over Na$_2$SO$_4$, filtered and concentrated under vacuum. The crude material was purified by flash column chromatograph eluted with hexanes/ethyl acetate (12/1 to 10/1) to removed byproduct and then with pure ethyl acetate to afford brown solid 2 (0.54 g, 36% yield). $^1$H NMR (300 MHz, CDCl$_3$) δ 7.79-7.69 (m, 3H), 7.68-7.67 (m, 2H), 7.65-7.52 (m, 2H), 4.82 (m, 2H) ppm.

Step c. A mixture of compound 2 (0.54 g, 1.46 mmol), pinacol diborane (0.82 g, 3.22 mmol), KOAc (0.86 g 8.76 mmol), and Pd catalyst (0.12 g, 0.15 mmol) in dioxane (28 mL) was heated at 110° C. for 30 h. The reaction mixture was cooled to rt and diluted with H$_2$O. The aqueous layer was extracted with ethyl acetate, and the organic layer was dried over Na$_2$SO$_4$, filtered and concentrated under vacuum. The crude material was purified by flash column chromatograph eluted with ethyl acetate to afford dark yellow solid 3 (0.49 g, 73% yield). $^1$H NMR (300 MHz, CDCl$_3$) δ 7.90-7.70 (m, 7H), 4.81 (s, 2H), 1.40-1.20 (m, 24H) ppm.

Step d. A mixture of 3 (400 mg, 0.87 mmol), iodoimidazole compound 4 (630 mg, 1.73 mmol) and Pd(PPh$_3$)$_4$ (200 mg, 0.17 mmol) and potassium carbonate (311 mg, 2.25 mmol) in DMSO (10 mL) and H$_2$O (3.5 mL) was heated at 100° C. for 14 h. The reaction mixture was cooled to rt and diluted with H$_2$O and extracted with dichloromethane. The combine organic layers were dried over Na$_2$SO$_4$, filtered and concentrated under vacuum. The crude material was purified by flash column chromatography (ethyl acetate/methanol=97/3 (v/v)) to afford 5 (357 mg, 61% yield) as a light yellow solid. $^1$H NMR (CDCl$_3$, 300 MHz) δ 7.95-6.90 (m, 9H), 4.95 (m, 2H), 3.41 (m, 4H), 2.95 (m, 2H), 2.28-1.85 (m, 6H), 1.50 (s, 9H), 1.48 (s, 9H) ppm.

Step e. To a stirred suspension of 5 (40 mg, 0.059 mmol) in THF (0.6 mL) at rt was added 4 N HCl solution in 1,4-dioxane (0.6 mL), and the mixture was stirred at rt for 4 h. The reaction mixture was concentrated in vacuo to give an HCl salt (37 mg, 100% yield), which was used without purification in the next step. LC-MS (ESI) m/z: [(M+2H)/2]$^+$ 478.5.

Step f. To a stirred solution of HCl salt from above (37 mg, 0.059 mmol) and N-methoxycarbonyl-L-valine (22.6 mg, 0.13 mmol) in DMF (2 mL) was added HATU (49 mg, 0.13 mmol) followed by diisopropylethyl amine (0.1 mL, 0.59 mmol). After being stirred at rt for 4 h, the reaction mixture was diluted with H$_2$O and extracted with dichloromethane. The combine organic layers were dried over Na$_2$SO$_4$, filtered and concentrated under vacuum to give the crude product, which was purified by prep HPLC to give 6 (6.4 mg, 14% yield) as a white solid. $^1$H NMR (CDCl$_3$, 300 MHz) δ 7.95-7.20 (m, 9H), 5.20 (m, 2H), 4.40-3.61 (m, 6H), 3.34 (s, 6H), 3.20-1.90 (m, 12H), 0.95 (dd, 6H), 0.90 (dd, 6H). LC-MS (ESI) m/z: [M−H]$^−$ 793.

Step g. Similarly, the six-membered analogs (2a, 2b, 2c) of compound 2 were prepared following published procedures. Compounds 2a, 2b and 2c were further transformed following the same synthetic sequences and conditions described above afford their perspective analogs of compound 6.

Scheme 12-9

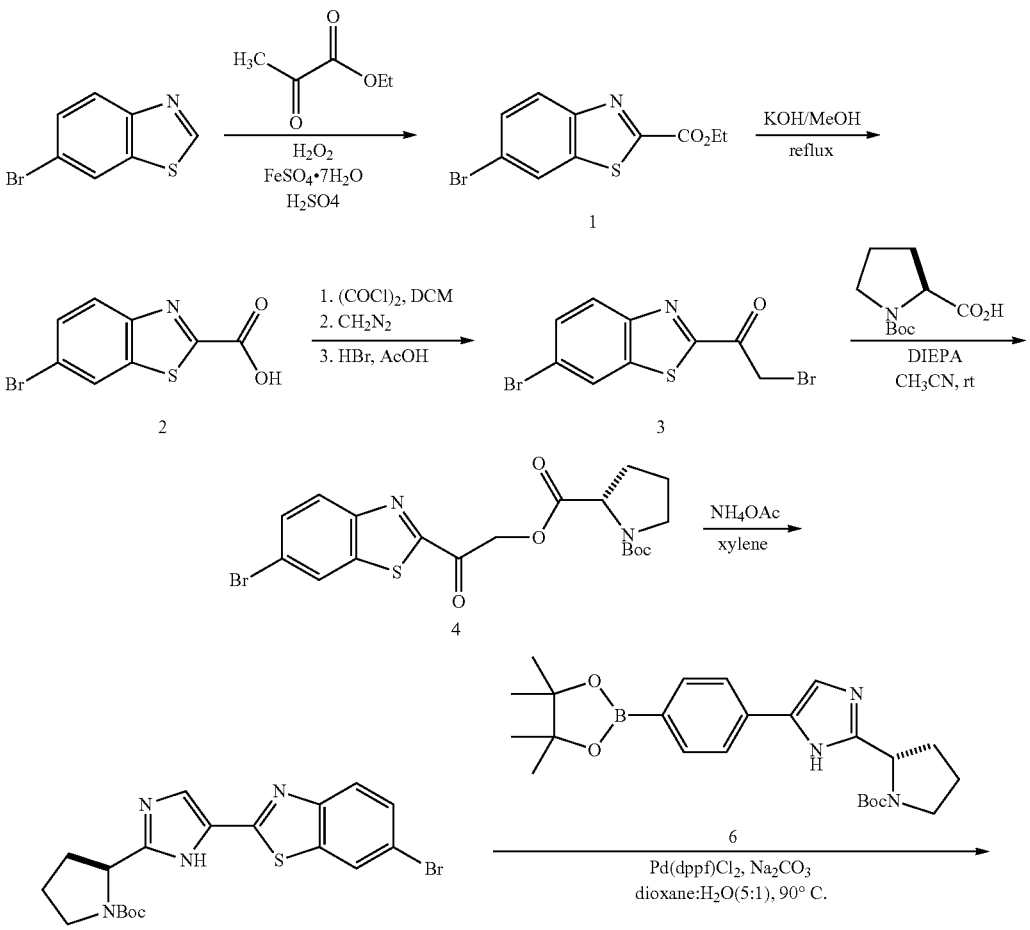

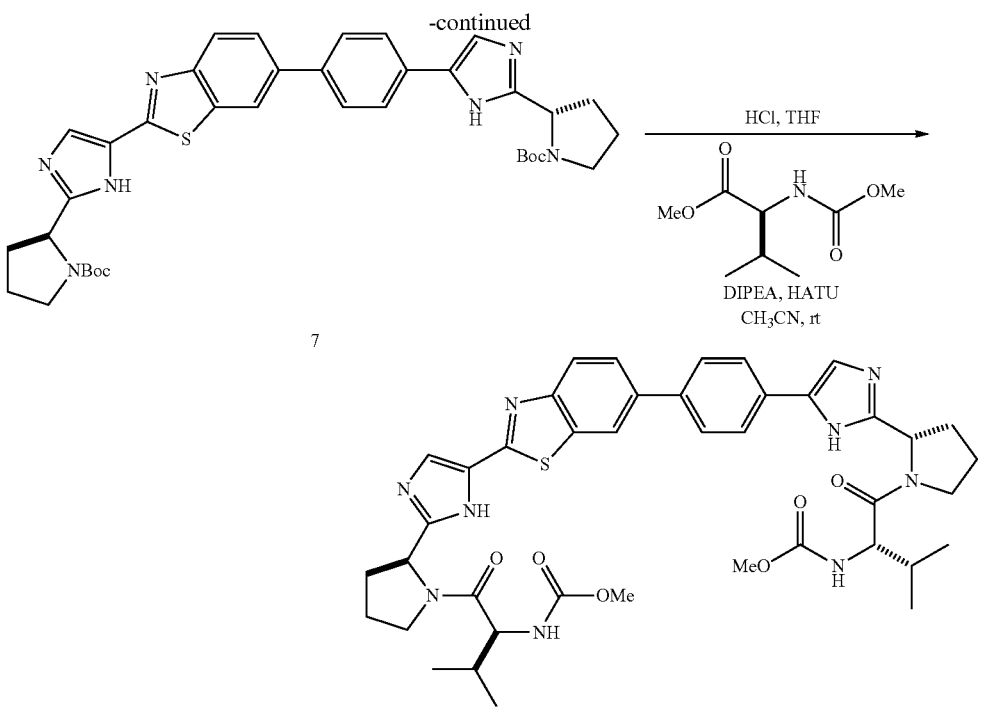

Step a. Referring to Scheme 12-9, to ethyl pyruvate (24.4 g, 23.4 mL, 210 mmol) was added dropwise $H_2O_2$ (35%, 13.6 g, 13.6 mL, 140 mmol) at 0° C. followed by stirring for 5 min To a mixture of 6-bromo-benzothiazole (10.0 g, 46.7 mmol) in $H_2O$ (45 mL) and $H_2SO_4$ (13.7 g, 7.5 mL, 140 mmol) was added simultaneously the fresh prepared ethyl pyruvate mixture and $FeSO_4·7H_2O$ (38.9 g, 140 mmol) in $H_2O$ (90 mL) at 0° C. The resulting mixture was kept at 0° C. and stirred at rt overnight. To the mixture was added additional $H_2SO_4$ (27.4 g, 15.0 mL, 280 mmol) followed by fresh prepared ethyl pyruvate mixture (28.8 g of ethyl pyruvate, 46.8 mL, 420 mmol and $H_2O_2$ 35%, 27.2 g, 27.2 mL, 280 mmol) and $FeSO_4·7H_2O$ (77.8 g, 280 mmol) in $H_2O$ (180 mL) at 0° C. After stirring at 0° C. for 7.5 h, excess ice was added to the reaction mixture and the pH was adjusted to 10-11 with a 2.0 M KOH solution. The basic mixture was extracted with EtOAc (5×300 mL), and the combined organic layers were dried over $Na_2SO_4$, filtered, and concentrated on a rotary evaporator to give yellow oil. The crude product 1 was used for the next step without further purification. LC-MS (ESI) m/z: $(M+1)^+$ 288.

Step b. To a crude mixture of 1 (~46.7 mmol) in MeOH (250 mL) was added KOH (25.2 g, 450 mmol). After the mixture was heated under reflux condition for 3 h, all volatile was removed on a rotary evaporator to give a brown solid. The brown solid was dissolved in $H_2O$ (200 mL) and then extracted with EtOAc (3×200 mL). The pH of the aqueous phase was adjusted to 3-4 with 10% HCl solution and extracted with EtOAc (5×200 mL). Combined organic layer was dried over $Na_2SO_4$, filtered, and concentrated on a rotary evaporator to give 2 as a yellow solid (9.66 g, 80% yield). LC-MS (ESI) m/z $(M+1)^+$ 260.

Step c. To a mixture of 2 (1.43 g, 5.5 mmol) in DCM (50 mL) was added slowly oxayl chloride (14.0 g, 9.5 mL, 110 mmol) followed by one drop of DMF at rt. After the resulting mixture was stirred at rt overnight (15 h), all volatiles were removed on a rotary evaporator. The crude mixture was used for the next step without purification.

Step d. To a solution of 6-bromo-benzothiazole-2-carbonyl chloride 2 (~5.5 mmol) in THF (50 mL) was added dropwise flash generated diazomethane solution (approximately 16.6 mmol of diazomethane solution generated from 25.1 mmol of 4-N,N-trimethyl-benzenesulfonamide) at 0° C. The resulting mixture was stirred at 0° C. for 30 min and then the temperature was allowed to warm to rt. After the stirring was continued at rt for 2.5 h, all volatile was removed on a rotary evaporator. The crude mixture was used for the next step without further purification.

Step e. To a mixture of 1-(6-bromo-benzothiazol-2-yl)-2-diazo-ethanone obtained from above (~5.5 mol) in AcOH (30 mL) was slowly added aqueous HBr (48%, 0.69 mL, 6.1 mmol) at rt. The resulting mixture was stirred at rt for an additional 2 h. All volatile was removed on a rotary evaporator to give dark solid. The crude mixture was further dried by azeotropic evaporation with toluene on a rotary evaporator (15 mL×2). Compound 3 was obtained as a dark brown solid, which was used for the next step without further purification.

Step f. To a crude mixture of 2-bromo-1-(6-bromo-benzothiazol-2-yl)-ethanone A7 (~5.5 mmol) in $CH_3CN$ (50 mL) was added pyrrolidine-1,2-dicarboxylic acid 1-tert-butyl ester (1.31 g, 6.1 mmol) followed by addition of DIPEA (2.14 g, 2.69 mL, 16.6 mmol) at rt. The resulting mixture was stirred at rt for 5 h, and then quenched with $H_2O$. The mixture was extracted with EtOAc (3×50 mL), and then the combined organic phases were washed with $H_2O$ (50 mL) and brined (50 mL), dried over $Na_2SO_4$, filtered, and concentrated on a rotary evaporator. The crude mixture was purified by column chromatography eluting with hexanes/EtOAc=6:1 to 4:1 (v/v) to give the title compounds as brown solid (297 mg, 12% for total 4 steps from 2). LC-MS (ESI) m/z: $(M+H)^+$ 493.

Step g. To a solution of (S)-2-(2-(6-bromobenzo[d]thiazol-2-yl)-2-oxoethyl) 1-tert-butyl pyrrolidine-1,2-dicarboxylate 4 (297 mg, 0.63 mmol) in xylene (5.0 mL) was added NH$_4$OAc (488 mg, 6.32 mmol). The resulting mixture was heated at 145° C. for 2 h, and then all solvent was removed on a rotary evaporator to give a crude mixture, which was subject to column chromatography eluting with hexanes:EtOAc (1:1 to 0:1 ratio). Compound 5 was obtained as brown solid (65 mg, 23%). LC-MS (ESI) m/z: (M+H)$^+$ 451.

Step h. A mixture of 5 (43 mg, 0.1 mmol), 6 (44 mg, 0.1 mmol, prepared as described previously), Pd(dppf)Cl$_2$ (4 mg, 5 µmol), and Na$_2$CO$_3$ (35 mg, 0.33 mmol) in dioxane/H$_2$O (2.0 mL/0.4 mL) was purged with N$_2$. The resulting mixture was stirred at 90° C. for 8 h, and then diluted with H$_2$O. The reaction mixture was extracted with EtOAc, and combined organic was dried over Na$_2$SO$_4$, filtered, and concentrated on a rotary evaporator. The crude mixture was purified by column chromatography eluting with hexanes:EtOAc=1:3 (v/v) to give 7a yellow solid (60 mg, 60% yield). LC-MS (ESI) m/z: (M+H)$^+$ 683; (M−H)$^−$ 681.

Step i. To a crude solution of compound 7 (717 mg, 1.056 mmol) in THF (7.5 mL) was added HCl (4.0 M in dioxane, 10 mL) at rt. The resulting mixture was stirred at rt for 16 h, and then all volatile was removed on a rotary evaporator to give yellow solid. The yellow solid was washed with diethyl ether (2×10 mL) and then further dried on a rotary evaporator to give yellow solid. The crude solid was used for the next step without further purification. The deprotected free amine from above (48 mg, ~0.1 mmol) was dissolved in CH$_3$CN (1.0 mL), was treated with N-methoxycarbonyl-L-valine (35 mg, 0.2 mmol), HATU (76 mg, 0.2 mmol) and DIEPA (52 mg, 65 µL, 0.4 mmol). The resulting mixture was stirred at rt for 2.5 h, and then all solvents were removed on a rotary evaporator to give crude mixture. The crude mixture was purified by prep-HPLC eluting H$_2$O to CH$_3$CN, and the isolated compound was ~80% purity. The product was further purified by prep-TLC eluting with EtOAc with 5% NH$_4$OH to give product 8 (4.5 mg) as a white solid. $^1$H NMR (300 MHz, CDCl$_3$) δ 8.12 (Br s, 1H), 7.58-7.84 (m, 5H), 7.28-7.46 (m, 4H), 5.38-5.58 (m, 4H), 4.36-4.42 (m, 2H), 3.87-3.98 (m, 2H), 3.71 (s, 3H), 3.69 (s, 3H), 2.10-2.40 (m, 2H), 1.20-1.40 (m, 8H), 0.81-0.91 (m, 12H). LC-MS (ESI) m/z: (M+H)$^+$ 795.

Biological Activity

Biological activity of the compounds of the invention was determined using an HCV replicon assay. The 1b_Huh-Luc/Neo-ET cell line persistently expressing a bicistronic genotype 1b replicon in Huh 7 cells was obtained from ReBLikon GMBH. This cell line was used to test compound inhibition using luciferase enzyme activity readout as a measurement of compound inhibition of replicon levels.

On Day 1 (the day after plating), each compound is added in triplicate to the cells. Plates incubated for 72 h prior to running the luciferase assay. Enzyme activity was measured using a Bright-Glo Kit (cat. number E2620) manufactured by Promega Corporation. The following equation was used to generate a percent control value for each compound.

% Control=(Average Compound Value/Average Control)*100

The EC$_{50}$ value was determined using GraphPad Prism and the following equation:

Y=Bottom+(Top−Bottom)/(1+10^((Log IC50−X)*Hill-Slope))

EC$_{50}$ values of compounds are repeated several times in the replicon assay.

Example compounds of the disclosed invention are illustrated in Tables 1 and 2. Table 1 includes inhibitory activity for many of the compounds with respect to HCV 1b. Additionally mass spectrometry results are provided. Table 2 provides additional example compounds of the invention. The biological activity is indicated as being *, , *, or ****, which corresponds to EC$_{50}$ ranges of >1000 nM, 999 nM to 10 nM, 9.9 nM to 1 nM, or <1 nM respectively.

Pharmaceutical Compositions

An eleventh aspect of the invention provides a pharmaceutical composition comprising compounds of the invention. In a first embodiment, the pharmaceutical composition further comprises one or more pharmaceutically acceptable excipients or vehicles, and optionally other therapeutic and/or prophylactic ingredients. Such excipients are known to those of skill in the art. The compounds of the present invention include, without limitation, basic compounds such as free bases. A thorough discussion of pharmaceutically acceptable excipients and salts is available in Remington's Pharmaceutical Sciences, 18th Edition (Easton, Pa.: Mack Publishing Company, 1990).

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

The invention includes a pharmaceutical composition comprising a compound of the present invention including isomers, racemic or non-racemic mixtures of isomers, or pharmaceutically acceptable salts or solvates thereof together with one or more pharmaceutically acceptable carriers and optionally other therapeutic and/or prophylactic ingredients.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate and the like.

For oral administration, the composition will generally take the form of a tablet, capsule, a softgel capsule nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents and the like.

A twelfth aspect of the invention provides use of the compounds of the invention in the manufacture of a medicament. In a first embodiment of the twelfth aspect, the medicament is for the treatment of hepatitis C.

A thirteenth aspect of the invention provides a method of treating hepatitis C comprising administering to a subject in need thereof, a therapeutically effective amount of a compound of the invention, optionally in a pharmaceutical composition. A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. The subject may be administered as many doses as is required to reduce and/or alleviate the signs, symptoms or causes of the disorder in question, or bring about any other desired alteration of a biological system. One of ordinary skill in the art of treating such diseases will be able, without undue experimentation and in reliance upon personal knowledge and the disclosure of this application, to ascertain a therapeutically effective amount of the compounds of this invention for a given disease.

Combination Therapy

The compounds of the present invention and their isomeric forms and pharmaceutically acceptable salts thereof are useful in treating and preventing HCV infection alone or when used in combination with other compounds targeting viral or cellular elements or functions involved in the HCV lifecycle. Classes of compounds useful in the invention may include, without limitation, all classes of HCV antivirals. For combination therapies, mechanistic classes of agents that may be useful when combined with the compounds of the present invention include, for example, nucleoside and non-nucleoside inhibitors of the HCV polymerase, protease inhibitors, helicase inhibitors, NS4B inhibitors and medicinal agents that functionally inhibit the internal ribosomal entry site (IRES) and other medicaments that inhibit HCV cell attachment or virus entry, HCV RNA translation, HCV RNA transcription, replication or HCV maturation, assembly or virus release. Specific compounds in these classes and useful in the invention include, but are not limited to, macrocyclic, heterocyclic and linear HCV protease inhibitors such as telaprevir (VX-950), boceprevir (SCH-503034), narlaprevir (SCH-900518), ITMN-191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor), VX-500, VX-813, PHX-1766, PHX2054, IDX-136, IDX-316, ABT-450 EP-013420 (and congeners) and VBY-376; the Nucleosidic HCV polymerase (replicase) inhibitors useful in the invention include, but are not limited to, R7128, PSI-7851, IDX-184, IDX-102, R1479, UNX-08189, PSI-6130, PSI-938 and PSI-879 and various other nucleoside and nucleotide analogs and HCV inhibitors including (but not limited to) those derived as 2'-C-methyl modified nucleos(t)ides, 4'-aza modified nucleos(t)ides, and 7'-deaza modified nucleos(t)ides. Non-nuclosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, NS5A inhibitors of the present invention may be used in combination with cyclophyllin and immunophyllin antagonists (eg, without limitation, DEBIO compounds, NM-811 as well as cyclosporine and its derivatives), kinase inhibitors, inhibitors of heat shock proteins (e.g., HSP90 and HSP70), other immunomodulatory agents that may include, without limitation, interferons (-alpha, -beta, -omega, -gamma, -lambda or synthetic) such as Intron A™, Roferon-A™, Canferon-A300™, Advaferon™, Infergen™, Humoferon™, Sumiferon MP™, Alfaferone™, IFN-β™, Feron™ and the like; polyethylene glycol derivatized (pegylated) interferon compounds, such as PEG interferon-α-2a (Pegasys™), PEG interferon-α-2b (PEGIntron™), pegylated IFN-α-con1 and the like; long acting formulations and derivatizations of interferon compounds such as the albumin-fused interferon, Albuferon™, Locteron™ and the like; interferons with various types of controlled delivery systems (e.g. ITCA-638, omega-interferon delivered by the DUROS™ subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isotorabine, ANA773 and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as InnoVac C, HCV E1 E2/MF59 and the like. In addition, any of the above-described methods involving administering an NS5A inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL™, REMICADE™ and HUMIRA™.

In addition, NS5A inhibitors of the present invention may be used in combination with antiprotozoans and other antivirals thought to be effective in the treatment of HCV infection, such as, without limitation, the prodrug nitazoxanide. Nitazoxanide can be used as an agent in combination the compounds disclosed in this invention as well as in combination with other agents useful in treating HCV infection such as peginterferon alfa-2a and ribavarin (see, for example, Rossignol, J F and Keeffe, E B, $Future\ Microbiol.$ 3:539-545, 2008).

NS5A inhibitors of the present invention may also be used with alternative forms of interferons and pegylated interferons, ribavirin or its analogs (e.g., tarabavarin, levoviron), microRNA, small interfering RNA compounds (e.g., SIRPLEX-140-N and the like), nucleotide or nucleoside analogs, immunoglobulins, hepatoprotectants, anti-inflammatory agents and other inhibitors of NS5A Inhibitors of other targets in the HCV lifecycle include NS3 helicase inhibitors; NS4A co-factor inhibitors; antisense oligonucleotide inhibitors, such as ISIS-14803, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative HCV inhibitor compounds include those disclosed in the following publications: U.S. Pat. No. 5,807,876; U.S. Pat. No. 6,498,178; U.S. Pat. No. 6,344,465; U.S. Pat. No. 6,054,472; WO97/40028; WO98/40381; WO00/56331, WO 02/04425; WO 03/007945; WO 03/010141; WO 03/000254; WO 01/32153; WO 00/06529; WO 00/18231; WO 00/10573; WO 00/13708; WO 01/85172; WO 03/037893; WO 03/037894; WO 03/037895; WO 02/100851; WO 02/100846; EP 1256628; WO 99/01582; WO 00/09543; WO02/18369; WO98/17679, WO00/056331; WO 98/22496; WO 99/07734; WO 05/073216, WO 05/073195 and WO 08/021,927.

Additionally, combinations of, for example, ribavirin and interferon, may be administered as multiple combination therapy with at least one of the compounds of the present invention. The present invention is not limited to the aforementioned classes or compounds and contemplates known and new compounds and combinations of biologically active agents (see, Strader, D. B., Wright, T., Thomas, D. L. and Seeff, L. B., $AASLD\ Practice\ Guidelines.$ 1-22, 2009 and Manns, M. P., Foster, G. R., Rockstroh, J. K., Zeuzem, S., Zoulim, F. and Houghton, M., $Nature\ Reviews\ Drug\ Discovery.$ 6:991-1000, 2007, Pawlotsky, J-M., Chevaliez, S, and McHutchinson, J. G., $Gastroenterology.$ 132:179-1998, 2007, Lindenbach, B. D. and Rice, C. M., $Nature$ 436:933-938, 2005. Klebl, B. M., Kurtenbach, A., Salassidis, K., Daub, H. and Herget, T., $Antiviral\ Chemistry\ \&\ Chemotherapy.$ 16:69-90, 2005. Beaulieu, P. L., $Current\ Opinion\ in\ Investigational\ Drugs.$ 8:614-634, 2007. Kim, S-J., Kim, J-H., Kim, Y-G., Lim, H-S, and Oh, W-J., *The Journal of Biological Chemistry.* 48:50031-50041, 2004, Okamoto, T., Nishimura, Y., Ichimura, T., Suzuki, K., Miyamura, T., Suzuki, T., Moriishi, K. and Matsuura, Y., *The EMBO Journal.* 1-11, 2006, Soriano, V., Peters, M. G. and Zeuzem, S. *Clinical Infectious Diseases.* 48:313-320, 2009, Huang, Z., Murray, M. G. and Secrist, J. A., *Antiviral Research.* 71:351-362, 2006 and Neyts, J., *Antiviral Research.* 71:363-371, 2006, each of which is incorporated by reference in their entirety herein). It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the professional judgment of the person administering or supervising the administration of the combination therapy.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

The invention claimed is:
1. A compound having formula I:

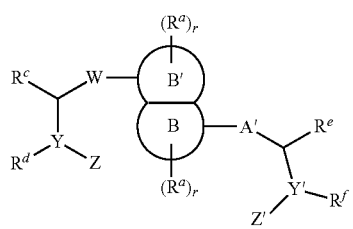

or a pharmaceutically acceptable salt thereof, wherein:
A' is a heteroaryl group selected from the group consisting of

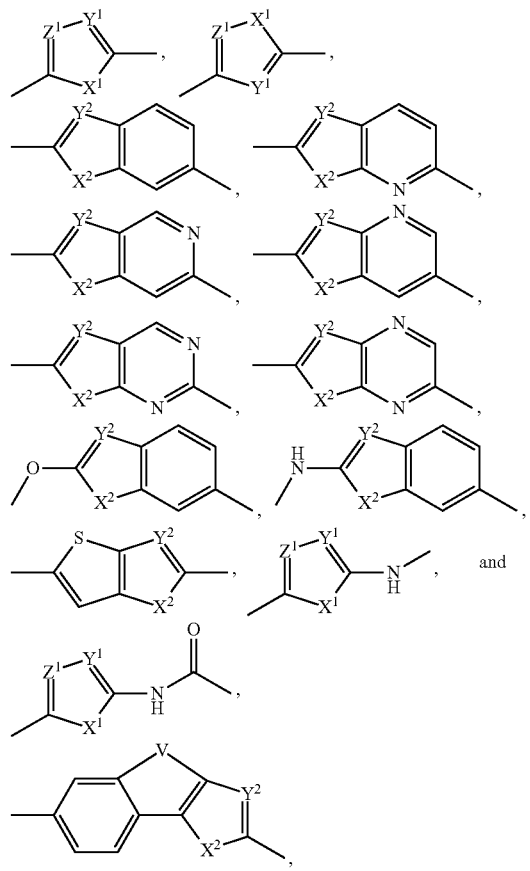

wherein:
$X^1$ is $CH_2$, NH, O or S,
$Y^1$, $Y^2$ and $Z^1$ are each independently CH or N,
$X^2$ is NH, O or S,
the carbons of the heteroaryl group are each independently optionally substituted with a substituent selected from the group consisting of halogen, —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
the nitrogens, if present, of the heteroaryl group are each independently optionally substituted with a substituent selected from the group consisting of —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide,
wherein B is alternatively attached to either side of A' so that in the example of A' being

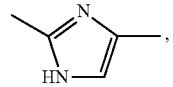

the W-B-A' is

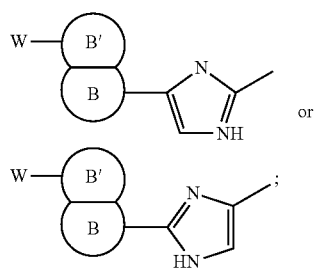

B and B' are each phenyl, such that the moiety B-B' is naphthyl;
each $R^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
each r is independently 0, 1, 2 or 3;
W is independently selected from

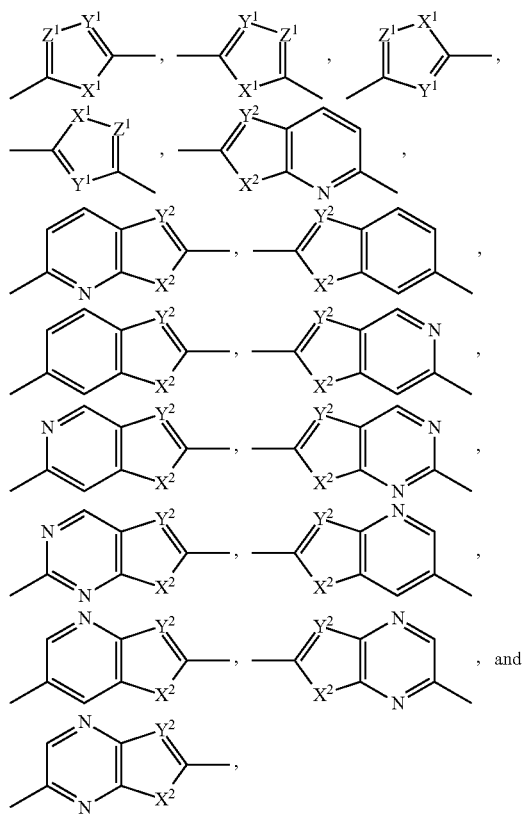

wherein:
$X^1$ is CH$_2$, NH, O or S,
$Y^1$, $Y^2$ and $Z^1$ are each independently CH or N,
$X^2$ is NH, O or S,
W is optionally substituted with one or more substituents selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, W and ring B' are connected through a carbon atom on B', and each $R^c$, $R^d$, $R^e$ and $R^f$ is independently selected from the group consisting of: hydrogen, C$_1$ to C$_8$ alkyl, C$_1$ to C$_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by C$_1$ to C$_8$ alkyl, C$_1$ to C$_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 5-membered heterocycle or heteroaryl ring, and $R^e$ and $R^f$ are optionally joined to form a 4- to 8-membered heterocycle which is optionally fused to another 3- to 5-membered heterocycle or heteroaryl ring;

Y and Y' are each independently carbon or nitrogen; and
Z and Z' are independently selected from the group consisting of 1-3 amino acids, —[U—(CR$^4_2$)$_t$—NR$^5$—C(R$^4_2$)$_t$]$_u$—U—(CR$^4_2$)$_t$—NR$^7$—(CR$^4_2$)$_t$—R$^8$, —U—(CR$^4_2$)$_t$—R$^8$, and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein, U is selected from the group consisting of —C(O)—, —C(S)— and —S(O)$_2$—, each $R^4$, $R^5$ and $R^7$ is independently selected from the group consisting of hydrogen, C$_1$ to C$_8$ alkyl, C$_1$ to C$_8$ heteroalkyl, cycloalkyl, heterocycle, aryl, heteroaryl and aralkyl, $R^8$ is selected from the group consisting of hydrogen, C$_1$ to C$_8$ alkyl, C$_1$ to C$_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each $R^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

2. The compound of claim 1, wherein $R^c$, $R^d$, $R^e$ and $R^f$ are each independently selected from the group consisting of: hydrogen, C$_1$ to C$_8$ alkyl and C$_1$ to C$_8$ heteroalkyl, wherein, each hetero atom, if present, is independently N, O or S, $R^c$ and $R^d$ are optionally joined to form a 4- to 8-membered heterocycle which is optionally fused to another 3- to 5-membered heterocycle, and $R^e$ and $R^f$ are optionally joined to form a 4- to 8-membered heterocycle which is optionally fused to another 3- to 5-membered heterocycle.

3. The compound of claim 2 wherein
a) $R^c$ and $R^d$ are joined and form a heterocyclic fused ring system selected from the group consisting of:

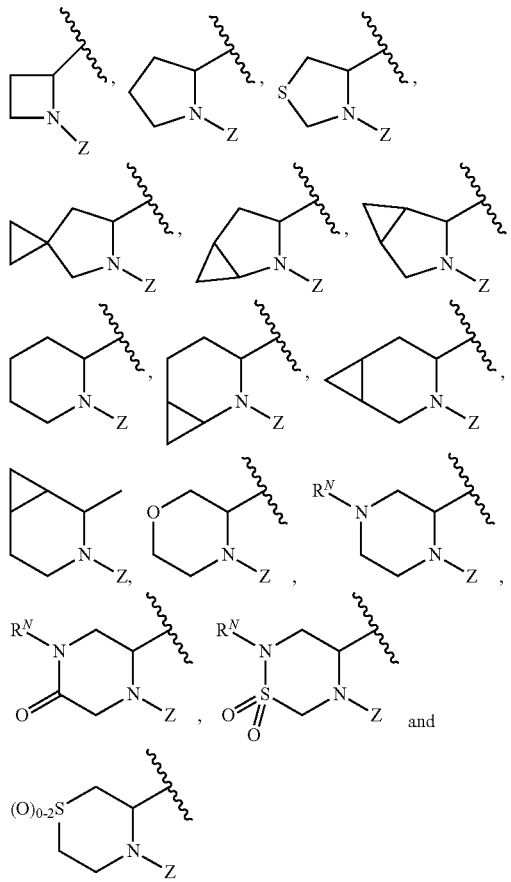

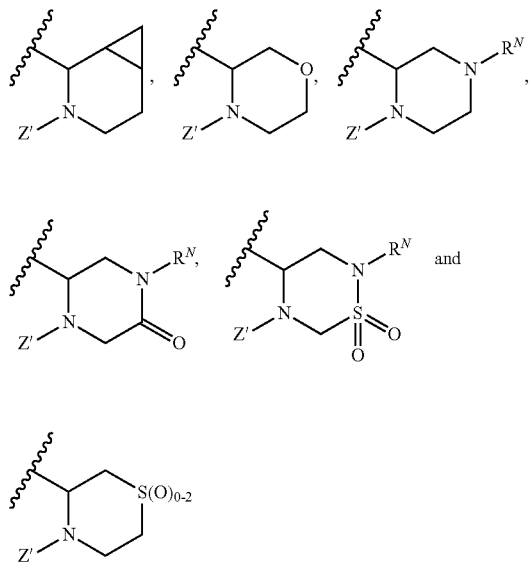

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, or b) wherein $R^e$ and $R^f$ are joined and form a heterocyclic fused ring system selected from the group consisting of:

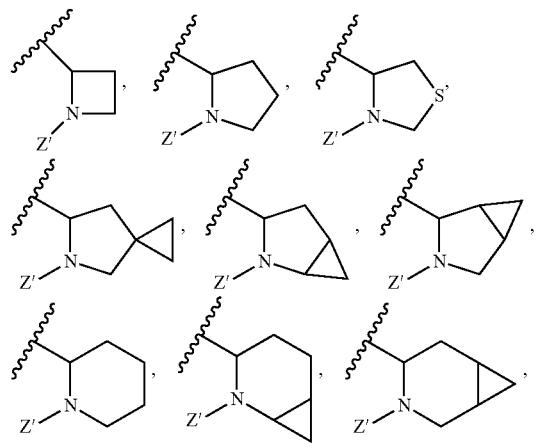

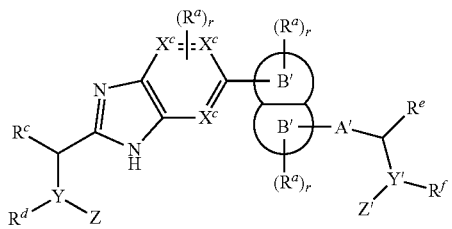

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

4. The compound of claim 1 having formula III:

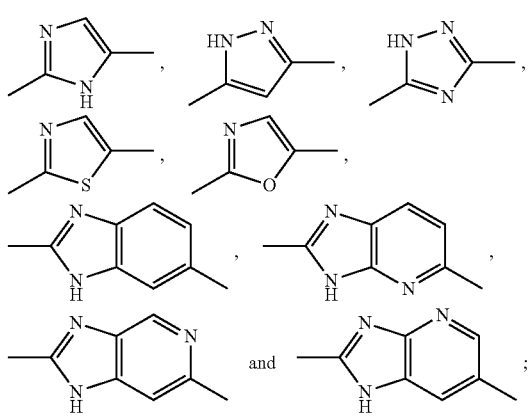

wherein

A' is selected from the group consisting of a single bond, and each $X^c$ is independently C or N.

5. The compound of claim 4 having formula selected from the group consisting of:
a) formula IIIa:

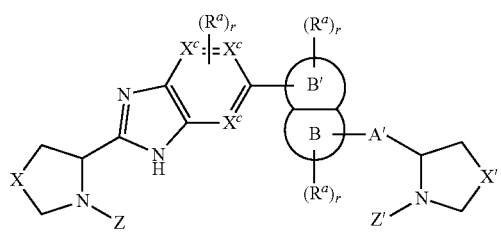

wherein X and X' are each independently selected from the group consisting of a bond, —CH₂—, —CH₂—CH₂—, —CH=CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl, b) formula IIIc:

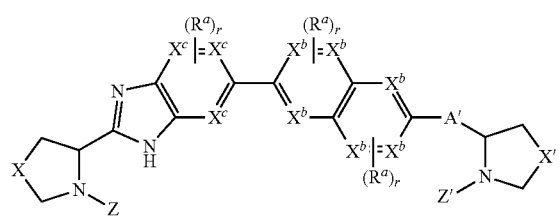

wherein X and X' are each independently selected from the group consisting of a bond, —CH₂—, —CH₂—CH₂—, —CH=CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl, c) formula IIId:

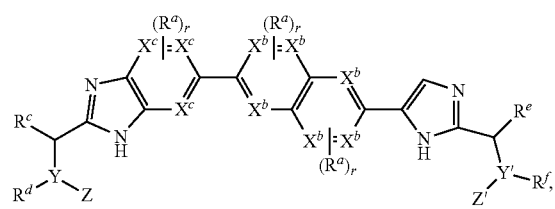

d) formula IIIe:

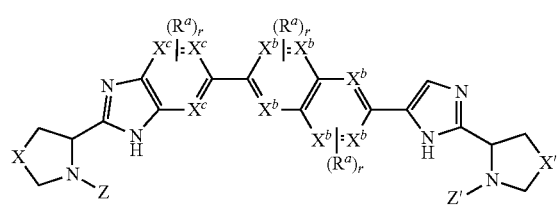

wherein X and X' are each independently selected from the group consisting of a bond, —CH₂—, —CH₂—CH₂—, —CH=CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl, e) formula IIIf:

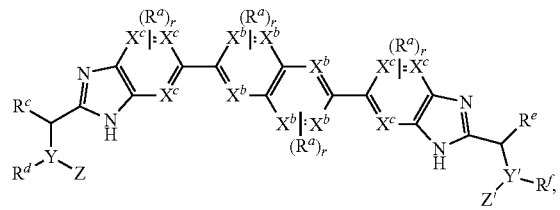

and f) formula IIIg:

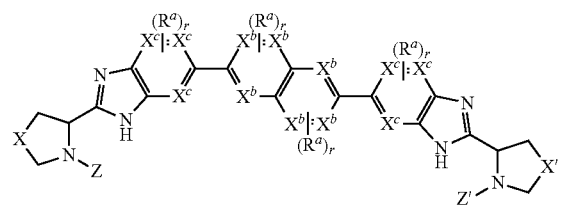

wherein X and X' are each independently selected from the group consisting of a bond, —CH₂—, —CH₂—CH₂—, —CH=CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl.

6. The compound of claim 1, having formula IIIk:

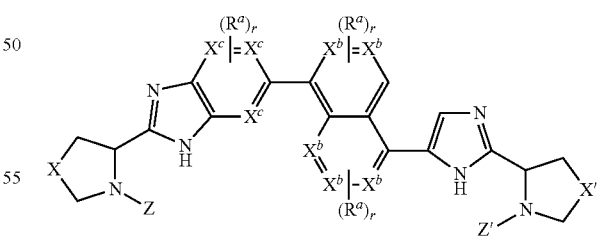

wherein X and X' are each independently selected from the group consisting of a bond, —CH₂—, —CH₂—CH₂—, —CH=CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl.

7. The compound of claim 1, having formula IIIm:

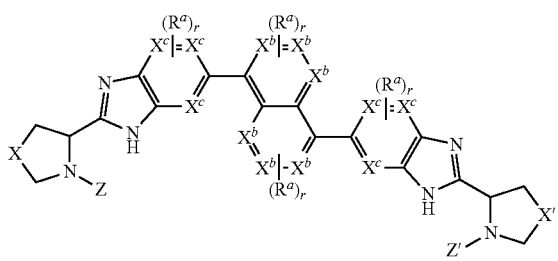

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

8. The compound of claim 1, having formula IIIq:

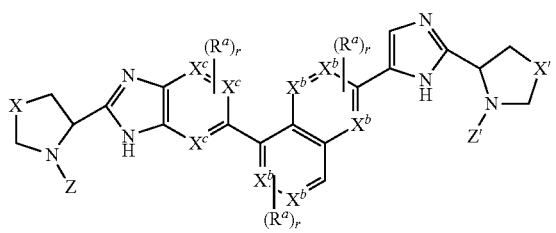

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl, and each X$^b$ is C and each X$^c$ is independently C or N.

9. The compound of claim 1, wherein R$^c$, R$^d$, R$^e$ and R$^f$ are each independently selected from the group consisting of: hydrogen, C$_1$ to C$_8$ alkyl and C$_1$ to C$_8$ heteroalkyl, wherein,
each hetero atom, if present, is independently N, O or S,
R$^c$ and R$^d$ are optionally joined to form a 4- to 8-membered heterocycle which is optionally fused to another 3- to 5-membered heterocycle, and
R$^e$ and R$^f$ are optionally joined to form a 4- to 8-membered heterocycle which is optionally fused to another 3- to 5-membered heterocycle.

10. The compound of claim 1, wherein each R$^a$ is independently —CN, —OCHF$_2$, —OCF$_3$, —CF$_3$, or —F.

11. The compound of claim 1, wherein one of Y and Y' is N.

12. The compound of claim 1, wherein A' is

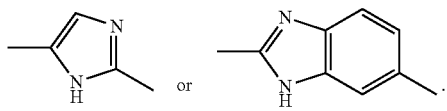

13. The compound of claim 1, wherein Z and Z' are each 1-3 amino acids.

14. The compound of claim 13 wherein the amino acids are in the D configuration.

15. The compound of claim 1, selected from the group consisting of

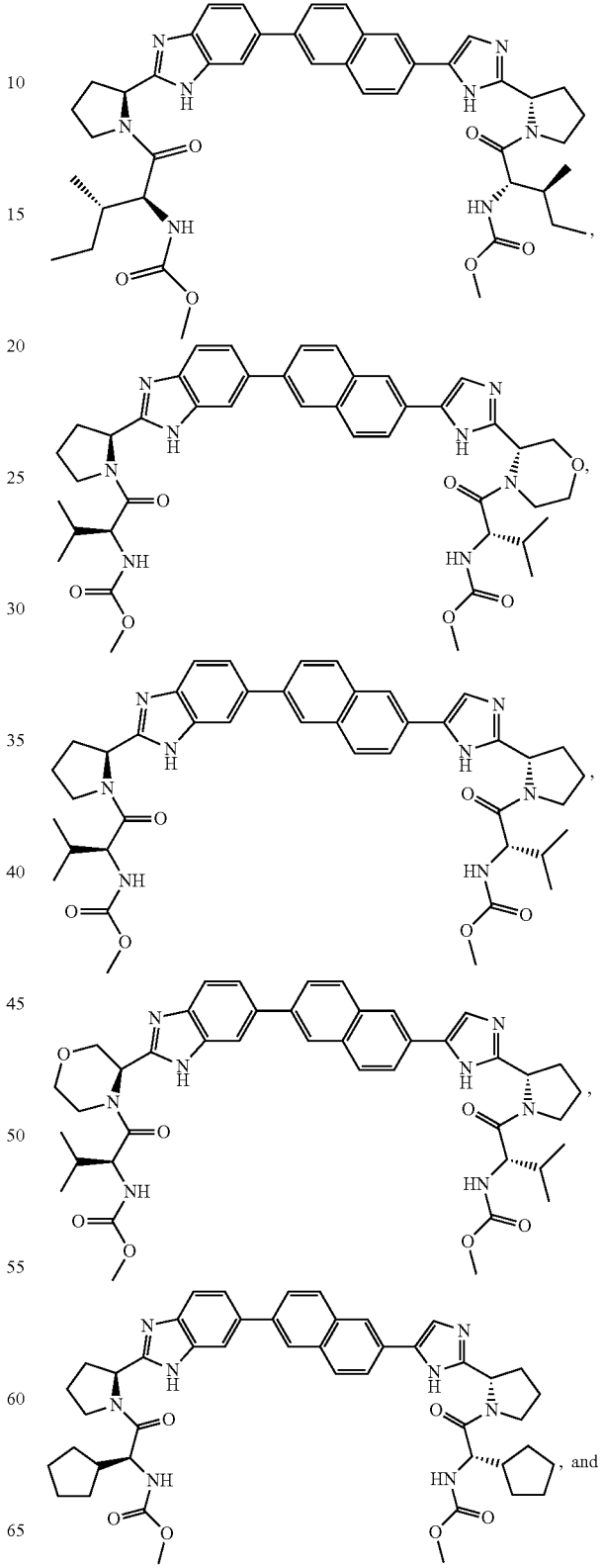

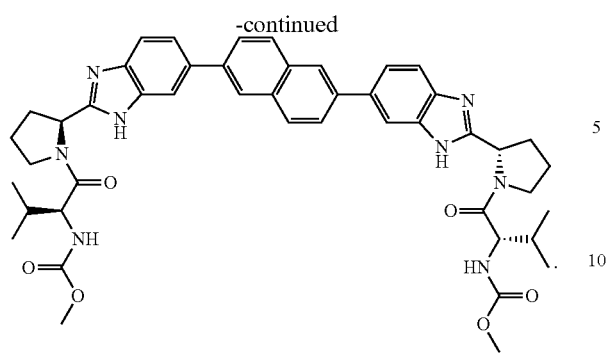
16. A pharmaceutical composition comprising a compound of claim 1 and one or more pharmaceutically acceptable excipients or vehicles.
17. A method of treating hepatitis C comprising administering to a subject in need thereof, a therapeutically effective amount of claim 1.
* * * * *